US007553831B2

(12) United States Patent  (10) Patent No.: US 7,553,831 B2
Beck et al.  (45) Date of Patent: Jun. 30, 2009

(54) COMPOUNDS TO TREAT ALZHEIMER'S DISEASE

(75) Inventors: James Beck, Kalamazoo, MI (US); Andrea Gailunas, San Francisco, CA (US); Roy Hom, San Francisco, CA (US); Barbara Jagodinska, Redwood City, CA (US); Varghese John, San Francisco, CA (US); Michael Maillaird, San Francisco, CA (US)

(73) Assignee: Elan Pharmaceuticals, Inc., So. San Francisco, CA (US)

( * ) Notice: Subject to any disclaimer, the term of this patent is extended or adjusted under 35 U.S.C. 154(b) by 472 days.

(21) Appl. No.: 11/042,695

(22) Filed: Jan. 25, 2005

(65) Prior Publication Data

US 2005/0203096 A1  Sep. 15, 2005

Related U.S. Application Data

(62) Division of application No. 09/895,843, filed on Jun. 29, 2001, now Pat. No. 6,846,813.

(60) Provisional application No. 60/215,323, filed on Jun. 30, 2000.

(51) Int. Cl.
A61K 31/33 (2006.01)
A61K 31/495 (2006.01)
C07D 241/04 (2006.01)
C07D 241/00 (2006.01)

(52) U.S. Cl. .................. 514/183; 514/252.12; 514/616; 514/617; 544/358; 544/398; 544/402

(58) Field of Classification Search .................. 514/183, 514/252.12, 616, 617; 544/358, 398, 402
See application file for complete search history.

(56) References Cited

U.S. PATENT DOCUMENTS

| 4,224,179 A | 9/1980 | Schneider |
| 4,231,877 A | 11/1980 | Yamauchi et al. |
| 4,235,871 A | 11/1980 | Papahadjopoulous et al. |
| 4,247,411 A | 1/1981 | Vanlerberghe et al. |
| 4,394,448 A | 7/1983 | Szoka, Jr. et al. |
| 4,399,216 A | 8/1983 | Axel et al. |
| 4,522,811 A | 6/1985 | Eppstein et al. |
| 4,616,088 A | 10/1986 | Ryono et al. |
| 4,636,491 A | 1/1987 | Bock et al. |
| 4,665,193 A | 5/1987 | Ryono et al. |
| 4,668,770 A | 5/1987 | Boger et al. |
| 4,673,567 A | 6/1987 | Jizomoto |
| 4,676,980 A | 6/1987 | Segal et al. |
| 4,736,866 A | 4/1988 | Leder et al. |
| 4,749,792 A | 6/1988 | Natarajan et al. |
| 4,753,788 A | 6/1988 | Gamble |
| 4,814,270 A | 3/1989 | Piran |
| 4,816,567 A | 3/1989 | Cabilly et al. |
| 4,870,009 A | 9/1989 | Evans et al. |
| 4,880,781 A | 11/1989 | Hester, Jr. et al. |
| 4,897,355 A | 1/1990 | Eppstein et al. |
| 5,010,182 A | 4/1991 | Brake et al. |
| 5,142,056 A | 8/1992 | Kempe et al. |
| 5,145,684 A | 9/1992 | Liversidge et al. |
| 5,162,538 A | 11/1992 | Voges et al. |
| 5,175,281 A | 12/1992 | McCall et al. |
| 5,250,565 A | 10/1993 | Brooks et al. |
| 5,364,934 A | 11/1994 | Drayna et al. |
| 5,374,652 A | 12/1994 | Buzzetti et al. |
| 5,376,542 A | 12/1994 | Schlegal |
| 5,387,742 A | 2/1995 | Cordell |
| 5,441,870 A | 8/1995 | Seubert et al. |
| 5,461,067 A | 10/1995 | Norbeck et al. |
| 5,475,138 A | 12/1995 | Pal et al. |
| 5,481,011 A | 1/1996 | Chen et al. |
| 5,482,947 A | 1/1996 | Talley et al. |
| 5,502,061 A | 3/1996 | Hui et al. |
| 5,502,187 A | 3/1996 | Ayer et al. |
| 5,508,294 A | 4/1996 | Vazquez et al. |
| 5,510,349 A | 4/1996 | Talley et al. |
| 5,510,388 A | 4/1996 | Vazquez et al. |
| 5,516,784 A | 5/1996 | Bennett et al. |

(Continued)

FOREIGN PATENT DOCUMENTS

DE  3610593  10/1987

(Continued)

OTHER PUBLICATIONS

Atsuumi et al., "Renin Inhibitors. I. Synthesis and Structure-Activity Relationships of Transition-State Inhibitors Containing Homostatine Analogues at the Scissile Bond," Chemical and Pharmaceutical Bulletin, 40(2), 364-370 (1992).

(Continued)

*Primary Examiner*—James O. Wilson
*Assistant Examiner*—Paul V. Ward
(74) *Attorney, Agent, or Firm*—McDonnell Boehnen Hulbert & Berghoff LLP

(57) ABSTRACT

The present invention is disubstituted amines of formula (I)

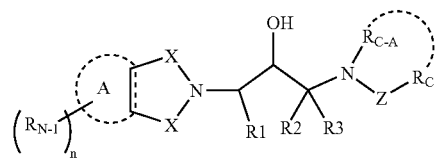

(I)

and disubstituted amines of formula (II)

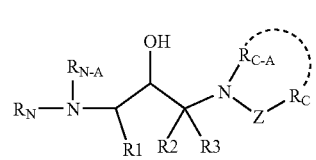

(II)

useful in treating Alzheimer's disease and other similar diseases.

14 Claims, No Drawings

U.S. PATENT DOCUMENTS

| | | | |
|---|---|---|---|
| 5,521,219 A | 5/1996 | Vazquez et al. |
| 5,545,640 A | 8/1996 | Beaulieu et al. |
| 5,593,846 A | 1/1997 | Schenk et al. |
| 5,602,169 A | 2/1997 | Hewawasam et al. |
| 5,602,175 A | 2/1997 | Talley et al. |
| 5,604,102 A | 2/1997 | McConlogue et al. |
| 5,610,190 A | 3/1997 | Talley et al. |
| 5,612,486 A | 3/1997 | McConlogue et al. |
| 5,625,031 A | 4/1997 | Webster et al. |
| 5,631,405 A | 5/1997 | Pal et al. |
| 5,639,769 A | 6/1997 | Vazquez et al. |
| 5,648,511 A | 7/1997 | Ng et al. |
| 5,663,200 A | 9/1997 | Bold et al. |
| 5,703,129 A | 12/1997 | Felsenstein et al. |
| 5,708,004 A | 1/1998 | Talley et al. |
| 5,720,936 A | 2/1998 | Wadsworth et al. |
| 5,721,130 A | 2/1998 | Seubert et al. |
| 5,733,882 A | 3/1998 | Carr et al. |
| 5,744,346 A | 4/1998 | Chrysler et al. |
| 5,753,652 A | 5/1998 | Fassler et al. |
| 5,760,064 A | 6/1998 | Vazquez et al. |
| 5,760,076 A | 6/1998 | Vazquez et al. |
| 5,766,846 A | 6/1998 | Schlossmacher et al. |
| 5,807,870 A | 9/1998 | Anderson et al. |
| 5,807,891 A | 9/1998 | Bold et al. |
| 5,811,633 A | 9/1998 | Wadsworth et al. |
| 5,827,891 A | 10/1998 | Dressman et al. |
| 5,830,897 A | 11/1998 | Vazquez et al. |
| 5,831,117 A | 11/1998 | Ng et al. |
| 5,847,169 A | 12/1998 | Nummy et al. |
| 5,849,911 A | 12/1998 | Fassler et al. |
| 5,850,003 A | 12/1998 | McLonlogue et al. |
| 5,863,902 A | 1/1999 | Munoz et al. |
| 5,872,101 A | 2/1999 | Munoz et al. |
| 5,877,015 A | 3/1999 | Hardy et al. |
| 5,877,399 A | 3/1999 | Hsiao et al. |
| 5,886,046 A | 3/1999 | Hirschmann et al. |
| 5,912,410 A | 6/1999 | Cordell |
| 5,922,770 A | 7/1999 | Peschke et al. |
| 5,935,976 A | 8/1999 | Bold et al. |
| 5,942,400 A | 8/1999 | Anderson et al. |
| 5,962,419 A | 10/1999 | McDonald et al. |
| 5,965,588 A | 10/1999 | Vazquez et al. |
| 6,001,813 A | 12/1999 | Gyorkos et al. |
| 6,013,658 A | 1/2000 | Lau et al. |
| 6,022,872 A | 2/2000 | Vazquez et al. |
| 6,045,829 A | 4/2000 | Liversidge et al. |
| 6,051,684 A | 4/2000 | McDonald et al. |
| 6,060,476 A | 5/2000 | Vazquez et al. |
| 6,150,344 A | 11/2000 | Carroll et al. |
| 6,153,652 A | 11/2000 | Wu et al. |
| 6,191,166 B1 | 2/2001 | Audia et al. |
| 6,221,670 B1 | 4/2001 | Cordell |
| 2002/0016320 A1 | 2/2002 | Fang et al. |

FOREIGN PATENT DOCUMENTS

| | | |
|---|---|---|
| DE | 3721855 | 9/1988 |
| DE | 4003575 | 8/1991 |
| EP | 0036776 | 9/1981 |
| EP | 0073657 | 3/1983 |
| EP | 0117058 | 8/1984 |
| EP | 0117060 | 8/1984 |
| EP | 0173441 | 5/1986 |
| EP | 0209897 | 1/1987 |
| EP | 0212903 | 3/1987 |
| EP | 0264106 | 4/1988 |
| EP | 274259 | 7/1988 |
| EP | 0320205 | 6/1989 |
| EP | 0337714 | 10/1989 |
| EP | 0362179 | 4/1990 |
| EP | 0432694 | 6/1991 |
| EP | 0437729 | 7/1991 |
| EP | 0609625 | 8/1994 |
| EP | 0652009 | 5/1995 |
| EP | 0372537 | 2/2008 |
| GB | 223740 | 10/1988 |
| GB | 2211504 | 7/1989 |
| JP | 7126286 | 5/1995 |
| WO | 8702986 | 5/1987 |
| WO | 8704349 | 7/1987 |
| WO | 8705330 | 9/1987 |
| WO | 8900161 | 1/1989 |
| WO | 8901488 | 2/1989 |
| WO | 8905859 | 6/1989 |
| WO | 9013646 | 11/1990 |
| WO | 9100360 | 1/1991 |
| WO | 9200750 | 1/1992 |
| WO | 9217490 | 10/1992 |
| WO | 9220373 | 11/1992 |
| WO | 9320257 | 2/1993 |
| WO | 9308829 | 5/1993 |
| WO | 9317003 | 9/1993 |
| WO | 9404492 | 3/1994 |
| WO | 9506030 | 3/1995 |
| WO | 9509843 | 4/1995 |
| WO | 9509843 | 5/1995 |
| WO | 9622287 | 7/1996 |
| WO | 9635414 | 11/1996 |
| WO | 9730072 | 8/1997 |
| WO | 9822597 | 5/1998 |
| WO | 9829401 | 7/1998 |
| WO | 9833795 | 8/1998 |
| WO | 9838167 | 9/1998 |
| WO | 9850342 | 11/1998 |
| WO | 9941266 | 8/1999 |
| WO | 9954293 | 10/1999 |
| WO | 9965870 | 12/1999 |
| WO | 0017369 | 3/2000 |
| WO | 0047618 | 8/2000 |
| WO | 0056335 | 9/2000 |
| WO | 0061748 | 10/2000 |
| WO | 0069262 | 11/2000 |
| WO | 0077030 | 12/2000 |
| WO | 0100663 | 1/2001 |
| WO | 0100665 | 1/2001 |
| WO | 0110387 | 2/2001 |
| WO | 0119797 | 3/2001 |
| WO | 0123533 | 4/2001 |
| WO | 0129563 | 4/2001 |
| WO | 0151659 | 7/2001 |

OTHER PUBLICATIONS

Chen et al., "Aminodiol HIV Protease Inhibitors. Synthesis and Structure-Activity Relationships of P1/P1' Compounds: Correlation between Lipophilicity and Cytotoxicity," J. Med. Chem., vol. 39, No. 10, pp. 1991-2007 (1996).

Raddatz et al., "Substrate Analogue Renin Inhibitors Containing Replacements of Histidine in P2 or Isosteres of the Amide bond Between P3 and P2 Sites," J. Med. Chem., 34:11, 3267-3280 (1991).

Nishi et al., "Diastereoselective Synthesis of the Hydroxyethylene Dipeptide Isostere of Leu-Val," Chemistry Letters, 1983-1996 (1989).

Harbeson et al., "Inhibition of Aminopeptidases by Peptides Containing Ketomethylene and Hydroxyethylene Amide Bond Replacements," J. of Med. Chem., 32:6, 1378-1392 (1989).

Thaisrivongs et al., "Conformationally Constrained Renin Inhibitory Peptides: γ-Lactam-Bridged Dipeptide Isostere as Conformational Restriction," J. Med. Chem., 31, 7, 1369-1376 (1988).

Nakano et al., "Synthesis of a Homostatine-Containing Renin Inhibitor Which Incorporates a Sulfonemethylene Isostere at Its N-Terminus," Bulletin of the Chemical Society of Japan, 63:8, 224-2232 (1990).

Kaltenbronn et al., "Renin Inhibitors Containing Isosteric Replacements of the Amide Bond Connecting the P3 and P2 Sites," J. Med. Chem., 33, 2, 838-845 (1990).

Plummer et al., "Potent and Selective Bicyclic Lactam Inhibitors of Thrombin: Part 3:P1' Modifications," Bioorganic & Medicinal Chemistry Letters, 9, 835-840 (1999).

Abbenante et al., "Inhibitors of .beta.-Amyloid Formation Based on the .beta.-Secretase Cleavage Site," Biochemical and Biophysical Research Communications, 268:133-135 (2000).

Alterman et al., "Design and Synthesis of New Potent C.sub.3-Symmetric HIV-1 Protease Inhibitors, Use of L-Mannaric Acid asa Peptiodomimetic Scaffold," J. Med. Chem., 41, 3782-3792 (1998).

Amblard et al., "Synthesis and Characterization of Bradykinin B.sub.2 Receptor Agonists Containing Constrained Dipeptide Mimics," J. Med. Chem., 42:20, 4193-4201 (1999).

Arrowsmith et al., "Amino-Alcohol Dipeptide Analogues: A Simple Synthesis of a Versatile Isostere for the Development of Proteinase Inhibitors," 28:45, 5569-5572 (1987).

Askin et al., "Highly Disastrous Alkylations of Chiral Amide Enolates: New Routes to Hydroxyethylene Dipeptide Isostere Inhibitors of HIV-1 Protease," The Journal of Organic Chemistry, 57:10, 2771-2773 (1992).

Balicki et al., "Mild and Efficient Conversion of Nitriles to Amides with Basic Urea-Hydrogen Peroxide Adduct," Synth. Comm., 23(22), 3149-3155 (1993).

Barton, "Protection of N-H Bonds and NR.sub.3," Protective Groups in Organic Chemistry, Chapter 2, 43-93 (1976).

Basu et al., "Efficient Transformation of Nitrile into Amide under Mild Condition," Tetrahedron Letters, 39, 3005-3006 (1998).

Bennett et al., "The Synthesis of Novel HIV-Protease-Inhibitors via Silica Gel Asisted-Addition of Amines to Epoxides," Synlett, 9, 703-704 (1993).

Berge et al., "Pharmaceutical Salts," Journal of Pharmaceutical Sciences, 66:1, 1-19 (1977).

Blatt, "Heptaldoxime," Organic Syntheses, Collective vol. 2, 312-315.

Bodendorf et al., "A Splice Variant of .beta.-Secretase Deficient in the Amyloidogenic Processings of the Amyloid Precursor Protein," The Journal of Biological Chemistry, 276:15, 12019-12023 (2001).

Lin et al., "Human Aspartic Protease Memapsin 2 Cleaves the .beta.-Amyloid Precursor Protein," PNAS, 97:4, 1456-1460 (2000).

Luly et al., "A Synthesis of Protected AminoalkylEpoxides from Alpha Amino Acids," Journal of Organic Chemistry, 52:8, 1487-1492 (1987).

Luo et al., "Mice Deficient in BACE1, the Alzheimer's .beta.-secretase have Normal Phenotype and Abolished .beta.-amyloid Generation," Nature Neuroscience, 4:3, 231-232 (2001).

March, "Aliphatic Nucleophilic Substitution," Advanced Organic Chemistry: Reactions, Mechanisms and Structure, 3d Edition, 380-381.

Martin et al., "Application of Almez-Mediated Amidation Reactions to Solution Phase Peptide Synthesis," Tetrahedron Letters, 39, 1517-1520 (1998).

Mashraqui et al., "Cyclophanes. 14. Synthesis, Structure Assignment, and Conformational Properties of [2.2](2,5) Oxazolo- and Thiazolophanes," J. Am. Chem. Soc., 104, 4461-4465 (1982).

McLendon et al., "Cell-Free Assays for Gamma-Secretase Activity," The FASEB Journal, 14:15, 2383-2386 (2000).

Miyaura et al., "Palladium-Catalyzed Cross-Coupling Reactions of Organoboron Compounds," Chem. Rev., 2457-2483 (2000).

Moersch et al., "The Synthesis of Alpha-Hydroxcarboxylic Acids by Aeration of Lithiated CArboxylic Acids in Tetrahydrofuran Solution," Synthesis, 12, 627-649 (1971).

Murahashi et al., "Ruthenium-Catalyzed Hydration of Nitriles and Transformation of .delta.-Keto Nitriles to Ene-Lactams," J. Org. Chem., 57:9, 2521-2523 (1992).

Norman et al., "Structure-Activity Relationships of a Series of Pyrrolo[3,2-d]pyrimidien Derivatives and Related Compounds as Neuropeptide Y5 Receptor Antagonists," J. Med. Chem., 43, 4288-4312 (2000).

Owa et al., Discovery of Novel Anittumor Sulfoamides Targeting G1 Phase of the Cell Cycle, J. Med. Chem., 42, 3789-3799 (1999).

Pirttita et al., "Longitudinal Study of Cerebrospinal Fluid Amyloid Proteins and Apolipoprotein E in Patients with Probable Alzheimers's Disease," Neuroscience Letter, 249, 21-24 (1998).

Reetz et al., "Protective Group Tuning in the Stereoselective Conversion of .alpha. Amino Aldehydes into Aminoalkyl Epoxides," Tetrahedron Letters, 30:40, 5425-5428 (1989).

Sabbagh et al., ".beta.-Amyloid and Treatment Opportunities for Alzheimer's Disease," Alzheimer's Disease Review, 3:1-19 (1998).

Sakurai et al., "Studies of HIV-1 Protease Inhibitors, II, Incorporation of Four Types of Hydroxyethylene Dipeptide Isosteres at the Scissle Site of Substrate Sequences," Chemical & Pharmaceutical Bulletin, 41:8, 1378-1386 (1993).

Sakurai et al., "A New Synthethic Route for the Gamma-Lactone Precursors of Hydroxyethylene Dipeptide Isosteres," Tetrahedron Letters, 34:10, 5939-5942 (1993).

Sebti et al., "Catalysie Heterogene de L'Hydration des Nitriles en Amides par le Phosphate Naturel Dope par KF et le Phosphate Trisodique," Tehtrahedron Letters, 37:36, 6555-6556 (1996).

Selkoe, "The Molecular Pathology of Alzheimer's Disease," Neuron, 6:4, 487-498 (1991).

Selkoe, "Translating Cell Biology into Therapeutic Advances in Alzheimer's Disease," Nature, 399:6738, pp. A-23-A31 (1999).

Seubert et al., "Isolation and Quantification of Soluble Alzheimer's .beta.-peptide from Biological Fluids," Nature, 359:6393, 325-327 (1992).

Shearman et al., "L-685, 458, and Aspartyl Protease Transition State Mimic, is a Potent Inhibitor of Amyloid .beta.-Portein Precursor. gamma.-Secretase Activity," Biochemistry, 39, 8698-9704 (2000).

Shibata et al., "An Expeditious Synthesis of (2R,3S)-3-tertButoxycarbonlamino-1, isobutylamino-4-phenyl-2-2butanol, a Key Building Block of HIV Protease Inhibitors," Tetrahedron Letters, 38:4, 619-620 (1997).

Sinha et al., "Purification and Cloning of Amyloid Precursor Protein. beta.-secretase from Human Brain," Nature, 402:6761, 537-540 (1999).

Smith et al., "Reduction of Carboxylic Acids and Esters to Alkanese," Advances Organic Chemistry-Reactions, Mechanisms and Structure, 5th Ed., Chapt. 19, 1552-1554 (2001).

Snyder et al., "Organoboron Compounds and the Study of Reaction Mechanisms, Primary Aliphatic Boroaic Acids," J. Am. Chem. Soc. 105-111 (Jan.-Jun. 1938).

Thurksuf et al., Synthesis and Anticonvulsant Activity of 1-Phenylcyclohexylamine Analogues, 33:1452-1458 (1990).

Tucker et al., A Series of Potent HIV-1 Protease Inhibitors Containing a Hydroxyethyl Secondary Amine Transition State Isostere: Synthesis, Enzyme Inhibition, and Antiviral Activity, 35:14, 2525-2533 (1992).

Vassar et al., ".beta.-Secretase Cleavage of Alzheimers' AMyloid Precursor Protein by the Transmembrane Aspartic Protease BACE," Science, 286:5440, 735-741 (1999).

Vazquez et al., "Inhibitors of HIV-1 Protease Containing the Novel and Potent .RTM.-Hydroxyethyl sulfonamide Isostere," J. of Med. Chem., 38:4, 581-584 (1995).

Wang et al., "Preparation of .alpha.-Chloroketones by the Chloracetate Claisen Reaction," Synlett, 6, 902-904 (Jun. 2000).

Werner et al., "Cyclobutylamine," Organic Syntheses, vol. 5, 273-276 (1973).

Wilgus et al., "The Acid-Catalyzed and Uncatalyzed Hydrolysis of Nitriles on Unactivated Alumina," 36:20, 3469-3472 (1995).

Yan et al., Membrane-anchored Aspartyl Protease with Alzheimer's Disease .beta.-secretase Activity, Nature, 402:6761, 533-537 (1999).

Flynn et al., "Chemical Library Purification Strategies Based on Principles of Complementary Molecular Reactivity and Molecular Recognition," J. Am. Chem. Soc., 119, 487-4881 (1997).

Chevallier N. et al., "Cathepsin D displays in vitro β-secretase-like specificity," Brain Research, 750, 11-19 (1997).

Kick E.K. et al., "Structure-based design and combinatorial chemistry yield low nanomolar inhibitors of cathepsin D," Chemistry and Biology, 4:297-307 (1997).

Nj, J.S. et al., "A practical synthesis of an HIV protease inhibitor intermediate—Diastereoselective epoxide formation from chiral α-aminoaldehydes," Tetrahedron, 51:23, 6397-6410 (1995).

Bose et al., "A Facile Hydrataion of Nitriles by Dimnethyldioxirane," Synth. Comm., 27(18):3119-3123 (1997).

Calderwood et al., "Organocerium REactions of Benzamides and Thiobenzamides: A Direct Synthesis of Tertiary Carbinamines," Tetrahedron Letters, 38:7, 1241-1244 (1997).

Chen et al., "A Practical Method for the Preparation of a α-Chloroketones of N-Carbamate Protected-α-Aminoacids," Tetrahedron—Mannaric Acid Letters, 38:18, 3175-3178 (1997).

Ciganek, "Tertiary Carbinamines by Addition of Organocerium Reagents to Nitriles and Ketimines," J. Org. Chem., 57:16, 4521-4527 (1992).

Citron et al., "Mutation of the β-amyloid Precursor Protein in Familial Alzheimer's Disease Increases β-Protein Production," Nature, 360:6405, 672-674 (1992).

Cushman et al., "Synthesis of Analogs of 2-Methoxyestradiol with Enhanced Inhibitory Effects on Tubulin Polymerization and Cancer Cell Growth," J. Med. Che., 40:15, 2323-2331 (1997).

Deno et al., "Protonated Cyclopropane Intermediates in the Ractions of Cyclopropanecarboxylic Acids," J. Am. Chem. Soc., 92:7, 3700-3703 (1970).

Diederich et al., "Stereoselective Synthesis of a Hydroxyethylene Dipeptide Isotere," Tetrahedron Letters, 34:39, 6169-6172 (1993).

Diercks et al., "Tris (benzocyclobutadieno) benzene, the Triangular [4] Phenylene with a Completely Bond-Fixed Cyclohexatriene Ring: Cobalt-Catalyzed Synthesis from Hexaethynlbenzene and Thermal Ring Opening to 1,2:5,6:9,10-Tribenzo-3,4,7,8,11,12 hexadehydro[12]-annulene," J. Am. Chem. Soc., 108:11, 3150-3152 (1986).

Dovey et al., "Funcational Gamma-Secretase Inhibitors Reduce Beta0Amyloid Peptide Levels in Brain," Journal of Neurochemistry, 76, 173-181 (2001).

Dragovich et al., "Structure-Based Desing, Synthesis, and Biological Evaluation of Irrevertible Human Rhinovirus 3C Protease Inhibitors," Journal of Medicinal Chemistry, 42:7, 1203-1212 (1999).

Emilien et al., "Prospects for Pharmacological Intervention in Alzheimer Disease," Neurological Review, 57, 454-459 (2000).

Felman et al., "Synthesis and Antiulcer Activity of Novel 5-(2-Ethenyl Substituted)-3(2H)furanones," J. Med. Chem., 35:7, 1183-1190 (1992).

Games et al., "Alzheimer-type Neuropathology in Trasgenic Mice Overexpressing V717Fβ-amyloid Precursor Protein," Letters to Nature, 373:6614, 523-527 (1995).

Gao et al., "Asymmetric Hetero Diels-Alder Reaction Catalyzed by Stable and Easily Prepared CAB Catalysts," Tetrahedron Letters, 50:4, 979-988 (1994).

Getman et al., "Discovery of a Novel Class of Potent HIV-1 Protease Inhibitors Containing the (r)-(Hydroxyethyl) urea Isostere," J. Med. Chem., 36:2, 288-291 (1993).

Ghosh et al., "Design of Potent Inhibitors for Human Brain Memapsin 2 β-Secretase," J. Am. Chem. Soc., 122, 3522-3523 (2000).

Ghosh et al., "Potent HIV Protease Inhibitors: The Development of Tetrahydrofuranylglycines as Novel P2-Ligands and Pyrazine Amides as P3-Ligands," J. Med. Chem., 36, 2300-2310 (1993).

Gould, "Salt Selection for Basic Drugs," International Journal of Pharmaceutics, 33:1-3, 201-217 (1986).

Greene et al., "Protection for the Amino Group," Protective Groups in Organic Synthesis: 2nd Ed., Chpt. 7, 309-405 (1991).

Greene et al., "Protection for the Amino Group," Protective Groups in Organic Synthesis, Chpt. 7, 218-287 (1981).

Hardy et al., "Framing β-Amyloid," Nature Genetics, 1, 233-234 (1992).

Heck, "Carbonylation of Aromatic Compounds to Acids, Acid Derivatives, Aldehydes and Ketones," Palladium Reagents in Organic Syntheses, Chpt. 8.2, 342-365 (1985).

Henning, "A. Synthetic Routs to Different Classes of Natural Products and Analogs Thereof—Synthesis of Hydroxyethylene Isoteric Dipeptides," Organic Synthesis Highlights II, 251-259 (1995).

Hon et al., "The Studies of Metal Ion Catalyzed Carbon-Hdyrogen Insertion of α-Alkoxy-α'-Diazoketones Derived from Mandelic and Lactic Acids," Heterocycles, 31:10, 1745-1750 (1990).

Hong et al., "Structure of the Protease Domain of Memapsin 2 (β-Secretase) Complexed with Inhibitor," Science, 290:5489, 150-153 (2000).

Hussain et al., Identification of a Novel Aspartic Protease (asp 2) as β-Secretase, Molecular and Cellular Neuroscience, 14, 419-427 (1999).

Kabalka et al., "The Transformation of Nitriles into Amides," Synth. Comm., 20(1), 1445-1451 (1990).

Kaldor et al., "Isophthalic Acid Derivatives: Amino Acid Surrogates for the Inhibition of HIV-1 Protease," Bioorganic and Medicinal Chemistry Letters, 5:7, 721-726 (1995).

Kang et al., "The Precursor of Alzheimer's Disease Amyloid A4 Protein Resembles a Cell-Surface Receptor," 325:6106, 733-736 (1987).

Kitaguchi et al., "Novel Precursor of Alzheimer's Disease Amloid Protein Shows Protease Inhibitory Activity," Nature, 331:6156, 530-532 (1988).

Klumpp et al., "Lithiation of Cyclopropylcarbinols," J. Am. Chem. Soc., 101:23 (1979).

Lakouraj et al., "Selective Conversion of Nitriles of Amides by Amberlyst A-26 Supported Hydroperoxide," Indian Journal of Chemistry, 38B, 974-975 (1999).

Larock, "Carboxylic Acids to Amides," Comprehensive Organic Transformations, Chpt. 4, 972-985 (1986).

Li et al., "Photoactivated V-secretase Inhibitors Directed to the Active Site Covalently Label Presenilin I," Nature, 405, 689-694 (2000).

Demerle-Pallardy et al., "In Vitro Antioxidant Neuroprotective Activity of BN 80933, a Dual Inhibitor of Neuronal Nitric Oxide Synthase and Lipid Peroxidation" J. Neurochem., V. 74/5, 2079-2086 (2000).

Chabrier et al., "Nitric oxide synthases: targets for therapeutic strategies in neurological diseases," CMLS Cell Mol. Life Sci., 55, 1029-1035 (1999).

CAS Abstract #123:169523-1995:772556.

COMPOUNDS TO TREAT ALZHEIMER'S DISEASE

CROSS-REFERENCE TO RELATED APPLICATIONS

This application claims priority to the following provisional application: U.S. provisional application Ser. No. 60/215,323, filed Jun. 30, 2000.

BACKGROUND OF THE INVENTION

1. Field of the Invention

The present invention is directed to compounds useful in treatment of Alzheimer's disease and similar diseases.

2. Description of the Related Art

Alzheimer's disease (AD) is a progressive degenerative disease of the brain primarily associated with aging. Clinical presentation of AD is characterized by loss of memory, cognition, reasoning, judgement, and orientation. As the disease progresses, motor, sensory, and linguistic abilities are also affected until there is global impairment of multiple cognitive functions. These cognitive losses occur gradually, but typically lead to severe impairment and eventual death in the range of four to twelve years.

Alzheimer's disease is characterized by two major pathologic observations in the brain: neurofibrillary tangles and beta amyloid (or neuritic) plaques, comprised predominantly of an aggregate of a peptide fragment know as A beta. Individuals with AD exhibit characteristic beta-amyloid deposits in the brain (beta amyloid plaques) and in cerebral blood vessels (beta amyloid angiopathy) as well as neurofibrillary tangles. Neurofibrillary tangles occur not only in Alzheimer's disease but also in other dementia-inducing disorders. On autopsy, large numbers of these lesions are generally found in areas of the human brain important for memory and cognition.

Smaller numbers of these lesions, in a more restricted anatomical distribution, are found in the brains of most aged humans who do not have clinical AD. Amyloidogenic plaques and vascular amyloid angiopathy also characterize the brains of individuals with Trisomy 21 (Down's Syndrome), Hereditary Cerebral Hemorrhage with Amyloidosis of the Dutch-Type (HCHW A-D), and other neurogenerative disorders. Beta-amyloid is a defining feature of AD, now believed to be a causative precursor or factor in the development of the disease. Deposition of A beta in areas of the brain responsible for cognitive activities is a major factor in the development of AD. Beta-amyloid plaques are predominantly composed of amyloid beta peptide (A beta, also sometimes designated betaA4). A beta peptide is derived by proteolysis of the amyloid precursor protein (APP) and is comprised of 39-42 amino acids. Several proteases called secretases are involved in the processing of APP.

Cleavage of APP at the N-terminus of the A beta peptide by beta-secretase and at the C-terminus by one or more gamma-secretases constitutes the beta-amyloidogenic pathway, i.e. the pathway by which A beta is formed. Cleavage of APP by alpha-secretase produces alpha-sAPP, a secreted form of APP that does not result in beta-amyloid plaque formation. This alternate pathway precludes the formation of A beta peptide. A description of the proteolytic processing fragments of APP is found, for example, in U.S. Pat. Nos. 5,441,870; 5,721,130; and 5,942,400.

An aspartyl protease has been identified as the enzyme responsible for processing of APP at the beta-secretase cleavage site. The beta-secretase enzyme has been disclosed using varied nomenclature, including BACE, Asp, and Memapsin. See, for example, Sinha et. al., 1999, *Nature* 402:537-554 (p 501) and published PCT application WO00/17369.

Several lines of evidence indicate that progressive cerebral deposition of beta-amyloid peptide (A beta) plays a seminal role in the pathogenesis of AD and can precede cognitive symptoms by years or decades. See, for example, Selkoe, 1991, *Neuron* 6:487. Release of A beta from neuronal cells grown in culture and the presence of A beta in cerebrospinal fluid (CSF) of both normal individuals and AD patients has been demonstrated. See, for example, Seubert et al., 1992, *Nature* 359:325-327.

It has been proposed that A beta peptide accumulates as a result of APP processing by beta-secretase, thus inhibition of this enzyme's activity is desirable for the treatement of AD. In vivo processing of APP at the beta-secretase cleavage site is thought to be a rate-limiting step in A beta production, and is thus a therapeutic target for the treatment of AD. See for example, Sabbagh, M., et al., 1997, *Alz. Dis. Rev.* 3, 1-19.

BACE1 knockout mice fail to produce A beta, and present a normal phenotype. When crossed with transgenic mice that overexpress APP, the progeny show reduced amounts of A beta in brain extracts as compared with control animals (Luo et. al., 2001 *Nature Neuroscience* 4:231-232). This evidence further supports the proposal that inhibition of beta-secretase activity and reduction of A beta in the brain provides a therapeutic method for the treatment of AD and other beta amyloid disorders.

Published PCT application WO00/47618 entitled "Beta-Secretase Enzyme Compositions and Methods" identifies the beta-secretase enzyme and methods of its use. This publication also discloses oligopeptide inhibitors that bind the enzyme's active site and are useful in affinity column purification of the enzyme. In addition, WO00/77030 discloses tetrapeptide inhibitors of beta-secretase activity that are based on a statine molecule.

Various pharmaceutical agents have been proposed for the treatment of Alzheimer's disease but without any real success. U.S. Pat. No. 5,175,281 discloses 21-aminosteroids as being useful for treating Alzheimer's disease. U.S. Pat. No. 5,502,187 discloses bicyclic heterocyclic amines as being useful for treating Alzheimer's disease.

U.S. Pat. Nos. 4,616,088 and 4,665,193 discloses hydroxyethylamine compounds as anti-hypertensive agents due to their ability to inhibit renin.

U.S. Pat. No. 4,636,491 discloses various tetrapeptides which are useful as renin inhibitors.

U.S. Pat. No. 4,749,792 discloses amino compounds useful as analgesics because of their ability to inhibit an enkephalin-degrading aminopeptidase.

U.S. Pat. No. 5,142,056 discloses peptide derivatives with a $C_2$-symmetric dihydroxyethylene core as retroviral protease inhibitors.

U.S. Pat. Nos. 5,461,067 and 5,753,652 disclose the synthesis of retroviral protease inhibitors.

U.S. Pat. Nos. 5,475,138 and 5,631,405 disclose processes and various intermediates useful in the synthesis of selected protease inhibitors.

U.S. Pat. No. 5,502,061 discloses HIV protease inhibitors containing an unsaturated carbocycle or heterocycle at the C-terminus.

U.S. Pat. No. 5,545,640 discloses compounds which inhibit HIV protease activity.

U.S. Pat. No. 5,516,784 discloses compounds active against retroviruses, including HIV.

U.S. Pat. No. 5,602,175 discloses hydroxyethylamine compounds as retroviral protease inhibitors.

U.S. Pat. No. 5,631,405 discloses a process for the formation of intermediates useful in the synthesis of selected protease inhibitors.

U.S. Pat. No. 5,733,882 and International Publications WO 93/02057 and WO 93/17003 disclose dipeptide analogs as retroviral protease inhibitors.

U.S. Pat. No. 5,760,076 discloses hydroxyethylamino sulfonamide compounds as retrovirus protease inhibitors.

U.S. Pat. No. 5,807,870 discloses hydroxyethylamine compounds for the inhibition of HIV protease.

U.S. Pat. No. 5,827,891 discloses HIV protease inhibitors.

U.S. Pat. No. 5,830,897 discloses hydroxyethylamino sulfonamide compounds as retrovirus protease inhibitors.

U.S. Pat. No. 5,831,117 discloses a process and intermediates useful in retroviral protease inhibitor intermediates.

U.S. Pat. No. 5,847,169 discloses a process for preparing aminoepoxides involving the activation of the terminal hydroxyl of an aminodiol.

U.S. Pat. No. 5,849,911 discloses hydroxyethylamine HIV protease inhibitors which form hydrazines with one of the amino groups; this amino group must also be alkylated.

U.S. Pat. No. 5,922,770 discloses peptide derivatives which are useful in treating disorders resulting from a deficiency in growth hormone.

U.S. Pat. No. 6,013,658 discloses peptide derivatives which are useful in treating disorders resulting from a deficiency in growth hormone.

U.S. Pat. No. 6,022,872 discloses hydroxyethylamino sulfonyl urea compounds as HIV protease inhibitors.

U.S. Pat. No. 6,060,476 discloses hydroxyethylamino sulfonamide compounds as HIV protease inhibitors.

International Publication WO 89/01488 discloses renin inhibiting peptides with a hydroxyethylene or dihydroxyethylene isostere in the 10,11-position of the renin substrate angiotensinogen.

International Publication WO92/00750 discloses retroviral protease inhibitors.

International Publication WO 94/04492 discloses hydroxyethylamine intermediates useful for the treatment of retroviral diseases such as HIV. This disclosure also presents epoxides as intermediates for the retroviral inhibitors.

International Publication WO 95/06030 discloses epoxides, chloromethyl ketones, and alcohols prepared as intermediates for HIV protease inhibitors, with a single protecting group on the amine and arylalkyl side chain substituted with alkyl, nitro, nitrile, alkoxy, and thioalkoxy; a preferred side chain is 4-fluorophenylmethyl.

International Publication WO98/29401 discloses a method for the preparation of aminoepoxides from aminoaldehydes by which the aminoaldehyde continuously flows into a mixing zone containing an in situ generated halomethyl organometallic reagent.

International Publication WO98/33795 discloses non-peptide inhibitors of cathepsin D.

International Publication WO98/50342 discloses bis aminomethyl carbonyl compounds as inhibitors of cysteine and serine proteases.

International Publication WO00/056335 discloses non-peptide inhibitors of aspartyl proteases. These compounds influence processing of the amyloid precursor protein APP.

EP 0 609 625 discloses HIV protease inhibitors with only one noncyclized nitrogen atom.

Bioorganic & Medicinal Chemistry Letters, 5, 721-726 (1995) describes the synthesis of compounds useful for the inhibition of HIV protease in which the C-terminal nitrogen of the hydroxyethylamine compound is incorporated into a ring system such that a piperidine ring, with an amide substituent next to the nitrogen, is formed.

The hydroxyethylamine "nucleus" or isostere, which is present in the compounds of the present invention has been employed with success in the area of HIV protease inhibition. Many of these hydroxyethylamine compounds are known as well as how to make them. See for example, J. Am. Chem. Soc., 93, 288-291 (1993), Tetrahedron Letters, 28(45) 5569-5572 (1987), J. Med. Chem., 38(4), 581-584 (1994), Tetrahedron Letters, 38(4), 619-620 (1997).

U.S. Pat. No. 5,648,511 discloses a diprotected aralkyl epoxide.

U.S. Pat. Nos. 5,482,947; 5,508,294; 5,510,349; 5,510,388; 5,521,219; 5,610,190; 5,639,769; 5,760,064; and 5,965,588 disclose monoprotected (substituted) aralkyl epoxides.

Tetrahedron Lett., 30(40), 5425-5428 (1989) discloses a process in which doubly protected alpha-amino aldehydes are transformed into the corresponding aminoalkyl epoxides.

J. Med. Chem., 36, 2300 (1993) discloses an azide substituted benzyl epoxide.

Tetrahedron Lett., 38, 3175 (1997) discloses a process for the preparation of N-BOC protected epoxides from protected amino acid esters.

J. Med. Chem., 35, 2525 (1992) discloses hydroxyethylamine inhibitors of HIV protease.

U.S. Pat. No. 5,481,011 discloses arylalkyl amino epoxides in which the amino group is protected by a carbamate functionality.

Synlett, 6, 902 (2000) discloses the preparation of alpha-chloroketones of aminoprotected-(substituted)benzyl esters.

U.S. Pat. No. 5,648,511 discloses a diprotected aralkyl alcohol.

U.S. Pat. Nos. 5,482,947; 5,508,294; 5,510,349; 5,510,388; 5,521,219; 5,610,190; 5,639,769; 5,760,064; and 5,965,588 disclose monoprotected (substituted) aralklyl alcohols.

U.S. Pat. Nos. 5,482,947; 5,508,294; 5,510,349; 5,510,388; 5,521,219; 5,610,190; 5,639,769; 5,760,064; and 5,965,588 disclose a process for removing the protecting group of the monoprotected (substituted) aralklyl alcohols to give the free amino alcohol product as the amine salt.

U.S. Pat. No. 5,648,511 discloses the removal of the amino protecting group of the protected amino-alcohol to give a free amino-alcohol.

U.S. Pat. No. 6,150,344 discloses phosphate containing compounds useful in treating Alzheimer's disease.

EP 652 009 A1 discloses inhibitors of aspartyl protease which inhibit beta-amyloid peptide production in cell culture and in vivo. The compounds which inhibit intracellular beta-amyloid peptide production are useful in treating Alzheimer's Disease.

WO00/69262 discloses a new beta-secretase and its use in assays to screen for potential drug candidates against Alzheimer's disease.

WO01/00663 discloses memapsin 2 (human beta-secretase) as well as catalytically active recombinant enzyme. In addition, a method of identifying inhibitors of memapsin 2, as well as two inhibitors are disclosed. Both inhibitors that are disclosed are peptides.

WO01/00665 discloses inhibitors of memapsin 2 that are useful in treating Alzheimer's disease.

WO01/19797 discloses lactams of the formula —C—C—CO—N-lactam-W—X-Y-Z which are useful in treating Alzheimer's disease.

At present there are no effective treatments for halting, preventing, or reversing the progression of Alzheimer's disease. Therefore, there is an urgent need for pharmaceutical agents capable of slowing the progression of Alzheimer's disease and/or preventing it in the first place.

Compounds that are effective inhibitors of beta-secretase, that inhibit beta-secretase-mediated cleavage of APP, that are effective inhibitors of A beta production, and/or are effective to reduce amyloid beta deposits or plaques, are needed for the treatment and prevention of disease characterized by amyloid beta deposits or plaques, such as AD.

SUMMARY OF INVENTION

The present invention includes a disubstituted amine of formula I is:

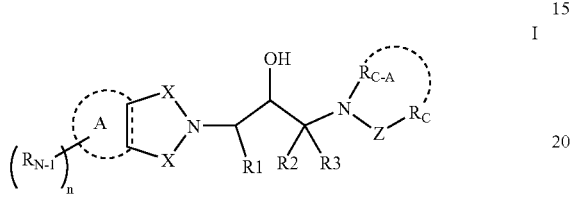

where $R_1$ is:
- (I) $C_1$-$C_6$ alkyl, optionally substituted with one, two or three substituents selected from the group consisting of $C_1$-$C_3$ alkyl, $C_1$-$C_7$ alkyl (optionally substituted with $C_1$-$C_3$ alkyl and $C_1$-$C_3$ alkoxy), —F, —Cl, —Br, —I, —OH, —SH, —C≡N, —CF$_3$, $C_1$-$C_3$ alkoxy, $NR_{1-a}R_{1-b}$ where $R_{1-a}$ and $R_{1-b}$ are —H or $C_1$-$C_6$ alkyl, and —OC=O $NR_{1-a}R_{1-b}$ where $R_{1-a}$ and $R_{1-b}$ are as defined above,
- (II) —CH$_2$—S(O)$_{0-2}$—($C_1$-$C_6$ alkyl),
- (III) —CH$_2$—CH$_2$—S(O)$_{0-2}$—($C_1$-$C_6$ alkyl),
- (IV) $C_2$-$C_6$ alkenyl with one or two double bonds, optionally substituted with one, two or three substituents selected from the group consisting of —F, —Cl, —OH, —SH, —C≡N, —CF$_3$, $C_1$-$C_3$ alkoxy, and —$NR_{1-a}R_{1-b}$ where $R_{1-a}$ and $R_{1-b}$ are —H or $C_1$-$C_6$ alkyl,
- (V) $C_2$-$C_6$ alkynyl with one or two triple bonds, optionally substituted with one, two or three substituents selected from the group consisting of —F, —Cl, —OH, —SH, —C≡N, —CF$_3$, $C_1$-$C_3$ alkoxy, and —$NR_{1-a}R_{1-b}$ where $R_{1-a}$ and $R_{1-b}$ are —H or $C_1$-$C_6$ alkyl,
- (VI) —(CH$_2$)$_{n1}$—($R_{1-aryl}$) where $n_1$ is zero or one and where $R_{1-aryl}$ is phenyl, 1-naphthyl, 2-naphthyl and indanyl, indenyl, dihydronaphthalyl, or tetralinyl optionally substituted with one, two, three, or four of the following substituents on the aryl ring:
  - (A) $C_1$-$C_6$ alkyl optionally substituted with one, two or three substituents selected from the group consisting of $C_1$-$C_3$ alkyl, —F, —Cl, —Br, —I, —OH, —SH, —C≡N, —CF$_3$, $C_1$-$C_3$ alkoxy, and —$NR_{1-a}$ $R_{1-b}$ where $R_{1-a}$ and $R_{1-b}$ are as defined above,
  - (B) $C_2$-$C_6$ alkenyl with one or two double bonds, optionally substituted with one, two or three substituents selected from the group consisting of —F, —Cl, —OH, —SH, —C≡N, —CF$_3$, $C_1$-$C_3$ alkoxy, —$NR_{1-a}R_{1-b}$ where $R_{1-a}$ and $R_{1-b}$ are —H or $C_1$-$C_6$ alkyl,
  - (C) $C_2$-$C_6$ alkynyl with one or two triple bonds, optionally substituted with one, two or three substituents selected from the group consisting of —F, —Cl, —OH, —SH, —C≡N, —CF$_3$, $C_1$-$C_3$ alkoxy, and —$NR_{1-a}R_{1-b}$ where $R_{1-a}$ and $R_{1-b}$ are —H or $C_1$-$C_6$ alkyl,
  - (D) —F, Cl, —Br or —I,
  - (F) —$C_1$-$C_6$ alkoxy optionally substituted with one, two, or three —F,
  - (G) —$NR_{N-2}R_{N-3}$ where $R_{N-2}$ and $R_{N-3}$ are as defined below,
  - (H) —OH,
  - (I) —C≡N,
  - (J) $C_3$-$C_7$ cycloalkyl, optionally substituted with one, two or three substituents selected from the group consisting of —F, —Cl, —OH, —SH, —C≡N, —CF$_3$, $C_1$-$C_3$ alkoxy, and —$NR_{1-a}R_{1-b}$ where $R_{1-a}$ and $R_{1-b}$ are —H or $C_1$-$C_6$ alkyl,
  - (K) —CO—($C_1$-$C_4$ alkyl),
  - (L) —SO$_2$—$NR_{1-a}R_{1-b}$ where $R_{1-a}$ and $R_{1-b}$ are as defined above,
  - (M) —CO—$NR_{1-a}R_{1-b}$ where $R_{1-a}$ and $R_{1-b}$ are as defined above, or
  - (N) —SO$_2$—($C_1$-$C_4$ alkyl),
- (VII) —(CH$_2$)$_{n1}$—($R_{1-heteroaryl}$) where $n_1$ is as defined above and where $R_{1-heteroaryl}$ is selected from the group consisting of:
  - pyridinyl,
  - pyrimidinyl,
  - quinolinyl,
  - benzothienyl,
  - indolyl,
  - indolinyl,
  - pryidazinyl,
  - pyrazinyl,
  - isoquinolyl,
  - quinazolinyl,
  - quinoxalinyl,
  - phthalazinyl,
  - imidazolyl,
  - isoxazolyl,
  - pyrazolyl,
  - oxazolyl,
  - thiazolyl,
  - indolizinyl,
  - indazolyl,
  - benzothiazolyl,
  - benzimidazolyl,
  - benzofuranyl,
  - furanyl,
  - thienyl,
  - pyrrolyl,
  - oxadiazolyl,
  - thiadiazolyl,
  - triazolyl,
  - tetrazolyl,
  - oxazolopyridinyl,
  - imidazopyridinyl,
  - isothiazolyl,
  - naphthyridinyl,
  - cinnolinyl,
  - carbazolyl,
  - beta-carbolinyl,
  - isochromanyl,
  - chromanyl,
  - tetrahydroisoquinolinyl,
  - isoindolinyl,
  - isobenzotetrahydrofuranyl,
  - isobenzotetrahydrothienyl,
  - isobenzothienyl, benzoxazolyl,
pyridopyridinyl,
benzotetrahydrofuranyl,
benzotetrahydrothienyl,
purinyl,
benzodioxolyl,
triazinyl,
phenoxazinyl,
phenothiazinyl,
pteridinyl,
benzothiazolyl,
imidazopyridinyl,
imidazothiazolyl,
dihydrobenzisoxazinyl,
benzisoxazinyl,
benzoxazinyl,
dihydrobenzisothiazinyl,
benzopyranyl,
benzothiopyranyl,
coumarinyl,
isocoumarinyl,
chromonyl,
chromanonyl,
pyridinyl-N-oxide,
tetrahydroquinolinyl
dihydroquinolinyl
dihydroquinolinonyl
dihydroisoquinolinonyl
dihydrocoumarinyl
dihydroisocoumarinyl
isoindolinonyl
benzodioxanyl
benzoxazolinonyl
pyrrolyl N-oxide,
pyrimidinyl N-oxide,
pyridazinyl N-oxide,
pyrazinyl N-oxide,
quinolinyl N-oxide,
indolyl N-oxide,
indolinyl N-oxide,
isoquinolyl N-oxide,
quinazolinyl N-oxide,
quinoxalinyl N-oxide,
phthalazinyl N-oxide,
imidazolyl N-oxide,
isoxazolyl N-oxide,
oxazolyl N-oxide,
thiazolyl N-oxide,
indolizinyl N-oxide,
indazolyl N-oxide,
benzothiazolyl N-oxide,
benzimidazolyl N-oxide,
pyrrolyl N-oxide,
oxadiazolyl N-oxide,
thiadiazolyl N-oxide,
triazolyl N-oxide,
tetrazolyl N-oxide,
benzothiopyranyl S-oxide, and
benzothiopyranyl S,S-dioxide,
where the $R_{1\text{-}heteroaryl}$ group is bonded to —$(CH_2)_{n1}$— by any ring atom of the parent $R_{N\text{-}heteroaryl}$ group substituted by hydrogen such that the new bond to the $R_{1\text{-}heteroaryl}$ group replaces the hydrogen atom and its bond, where heteroaryl is optionally substituted with one, two, three, or four:

(1) $C_1$-$C_6$ alkyl optionally substituted with one, two or three substituents selected from the group consisting of $C_1$-$C_3$ alkyl, —F, —Cl, —Br, —I, —OH, —SH, —C≡N, —$CF_3$, $C_1$-$C_3$ alkoxy, and —$NR_{1\text{-}a}R_{1\text{-}b}$ where $R_{1\text{-}a}$ and $R_{1\text{-}b}$ are as defined above, (2) $C_2$-$C_6$ alkenyl with one or two double bonds, optionally substituted with one, two or three substituents selected from the group consisting of —F, —Cl, —OH, —SH, —C≡N, —$CF_3$, $C_1$-$C_3$ alkoxy, and —$NR_{1\text{-}a}R_{1\text{-}b}$ where $R_{1\text{-}a}$ and $R_{1\text{-}b}$ are —H or $C_1$-$C_6$ alkyl, (3) $C_2$-$C_6$ alkynyl with one or two triple bonds, optionally substituted with one, two or three substituents selected from the group consisting of —F, —Cl, —OH, —SH, —C≡N, —$CF_3$, $C_1$-$C_3$ alkoxy, and —$NR_{1\text{-}a}R_{1\text{-}b}$ where $R_{1\text{-}a}$ and $R_{1\text{-}b}$ are —H or $C_1$-$C_6$ alkyl, (4) —F, Cl, —BR, or —I, (6) —$C_1$-$C_6$ alkoxy optionally substituted with one, two, or three —F, (7) —$NR_{N\text{-}2}R_{N\text{-}3}$ where $R_{N\text{-}2}$ and $R_{N\text{-}3}$ are as defined below, (8) —OH, (9) —C≡N,

(10) $C_3$-$C_7$ cycloalkyl, optionally substituted with one, two or three substituents selected from the group consisting of —F, —Cl, —OH, —SH, —C≡N, —$CF_3$, $C_1$-$C_3$ alkoxy, and —$NR_{1\text{-}a}R_{1\text{-}b}$ where $R_{1\text{-}a}$ and $R_{1\text{-}b}$ are —H or $C_1$-$C_6$ alkyl,

(11) —CO—($C_1$-$C_4$ alkyl),

(12) —$SO_2$—$NR_{1\text{-}a}R_{1\text{-}b}$ where $R_{1\text{-}a}$ and $R_{1\text{-}b}$ are as defined above,

(13) —CO—$NR_{1\text{-}a}R_{1\text{-}b}$ where $R_{1\text{-}a}$ and $R_{1\text{-}b}$ are as defined above, or

(14) —$SO_2$—($C_1$-$C_4$ alkyl), with the proviso that when $n_1$ is zero $R_{1\text{-}heteroaryl}$ is not bonded to the carbon chain by nitrogen, or (VIII) —$(CH_2)_{n1}$—($R_{1\text{-}heterocycle}$) where $n_1$ is as defined above and $R_{1\text{-}heterocycle}$ is selected from the group consisting of:
morpholinyl,
thiomorpholinyl,
thiomorpholinyl S-oxide,
thiomorpholinyl S,S-dioxide,
piperazinyl,
homopiperazinyl,
pyrrolidinyl,
pyrrolinyl,
tetrahydropyranyl,
piperidinyl,
tetrahydrofuranyl,
tetrahydrothienyl,
homopiperidinyl,
homomorpholinyl,
homothiomorpholinyl,
homothiomorpholinyl S,S-dioxide,
oxazolidinonyl,
dihydropyrazolyl,
dihydropyrrolyl,
dihydropyrazinyl,
dihydropyridinyl,
dihydropyrimidinyl,
dihydrofuryl,
dihydropyranyl,
tetrahydrothienyl S-oxide,
tetrahydrothienyl S,S-dioxide, and
homothiomorpholinyl S-oxide,
where the $R_{1\text{-}heterocycle}$ group is bonded by any atom of the parent $R_{1\text{-}heterocycle}$ group substituted by hydrogen such that the new bond to the $R_{1\text{-}heterocycle}$ group replaces the hydrogen atom and its bond, where heterocycle is optionally substituted with one, two, three, or four:

(1) $C_1$-$C_6$ alkyl optionally substituted with one, two or three substituents selected from the group consisting of $C_1$-$C_3$ alkyl, —F, —Cl, —Br, —I, —OH, —SH, —C≡N, —CF$_3$, $C_1$-$C_3$ alkoxy, and —NR$_{1\text{-}a}$R$_{1\text{-}b}$ where $R_{1\text{-}a}$ and $R_{1\text{-}b}$ are as defined above, (2) $C_2$-$C_6$ alkenyl with one or two double bonds, optionally substituted with one, two or three substituents selected from the group consisting of —F, —Cl, —OH, —SH, —C≡N, —CF$_3$, $C_1$-$C_3$ alkoxy, and —NR$_{1\text{-}a}$R$_{1\text{-}b}$ where $R_{1\text{-}a}$ and $R_{1\text{-}b}$ are —H or $C_1$-$C_6$ alkyl, (3) $C_2$-$C_6$ alkynyl with one or two triple bonds, optionally substituted with one, two or three substituents selected from the group consisting of —F, —Cl, —OH, —SH, —C≡N, —CF$_3$, $C_1$-$C_3$ alkoxy, and —NR$_{1\text{-}a}$R$_{1\text{-}b}$ where $R_{1\text{-}a}$ and $R_{1\text{-}b}$ are —H or $C_1$-$C_6$ alkyl, (4) —F, Cl, —Br, or —I, (5) $C_1$-$C_6$ alkoxy, (6) —$C_1$-$C_6$ alkoxy substituted with one, two, or three —F, (7) —NR$_{N\text{-}2}$R$_{N\text{-}3}$ where $R_{N\text{-}2}$ and $R_{N\text{-}3}$ are as defined below, (8) —OH, (9) —C≡N,

(10) $C_3$-$C_7$ cycloalkyl, optionally substituted with one, two or three substituents selected from the group consisting of —F, —Cl, —OH, —SH, —C≡N, —CF$_3$, $C_1$-$C_3$ alkoxy, and —NR$_{1\text{-}a}$R$_{1\text{-}b}$ where $R_{1\text{-}a}$ and $R_{1\text{-}b}$ are —H or $C_1$-$C_6$ alkyl,

(11) —CO—($C_1$-$C_4$ alkyl),

(12) —SO$_2$—NR$_{1\text{-}a}$R$_{1\text{-}b}$ where $R_{1\text{-}a}$ and $R_{1\text{-}b}$ are as defined above,

(13) —CO—NR$_{1\text{-}a}$R$_{1\text{-}b}$ where $R_{1\text{-}a}$ and $R_{1\text{-}b}$ are as defined above,

(14) —SO$_2$—($C_1$-$C_4$ alkyl), or

(15) =O, with the proviso that when n, is zero $R_{1\text{-}heterocycle}$ is not bonded to the carbon chain by nitrogen;

where $R_2$ is:

(I) —H, (II) $C_1$-$C_6$ alkyl, optionally substituted with one, two or three substituents selected from the group consisting of $C_1$-$C_3$ alkyl, —F, —Cl, —Br, —I, —OH, —SH, —C≡N, —CF$_3$, $C_1$-$C_3$ alkoxy, and —NR$_{1\text{-}a}$R$_{1\text{-}b}$ where $R_{1\text{-}a}$ and $R_{1\text{-}b}$ are as defined above, (III) —(CH$_2$)$_{0\text{-}4}$—R$_{2\text{-}1}$ where $R_{2\text{-}1}$ is $R_{1\text{-}aryl}$ or $R_{1\text{-}heteroaryl}$ where $R_{1\text{-}aryl}$ and $R_{1\text{-}heteroaryl}$ are as defined above;

(IV) $C_2$-$C_6$ alkenyl with one or two double bonds, optionally substituted with one, two or three substituents selected from the group consisting of —F, —Cl, —OH, —SH, —C≡N, —CF$_3$, $C_1$-$C_3$ alkoxy, and —NR$_{1\text{-}a}$R$_{1\text{-}b}$ where $R_{1\text{-}a}$ and $R_{1\text{-}b}$ are —H or $C_1$-$C_6$ alkyl, (V) $C_2$-$C_6$ alkynyl with one or two triple bonds, optionally substituted with one, two or three substituents selected from the group consisting of —F, —Cl, —OH, —SH, —C≡N, —CF$_3$, $C_1$-$C_3$ alkoxy, and —NR$_{1\text{-}a}$R$_{1\text{-}b}$ where $R_{1\text{-}a}$ and $R_{1\text{-}b}$ are —H or $C_1$-$C_6$ alkyl, or (VI) —(CH$_2$)$_{0\text{-}4}$—$C_3$-$C_7$ cycloalkyl, optionally substituted with one, two or three substituents selected from the group consisting of —F, —Cl, —OH, —SH, —C≡N, —CF$_3$, $C_1$-$C_3$ alkoxy, and —NR$_{1\text{-}a}$R$_{1\text{-}b}$ where $R_{1\text{-}a}$ and $R_{1\text{-}b}$ are —H or $C_1$-$C_6$ alkyl, where $R_3$ is:

(I) —H, (II) $C_1$-$C_6$ alkyl, optionally substituted with one, two or three substituents selected from the group consisting of $C_1$-$C_3$ alkyl, —F, —Cl, —Br, —I, —OH, —SH, —C≡N, —CF$_3$, $C_1$-$C_3$ alkoxy, and —NR$_{1\text{-}a}$R$_{1\text{-}b}$ where $R_{1\text{-}a}$ and $R_{1\text{-}b}$ are as defined above, (III) —(CH$_2$)$_{0\text{-}4}$—R$_{2\text{-}1}$ where $R_{2\text{-}1}$ is $R_{1\text{-}aryl}$ or $R_{1\text{-}heteroaryl}$ where $R_{1\text{-}aryl}$ and $R_{1\text{-}heteroaryl}$ are as defined above;

(IV) $C_2$-$C_6$ alkenyl with one or two double bonds, (V) $C_2$-$C_6$ alkynyl with one or two triple bonds, or (VI) —(CH$_2$)$_{0\text{-}4}$—$C_3$-$C_7$ cycloalkyl, optionally substituted with one, two or three substituents selected from the group consisting of —F, —Cl, —OH, —SH, —C≡N, —CF$_3$, $C_1$-$C_3$ alkoxy, and —NR$_{1\text{-}a}$R$_{1\text{-}b}$ where $R_{1\text{-}a}$ and $R_{1\text{-}b}$ are —H or $C_1$-$C_6$ alkyl, where $R_2$ and $R_3$ are taken together with the carbon to which they are attached to form a carbocycle of three, four, five, six or seven carbon atoms, optionally where one carbon atom is replaced by a heteroatom selected from the group consisting of —O—, —S—, —SO$_2$—, and —NR$_{N\text{-}2}$—, where $R_{N\text{-}2}$ is selected from the group consisting of:

(a) —H, (b) —$C_1$-$C_6$ alkyl optionally substituted with one substituent selected from the group consisting of:
  (i) —OH, and
  (ii) —NH$_2$, (c) —$C_1$-$C_6$ alkyl optionally substituted with one to three —F, —Cl, —Br, or —I, (d) —$C_3$-$C_7$ cycloalkyl, (e) —($C_1$-$C_2$ alkyl)-($C_3$-$C_7$ cycloalkyl), (f) —($C_1$-$C_6$ alkyl)-O—($C_1$-$C_3$ alkyl), (g) —$C_2$-$C_6$ alkenyl with one or two double bonds, (h) —$C_2$-$C_6$ alkynyl with one or two triple bonds, (i) —$C_1$-$C_6$ alkyl chain with one double bond and one triple bond, (j) —$R_{1\text{-}aryl}$ where $R_{1\text{-}aryl}$ is as defined above, and (k) —$R_{1\text{-}heteroaryl}$ where $R_{1\text{-}heteroaryl}$ is as defined above;

where X is independently chosen from the group consisting of:

—C(O)—,

—CH$_2$—,

—CH$_2$—CH$_2$—, and

—CH$_2$—C(O)—;

wherein in the rings drawn, a dotted line indicates an optional double bond or an optional ring;

wherein ring A is phenyl, cyclohexyl, cyclopentyl, pyridyl, pyrimidinyl, pyrazinyl or is absent;

and where $R_{N\text{-}1}$ is selected from the group consisting of:

(1) $C_1$-$C_6$ alkyl, optionally substituted with one, two or three substituents selected from the group consisting of $C_1$-$C_3$ alkyl, —F, —Cl, —Br, —I, —OH, —SH, —C≡N, —CF$_3$, $C_1$-$C_3$ alkoxy, and —NR$_{1\text{-}a}$R$_{1\text{-}b}$ where $R_{1\text{-}a}$ and $R_{1\text{-}b}$ are as defined above, (2) —OH, (3) —NO$_2$, (4) —F, —Cl, —Br, or —I, (5) —CO—OH, (6) —C≡N, (7) —(CH$_2$)$_{0\text{-}4}$—CO—NR$_{N\text{-}2}$R$_{N\text{-}3}$ where $R_{N\text{-}2}$ and $R_{N\text{-}3}$ are the same or different and are selected from the group consisting of:

(a) —H,
(b) —$C_1$-$C_6$ alkyl optionally substituted with one substituent selected from the group consisting of:
  (i) —OH, and
  (ii) —$NH_2$,
(c) —$C_1$-$C_6$ alkyl optionally substituted with one to three —F, —Cl, —Br, or —I,
(d) —$C_3$-$C_7$ cycloalkyl,
(e) —($C_1$-$C_2$ alkyl)-($C_3$-$C_7$ cycloalkyl),
(f) —($C_1$-$C_6$ alkyl)-O—($C_1$-$C_3$ alkyl),
(g) —$C_2$-$C_6$ alkenyl with one or two double bonds,
(h) —$C_2$-$C_6$ alkynyl with one or two triple bonds,
(i) —$C_1$-$C_6$ alkyl chain with one double bond and one triple bond,
(j) —$R_{1\text{-}aryl}$ where $R_{1\text{-}aryl}$ is as defined above, and
(k) —$R_{1\text{-}heteroaryl}$ where $R_{1\text{-}heteroaryl}$ is as defined above,
(8) —$(CH_2)_{0\text{-}4}$—CO—($C_1$-$C_{12}$ alkyl),
(9) —$(CH_2)_{0\text{-}4}$—CO—($C_2$-$C_{12}$ alkenyl with one, two, or three double bonds),
(10) —$(CH_2)_{0\text{-}4}$—CO—($C_2$-$C_{12}$ alkynyl with one, two, or three triple bonds),
(11) —$(CH_2)_{0\text{-}4}$—CO—($C_3$-$C_7$ cycloalkyl),
(12) —$(CH_2)_{0\text{-}4}$—CO—$R_{1\text{-}aryl}$ where $R_{1\text{-}aryl}$ is as defined above,
(13) —$(CH_2)_{0\text{-}4}$—CO—$R_{1\text{-}heteroaryl}$ where $R_{1\text{-}heteroaryl}$ is as defined above,
(14) —$(CH_2)_{0\text{-}4}$—CO—$R_{1\text{-}heterocycle}$ where $R_{1\text{-}heterocycle}$ is as defined above,
(15) —$(CH_2)_{0\text{-}4}$—CO—$R_{N\text{-}4}$ where $R_{N\text{-}4}$ is selected from the group consisting of morpholinyl, thiomorpholinyl, piperazinyl, piperidinyl, homomorpholinyl, homothiomorpholinyl, homoythiomorpholinyl S-oxide, homothiomorpholinyl S,S-dioxide, pyrrolinyl and pyrrolidinyl where each group is optionally substituted with one, two, three, or four of: $C_1$-$C_6$ alkyl,
(16) —$(CH_2)_{0\text{-}4}$—CO—O—$R_{N\text{-}5}$ where $R_{N\text{-}5}$ is selected from the group consisting of:
  (a) $C_1$-$C_6$ alkyl,
  (b) —$(CH_2)_{0\text{-}2}$—($R_{1\text{-}aryl}$) where $R_{1\text{-}aryl}$ is as defined above,
  (c) $C_2$-$C_6$ alkenyl containing one, or two double bonds,
  (d) $C_2$-$C_6$ alkynyl containing one, or two triple bonds,
  (e) $C_3$-$C_7$ cycloalkyl, and
  (f) —$(CH_2)_{0\text{-}2}$—($R_{1\text{-}heteroaryl}$) where $R_{1\text{-}heteroaryl}$ is as defined above,
(17) —$(CH_2)_{0\text{-}4}$—$SO_2$—$NR_{N\text{-}2}R_{N\text{-}3}$ where $R_{N\text{-}2}$ and $R_{N\text{-}3}$ are as defined above,
(18) —$(CH_2)_{0\text{-}4}$—SO—($C_1$-$C_8$ alkyl),
(19) —$(CH_2)_{0\text{-}4}$—$SO_2$—($C_1$-$C_{12}$ alkyl),
(20) —$(CH_2)_{0\text{-}4}$—$SO_2$—($C_3$-$C_7$ cycloalkyl),
(21) —$(CH_2)_{0\text{-}4}$—N(H or $R_{N\text{-}5}$)—CO—O—$R_{N\text{-}5}$ where $R_{N\text{-}5}$ can be the same or different and is as defined above,
(22) —$(CH_2)_{0\text{-}4}$—N(H or $R_{N\text{-}5}$)—CO—N($R_{N\text{-}5}$)$_2$, where $R_{N\text{-}5}$ can be the same or different and is as defined above,
(23) —$(CH_2)_{0\text{-}4}$—N—CS—N($R_{N\text{-}5}$)$_2$, where $R_{N\text{-}5}$ can be the same or different and is as defined above,
(24) —$(CH_2)_{0\text{-}4}$—N(—H or $R_{N\text{-}5}$)—CO—$R_{N\text{-}2}$ where $R_{N\text{-}5}$ and $R_{N\text{-}2}$ can be the same or different and are as defined above,
(25) —$(CH_2)_{0\text{-}4}$—$NR_{N\text{-}2}R_{N\text{-}3}$ where $R_{N\text{-}2}$ and $R_{N\text{-}3}$ can be the same or different and are as defined above,
(26) —$(CH_2)_{0\text{-}4}$—$R_{N\text{-}4}$ where $R_{N\text{-}4}$ is as defined above,
(27) —$(CH_2)_{0\text{-}4}$—O—CO—($C_1$-$C_6$ alkyl),
(28) —$(CH_2)_{0\text{-}4}$—O—P(O)—($OR_{N\text{-}aryl\text{-}1}$)$_2$ where $R_{N\text{-}aryl\text{-}1}$ is —H or $C_1$-$C_4$ alkyl,
(29) —$(CH_2)_{0\text{-}4}$—O—CO—N($R_{N\text{-}5}$)$_2$ where $R_{N\text{-}5}$ is as defined above,
(30) —$(CH_2)_{0\text{-}4}$—O—CS—N($R_{N\text{-}5}$)$_2$ where $R_{N\text{-}5}$ is as defined above,
(31) —$(CH_2)_{0\text{-}4}$—O—($R_{N\text{-}5}$)$_2$ where $R_{N\text{-}5}$ is as defined above,
(32) —$(CH_2)_{0\text{-}4}$—O—($R_{N\text{-}5}$)$_2$—COOH where $R_{N\text{-}5}$ is as defined above,
(33) —$(CH_2)_{0\text{-}4}$—S—($R_{N\text{-}5}$)$_2$ where $R_{N\text{-}5}$ is as defined above,
(34) —$(CH_2)_{0\text{-}4}$—O—($C_1$-$C_6$ alkyl optionally substituted with one, two, three, four, or five of: —F),
(35) $C_3$-$C_7$ cycloalkyl,
(36) $C_2$-$C_6$ alkenyl with one or two double bonds optionally substituted with $C_1$-$C_3$ alkyl, —F, —Cl, —Br, —I, —OH, —SH, —C≡N, —$CF_3$, $C_1$-$C_3$ alkoxy, or —$NR_{1\text{-}a}R_{1\text{-}b}$ where $R_{1\text{-}a}$ and $R_{1\text{-}b}$ are as defined above,
(37) $C_2$-$C_6$ alkynyl with one or two triple bonds optionally substituted with $C_1$-$C_3$ alkyl, —F, —Cl, —Br, —I, —OH, —SH, —C≡N, —$CF_3$, $C_1$-$C_3$ alkoxy, or —$NR_{1\text{-}a}R_{1\text{-}b}$ where $R_{1\text{-}a}$ and $R_{1\text{-}b}$ are as defined above,
(38) —$(CH_2)_{0\text{-}4}$—N(—H or $R_{N\text{-}5}$)—$SO_2$—$R_{N\text{-}2}$ where $R_{N\text{-}5}$ and $R_{N\text{-}2}$ can be the same of different and are as described above, and
(39) —$(CH_2)_{0\text{-}4}$—$C_3$-$C_7$ cycloalkyl;
where n is equal to 0, 1, 2 or 3;
where Z is selected from the group consisting of:
  (A) —C(O)—,
  (B) —S(O)$_{1\text{-}2}$—,
  (C) —C(O)—$X_{N\text{-}1}$— where $X_{N\text{-}1}$ is selected from the group consisting of —O—, —S— and —NR'— and where R' is as defined above; and
  (D) a single bond;
where $R_C$ is:
  (I) —$C_1$-$C_{10}$ alkyl optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, —$NR_{1\text{-}a}R_{1\text{-}b}$ where $R_{1\text{-}a}$ and $R_{1\text{-}b}$ are as defined above, —OC═O $NR_{1\text{-}a}R_{1\text{-}b}$ where $R_{1\text{-}a}$ and $R_{1\text{-}b}$ are as defined above, —S(═O)$_{0\text{-}2}R_{1\text{-}a}$ where $R_{1\text{-}a}$ is as defined above, —$NR_{1\text{-}a}$C═O $NR_{1\text{-}a}R_{1\text{-}b}$ where $R_{1\text{-}a}$ and $R_{1\text{-}b}$ are as defined above, —C═O $NR_{1\text{-}a}R_{1\text{-}b}$ where $R_{1\text{-}a}$ and $R_{1\text{-}b}$ are as defined above, and —S(═O)$_2NR_{1\text{-}a}R_{1\text{-}b}$ where $R_{1\text{-}a}$ and $R_{1\text{-}b}$ are as defined above,
  (II) —$(CH_2)_{0\text{-}3}$—($C_3$-$C_8$)cycloalkyl where cycloalkyl can be optionally substituted with one, two, or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, —CO—OH, —CO—O—($C_1$-$C_4$ alkyl), and —$NR_{1\text{-}a}R_{1\text{-}b}$ where $R_{1\text{-}a}$ and $R_{1\text{-}b}$ are as defined above,
  (III) —$(CR_{C\text{-}x}R_{C\text{-}y})_{0\text{-}4}$—$R_{C\text{-}aryl}$ where $R_{C\text{-}x}$ and $R_{C\text{-}y}$ are
    (A) —H,
    (B) $C_1$-$C_4$ alkyl optionally substituted with one or two —OH,
    (C) $C_1$-$C_4$ alkoxy optionally substituted with one, two, or three —F,
    (D) —$(CH_2)_{0\text{-}4}$—$C_3$-$C_7$ cycloalkyl,
    (E) $C_2$-$C_6$ alkenyl containing one or two double bonds,
    (F) $C_2$-$C_6$ alkynyl containing one or two triple bonds, (G) phenyl-, (H) $C_0$-$C_4$ alkylC(O)$NR_{1-a}R_{1-b}$ where $R_{1-a}$ and $R_{1-b}$ are as defined above, and where $R_{C-x}$ and $R_{C-y}$ are taken together with the carbon to which they are attached to form a carbocycle of three, four, five, six, or seven carbon atoms, optionally where one carbon atom is replaced by a heteroatom selected from the group consisting of —O—, —S—, —$SO_2$—, —$NR_{N-2}$— and $R_{C-aryl}$ is the same as $R_{N-aryl}$ and where $R_{C-aryl}$ may optionally be substituted with —$C_0$-$C_4$ alkyl-C(O)$NR_{1-a}R_{1-b}$, $C_0$-$C_4$ alkylC(O)$OR_{1-a}$ where $R_{1-a}$ and $R_{1-b}$ are as defined above, (IV) —$(CR_{C-x}R_{C-y})_{0-4}$—$R_{C-heteroaryl}$ where $R_{C-heteroaryl}$ is the same as $R_{N-heteroaryl}$ and $R_{C-x}$ and $R_{C-y}$ are as defined above, (V) —$(CR_{C-x}R_{C-y})_{0-4}$—$R_{C-aryl}$—$R_{C-aryl}$ where $R_{C-aryl}$, $R_{C-x}$ and $R_{C-y}$ are as defined above, (VI) —$(CR_{C-x}R_{C-y})_{0-4}$—$R_{C-aryl}$—$R_{C-heteroaryl}$ where $R_{C-aryl}$, $R_{C-heteroaryl}$, $R_{C-x}$ and $R_{C-y}$ are as defined above, (VII) —$(CR_{C-x}R_{C-y})_{0-4}$—$R_{C-heteroaryl}$—$R_{C-aryl}$ where $R_{C-heteroaryl}$, $R_{C-aryl}$, $R_{C-x}$ and $R_{C-y}$ are as defined above, (VIII) —$(CR_{C-x}R_{C-y})_{0-4}$—$R_{C-heteroaryl}$—$R_{C-heteroaryl}$ where $R_{C-heteroaryl}$, $R_{C-x}$ and $R_{C-y}$ are as defined above, (IX) —$(CR_{C-x}R_{C-y})_{0-4}$—$R_{C-aryl}$—$R_{C-heterocycle}$ where $R_{C-heterocycle}$ is the same as $R_{1-heterocycle}$, and $R_{C-aryl}$, $R_{C-x}$ and $R_{C-y}$ are as defined above, (X) —$(CR_{C-x}R_{C-y})_{0-4}$—$R_{C-heteroaryl}$—$R_{C-heterocycle}$ where $R_{C-heteroaryl}$, $R_{C-heterocycle}$, $R_{C-x}$ and $R_{C-y}$ are as defined above, (XI) —$(CR_{C-x}R_{C-y})_{0-4}$—$R_{C-heterocycle}$—$R_{C-aryl}$ where $R_{C-heterocycle}$, $R_{C-aryl}$, $R_{C-x}$ and $R_{C-y}$ are as defined above, (XII) —$(CR_{C-x}R_{C-y})_{0-4}$—$R_{C-heterocycle}$—$R_{C-heteroaryl}$ where $R_{C-heterocycle}$, $R_{C-heteroaryl}$, $R_{C-x}$ and $R_{C-y}$ are as defined above, (XIII) —$(CR_{C-x}R_{C-y})_{0-4}$—$R_{C-heterocycle}$—$R_{C-heterocycle}$ where $R_{C-heterocycle}$, $R_{C-x}$ and $R_{C-y}$ are as defined above, (XIV) —$(CR_{C-x}R_{C-y})_{0-4}$—$R_{C-heterocycle}$ where $R_{C-heterocycle}$, $R_{C-x}$ and $R_{C-y}$ are as defined above, (XV) —$[C(R_{C-1})(R_{C-2})]_{1-3}$—CO—N—$(R_{C-3})_2$ where $R_{C-3}$ is as defined below and $R_{C-1}$, $R_{C-2}$ are the same or different and are selected from the group consisting of:

(A) —H, (B) —$C_1$-$C_6$ alkyl, optionally substituted with one, two, or three substituents independently selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above, (D) $C_2$-$C_6$ alkenyl with one, or two double bonds, optionally substituted with one, two, or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above, (E) $C_2$-$C_6$ alkynyl with one or two triple bonds, optionally substituted with one, two, or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above, (F) —$(CH_2)_{1-2}$—$S(O)_{0-2}$—$(C_1$-$C_6$ alkyl), (F) —$(CH_2)_{0-4}$—$C_3$-$C_7$ cycloalkyl, optionally substituted with one, two, or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and $NR_{1-a}R_{1-b}$ where $R_{1-a}$ and $R_{1-b}$ are as defined above, (G) —$(C_1$-$C_4$ alkyl)-$R_{C'-aryl}$ where $R_{C'-aryl}$ is as defined for $R_{1-aryl}$, (H) —$(C_1$-$C_4$ alkyl)-$R_{C-heteroaryl}$ where $R_{C-heteroaryl}$ is as defined above, (I) —$(C_1$-$C_4$ alkyl)-$R_{C-heterocycle}$ where $R_{C-heterocycle}$ is as defined above, (J) —$R_{C-heteroaryl}$ where $R_{C-heteroaryl}$ is as defined above, (K) —$R_{C-heterocycle}$ where $R_{C-heterocycle}$ is as defined above, (M) —$(CH_2)_{1-4}$—$R_{C-4}$—$(CH_2)_{0-4}$—$R_{C-aryl}$ where $R_{C-4}$ is —O—, —S— or —$NR_{C-5}$— where $R_{C-5}$ is $C_1$-$C_6$ alkyl, and where $R_{C-aryl}$ is defined above, (N) —$(CH_2)_{1-4}$—$R_{C-4}$—$(CH_2)_{0-4}$—$R_{C-heteroaryl}$ where $R_{C-4}$ and $R_{C-heteroaryl}$ are as defined above, and (O) —$R_{C'-aryl}$ where $R_{C'-aryl}$ is as defined above, and where $R_{C-3}$ is the same or different and is:

(a) —H, (b) —$C_1$-$C_6$ alkyl optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above, (c) $C_2$-$C_6$ alkenyl with one or two double bonds, optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above, (d) $C_2$-$C_6$ alkynyl with one, or two triple bonds, optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above, (e) —$(CH_2)_{0-4}$—$C_3$-$C_7$ cycloalkyl, optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above, (f) —$R_{C'-aryl}$ where $R_{C'-aryl}$ is as defined above, (g) —$R_{C-heteroaryl}$ where $R_{C-heteroaryl}$ is as defined above, (h) —$R_{C-heterocycle}$ where $R_{C-heterocycle}$ is as defined above, (i) —$(C_1$-$C_4$ alkyl)-$R_{C'-aryl}$ where $R_{C'-aryl}$ is as defined above, (j) —$(C_1$-$C_4$ alkyl)-$R_{C-heteroaryl}$ where $R_{C-heteroaryl}$ is as defined above, (k) —$(C_1$-$C_4$ alkyl)-$R_{C-heterocycle}$ where $R_{C-heterocycle}$ is as defined above, (XVI) —CH(R$_{C-aryl}$)$_2$ where R$_{C-aryl}$ are the same or different and are as defined above, (XVII) —CH(R$_{C-heteroaryl}$)$_2$ where R$_{C-heteroaryl}$ are the same or different and are as defined above, (XVIII) —CH(R$_{C-aryl}$)(R$_{C-heteroaryl}$) where R$_{C-aryl}$ and R$_{C-heteroaryl}$ are as defined above, (XIX) -cyclopentyl, -cyclohexyl, or -cycloheptyl ring fused to R$_{C-aryl}$ or R$_{C-heteroaryl}$ or R$_{C-heterocycle}$ where R$_{C-aryl}$ or R$_{C-heteroaryl}$ or R$_{C-heterocycle}$ are as defined above where one carbon of cyclopentyl, cyclohexyl, or cycloheptyl is optionally replaced with NH, NR$_{N-5}$, O, or S(=O)$_{0-2}$, and where cyclopentyl, cyclohexyl, or cycloheptyl can be optionally substituted with one, or two —C$_1$-C$_3$ alkyl, —F, —OH, —SH, —C≡N, —CF$_3$, C$_1$-C$_6$ alkoxy, =O, or —NR$_{1-a}$R$_{1-b}$ where R$_{1-a}$ and R$_{1-b}$ are as defined above, (XX) C$_2$-C$_{10}$ alkenyl containing one or two double bonds optionally substituted with one, two, or three substituents selected from the group consisting of C$_1$-C$_3$ alkyl, —F, —Cl, —Br, —I, —OH, —SH, —C≡N, —CF$_3$, C$_1$-C$_6$ alkoxy, —O-phenyl, and —NR$_{1-a}$R$_{1-b}$ where R$_{1-a}$ and R$_{1-b}$ are as defined above, (XXI) C$_2$-C$_{10}$ alkynyl containing one, or two triple bonds optionally substituted with one, two, or three substituents selected from the group consisting of C$_1$-C$_3$ alkyl, —F, —Cl, —Br, —I, —OH, —SH, —C≡N, —CF$_3$, C$_1$-C$_6$ alkoxy, —O-phenyl, and —NR$_{1-a}$R$_{1-b}$ where R$_{1-a}$ and R$_{1-b}$ are as defined above, (XXI) —(CH$_2$)$_{0-1}$—CHR$_{C-6}$—(CH$_2$)$_{0-1}$—R$_{C-aryl}$ where R$_{C-aryl}$ is as defined above and R$_{C-6}$ is —(CH$_2$)$_{0-6}$—OH, (XXII) —(CH$_2$)$_{0-1}$—CHR$_{C-6}$—(CH$_2$)$_{0-1}$—R$_{C-heteroaryl}$ where R$_{C-heteroaryl}$ and R$_{C-6}$ is as defined above, (XXIII) —CH(—R$_{C-aryl}$ or R$_{C-heteroaryl}$)—CO—O(C$_1$-C$_4$ alkyl) where R$_{C-aryl}$ and R$_{C-heteroaryl}$ are as defined above, (XXIV) —CH(—CH$_2$—OH)—CH(—OH)-phenyl-NO$_2$, (XXV) (C$_1$-C$_6$ alkyl)-O—(C$_1$-C$_6$ alkyl)-OH, (XXVII) —CH$_2$—NH—CH$_2$—CH(—O—CH$_2$—CH$_3$)$_2$, or (XXVIII) —(CH$_2$)$_{0-6}$—C(=NR$_{1-a}$)(NR$_{1-a}$R$_{1-b}$) where R$_{1-a}$ and R$_{1-b}$ are as defined above, where R$_{C-A}$ is H, C$_1$-C$_{10}$ alkyl, C$_2$-C$_{10}$ alkenyl and alkynyl, phenyl, C$_1$-C$_4$ alkyl-R$_{N-aryl}$, C$_1$-C$_4$ alkyl-R$_{N-heteroaryl}$, C$_1$-C$_4$ alkyl-C$_3$-C$_7$ cycloalkyl, or C$_1$-C$_4$ alkyl-R$_{1-heterocycle}$, wherein each multi-atom group may be optionally substituted with one, two, or three substituents independently selected from the group consisting of —F, —Cl, —OH, —SH, —C≡N, —CF$_3$, C$_1$-C$_3$ alkoxy, —C(O)O—R$_{1-a}$, and —NR$_{1-a}$R$_{1-b}$ where R$_{1-a}$ and R$_{1-b}$ are —H, C$_1$-C$_6$ alkyl or phenyl;

where R$_{C-A}$, -Z-R$_C$, and the nitrogen atom to which they attach may cyclize to form a ring or fused rings chosen from the group consisting of 5-8 membered heterocyclics having up to 2 heteroatoms in addition to the ring nitrogen defined above chosen from the group consisting of N, O, and S, which may optionally be fused with one, or two phenyl, pyridyl, cyclohexyl, piperidinyl or morpholinyl, where the ring or fused rings may optionally have one, two, or three substituents independently chosen from the group of:

(1) C$_1$-C$_6$ alkyl,

C$_2$-C$_6$ alkenyl with one or two double bonds, or

C$_2$-C$_6$ alkynyl with one or two triple bonds, wherein each may be optionally substituted with one, two, or three substituents selected from the group consisting of —F, —Cl, —OH, —SH, —C≡N, —CF$_3$, C$_1$-C$_3$ alkoxy, and —NR$_{1-a}$R$_{1-b}$ where R$_{1-a}$ and R$_{1-b}$ are —H or C$_1$-C$_6$ alkyl, (2) —F, Cl, —Br, or —I, (3) —C$_1$-C$_6$ alkoxy optionally substituted with one, two, or three —F, (4) —NR$_{N-2}$R$_{N-3}$ where R$_{N-2}$ and R$_{N-3}$ are as defined below, (5) —OH, (6) —C≡N, (7) =O (oxo), (8) —CO—(C$_1$-C$_4$ alkyl), (9) —SO$_2$—NR$_{1-a}$R$_{1-b}$ where R$_{1-a}$ and R$_{1-b}$ are as defined above, or

(10) —CO—NR$_{1-a}$R$_{1-b}$ where R$_{1-a}$ and R$_{1-b}$ are as defined above, or a pharmaceutically acceptable salt thereof.

Additionally, the present invention includes a second disubstituted amine of formula II:

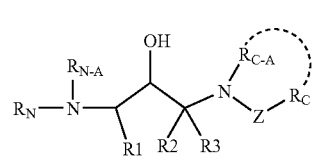

II where R$_1$ is:

(I) C$_1$-C$_6$ alkyl, optionally substituted with one, two or three substituents selected from the group consisting of C$_1$-C$_3$ alkyl, C$_1$-C$_7$ alkyl (optionally substituted with C$_1$-C$_3$ alkyl and C$_1$-C$_3$ alkoxy), —F, —Cl, —Br, —I, —OH, —SH, —C≡N, —CF$_3$, C$_1$-C$_3$ alkoxy, —NR$_{1-a}$R$_{1-b}$ where R$_{1-a}$ and R$_{1-b}$ are —H or C$_1$-C$_6$ alkyl, and —OC=O NR$_{1-a}$R$_{1-b}$ where R$_{1-a}$ and R$_{1-b}$ are as defined above, (II) —CH$_2$—S(O)$_{0-2}$—(C$_1$-C$_6$ alkyl), (III) —CH$_2$—CH$_2$—S(O)$_{0-2}$—(C$_1$-C$_6$ alkyl), (IV) C$_2$-C$_6$ alkenyl with one or two double bonds, optionally substituted with one, two or three substituents selected from the group consisting of —F, —Cl, —OH, —SH, —C≡N, —CF$_3$, C$_1$-C$_3$ alkoxy, and —NR$_{1-a}$R$_{1-b}$ where R$_{1-a}$ and R$_{1-b}$ are —H or C$_1$-C$_6$ alkyl, (V) C$_2$-C$_6$ alkynyl with one or two triple bonds, optionally substituted with one, two or three substituents selected from the group consisting of —F, —Cl, —OH, —SH, —C≡N, —CF$_3$, C$_1$-C$_3$ alkoxy, and —NR$_{1-a}$R$_{1-b}$ where R$_{1-a}$ and R$_{1-b}$ are —H or C$_1$-C$_6$ alkyl, (VI) —(CH$_2$)$_{n1}$—(R$_{1-aryl}$) where n$_1$ is zero or one and where R$_{1-aryl}$ is phenyl, 1-naphthyl, 2-naphthyl and indanyl, indenyl, dihydronaphthalyl, or tetralinyl optionally substituted with one, two, three, or four of the following substituents on the aryl ring:

(A) C$_1$-C$_6$ alkyl optionally substituted with one, two or three substituents selected from the group consisting of C$_1$-C$_3$ alkyl, —F, —Cl, —Br, —I, H, —SH, —C≡N, —CF$_3$, C$_1$-C$_3$ alkoxy, and —NR$_{1-a}$R$_{1-b}$ where R$_{1-a}$ and R$_{1-b}$ are as defined above, (B) $C_2$-$C_6$ alkenyl with one or two double bonds, optionally substituted with one, two or three substituents selected from the group consisting of —F, —Cl, —OH, —SH, —C≡N, —$CF_3$, $C_1$-$C_3$ alkoxy, —$NR_{1-a}R_{1-b}$ where $R_{1-a}$ and $R_{1-b}$ are —H or $C_1$-$C_6$ alkyl,
(C) $C_2$-$C_6$ alkynyl with one or two triple bonds, optionally substituted with one, two or three substituents selected from the group consisting of —F, —Cl, —OH, —SH, —C≡N, —$CF_3$, $C_1$-$C_3$ alkoxy, and —$NR_{1-a}R_{1-b}$ where $R_{1-a}$ and $R_{1-b}$ are —H or $C_1$-$C_6$ alkyl,
(D) —F, Cl, —Br or —I,
(F) —$C_1$-$C_6$ alkoxy optionally substituted with one, two, or three —F,
(G) —$NR_{N-2}R_{N-3}$ where $R_{N-2}$ and $R_{N-3}$ are as defined below,
(H) —OH,
(I) —C≡N,
(J) $C_3$-$C_7$ cycloalkyl, optionally substituted with one, two or three substituents selected from the group consisting of —F, —Cl, —OH, —SH, —C≡N, —$CF_3$, $C_1$-$C_3$ alkoxy, and —$NR_{1-a}R_{1-b}$ where $R_{1-a}$ and $R_{1-b}$ are —H or $C_1$-$C_6$ alkyl,
(K) —CO—($C_1$-$C_4$ alkyl),
(L) —$SO_2$—$NR_{1-a}R_{1-b}$ where $R_{1-a}$ and $R_{1-b}$ are as defined above,
(M) —CO—$NR_{1-a}R_{1-b}$ where $R_{1-a}$ and $R_{1-b}$ are as defined above, or
(N) —$SO_2$—($C_1$-$C_4$ alkyl),
(VII) —$(CH_2)_{n1}$—$(R_{1-heteroaryl})$ where $n_1$ is as defined above and where $R_{1-heteroaryl}$ is selected from the group consisting of:
pyridinyl,
pyrimidinyl,
quinolinyl,
benzothienyl,
indolyl,
indolinyl,
pryidazinyl,
pyrazinyl,
isoquinolyl,
quinazolinyl,
quinoxalinyl,
phthalazinyl,
imidazolyl,
isoxazolyl,
pyrazolyl,
oxazolyl,
thiazolyl,
indolizinyl,
indazolyl,
benzothiazolyl,
benzimidazolyl,
benzofuranyl,
furanyl,
thienyl,
pyrrolyl,
oxadiazolyl,
thiadiazolyl,
triazolyl,
tetrazolyl,
oxazolopyridinyl,
imidazopyridinyl,
isothiazolyl,
naphthyridinyl,
cinnolinyl,
carbazolyl,
beta-carbolinyl,
isochromanyl,
chromanyl,
tetrahydroisoquinolinyl,
isoindolinyl,
isobenzotetrahydrofuranyl,
isobenzotetrahydrothienyl,
isobenzothienyl,
benzoxazolyl,
pyridopyridinyl,
benzotetrahydrofuranyl,
benzotetrahydrothienyl,
purinyl,
benzodioxolyl,
triazinyl,
phenoxazinyl,
phenothiazinyl,
pteridinyl,
benzothiazolyl,
imidazopyridinyl,
imidazothiazolyl,
dihydrobenzisoxazinyl,
benzisoxazinyl,
benzoxazinyl,
dihydrobenzisothiazinyl,
benzopyranyl,
benzothiopyranyl,
coumarinyl,
isocoumarinyl,
chromonyl,
chromanonyl,
pyridinyl-N-oxide,
tetrahydroquinolinyl
dihydroquinolinyl
dihydroquinolinonyl
dihydroisoquinolinonyl
dihydrocoumarinyl
dihydroisocoumarinyl
isoindolinonyl
benzodioxanyl
benzoxazolinonyl
pyrrolyl N-oxide,
pyrimidinyl N-oxide,
pyridazinyl N-oxide,
pyrazinyl N-oxide,
quinolinyl N-oxide,
indolyl N-oxide,
indolinyl N-oxide,
isoquinolyl N-oxide,
quinazolinyl N-oxide,
quinoxalinyl N-oxide,
phthalazinyl N-oxide,
imidazolyl N-oxide,
isoxazolyl N-oxide,
oxazolyl N-oxide,
thiazolyl N-oxide,
indolizinyl N-oxide,
indazolyl N-oxide,
benzothiazolyl N-oxide,
benzimidazolyl N-oxide,
pyrrolyl N-oxide,
oxadiazolyl N-oxide,
thiadiazolyl N-oxide,
triazolyl N-oxide,
tetrazolyl N-oxide,
benzothiopyranyl S-oxide, and
benzothiopyranyl S,S-dioxide, where the $R_{1\text{-}heteroaryl}$ group is bonded to —(CH$_2$)$_{n1}$— by any ring atom of the parent $R_{N\text{-}heteroaryl}$ group substituted by hydrogen such that the new bond to the $R_{1\text{-}heteroaryl}$ group replaces the hydrogen atom and its bond, where heteroaryl is optionally substituted with one, two, three, or four:
  (1) $C_1$-$C_6$ alkyl optionally substituted with one, two or three substituents selected from the group consisting of $C_1$-$C_3$ alkyl, —F, —Cl, —Br, —I, —OH, —SH, —C≡N, —CF$_3$, $C_1$-$C_3$ alkoxy, and —NR$_{1\text{-}a}$R$_{1\text{-}b}$ where R$_{1\text{-}a}$ and R$_{1\text{-}b}$ are as defined above,
  (2) $C_2$-$C_6$ alkenyl with one or two double bonds, optionally substituted with one, two or three substituents selected from the group consisting of —F, —Cl, —OH, —SH, —C≡N, —CF$_3$, $C_1$-$C_3$ alkoxy, and —NR$_{1\text{-}a}$R$_{1\text{-}b}$ where R$_{1\text{-}a}$ and R$_{1\text{-}b}$ are —H or $C_1$-$C_6$ alkyl,
  (3) $C_2$-$C_6$ alkynyl with one or two triple bonds, optionally substituted with one, two or three substituents selected from the group consisting of —F, —Cl, —OH, —SH, —C≡N, —CF$_3$, $C_1$-$C_3$ alkoxy, and —NR$_{1\text{-}a}$R$_{1\text{-}b}$ where R$_{1\text{-}a}$ and R$_{1\text{-}b}$ are —H or $C_1$-$C_6$ alkyl,
  (4) —F, Cl, —BR, or —I,
  (6) —$C_1$-$C_6$ alkoxy optionally substituted with one, two, or three —F,
  (7) —NR$_{N\text{-}2}$R$_{N\text{-}3}$ where R$_{N\text{-}2}$ and R$_{N\text{-}3}$ are as defined below,
  (8) —OH,
  (9) —C≡N,
  (10) $C_3$-$C_7$ cycloalkyl, optionally substituted with one, two or three substituents selected from the group consisting of —F, —Cl, —OH, —SH, —C≡N, —CF$_3$, $C_1$-$C_3$ alkoxy, and —NR$_{1\text{-}a}$R$_{1\text{-}b}$ where R$_{1\text{-}a}$ and R$_{1\text{-}b}$ are —H or $C_1$-$C_6$ alkyl,
  (11) —CO—($C_1$-$C_4$ alkyl),
  (12) —SO$_2$—NR$_{1\text{-}a}$R$_{1\text{-}b}$ where R$_{1\text{-}a}$ and R$_{1\text{-}b}$ are as defined above,
  (13) —CO—NR$_{1\text{-}a}$R$_{1\text{-}b}$ where R$_{1\text{-}a}$ and R$_{1\text{-}b}$ are as defined above, or
  (14) —SO$_2$—($C_1$-$C_4$ alkyl), with the proviso that when n$_1$ is zero R$_{1\text{-}heteroaryl}$ is not bonded to the carbon chain by nitrogen, or
(VIII) —(CH$_2$)$_{n1}$—(R$_{1\text{-}heterocycle}$) where n$_1$ is as defined above and R$_{1\text{-}heterocycle}$ is selected from the group consisting of:
  morpholinyl,
  thiomorpholinyl,
  thiomorpholinyl S-oxide,
  thiomorpholinyl S,S-dioxide,
  piperazinyl,
  homopiperazinyl,
  pyrrolidinyl,
  pyrrolinyl,
  tetrahydropyranyl,
  piperidinyl,
  tetrahydrofuranyl,
  tetrahydrothienyl,
  homopiperidinyl,
  homomorpholinyl,
  homothiomorpholinyl,
  homothiomorpholinyl S,S-dioxide,
  oxazolidinonyl,
  dihydropyrazolyl,
  dihydropyrrolyl,
  dihydropyrazinyl,
  dihydropyridinyl,
  dihydropyrimidinyl,
  dihydrofuryl,
  dihydropyranyl,
  tetrahydrothienyl S-oxide,
  tetrahydrothienyl S,S-dioxide, and
  homothiomorpholinyl S-oxide,
where the R$_{1\text{-}heterocycle}$ group is bonded by any atom of the parent R$_{1\text{-}heterocycle}$ group substituted by hydrogen such that the new bond to the R$_{1\text{-}heterocycle}$ group replaces the hydrogen atom and its bond, where heterocycle is optionally substituted with one, two, three, or four:
  (1) $C_1$-$C_6$ alkyl optionally substituted with one, two or three substituents selected from the group consisting of $C_1$-$C_3$ alkyl, —F, —Cl, —Br, —I, —OH, —SH, —C≡N, —CF$_3$, $C_1$-$C_3$ alkoxy, and —NR$_{1\text{-}a}$R$_{1\text{-}b}$ where R$_{1\text{-}a}$ and R$_{1\text{-}b}$ are as defined above,
  (2) $C_2$-$C_6$ alkenyl with one or two double bonds, optionally substituted with one, two or three substituents selected from the group consisting of —F, —Cl, —OH, —SH, —C≡N, —CF$_3$, $C_1$-$C_3$ alkoxy, and —NR$_{1\text{-}a}$R$_{1\text{-}b}$ where R$_{1\text{-}a}$ and R$_{1\text{-}b}$ are —H or $C_1$-$C_6$ alkyl,
  (3) $C_2$-$C_6$ alkynyl with one or two triple bonds, optionally substituted with one, two or three substituents selected from the group consisting of —F, —Cl, —OH, —SH, —C≡N, —CF$_3$, $C_1$-$C_3$ alkoxy, and —NR$_{1\text{-}a}$R$_{1\text{-}b}$ where R$_{1\text{-}a}$ and R$_{1\text{-}b}$ are —H or $C_1$-$C_6$ alkyl,
  (4) —F, Cl, —Br, or —I,
  (5) $C_1$-$C_6$ alkoxy,
  (6) —$C_1$-$C_6$ alkoxy substituted with one, two, or three —F,
  (7) —NR$_{N\text{-}2}$R$_{N\text{-}3}$ where R$_{N\text{-}2}$ and R$_{N\text{-}3}$ are as defined below,
  (8) —OH,
  (9) —C≡N,
  (10) $C_3$-$C_7$ cycloalkyl, optionally substituted with one, two or three substituents selected from the group consisting of —F, —Cl, —OH, —SH, —C≡N, —CF$_3$, $C_1$-$C_3$ alkoxy, and —NR$_{1\text{-}a}$R$_{1\text{-}b}$ where R$_{1\text{-}a}$ and R$_{1\text{-}b}$ are —H or $C_1$-$C_6$ alkyl,
  (11) —CO—($C_1$-$C_4$ alkyl),
  (12) —SO$_2$—NR$_{1\text{-}a}$R$_{1\text{-}b}$ where R$_{1\text{-}a}$ and R$_{1\text{-}b}$ are as defined above,
  (13) —CO—NR$_{1\text{-}a}$R$_{1\text{-}b}$ where R$_{1\text{-}a}$ and R$_{1\text{-}b}$ are as defined above,
  (14) —SO$_2$—($C_1$-$C_4$ alkyl), or
  (15) =O, with the proviso that when n$_1$ is zero R$_{1\text{-}heterocycle}$ is not bonded to the carbon chain by nitrogen;
where R$_2$ is:
  (I) —H,
  (II) $C_1$-$C_6$ alkyl, optionally substituted with one, two or three substituents selected from the group consisting of $C_1$-$C_3$ alkyl, —F, —Cl, —Br, —I, —OH, —SH, —C≡N, —CF$_3$, $C_1$-$C_3$ alkoxy, and —NR$_{1\text{-}a}$R$_{1\text{-}b}$ where R$_{1\text{-}a}$ and R$_{1\text{-}b}$ are as defined above,
  (III) —(CH$_2$)$_{0\text{-}4}$—R$_{2\text{-}1}$ where R$_{2\text{-}1}$ is R$_{1\text{-}aryl}$ or R$_{1\text{-}heteroaryl}$ where R$_{1\text{-}aryl}$ and R$_{1\text{-}heteroaryl}$ are as defined above;
  (IV) $C_2$-$C_6$ alkenyl with one or two double bonds, optionally substituted with one, two or three substituents selected from the group consisting of —F, —Cl, —OH, —SH, —C≡N, —CF$_3$, $C_1$-$C_3$ alkoxy, and —NR$_{1\text{-}a}$R$_{1\text{-}b}$ where R$_{1\text{-}a}$ and R$_{1\text{-}b}$ are —H or $C_1$-$C_6$ alkyl,

21

(V) $C_2$-$C_6$ alkynyl with one or two triple bonds, optionally substituted with one, two or three substituents selected from the group consisting of —F, —Cl, —OH, —SH, —C≡N, —CF$_3$, $C_1$-$C_3$ alkoxy, and —NR$_{1\text{-}a}$R$_{1\text{-}b}$ where R$_{1\text{-}a}$ and R$_{1\text{-}b}$ are —H or $C_1$-$C_6$ alkyl, or (VI) —(CH$_2$)$_{0\text{-}4}$—$C_3$-$C_7$ cycloalkyl, optionally substituted with one, two or three substituents selected from the group consisting of —F, —Cl, —OH, —SH, —C≡N, —CF$_3$, $C_1$-$C_3$ alkoxy, and —NR$_{1\text{-}a}$R$_{1\text{-}b}$ where R$_{1\text{-}a}$ and R$_{1\text{-}b}$ are —H or $C_1$-$C_6$ alkyl, where R$_3$ is selected from the group consisting of:
- (I) —H,
- (II) $C_1$-$C_6$ alkyl, optionally substituted with one, two or three substituents selected from the group consisting of $C_1$-$C_3$ alkyl, —F, —Cl, —Br, —I, —OH, —SH, —C≡N, —CF$_3$, $C_1$-$C_3$ alkoxy, and —NR$_{1\text{-}a}$R$_{1\text{-}b}$ where R$_{1\text{-}a}$ and R$_{1\text{-}b}$ are as defined above,
- (III) —(CH$_2$)$_{0\text{-}4}$—R$_{2\text{-}1}$ where R$_{2\text{-}1}$ is R$_{1\text{-}aryl}$ or R$_{1\text{-}heteroaryl}$ where R$_{1\text{-}aryl}$ and R$_{1\text{-}heteroaryl}$ are as defined above;
- (IV) $C_2$-$C_6$ alkenyl with one or two double bonds,
- (V) $C_2$-$C_6$ alkynyl with one or two triple bonds, or
- (VI) —(CH$_2$)$_{0\text{-}4}$—$C_3$-$C_7$ cycloalkyl, optionally substituted with one, two or three substituents selected from the group consisting of —F, —Cl, —OH, —SH, —C≡N, —CF$_3$, $C_1$-$C_3$ alkoxy, and —NR$_{1\text{-}a}$R$_{1\text{-}b}$ where R$_{1\text{-}a}$ and R$_{1\text{-}b}$ are —H or $C_1$-$C_6$ alkyl, and where R$_2$ and R$_3$ are taken together with the carbon to which they are attached to form a carbocycle of three, four, five, six or seven carbon atoms, optionally where one carbon atom is replaced by a heteroatom selected from the group consisting of —O—, —S—, —SO$_2$—, and —NR$_{N\text{-}2}$—, where R$_{N\text{-}2}$ is selected from the group consisting of:
- (a) —H,
- (b) —$C_1$-$C_6$ alkyl optionally substituted with one substituent selected from the group consisting of:
  - (i) —OH, and
  - (ii) —NH$_2$,
- (c) —$C_1$-$C_6$ alkyl optionally substituted with one to three —F, —Cl, —Br, or —I,
- (d) —$C_3$-$C_7$ cycloalkyl,
- (e) —($C_1$-$C_2$ alkyl)-($C_3$-$C_7$ cycloalkyl),
- (f) —($C_1$-$C_6$ alkyl)-O—($C_1$-$C_3$ alkyl),
- (g) —$C_2$-$C_6$ alkenyl with one or two double bonds,
- (h) —$C_2$-$C_6$ alkynyl with one or two triple bonds,
- (i) —$C_1$-$C_6$ alkyl chain with one double bond and one triple bond,
- (j) —R$_{1\text{-}aryl}$ where R$_{1\text{-}aryl}$ is as defined above, and
- (k) —R$_{1\text{-}heteroaryl}$ where R$_{1\text{-}heteroaryl}$ is as defined above;

where R$_N$ is:
- (I) R$_{N\text{-}1}$—X$_N$— where X$_N$ is selected from the group consisting of:
  - (A) —CO—,
  - (B) —SO$_2$—,
  - (C) —(CR'R'')$_{1\text{-}6}$ where R' and R'' are the same or different and are —H or $C_1$-$C_4$ alkyl,
  - (D) —CO—(CR'R'')$_{1\text{-}6}$—X$_{N\text{-}1}$ where X$_{N\text{-}1}$ is selected from the group consisting of —O—, —S— and —NR'— and where R' and R'' are as defined above, and
  - (E) a single bond;

where R$_{N\text{-}1}$ is selected from the group consisting of:
- (A) R$_{N\text{-}aryl}$ where R$_{N\text{-}aryl}$ is phenyl, 1-naphthyl, 2-naphthyl, tetralinyl, indanyl, or 6,7,8,9-tetrahydro-5H-benzo[a]cycloheptenyl, or dihydronaphthyl optionally substituted with one, two or three of the following substituents which can be the same or different and are:
  - (1) $C_1$-$C_6$ alkyl, optionally substituted with one, two or three substituents selected from the group consisting of $C_1$-$C_3$ alkyl, —F, —Cl, —Br, —I, —OH, —SH, —C≡N, —CF$_3$, $C_1$-$C_3$ alkoxy, and —NR$_{1\text{-}a}$ R$_{1\text{-}b}$ where R$_{1\text{-}a}$ and R$_{1\text{-}b}$ are as defined above,
  - (2) —OH,
  - (3) —NO$_2$,
  - (4) —F, —Cl, —Br, or —I,
  - (5) —CO—OH,
  - (6) —C≡N,
  - (7) —(CH$_2$)$_{0\text{-}4}$—CO—NR$_{N\text{-}2}$R$_{N\text{-}3}$ where R$_{N\text{-}2}$ and R$_{N\text{-}3}$ are the same or different and are selected from the group consisting of:
    - (a) —H,
    - (b) —$C_1$-$C_6$ alkyl optionally substituted with one substituent selected from the group consisting of:
      - (i) —OH, and
      - (ii) —NH$_2$,
    - (c) —$C_1$-$C_6$ alkyl optionally substituted with one to three —F, —Cl, —Br, or —I,
    - (d) —$C_3$-$C_7$ cycloalkyl,
    - (e) —($C_1$-$C_2$ alkyl)-($C_3$-$C_7$ cycloalkyl),
    - (f) —($C_1$-$C_6$ alkyl)-O—($C_1$-$C_3$ alkyl),
    - (g) —$C_2$-$C_6$ alkenyl with one or two double bonds,
    - (h) —$C_2$-$C_6$ alkynyl with one or two triple bonds,
    - (i) —$C_1$-$C_6$ alkyl chain with one double bond and one triple bond,
    - (j) —R$_{1\text{-}aryl}$ where R$_{1\text{-}aryl}$ is as defined above, and
    - (k) —R$_{1\text{-}heteroaryl}$ where R$_{1\text{-}heteroaryl}$ is as defined above,
  - (8) —(CH$_2$)$_{0\text{-}4}$—CO—($C_1$-$C_{12}$ alkyl),
  - (9) —(CH$_2$)$_{0\text{-}4}$—CO—($C_2$-$C_{12}$ alkenyl with one, two or three double bonds),
  - (10) —(CH$_2$)$_{0\text{-}4}$—CO—($C_2$-$C_{12}$ alkynyl with one, two or three triple bonds),
  - (11) —(CH$_2$)$_{0\text{-}4}$—CO—($C_3$-$C_7$ cycloalkyl),
  - (12) —(CH$_2$)$_{0\text{-}4}$—CO—R$_{1\text{-}aryl}$ where R$_{1\text{-}aryl}$ is as defined above,
  - (13) —(CH$_2$)$_{0\text{-}4}$—CO—R$_{1\text{-}heteroaryl}$ where R$_{1\text{-}heteroaryl}$ is as defined above,
  - (14) —(CH$_2$)$_{0\text{-}4}$—CO—R$_{1\text{-}heterocycle}$ where R$_{1\text{-}heterocycle}$ is as defined above,
  - (15) —(CH$_2$)$_{0\text{-}4}$—CO—R$_{N\text{-}4}$ where R$_{N\text{-}4}$ is selected from the group consisting of morpholinyl, thiomorpholinyl, piperazinyl, piperidinyl, homomorpholinyl, homothiomorpholinyl, homothiomorpholinyl S-oxide, homothiomorpholinyl S,S-dioxide, pyrrolinyl and pyrrolidinyl where each group is optionally substituted with one, two, three, or four of: $C_1$-$C_6$ alkyl,
  - (16) —(CH$_2$)$_{0\text{-}4}$—CO—O—R$_{N\text{-}5}$ where R$_{N\text{-}5}$ is selected from the group consisting of:
    - (a) $C_1$-$C_6$ alkyl,
    - (b) —(CH$_2$)$_{0\text{-}2}$—(R$_{1\text{-}aryl}$) where R$_{1\text{-}aryl}$ is as defined above,
    - (c) $C_2$-$C_6$ alkenyl containing one or two double bonds,
    - (d) $C_2$-$C_6$ alkynyl containing one or two triple bonds,
    - (e) $C_3$-$C_7$ cycloalkyl,
    - (f) —(CH$_2$)$_{0\text{-}2}$—(R$_{1\text{-}heteroaryl}$) where R$_{1\text{-}heteroaryl}$ is as defined above,

(17) —$(CH_2)_{0-4}$—$SO_2$—$NR_{N-2}R_{N-3}$ where $R_{N-2}$ and $R_{N-3}$ are as defined above,
(18) —$(CH_2)_{0-4}$—SO—($C_1$-$C_8$ alkyl),
(19) —$(CH_2)_{0-4}$—$SO_2$—($C_1$-$C_{12}$ alkyl),
(20) —$(CH_2)_{0-4}$—$SO_2$—($C_3$-$C_7$ cycloalkyl),
(21) —$(CH_2)_{0-4}$—N(H or $R_{N-5}$)—CO—O—$R_{N-5}$ where $R_{N-5}$ can be the same or different and is as defined above,
(22) —$(CH_2)_{0-4}$—N(H or $R_{N-5}$)—CO—N($R_{N-5}$)$_2$, where $R_{N-5}$ can be the same or different and is as defined above,
(23) —$(CH_2)_{0-4}$—N—CS—N($R_{N-5}$)$_2$, where $R_{N-5}$ can be the same or different and is as defined above,
(24) —$(CH_2)_{0-4}$—N(—H or $R_{N-5}$)—CO—$R_{N-2}$ where $R_{N-5}$ and $R_{N-2}$ can be the same or different and are as defined above,
(25) —$(CH_2)_{0-4}$—$NR_{N-2}R_{N-3}$ where $R_{N-2}$ and $R_{N-3}$ can be the same or different and are as defined above,
(26) —$(CH_2)_{0-4}$—$R_{N-4}$ where $R_{N-4}$ is as defined above,
(27) —$(CH_2)_{0-4}$—O—CO—($C_1$-$C_6$ alkyl),
(28) —$(CH_2)_{0-4}$—P(O)—$(OR_{N-aryl-1})_2$ where $R_{N-aryl-1}$ is —H or $C_1$-$C_4$ alkyl,
(29) —$(CH_2)_{0-4}$—O—CO—N($R_{N-5}$)$_2$ where $R_{N-5}$ is as defined above,
(30) —$(CH_2)_{0-4}$—O—CS—N($R_{N-5}$)$_2$ where $R_{N-5}$ is as defined above,
(31) —$(CH_2)_{0-4}$—O—($R_{N-5}$)$_2$ where $R_{N-5}$ is as defined above,
(32) —$(CH_2)_{0-4}$—O—($R_{N-5}$)$_2$—COOH where $R_{N-5}$ is as defined above,
(33) —$(CH_2)_{0-4}$—S—($R_{N-5}$)$_2$ where $R_{N-5}$ is as defined above,
(34) —$(CH_2)_{0-4}$—O—($C_1$-$C_6$ alkyl optionally substituted with one, two, three, four, or five —F),
(35) $C_3$-$C_7$ cycloalkyl,
(36) $C_2$-$C_6$ alkenyl with one or two double bonds optionally substituted with $C_1$-$C_3$ alkyl, —F, —Cl, —Br, —I, —OH, —SH, —C≡N, —$CF_3$, $C_1$-$C_3$ alkoxy, or —$NR_{1-a}R_{1-b}$ where $R_{1-a}$ and $R_{1-b}$ are as defined above,
(37) $C_2$-$C_6$ alkynyl with one or two triple bonds optionally substituted with $C_1$-$C_3$ alkyl, —F, —Cl, —Br, —I, —OH, —SH, —C≡N, —$CF_3$, $C_1$-$C_3$ alkoxy, or —$NR_{1-a}R_{1-b}$ where $R_{1-a}$ and $R_{1-b}$ are as defined above,
(38) —$(CH_2)_{0-4}$—N(—H or $R_{N-5}$)—$SO_2$—$R_{N-2}$ where $R_{N-5}$ and $R_{N-2}$ can be the same of different and are as described above, or
(39) —$(CH_2)_{0-4}$—$C_3$-$C_7$ cycloalkyl,
(B) —$R_{N-heteroaryl}$, where $R_{N-heteroaryl}$ is selected from the group as defined above in $R_{1-heteroaryl}$ and where the $R_{N-heteroaryl}$ group is bonded by any atom of the parent $R_{N-heteroaryl}$ group substituted by hydrogen such that the new bond to the $R_{N-heteroaryl}$ group replaces the hydrogen atom and its bond, where heteroaryl is optionally substituted with one, two, three, or four of:
(1) $C_1$-$C_6$ alkyl, optionally substituted with one, two or three substituents selected from the group consisting of $C_1$-$C_3$ alkyl, —F, —Cl, —Br, —I, —OH, —SH, —C≡N, —$CF_3$, $C_1$-$C_3$ alkoxy, and —$NR_{1-a}R_{1-b}$ where $R_{1-a}$ and $R_{1-b}$ are as defined above,
(2) —OH,
(3) —$NO_2$,
(4) —F, —Cl, —Br, or —I,
(5) —CO—OH,
(6) —C≡N,
(7) —$(CH_2)_{0-4}$—CO—$NR_{N-2}R_{N-3}$ where $R_{N-2}$ and $R_{N-3}$ are the same or different and are selected from the group consisting of:
(a) —H,
(b) —$C_1$-$C_6$ alkyl optionally substituted with one substituent selected from the group consisting of:
(i) —OH, and
(ii) —$NH_2$,
(c) —$C_1$-$C_6$ alkyl optionally substituted with one to three —F, —Cl, —Br, or —I,
(d) —$C_3$-$C_7$ cycloalkyl,
(e) —($C_1$-$C_2$ alkyl)-($C_3$-$C_7$ cycloalkyl),
(f) —($C_1$-$C_6$ alkyl)-O—($C_1$-$C_3$ alkyl),
(g) —$C_2$-$C_6$ alkenyl with one or two double-bonds,
(h) —$C_2$-$C_6$ alkynyl with one or two triple bonds,
(i) —$C_1$-$C_6$ alkyl chain with one double bond and one triple bond,
(j) —$R_{1-aryl}$ where $R_{1-aryl}$ is as defined above, and
(k) —$R_{1-heteroaryl}$ where $R_{1-heteroaryl}$ is as defined above,
(8) —$(CH_2)_{0-4}$—CO—($C_1$-$C_{12}$ alkyl),
(9) —$(CH_2)_{0-4}$—CO—($C_2$-$C_{12}$ alkenyl with one, two, or three double bonds),
(10) —$(CH_2)_{0-4}$—CO—($C_2$-$C_{12}$ alkynyl with one, two, or three triple bonds),
(11) —$(CH_2)_{0-4}$—CO—($C_3$-$C_7$ cycloalkyl),
(12) —$(CH_2)_{0-4}$—CO—$R_{1-aryl}$ where $R_{1-aryl}$ is as defined above,
(13) —$(CH_2)_{0-4}$—CO—$R_{1-heteroaryl}$ where $R_{1-heteroaryl}$ is as defined above,
(14) —$(CH_2)_{0-4}$—CO—$R_{1-heterocycle}$ where $R_{1-heterocycle}$ is as defined above,
(15) —$(CH_2)_{0-4}$—CO—$R_{N-4}$ where $R_{N-4}$ is selected from the group consisting of morpholinyl, thiomorpholinyl, piperazinyl, piperidinyl, homomorpholinyl, homothiomorpholinyl, homothiomorpholinyl S-oxide, homothiomorpholinyl S,S-dioxide, pyrrolinyl and pyrrolidinyl where each group is optionally substituted with one, two, three, or four of: $C_1$-$C_6$ alkyl,
(16) —$(CH_2)_{0-4}$—CO—O—$R_{N-5}$ where $R_{N-5}$ is selected from the group consisting of:
(a) $C_1$-$C_6$ alkyl,
(b) —$(CH_2)_{0-2}$—($R_{1-aryl}$) where $R_{1-aryl}$ is as defined above,
(c) $C_2$-$C_6$ alkenyl containing one or two double bonds,
(d) $C_2$-$C_6$ alkynyl containing one or two triple bonds,
(e) $C_3$-$C_7$ cycloalkyl, and
(f) —$(CH_2)_{0-2}$—($R_{1-heteroaryl}$) where $R_{1-heteroaryl}$ is as defined above,
(17) —$(CH_2)_{0-4}$—$SO_2$—$NR_{N-2}R_{N-3}$ where $R_{N-2}$ and $R_{N-3}$ are as defined above,
(18) —$(CH_2)_{0-4}$—SO—($C_1$-$C_8$ alkyl),
(19) —$(CH_2)_{0-4}$—$SO_2$—($C_1$-$C_{12}$ alkyl),
(20) —$(CH_2)_{0-4}$—$SO_2$—($C_3$-$C_7$ cycloalkyl),
(21) —$(CH_2)_{0-4}$—N(H or $R_{N-5}$)—CO—O—$R_{N-5}$ where $R_{N-5}$ can be the same or different and is as defined above,
(22) —$(CH_2)_{0-4}$—N(H or $R_{N-5}$)—CO—N($R_{N-5}$)$_2$, where $R_{N-5}$ can be the same or different and is as defined above,

(23) —(CH$_2$)$_{0-4}$—N—CS—N(R$_{N-5}$)$_2$, where R$_{N-5}$ can be the same or different and is as defined above,

(24) —(CH$_2$)$_{0-4}$—N(—H or R$_{N-5}$)—CO—R$_{N-2}$ where R$_{N-5}$ and R$_{N-2}$ can be the same or different and are as defined above,

(25) —(CH$_2$)$_{0-4}$—NR$_{N-2}$R$_{N-3}$ where R$_{N-2}$ and R$_{N-3}$ can be the same or different and are as defined above,

(26) —(CH$_2$)$_{0-4}$—R$_{N-4}$ where R$_{N-4}$ is as defined above,

(27) —(CH$_2$)$_{0-4}$—O—CO—(C$_1$-C$_6$ alkyl),

(28) —(CH$_2$)$_{0-4}$—O—P(O)—(OR$_{N-aryl-1}$)$_2$ where R$_{N-aryl-1}$ is —H or C$_1$-C$_4$ alkyl,

(29) —(CH$_2$)$_{0-4}$—O—CO—N(R$_{N-5}$)$_2$ where R$_{N-5}$ is as defined above,

(30) —(CH$_2$)$_{0-4}$—O—CS—N(R$_{N-5}$)$_2$ where R$_{N-5}$ is as defined above,

(31) —(CH$_2$)$_{0-4}$—O—(R$_{N-5}$)$_2$ where R$_{N-5}$ is as defined above,

(32) —(CH$_2$)$_{0-4}$—O—(R$_{N-5}$)$_2$—COOH where R$_{N-5}$ is as defined above,

(33) —(CH$_2$)$_{0-4}$—S—(R$_{N-5}$)$_2$ where R$_{N-5}$ is as defined above,

(34) —(CH$_2$)$_{0-4}$—O—(C$_1$-C$_6$ alkyl optionally substituted with one, two, three, four, or five of —F),

(35) C$_3$-C$_7$ cycloalkyl,

(36) C$_2$-C$_6$ alkenyl with one or two double bonds optionally substituted with C$_1$-C$_3$ alkyl, —F, —Cl, —Br, —I, —OH, —SH, —C≡N, —CF$_3$, C$_1$-C$_3$ alkoxy, or —NR$_{1-a}$R$_{1-b}$ where R$_{1-a}$ and R$_{1-b}$ are as defined above,

(37) C$_2$-C$_6$ alkynyl with one or two triple bonds optionally substituted with C$_1$-C$_3$ alkyl, —F, —Cl, —Br, —I, —OH, —SH, —C≡N, —CF$_3$, C$_1$-C$_3$ alkoxy, or —NR$_{1-a}$R$_{1-b}$ where R$_{1-a}$ and R$_{1-b}$ are as defined above, or

(38) —(CH$_2$)$_{0-4}$—N(—H or R$_{N-5}$)—SO$_2$—R$_{N-2}$ where R$_{N-5}$ and R$_{N-2}$ can be the same of different and are as described above,

(39) —(CH$_2$)$_{0-4}$—C$_3$-C$_7$ cycloalkyl, (C) R$_{N-aryl}$—W—R$_{N-aryl}$, (D) R$_{N-aryl}$—W—R$_{N-heteroaryl}$, (E) R$_{N-aryl}$—W—R$_{N-1-heterocycle}$, where R$_{n-1-heterocycle}$ is the same as R$_{1-heterocycle}$, as defined above, (F) R$_{N-heteroaryl}$—W—R$_{N-aryl}$, (G) R$_{N-heteroaryl}$—W—R$_{N-heteroaryl}$, (H) R$_{N-heteroaryl}$—W—R$_{1-heterocycle}$, (I) R$_{1-heterocycle}$—W—R$_{N-aryl}$, (J) R$_{1-heterocycle}$—W—R$_{N-heteroaryl}$, and (K) R$_{1-heterocycle}$—W—R$_{1-heterocycle}$, where W is (1) —(CH$_2$)$_{0-4}$—, (2) —O—, (3) —S(O)$_{0-2}$—, (4) —N(R$_{N-5}$)— where R$_{N-5}$ is as defined above, or (5) —CO—;

(II) —CO—(C$_1$-C$_{10}$ alkyl) where alkyl is optionally substituted with one, two, or three substituents selected from the group consisting of:

(A) —OH, (B) —C$_1$-C$_6$ alkoxy, (C) —C$_1$-C$_6$ thioalkoxy, (D) —CO—O—R$_{N-8}$ where R$_{N-8}$ is —H, C$_1$-C$_6$ alkyl or -phenyl, (E) —CO—NR$_{N-2}$R$_{N-3}$ where R$_{N-2}$ and R$_{N-3}$ are the same or different and are as defined above, (F) —CO—R$_{N-4}$ where R$_{N-4}$ is as defined above, (G) —SO$_2$—(C$_1$-C$_8$ alkyl), (H) —SO$_2$—NR$_{N-2}$R$_{N-3}$ where R$_{N-2}$ and R$_{N-3}$ are the same or different and are as defined above, (I) —NH—CO—(C$_1$-C$_6$ alkyl), (J) —NH—CO—O—R$_{N-8}$ where R$_{N-8}$ is as defined above, (K) —NR$_{N-2}$R$_{N-3}$ where R$_{N-2}$ and R$_{N-3}$ are the same or different and are as defined above, (L) —R$_{N-4}$ where R$_{N-4}$ is as defined above, (M) —O—CO—(C$_1$-C$_6$ alkyl), (N) —O—CO—NR$_{N-8}$R$_{N-8}$ where R$_{N-8}$ are the same or different and are as defined above, (O) —O—(C$_1$-C$_5$ alkyl)-COOH, (P) —O—(C$_1$-C$_6$ alkyl optionally substituted with one, two, or three —F, —Cl, —Br, or —I), (Q) —NH—SO$_2$—(C$_1$-C$_6$ alkyl), and (R) —F, or —Cl, (III) —CO—(C$_1$-C$_6$ alkyl)-O—(C$_1$-C$_6$ alkyl) where alkyl is optionally substituted with one, two, or three substituents selected from the group consisting of:

(A) —OH, (B) —C$_1$-C$_6$ alkoxy, (C) —C$_1$-C$_6$ thioalkoxy, (D) —CO—O—R$_{N-8}$ where R$_{N-8}$ is —H, C$_1$-C$_6$ alkyl or, -phenyl, (E) —CO—NR$_{N-2}$R$_{N-3}$ where R$_{N-2}$ and R$_{N-3}$ are the same or different and are as defined above, (F) —CO—R$_{N-4}$ where R$_{N-4}$ is as defined above, (G) —SO$_2$—(C$_1$-C$_8$ alkyl), (H) —SO$_2$—NR$_{N-2}$R$_{N-3}$ where R$_{N-2}$ and R$_{N-3}$ are the same or different and are as defined above, (I) —NH—CO—(C$_1$-C$_6$ alkyl), (J) —NH—CO—O—R$_{N-8}$ where R$_{N-8}$ is as defined above, (K) —NR$_{N-2}$R$_{N-3}$ where R$_{N-2}$ and R$_{N-3}$ are the same or different and are as defined above, (L) —R$_{N-4}$ where R$_{N-4}$ is as defined above, (M) —O—CO—(C$_1$-C$_6$ alkyl), (N) —O—CO—NR$_{N-8}$R$_{N-8}$ where the R$_{N-8}$s are the same or different and are as defined above, (O) —O—(C$_1$-C$_5$ alkyl)-COOH, (P) —O—(C$_1$-C$_6$ alkyl optionally substituted with one, two, or three —F, —Cl, —Br, or —I), (Q) —NH—SO$_2$—(C$_1$-C$_6$ alkyl), and (R) —F, or —Cl, (IV) —CO—(C$_1$-C$_6$ alkyl)-S—(C$_1$-C$_6$ alkyl) where alkyl is optionally substituted with one, two, or three substituents selected from the group consisting of:

(A) —OH, (B) —C$_1$-C$_6$ alkoxy, (C) —C$_1$-C$_6$ thioalkoxy, (D) —CO—O—R$_{N-8}$ where R$_{N-8}$ is as defined above, (E) —CO—NR$_{N-2}$R$_{N-3}$ where R$_{N-2}$ and R$_{N-3}$ are the same or different and are as defined above, (F) —CO—R$_{N-4}$ where R$_{N-4}$ is as defined above, (G) —SO$_2$—(C$_1$-C$_8$ alkyl), (H) —SO$_2$—NR$_{N-2}$R$_{N-3}$ where R$_{N-2}$ and R$_{N-3}$ are the same or different and are as defined above, (I) —NH—CO—(C$_1$-C$_6$ alkyl), (J) —NH—CO—O—R$_{N-8}$ where R$_{N-8}$ is as defined above, (K) —NR$_{N-2}$R$_{N-3}$ where R$_{N-2}$ and R$_{N-3}$ are the same or different and are as defined above, (L) —R$_{N-4}$ where R$_{N-4}$ is as defined above, (M) —O—CO—(C$_1$-C$_6$ alkyl), (N) —O—CO—NR$_{N-8}$R$_{N-8}$ where R$_{N-8}$ are the same or different and are as defined above, (O) —O—($C_1$-$C_5$ alkyl)-COOH,
(P) —O—($C_1$-$C_6$ alkyl optionally substituted with one, two, or three —F, —Cl, —Br, or —I),
(Q) —NH—$SO_2$—($C_1$-$C_6$ alkyl), and
(R) —F, or —Cl, (V) —CO—CH(—($CH_2$)$_{0-2}$—O—$R_{N-10}$)—($CH_2$)$_{0-2}$—$R_{N-aryl}$/$R_{N-heteroaryl}$) where $R_{N-aryl}$ and $R_{N-heteroaryl}$ are as defined above, where $R_{N-10}$ is selected from the group consisting of:
(A) —H,
(B) $C_1$-$C_6$ alkyl,
(C) $C_3$-$C_7$ cycloalkyl,
(D) $C_2$-$C_6$ alkenyl with one double bond,
(E) $C_2$-$C_6$ alkynyl with one triple bond,
(F) $R_{1-aryl}$ where $R_{1-aryl}$ is as defined above, and
(G) $R_{N-heteroaryl}$ where $R_{N-heteroaryl}$ is as defined above, or (VI) —CO—($C_3$-$C_8$ cycloalkyl) where alkyl is optionally substituted with one or two substituents selected from the group consisting of:
(A) —($CH_2$)$_{0-4}$—OH,
(B) —($CH_2$)$_{0-4}$—$C_1$-$C_6$ alkoxy,
(C) —($CH_2$)$_{0-4}$—$C_1$-$C_6$ thioalkoxy,
(D) —($CH_2$)$_{0-4}$—CO—O—$R_{N-8}$ where $R_{N-8}$ is —H, $C_1$-$C_6$ alkyl or -phenyl,
(E) —($CH_2$)$_{0-4}$—CO—$NR_{N-2}R_{N-3}$ where $R_{N-2}$ and $R_{N-3}$ are the same or different and are as defined above,
(F) —($CH_2$)$_{0-4}$—CO—$R_{N-4}$ where $R_{N-4}$ is as defined above,
(G) —($CH_2$)$_{0-4}$—$SO_2$—($C_1$-$C_8$ alkyl),
(H) —($CH_2$)$_{0-4}$—$SO_2$—$NR_{N-2}R_{N-3}$ where $R_{N-2}$ and $R_{N-3}$ are the same or different and are as defined above,
(I) —($CH_2$)$_{0-4}$—NH—CO—($C_1$-$C_6$ alkyl),
(J) —NH—CO—O—$R_{N-8}$ where $R_{N-8}$ is as defined above,
(K) —($CH_2$)$_{0-4}$—$NR_{N-2}R_{N-3}$ where $R_{N-2}$ and $R_{N-3}$ are the same or different and are as defined above,
(L) —($CH_2$)$_{0-4}$—$R_{N-4}$ where $R_{N-4}$ is as defined above,
(M) —O—CO—($C_1$-$C_6$ alkyl),
(N) —O—CO—$NR_{N-8}R_{N-8}$ where $R_{N-8}$ are the same or different and are as defined above,
(O) —O—($C_1$-$C_5$ alkyl)-COOH,
(P) —O—($C_1$-$C_6$ alkyl optionally substituted with one, two, or three —F, —Cl, —Br, or —I),
(Q) —NH—$SO_2$—($C_1$-$C_6$ alkyl), and
(R) —F, or —Cl;

where $R_{N-4}$ is selected from the group consisting of H, $C_1$-$C_{10}$ alkyl, $C_2$-$C_{10}$ alkenyl and alkynyl, phenyl, $C_1$-$C_4$ alkyl-$R_{N-aryl}$, $C_1$-$C_4$ alkyl-$R_{N-heteroaryl}$, $C_1$-$C_4$ alkyl-$C_3$-$C_7$ cycloalkyl and $C_1$-$C_4$ alkyl-$R_{1-heterocycle}$, wherein each multi-atom group may be optionally substituted with one, two, or three substituents independently selected from the group consisting of —F, —Cl, —OH, —SH, —C≡N, —$CF_3$, $C_1$-$C_3$ alkoxy, —C(O)O—$R_{1-a}$, and —$NR_{1-a}R_{1-b}$ where $R_{1-a}$ and $R_{1-b}$ are —H, $C_1$-$C_6$ alkyl or phenyl;

where Z is selected from the group consisting of:
(A) —C(O)—,
(B) —S(O)$_{1-2}$—,
(C) —C(O)—$X_{N-1}$— where $X_{N-1}$ is selected from the group consisting of —O—, —S— and —NR'— and where R' is as defined above; and
(D) a single bond;

where $R_C$ is:
(I) —$C_1$-$C_{10}$ alkyl optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, —$NR_{1-a}R_{1-b}$ where $R_{1-a}$ and $R_{1-b}$ are as defined above, —OC=O $NR_{1-a}R_{1-b}$ where $R_{1-a}$ and $R_{1-b}$ are as defined above, —S(=O)$_{0-2}R_{1-a}$ where $R_{1-a}$ is as defined above, —$NR_{1-a}$C=O $NR_{1-a}R_{1-b}$ where $R_{1-a}$ and $R_{1-b}$ are as defined above, —C=O $NR_{1-a}R_{1-b}$ where $R_{1-a}$ and $R_{1-b}$ are as defined above, and —S(=O)$_2NR_{1-a}R_{1-b}$ where $R_{1-a}$ and $R_{1-b}$ are as defined above, (II) —($CH_2$)$_{0-3}$—($C_3$-$C_8$)cycloalkyl where cycloalkyl can be optionally substituted with one, two, or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, —CO—OH, —CO—O—($C_1$-$C_4$ alkyl), and —$NR_{1-a}R_{1-b}$ where $R_{1-a}$ and $R_{1-b}$ are as defined above, (III) —($CR_{C-x}R_{C-y}$)$_{0-4}$—$R_{C-aryl}$ where $R_{C-x}$ and $R_{C-y}$ are
(A) —H,
(B) $C_1$-$C_4$ alkyl optionally substituted with one, or two —OH,
(C) $C_1$-$C_4$ alkoxy optionally substituted with one, two, or three —F,
(D) —($CH_2$)$_{0-4}$—$C_3$-$C_7$ cycloalkyl,
(E) $C_2$-$C_6$ alkenyl containing one or two double bonds,
(F) $C_2$-$C_6$ alkynyl containing one or two triple bonds,
(G) phenyl-, or
(A) $C_0$-$C_4$ alkylC(O)$NR_{1-a}R_{1-b}$ where $R_{1-a}$ and $R_{1-b}$ are as defined above,
and where $R_{C-x}$ and $R_{C-y}$ are taken together with the carbon to which they are attached to form a carbocycle of three, four, five, six, or seven carbon atoms, optionally where one carbon atom is replaced by a heteroatom selected from the group consisting of —O—, —S—, —$SO_2$—, —$NR_{N-2}$— and $R_{C-aryl}$ where $R_{C-aryl}$ is the same as $R_{N-aryl}$ and where $R_{C-aryl}$ may optionally be substituted with —$C_0$-$C_4$ alkyl-C(O)$NR_{1-a}R_{1-b}$, $C_0$-$C_4$ alkylC(O)$OR_{1-a}$ where $R_{1-a}$ and $R_{1-b}$ are as defined above, (IV) —($CR_{C-x}R_{C-y}$)$_{0-4}$—$R_{C-heteroaryl}$ where $R_{C-heteroaryl}$ is the same as $R_{N-heteroaryl}$ and $R_{C-x}$ and $R_{C-y}$ are as defined above, (V) —($CR_{C-x}R_{C-y}$)$_{0-4}$—$R_{C-aryl}$—$R_{C-aryl}$ where $R_{C-aryl}$, $R_{C-x}$ and $R_{C-y}$ are as defined above, (VI) —($CR_{C-x}R_{C-y}$)$_{0-4}$—$R_{C-aryl}$—$R_{C-heteroaryl}$ where $R_{C-aryl}$, $R_{C-heteroaryl}$, $R_{C-x}$ and $R_{C-y}$ are as defined above, (VII) —($CR_{C-x}R_{C-y}$)$_{0-4}$—$R_{C-heteroaryl}$—$R_{C-aryl}$ where $R_{C-heteroaryl}$, $R_{C-aryl}$, $R_{C-x}$ and $R_{C-y}$ are as defined above, (VIII) —($CR_{C-x}R_{C-y}$)$_{0-4}$—$R_{C-heteroaryl}$—$R_{C-heteroaryl}$ where $R_{C-heteroaryl}$, $R_{C-x}$ and $R_{C-y}$ are as defined above, (IX) —($CR_{C-x}R_{C-y}$)$_{0-4}$—$R_{C-aryl}$—$R_{C-heterocycle}$ where $R_{C-heterocycle}$ is the same as $R_{1-heterocycle}$, and where $R_{C-aryl}$, $R_{C-x}$ and $R_{C-y}$ are as defined above, (X) —($CR_{C-x}R_{C-y}$)$_{0-4}$—$R_{C-heteroaryl}$—$R_{C-heterocycle}$ where $R_{C-heteroaryl}$, $R_{C-heterocycle}$, $R_{C-x}$ and $R_{C-y}$ are as defined above, (XI) —($CR_{C-x}R_{C-y}$)$_{0-4}$—$R_{C-heterocycle}$—$R_{C-aryl}$ where $R_{C-heterocycle}$, $R_{C-aryl}$, $R_{C-x}$ and $R_{C-y}$ are as defined above, (XII) —($CR_{C-x}R_{C-y}$)$_{0-4}$—$R_{C-heterocycle}$—$R_{C-heteroaryl}$ where $R_{C-heterocycle}$, $R_{C-heteroaryl}$, $R_{C-x}$ and $R_{C-y}$ are as defined above, (XIII) —($CR_{C-x}R_{C-y}$)$_{0-4}$—$R_{C-heterocycle}$—$R_{C-heterocycle}$ where $R_{C-heterocycle}$, $R_{C-x}$ and $R_{C-y}$ are as defined above, (XIV) —($CR_{C-x}R_{C-y}$)$_{0-4}$—$R_{C-heterocycle}$ where $R_{C-heterocycle}$, $R_{C-x}$ and $R_{C-y}$ are as defined above, (XV) —[$C(R_{C-1})(R_{C-2})$]$_{1-3}$—CO—N—($R_{C-3}$)$_2$ where $R_{C-3}$ is as defined below and $R_{C-1}$, $R_{C-2}$ are the same or different and are selected from the group consisting of:
- (A) —H,
- (B) —$C_1$-$C_6$ alkyl, optionally substituted with up to three substituents independently selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above,
- (D) $C_2$-$C_6$ alkenyl with one or two double bonds, optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above,
- (E) $C_2$-$C_6$ alkynyl with one or two triple bonds, optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above,
- (F) —($CH_2$)$_{1-2}$—$S(O)_{0-2}$—($C_1$-$C_6$ alkyl),
- (F) —($CH_2$)$_{0-4}$—$C_3$-$C_7$ cycloalkyl, optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above,
- (G) —($C_1$-$C_4$alkyl)-$R_{C'-aryl}$ where $R_{C'-aryl}$ is as defined for $R_{1-aryl}$,
- (H) —($C_1$-$C_4$ alkyl)-$R_{C-heteroaryl}$ where $F_{C-heteroaryl}$ is as defined above,
- (I) —($C_1$-$C_4$ alkyl)-$R_{C-heterocycle}$ where $R_{C-heterocycle}$ is as defined above,
- (J) —$R_{C-heteroaryl}$ where $R_{C-heteroaryl}$ is as defined above,
- (K) —$R_{C-heterocycle}$ where $R_{C-heterocycle}$ is as defined above,
- (M) —($CH_2$)$_{1-4}$—$R_{C-4}$—($CH_2$)$_{0-4}$—$R_{C'-aryl}$ where $R_{C-4}$ is —O—, —S— or —$NR_{C-5}$— where $R_{C-5}$ is $C_1$-$C_6$ alkyl, and where $R_{C'-aryl}$ is defined above,
- (N) —($CH_2$)$_{1-4}$—$R_{C-4}$—($CH_2$)$_{0-4}$—$R_{C-heteroaryl}$ where $R_{C-4}$ and $R_{C-heteroaryl}$ are as defined above, and
- (O) —$R_{C'-aryl}$ where $R_{C'-aryl}$ is as defined above, and where $R_{C-3}$ is the same or different and is:
- (A) —H,
- (B) —$C_1$-$C_6$ alkyl optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above,
- (C) $C_2$-$C_6$ alkenyl with one or two double bonds, optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above,
- (D) $C_2$-$C_6$ alkynyl with one or two triple bonds, optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above,
- (E) —($CH_2$)$_{0-4}$—$C_3$-$C_7$ cycloalkyl, optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, —$NR_{1-a}R_{1-b}$ where $R_{1-a}$ and $R_{1-b}$ are as defined above,
- (F) —$R_{C'-aryl}$ where $R_{C'-aryl}$ is as defined above,
- (G) —$R_{C-heteroaryl}$ where $R_{C-heteroaryl}$ is as defined above,
- (H) —$R_{C-heterocycle}$ where $R_{C-heterocycle}$ is as defined above,
- (I) —($C_1$-$C_4$ alkyl)-$R_{C'-aryl}$ where $R_{C'-aryl}$ is as defined above,
- (J) —($C_1$-$C_4$ alkyl)-$R_{C-heteroaryl}$ where $R_{C-heteroaryl}$ is as defined above, or
- (K) —($C_1$-$C_4$ alkyl)-$R_{C-heterocycle}$ where $R_{C-heterocycle}$ is as defined above, (XVI) —$CH(R_{C-aryl})_2$ where $R_{C-aryl}$ are the same or different and are as defined above, (XVII) —$CH(R_{C-heteroaryl})_2$ where $R_{C-heteroaryl}$ are the same or different and are as defined above, (XVIII) —$CH(R_{C-aryl})(R_{C-heteroaryl})$ where $R_{C-aryl}$ and $R_{C-heteroaryl}$ are as defined above, (XIX) -cyclopentyl, -cyclohexyl, or -cycloheptyl ring fused to $R_{C-aryl}$ or $R_{C-heteroaryl}$ or $R_{C-heterocycle}$ where $R_{C-aryl}$ or $R_{C-heteroaryl}$ or $R_{C-heterocycle}$ are as defined above where one carbon of cyclopentyl, cyclohexyl, or cycloheptyl is optionally replaced with NH, $NR_{N-5}$, O, or $S(=O)_{0-2}$, and where cyclopentyl, cyclohexyl, or cycloheptyl can be optionally substituted with one or two —$C_1$-$C_3$ alkyl, —F, —OH, —SH, —C≡N, —$CF_3$, $C_1$-$C_6$ alkoxy, =O, or —$NR_{1-a}R_{1-b}$ where $R_{1-a}$ and $R_{1-b}$ are as defined above, (XX) $C_2$-$C_{10}$ alkenyl containing one or two double bonds optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above, (XXI) $C_2$-$C_{10}$ alkynyl containing one or two triple bonds optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above, (XXI) —($CH_2$)$_{0-1}$—$CHR_{C-6}$—($CH_2$)$_{0-1}$—$R_{C-aryl}$ where $R_{C-aryl}$ is as defined above and $R_{C-6}$ is —($CH_2$)$_{0-6}$—OH, (XXII) —($CH_2$)$_{0-1}$—$CHR_{C-6}$—($CH_2$)$_{0-1}$—$R_{C-heteroaryl}$ where $R_{C-heteroaryl}$ and $R_{C-6}$ is as defined above, (XXIII) —CH(—$R_{C-aryl}$ or $R_{C-heteroaryl}$)—CO—O($C_1$-$C_4$ alkyl) where $R_{C-aryl}$ and $R_{C-heteroaryl}$ are as defined above, (XXIV) —CH(—$CH_2$—OH)—CH(—OH)-phenyl-$NO_2$, (XXV) ($C_1$-$C_6$ alkyl)-O—($C_1$-$C_6$ alkyl)-OH, (XXVII) —CH₂—NH—CH₂—CH(—O—CH₂—CH₃)₂, or (XXVIII) —(CH₂)₀₋₆—C(=NR₁₋ₐ)(NR₁₋ₐR₁₋ᵦ) where R₁₋ₐ and R₁₋ᵦ are as defined above, where $R_{C-A}$ is H, $C_1$-$C_{10}$ alkyl, $C_2$-$C_{10}$ alkenyl and alkynyl, phenyl, $C_1$-$C_4$ alkyl-$R_{N-aryl}$, $C_1$-$C_4$ alkyl-$R_{N-heteroaryl}$, $C_1$-$C_4$ alkyl-C3-C7 cycloalkyl, or $C_1$-$C_4$ alkyl-$R_{1-heterocycle}$, wherein each multi-atom group may be optionally substituted with one, two, or three substituents independently selected from the group consisting of —F, —Cl, —OH, —SH, —C≡N, —CF₃, $C_1$-$C_3$ alkoxy, —C(O)O—$R_{1-a}$, and —$NR_{1-a}R_{1-b}$ where $R_{1-a}$ and $R_{1-b}$ are —H, $C_1$-$C_6$ alkyl or phenyl;

where $R_{C-A}$, -Z-$R_C$, and the nitrogen atom to which they attach may cyclize to form a ring or fused rings chosen from the group consisting of 5-8 membered heterocyclics having up to 2 heteroatoms in addition to the ring nitrogen defined above chosen from the group consisting of N, O, and S, which may optionally be fused with one, or two phenyl, pyridyl, cyclohexyl, piperidinyl or morpholinyl, where the ring or fused rings may optionally have one, two, or three substituents independently chosen from the group of:

(1) $C_1$-$C_6$ alkyl,
$C_2$-$C_6$ alkenyl with one or two double bonds, or
$C_2$-$C_6$ alkynyl with one or two triple bonds, wherein each may be optionally substituted with one, two, or three substituents selected from the group consisting of —F, —Cl, —OH, —SH, —C≡N, —CF₃, $C_1$-$C_3$ alkoxy, and —$NR_{1-a}R_{1-b}$ where $R_{1-a}$ and $R_{1-b}$ are —H or $C_1$-$C_6$ alkyl, (2) —F, Cl, —Br, or —I,
(3) —$C_1$-$C_6$ alkoxy optionally substituted with one, two, or three —F,
(4) —$NR_{N-2}R_{N-3}$ where $R_{N-2}$ and $R_{N-3}$ are as defined below,
(5) —OH,
(6) —C≡N,
(7) =O (oxo),
(8) —CO—($C_1$-$C_4$ alkyl),
(9) —$SO_2$—$NR_{1-a}R_{1-b}$ where $R_{1-a}$ and $R_{1-b}$ are as defined above, or
(10) —CO—$NR_{1-a}R_{1-b}$ where $R_{1-a}$ and $R_{1-b}$ are as defined above, and pharmaceutically acceptable salts thereof.

Disclosed is a method of treating a patient who has, or in preventing a patient from getting, a disease or condition selected from the group consisting of Alzheimer's disease, for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, or diffuse Lewy body type of Alzheimer's disease and who is in need of such treatment which comprises administration of a therapeutically effective amount of a compound selected from the group consisting of a disubstituted amine of formula (I)

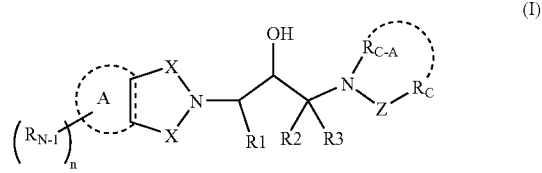

where $R_1$, $R_2$, $R_3$, $R_C$, $R_{C-A}$, $R_{N-1}$, A, X, Z, and n are as defined above for the disubstituted amine (I), and pharmaceutically acceptable salts thereof, and a disubstituted amine of formula (II)

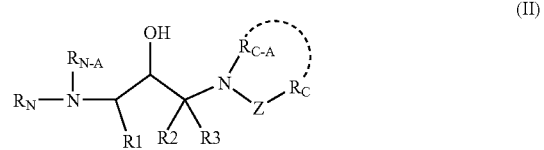

where $R_1$, $R_2$, $R_3$, $R_C$, $R_{C-A}$, $R_N$, $R_{N-A}$, and Z are as defined above for the disubstituted amine (II), and pharmaceutically acceptable salts thereof.

Also disclosed are methods for inhibiting beta-secretase activity, for inhibiting cleavage of amyloid precursor protein (APP), in a reaction mixture, at a site between Met596 and Asp597, numbered for the APP-695 amino acid isotype; or at a corresponding site of an isotype or mutant thereof, for inhibiting production of amyloid beta peptide (A beta) in a cell, for inhibiting the production of beta-amyloid plaque in an animal, and for treating or preventing a disease characterized by beta-amyloid deposits in the brain which comprise administration of a therapeutically effective amount of a disubstituted amine of formula (I)

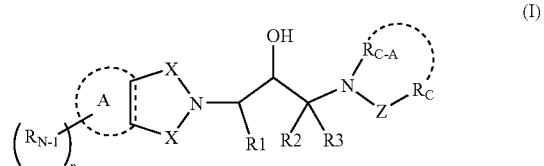

where $R_1$, $R_2$, $R_3$, $R_C$, $R_{C-A}$, $R_{N-1}$, A, X, Z, and n are as defined above for the disubstituted amine (I), and pharmaceutically acceptable salts thereof, and a disubstituted amine of formula (II)

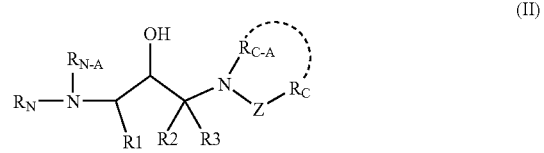

where $R_1$, $R_2$, $R_3$, $R_C$, $R_{C-A}$, $R_N$, $R_{N-A}$, and Z are as defined above for the disubstituted amine (II), and pharmaceutically acceptable salts thereof.

Disclosed is a pharmaceutical composition which comprises a disubstituted amine of formula (I)

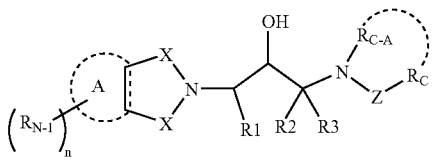

where $R_1$, $R_2$, $R_3$, $R_C$, $R_{C-A}$, $R_{N-1}$, A, X, Z, and n are as defined above for the disubstituted amine (I), and pharmaceutically acceptable salts thereof, and a disubstituted amine of formula (II)

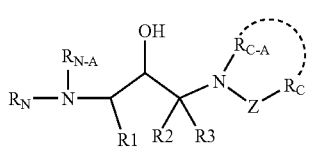

where $R_1$, $R_2$, $R_3$, $R_C$, $R_{C-A}$, $R_N$, $R_{N-A}$, and Z are as defined above for the disubstituted amine (II), and pharmaceutically acceptable salts thereof, and one or more pharmaceutically acceptable inert carriers.

The present invention provides compounds, compositions, kits, and methods for inhibiting beta-secretase-mediated cleavage of amyloid precursor protein (APP). More particularly, the compounds, compositions, and methods of the invention are effective to inhibit the production of A beta peptide and to treat or prevent any human or veterinary disease or condition associated with a pathological form of A beta peptide.

The compounds, compositions, and methods of the invention are useful for treating humans who have Alzheimer's Disease (AD), for helping prevent or delay the onset of AD, for treating patients with mild cognitive impairment (MCI), and preventing or delaying the onset of AD in those patients who would otherwise be expected to progress from MCI to AD, for treating Down's syndrome, for treating Hereditary Cerebral Hemorrhage with Amyloidosis of the Dutch Type, for treating cerebral beta-amyloid angiopathy and preventing its potential consequences such as single and recurrent lobar hemorrhages, for treating other degenerative dementias, including dementias of mixed vascular and degenerative origin, for treating dementia associated with Parkinson's disease, dementia associated with progressive supranuclear palsy, dementia associated with cortical basal degeneration, and diffuse Lewy body type AD.

The compounds of the invention possess beta-secretase inhibitory activity. The inhibitory activities of the compounds of the invention are readily demonstrated, for example, using one or more of the assays described herein or known in the art.

DETAILED DESCRIPTION OF THE INVENTION

The present invention is the disubstituted amines (I) and (II) that are useful in treating and preventing Alzheimer's disease. The anti-Alzheimer's disubstituted amines (I) and (II) are made by methods well known to those skilled in the art from starting compounds known to those skilled in the art. The process chemistry is well known to those skilled in the art. One example of a general process to prepare the disubstituted amines (I) and (II) of the present invention is set forth in CHART A, and for C-terminal amides and ureas may also alternatively be made by CHART A-1.

Compounds of the invention where Z is carbonyl or —C(O)—$X_{N-1}$— are obtained by reacting the epoxide (V) with a primary amine of the type $R_{C-A}$-$NH_2$ and then coupling the obtained secondary amine with an $R_C$ group suitably bearing a carboxy functionality or by reaction with an isocyanate function to provide a urea. CHART A-1 exemplifies these procedures.

The chemistry is straight forward and in summary involves the steps of N-protecting an amino acid (1) starting material to produce the corresponding protected amino acid (2), reaction of the protected amino acid (2) with diazomethane followed by work-up to add a carbon atom to produce the corresponding protected compound (III), reduction of the protected compound (III) to the corresponding alcohol (IV), formation of the corresponding epoxide (V), opening of the epoxide (V) with a C-terminal amine, $R_C$—$NH_2$ (VI) to produce the corresponding protected alcohol (VII) which then has the nitrogen protecting group removed to produce the corresponding amine (VIII), which is then reacted with an amide forming agent of the formula ($R_{N-1}$—$X_N$)$_2$O or $R_{N-1}$—$X_N$—$X_2$ or $R_{N-1}$—$X_N$—OH (IX) to produce the anti-Alzheimer disubstituted amine (II). One skilled in the art will appreciate that these are all well known reactions in organic chemistry. A chemist skilled in the art, knowing the chemical structure of the biologically active substituted amine end product (II) of the invention would be able to prepare them by known methods from known starting materials without any additional information. The explanation below therefore is not necessary but is deemed helpful to those skilled in the art who desire to make the compounds of the present invention.

The backbone of the compounds of the present invention is a hydroxyethylamine moiety, —NH—CH(R)—CH(OH)—. It can be readily prepared by methods disclosed in the literature and known to those skilled in the art. For example, *J. Med. Chem.*, 36, 288-291 (1992), *Tetrahedron Letters*, 28, 5569-5572 (1987), and *J. Med. Chem.*, 38, 581-584 (1994) and *Tetrahedron Letters*, 38, 619-620 (1997) both disclose processes to prepare hydroxyethylamine type compounds.

CHART A sets forth a general method used in the present invention to prepare the appropriately disubstituted N-terminal amines (I) and (II). The anti-Alzheimer disubstituted amines (I) and (II) of the present invention are prepared by starting with the corresponding amino acid (1). The amino acids are well known to those skilled in the art or can be readily prepared from known compounds by methods well known to those skilled in the art. The disubstituted amines (I) and (II) of the present invention have at least two enantiomeric centers which give four enantiomers. The first of these enantiomeric centers derives from the amino acid starting material. It is preferred to commercially obtain or produce the desired enantiomer (S) rather than produce an enantiomerically impure mixture and then have to separate out the desired enantiomer (S). It is preferred to start the process with enantiomerically pure (S)-amino acid of the same configuration as that of the disubstituted amine (I) or (II) products. For the amino acids, $R_1$ is:

(I) $C_1$-$C_6$ alkyl, optionally substituted with one, two or three substituents selected from the group consisting of $C_1$-$C_3$ alkyl, $C_1$-$C_7$ alkyl (optionally substituted with $C_1$-$C_3$ alkyl and $C_1$-$C_3$ alkoxy), —F, —Cl, —Br, —I, —OH, —SH, —C≡N, —CF$_3$, $C_1$-$C_3$ alkoxy, —$NR_{1-a}R_{1-b}$ where $R_{1-a}$ and $R_{1-b}$ are —H or $C_1$-$C_6$ alkyl, and —OC=O $NR_{1-a}R_{1-b}$ where $R_{1-a}$ and $R_{1-b}$ are as defined above, (II) —$CH_2$—$S(O)_{0-2}$—($C_1$-$C_6$ alkyl), (III) —CH$_2$—CH$_2$—S(O)$_{0-2}$—(C$_1$-C$_6$ alkyl),
(IV) C$_2$-C$_6$ alkenyl with one or two double bonds, optionally substituted with one, two or three substituents selected from the group consisting of —F, —Cl, —OH, —SH, —C≡N, —CF$_3$, C$_1$-C$_3$ alkoxy, and —NR$_{1-a}$R$_{1-b}$ where R$_{1-a}$ and R$_{1-b}$ are —H or C$_1$-C$_6$ alkyl,
(V) C$_2$-C$_6$ alkynyl with one or two triple bonds, optionally substituted with one, two or three substituents selected from the group consisting of —F, —Cl, —OH, —SH, —C≡N, —CF$_3$, C$_1$-C$_3$ alkoxy, and NR$_{1-a}$R$_{1-b}$ where R$_{1-a}$ and R$_{1-b}$ are —H or C$_1$-C$_6$ alkyl,
(VI) —(CH$_2$)$_{n1}$—(R$_{1-aryl}$) where n$_1$ is zero or one and where R$_{1-aryl}$ is phenyl, 1-naphthyl, 2-naphthyl and indanyl, indenyl, dihydronaphthalyl, or tetralinyl optionally substituted with one, two, three, or four of the following substituents on the aryl ring:
  (A) C$_1$-C$_6$ alkyl optionally substituted with one, two or three substituents selected from the group consisting of C$_1$-C$_3$ alkyl, —F, —Cl, —Br, —I, —OH, —SH, —C≡N, —CF$_3$, C$_1$-C$_3$ alkoxy, and —NR$_{1-a}$R$_{1-b}$ where R$_{1-a}$ and R$_{1-b}$ are as defined above,
  (B) C$_2$-C$_6$ alkenyl with one or two double bonds, optionally substituted with one, two or three substituents selected from the group consisting of —F, —Cl, —OH, —SH, —C≡N, —CF$_3$, C$_1$-C$_3$ alkoxy, —NR$_{1-a}$R$_{1-b}$ where R$_{1-a}$ and R$_{1-b}$ are —H or C$_1$-C$_6$ alkyl,
  (C) C$_2$-C$_6$ alkynyl with one or two triple bonds, optionally substituted with one, two or three substituents selected from the group consisting of —F, —Cl, —OH, —SH, —C≡N, —CF$_3$, C$_1$-C$_3$ alkoxy, and —NR$_{1-a}$R$_{1-b}$ where R$_{1-a}$ and R$_{1-b}$ are —H or C$_1$-C$_6$ alkyl,
  (D) —F, Cl, —Br or —I,
  (F) —C$_1$-C$_6$ alkoxy optionally substituted with one, two, or three —F,
  (G) —NR$_{N-2}$R$_{N-3}$ where R$_{N-2}$ and R$_{N-3}$ are as defined below,
  (H) —OH,
  (I) —C≡N,
  (J) C$_3$-C$_7$ cycloalkyl, optionally substituted with one, two or three substituents selected from the group consisting of —F, —Cl, —OH, —SH, —C≡N, —CF$_3$, C$_1$-C$_3$ alkoxy, and —NR$_{1-a}$R$_{1-b}$ where R$_{1-a}$ and R$_{1-b}$ are —H or C$_1$-C$_6$ alkyl,
  (K) —CO—(C$_1$-C$_4$ alkyl),
  (L) —SO$_2$—NR$_{1-a}$R$_{1-b}$ where R$_{1-a}$ and R$_{1-b}$ are as defined above,
  (M) —CO—NR$_{1-a}$R$_{1-b}$ where R$_{1-a}$ and R$_{1-b}$ are as defined above, or
  (N) —SO$_2$—(C$_1$-C$_4$ alkyl),
(VII) —(CH$_2$)$_{n1}$—(R$_{1-heteroaryl}$) where n$_1$ is as defined above and where R$_{1-heteroaryl}$ is selected from the group consisting of:
pyridinyl,
pyrimidinyl,
quinolinyl,
benzothienyl,
indolyl,
indolinyl,
pryidazinyl,
pyrazinyl,
isoquinolyl,
quinazolinyl,
quinoxalinyl,
phthalazinyl,
imidazolyl,
isoxazolyl,
pyrazolyl,
oxazolyl,
thiazolyl,
indolizinyl,
indazolyl,
benzothiazolyl,
benzimidazolyl,
benzofuranyl,
furanyl,
thienyl,
pyrrolyl,
oxadiazolyl,
thiadiazolyl,
triazolyl,
tetrazolyl,
oxazolopyridinyl,
imidazopyridinyl,
isothiazolyl,
naphthyridinyl,
cinnolinyl,
carbazolyl,
beta-carbolinyl,
isochromanyl,
chromanyl,
tetrahydroisoquinolinyl,
isoindolinyl,
isobenzotetrahydrofuranyl,
isobenzotetrahydrothienyl,
isobenzothienyl,
benzoxazolyl,
pyridopyridinyl,
benzotetrahydrofuranyl,
benzotetrahydrothienyl,
purinyl,
benzodioxolyl,
triazinyl,
phenoxazinyl,
phenothiazinyl,
pteridinyl,
benzothiazolyl,
imidazopyridinyl,
imidazothiazolyl,
dihydrobenzisoxazinyl,
benzisoxazinyl,
benzoxazinyl,
dihydrobenzisothiazinyl,
benzopyranyl,
benzothiopyranyl,
coumarinyl,
isocoumarinyl,
chromonyl,
chromanonyl,
pyridinyl-N-oxide,
tetrahydroquinolinyl,
dihydroquinolinyl,
dihydroquinolinonyl
dihydroisoquinolinonyl
dihydrocoumarinyl
dihydroisocoumarinyl
isoindolinonyl
benzodioxanyl
benzoxazolinonyl
pyrrolyl N-oxide,
pyrimidinyl N-oxide,
pyridazinyl N-oxide,
pyrazinyl N-oxide, quinolinyl N-oxide,
indolyl N-oxide,
indolinyl N-oxide,
isoquinolyl N-oxide,
quinazolinyl N-oxide,
quinoxalinyl N-oxide,
phthalazinyl N-oxide,
imidazolyl N-oxide,
isoxazolyl N-oxide,
oxazolyl N-oxide,
thiazolyl N-oxide,
indolizinyl N-oxide,
indazolyl N-oxide,
benzothiazolyl N-oxide,
benzimidazolyl N-oxide,
pyrrolyl N-oxide,
oxadiazolyl N-oxide,
thiadiazolyl N-oxide,
triazolyl N-oxide,
tetrazolyl N-oxide,
benzothiopyranyl S-oxide, and
benzothiopyranyl S,S-dioxide, where the $R_{1\text{-}heteroaryl}$ group is bonded to —$(CH_2)_{n1}$— by any ring atom of the parent $R_{N\text{-}heteroaryl}$ group substituted by hydrogen such that the new bond to the $R_{1\text{-}heteroaryl}$ group replaces the hydrogen atom and its bond, where heteroaryl is optionally substituted with one, two, three, or four:
  (1) $C_1$-$C_6$ alkyl optionally substituted with one, two or three substituents selected from the group consisting of $C_1$-$C_3$ alkyl, —F, —Cl, —Br, —I, —OH, —SH, —C≡N, —CF$_3$, $C_1$-$C_3$ alkoxy, and —NR$_{1\text{-}a}$R$_{1\text{-}b}$ where $R_{1\text{-}a}$ and $R_{1\text{-}b}$ are as defined above,
  (2) $C_2$-$C_6$ alkenyl with one or two double bonds, optionally substituted with one, two or three substituents selected from the group consisting of —F, —Cl, —OH, —SH, —C≡N, —CF$_3$, $C_1$-$C_3$ alkoxy, and —NR$_{1\text{-}a}$R$_{1\text{-}b}$ where $R_{1\text{-}a}$ and $R_{1\text{-}b}$ are —H or $C_1$-$C_6$ alkyl,
  (3) $C_2$-$C_6$ alkynyl with one or two triple bonds, optionally substituted with one, two or three substituents selected from the group consisting of —F, —Cl, —OH, —SH, —C≡N, —CF$_3$, $C_1$-$C_3$ alkoxy, and —NR$_{1\text{-}a}$R$_{1\text{-}b}$ where $R_{1\text{-}a}$ and $R_{1\text{-}b}$ are —H or $C_1$-$C_6$ alkyl,
  (4) —F, Cl, —BR, or —I,
  (6) —$C_1$-$C_6$ alkoxy optionally substituted with one, two, or three —F,
  (7) —NR$_{N\text{-}2}$R$_{N\text{-}3}$ where $R_{N\text{-}2}$ and $R_{N\text{-}3}$ are as defined below,
  (8) —OH,
  (9) —C≡N,
  (10) $C_3$-$C_7$ cycloalkyl, optionally substituted with one, two or three substituents selected from the group consisting of —F, —Cl, —OH, —SH, —C≡N, —CF$_3$, $C_1$-$C_3$ alkoxy, and —NR$_{1\text{-}a}$R$_{1\text{-}b}$ where $R_{1\text{-}a}$ and $R_{1\text{-}b}$ are —H or $C_1$-$C_6$ alkyl,
  (11) —CO—($C_1$-$C_4$ alkyl),
  (12) —SO$_2$—NR$_{1\text{-}a}$R$_{1\text{-}b}$ where $R_{1\text{-}a}$ and $R_{1\text{-}b}$ are as defined above,
  (13) —CO—NR$_{1\text{-}a}$R$_{1\text{-}b}$ where $R_{1\text{-}a}$ and $R_{1\text{-}b}$ are as defined above, or
  (14) —SO$_2$—($C_1$-$C_4$ alkyl), with the proviso that when n, is zero $R_{1\text{-}heteroaryl}$ is not bonded to the carbon chain by nitrogen,
(VIII) —$(CH_2)_{n1}$—($R_{1\text{-}heterocycle}$) where $n_1$ is as defined above and $R_{1\text{-}heterocycle}$ is selected from the group consisting of:
  morpholinyl,
  thiomorpholinyl,
  thiomorpholinyl S-oxide,
  thiomorpholinyl S,S-dioxide,
  piperazinyl,
  homopiperazinyl,
  pyrrolidinyl,
  pyrrolinyl,
  tetrahydropyranyl,
  piperidinyl,
  tetrahydrofuranyl,
  tetrahydrothienyl,
  homopiperidinyl,
  homomorpholinyl,
  homothiomorpholinyl,
  homothiomorpholinyl S,S-dioxide,
  oxazolidinonyl,
  dihydropyrazolyl,
  dihydropyrrolyl,
  dihydropyrazinyl,
  dihydropyridinyl,
  dihydropyrimidinyl,
  dihydrofuryl,
  dihydropyranyl,
  tetrahydrothienyl S-oxide,
  tetrahydrothienyl S,S-dioxide, and
  homothiomorpholinyl S-oxide, where the $R_{1\text{-}heterocycle}$ group is bonded by any atom of the parent $R_{1\text{-}heterocycle}$ group substituted by hydrogen such that the new bond to the $R_{1\text{-}heterocycle}$ group replaces the hydrogen atom and its bond, where heterocycle is optionally substituted with one, two, three, or four:
  (1) $C_1$-$C_6$ alkyl optionally substituted with one, two or three substituents selected from the group consisting of $C_1$-$C_3$ alkyl, —F, —Cl, —Br, —I, —OH, —SH, —C≡N, —CF$_3$, $C_1$-$C_3$ alkoxy, and —NR$_{1\text{-}a}$ R$_{1\text{-}b}$ where $R_{1\text{-}a}$ and $R_{1\text{-}b}$ are as defined above,
  (2) $C_2$-$C_6$ alkenyl with one or two double bonds, optionally substituted with one, two or three substituents selected from the group consisting of —F, —Cl, —OH, —SH, —C≡N, —CF$_3$, $C_1$-$C_3$ alkoxy, and —NR$_{1\text{-}a}$R$_{1\text{-}b}$ where $R_{1\text{-}a}$ and $R_{1\text{-}b}$ are —H or $C_1$-$C_6$ alkyl,
  (3) $C_2$-$C_6$ alkynyl with one or two triple bonds, optionally substituted with one, two or three substituents selected from the group consisting of —F, —Cl, —OH, —SH, —C≡N, —CF$_3$, $C_1$-$C_3$ alkoxy, and —NR$_{1\text{-}a}$R$_{1\text{-}b}$ where $R_{1\text{-}a}$ and $R_{1\text{-}b}$ are —H or $C_1$-$C_6$ alkyl,
  (4) —F, Cl, —Br, or —I,
  (5) $C_1$-$C_6$ alkoxy,
  (6) —$C_1$-$C_6$ alkoxy substituted with one, two, or three —F,
  (7) —NR$_{N\text{-}2}$R$_{N\text{-}3}$ where $R_{N\text{-}2}$ and $R_{N\text{-}3}$ are as defined below,
  (8) —OH,
  (9) —C≡N,
  (10) $C_3$-$C_7$ cycloalkyl, optionally substituted with one, two or three substituents selected from the group consisting of —F, —Cl, —OH, —SH, —C≡N, —CF$_3$, $C_1$-$C_3$ alkoxy, and —NR$_{1\text{-}a}$R$_{1\text{-}b}$ where $R_{1\text{-}a}$ and $R_{1\text{-}b}$ are —H or $C_1$-$C_6$ alkyl,
  (11) —CO—($C_1$-$C_4$ alkyl),
  (12) —SO$_2$—NR$_{1\text{-}a}$R$_{1\text{-}b}$ where $R_{1\text{-}a}$ and $R_{1\text{-}b}$ are as defined above,
  (13) —CO—NR$_{1\text{-}a}$R$_{1\text{-}b}$ where $R_{1\text{-}a}$ and $R_{1\text{-}b}$ are as defined above,
  (14) —SO$_2$—($C_1$-$C_4$ alkyl), or

(15) =O, with the proviso that when $n_1$ is zero $R_{1-heterocycle}$ is not bonded to the carbon chain by nitrogen.

It is preferred that $R_1$ be —$(CH_2)_{0-1}$—$(R_{1-aryl})$ or —$(CH_2)_{n1}$—$(R_{1-heteroaryl})$. It is more preferred that $R_1$ is —$(CH_2)$—$(R_{1-aryl})$ or —$(CH_2)$—$(R_{1-heteroaryl})$. It is further preferred that $R_1$ is —$(CH_2)$—$(R_{1-aryl})$ where $R_{1-aryl}$ is phenyl. It is even more preferred that $R_1$ is —$(CH_2)$—$(R_{1-aryl})$ where $R_{1-aryl}$ is phenyl substituted with two —F. It is additionally preferred that the —F substitution is 3,5-difluorobenzyl.

When $R_1$ is $R_{1-heteroaryl}$ or $R_{1-heterocycle}$ the bond from the $R_{1-heteroaryl}$ or $R_{1-heterocycle}$ group to the —$(CH_2)_{n1}$— group can be from any ring atom which has an available valence provided that such bond does not result in formation of a charged species or unstable valence. This means that the $R_{1-heteroaryl}$ or $R_{1-heterocycle}$ group is bonded to —$(CH_2)_{n1}$— by any ring atom of the parent $R_{1-heteroaryl}$ or $R_{1-heterocycle}$ group which was substituted by hydrogen such that the new bond to the $R_{1-heteroaryl}$ or $R_{1-heterocycle}$ group replaces the hydrogen atom and its bond.

The first step of the process is to protect the free amino group of an (S)-amino acid (1) with an amino protecting group to produce the (S)-protected amino acid (2) by methods well known to those skilled in the art. Amino protecting groups are well known to those skilled in the art. See for example, "Protecting Groups in Organic Synthesis", John Wiley and sons, New York, N.Y., 1981, Chapter 7; "Protecting Groups in Organic Chemistry", Plenum Press, New York, N.Y., 1973, Chapter 2. The function of the amino protecting group is to protect the free amino functionality (—$NH_2$) during subsequent reactions on the (S)-amino acid (1) which would not proceed well, either because the amino group would react and be functionalized in a way that is inconsistent with its need to be free for subsequent reactions, or the free amino group would interfere in the reaction. When the amino protecting group is no longer needed, it is removed by methods well known to those skilled in the art. By definition the amino protecting group must be readily removable as is known to those skilled in the art by methods well known to those skilled in the art. A suitable amino PROTECTING GROUP is selected from the group consisting of t-butoxycarbonyl, benzyloxycarbonyl, formyl, trityl, acetyl, trichloroacetyl, dichloroacetyl, chloroacetyl, trifluoroacetyl, difluoroacetyl, fluoroacetyl, 4-phenylbenzyloxycarbonyl, 2-methylbenzyloxycarbonyl, 4-ethoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycabonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, fluorenylmethoxycarbonyl, 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl and 1-piperidyloxycarbonyl, 9-fluorenylmethyl carbonate, —CH—CH=$CH_2$ and phenyl-C(=N—)—H.

It is preferred that the protecting group be t-butoxycarbonyl (BOC) and benzyloxycarbony (CBZ), it is more preferred that the protecting group be t-butoxycarbonyl. One skilled in the art will understand the preferred methods of introducing a t-butoxycarbonyl or benzyloxycarbonyl protecting group and may additionally consult T. W. Green and P. G. M. Wuts in "Protective Groups in Organic Chemistry," John Wiley and Sons, 1991 for guidance.

The (S)-protected amino acid (2) is transformed to the corresponding (S)-protected compound (III) by two different methods depending on the nature of $R_2$ and $R_3$. $R_2$ and $R_3$ are independently:

(I) —H, (II) $C_1$-$C_6$ alkyl, optionally substituted with one, two or three substituents selected from the group consisting of $C_1$-$C_3$ alkyl, —F, —Cl, —Br, —I, —OH, —SH, —C≡N, —$CF_3$, $C_1$-$C_3$ alkoxy, and —$NR_{13}R_{1-b}$ where $R_{1-a}$ and $R_{1-b}$ are as defined above, (III) —$(CH_2)_{0-4}$—$R_{2-1}$ where $R_{2-1}$ is $R_{1-aryl}$ or $R_{1-heteroaryl}$ where $R_{1-aryl}$ and $R_{1-heteroaryl}$ are as defined above;

(IV) $C_2$-$C_6$ alkenyl with one or two double bonds, (V) $C_2$-$C_6$ alkynyl with one or two triple bonds, or (VI) —$(CH_2)_{0-4}$—$C_3$-$C_7$ cycloalkyl, optionally substituted with one, two or three substituents selected from the group consisting of —F, —Cl, —OH, —SH, —C≡N, —$CF_3$, $C_1$-$C_3$ alkoxy, and —$NR_{1-a}R_{1-b}$ where $R_{1-a}$ and $R_{1-b}$ are —H or $C_1$-$C_6$ alkyl, where $R_2$ and $R_3$ are taken together with the carbon to which they are attached to form a carbocycle of three, four, five, six or seven carbon atoms, optionally where one carbon atom is replaced by a heteroatom selected from the group consisting of —O—, —S—, —$SO_2$—, and —$NR_{N-2}$—, where $R_{N-2}$ is selected from the group consisting of:

(a) —H, (b) —$C_1$-$C_6$ alkyl optionally substituted with one substituent selected from the group consisting of:
 (i) —OH, and
 (ii) —$NH_2$, (c) —$C_1$-$C_6$ alkyl optionally substituted with one to three —F, —Cl, —Br, or —I, (d) —$C_3$-$C_7$ cycloalkyl, (e) —($C_1$-$C_2$ alkyl)-($C_3$-$C_7$ cycloalkyl), (f) —($C_1$-$C_6$ alkyl)-O—($C_1$-$C_3$ alkyl), (g) —$C_2$-$C_6$ alkenyl with one or two double bonds, (h) —$C_2$-$C_6$ alkynyl with one or two triple bonds, (i) —$C_1$-$C_6$ alkyl chain with one double bond and one triple bond, (j) —$R_{1-heteroaryl}$ where $R_{1-heteroaryl}$ is as defined above, and (k) —$R_{1-heteroaryl}$ where $R_{1-heteroaryl}$ is as defined above;

It is preferred that $R_2$ and $R_3$ both be —H. If $R_2$ and $R_3$ are not the same, an additional enantiomeric center is added to the molecule. If it is desired that both $R_2$ and $R_3$ are —H, then the (S)-protected amino acid is reacted with diazomethane, as is well known to those skilled in the art under conditions that generate a diazoketone, followed by reaction with a compound of the formula H—$X_1$ to produce the (S)-protected compound (III). $X_1$ includes —Cl, —Br, —I, —O-tosylate, —O-mesylate, —O-mesylate; it is preferred that —$X_1$ be —Br or —Cl. Suitable reaction conditions include running the reaction in inert solvents, such as but not limited to ether or tetrahydrofuran or the like. The reactions from the (S)-protected amino acid (2) to the (S)-protected compound (III) are carried out for a period of time between 10 minutes and 1 day and at temperatures ranging from −78 degrees to 20-25 degrees C. It is preferred to conduct the reactions for a period of time between 1-4 hours and at temperatures between −30 degrees to −10 degrees C. This process adds one methylene group to the hydroxyethylamine backbone.

Alternatively, the (S)-protected compounds of formula (III) can be prepared by first converting the (S)-protected amino acid (2) to a corresponding methyl or ethyl ester, according to methods well established in the art, followed by treatment with a reagent of formula $X_1$—$C(R_2)(R_3)$—$X_1$ and a strong metal base. The base serves to affect a halogen-metal exchange, where the —$X_1$ undergoing exchange is a halogen selected from chlorine, bromine or iodine. The nucleophilic addition to the ester derivative gives the (S)-protected compound (III) directly. Suitable bases include, but are not limited to the alkyllithiums including, for example, sec-butyllithium, n-butyllithium, and t-butyllithium. The reactions are preferably conducted at low temperature, such as −78 degrees C. Suitable reaction conditions include running the reaction in inert solvents, such as but not limited to, ether, tetrahydrofuran and the like. Where $R_2$ and $R_3$ are both hydrogen, then examples of $X_1$—$C(R_2)(R_3)$—$X_1$ include dibromomethane, diiodomethane, chloroiodomethane, bromoiodomethane and bromochloromethane. One skilled in the art knows the preferred conditions required to conduct this reaction. Furthermore, if $R_2$ and/or $R_3$ are not —H, then the addition of —$C(R_2)(R_3)$—$X_1$ to esters of the (S)-protected amino acid to produce the (S)-protected compound (III), incorporating an additional chiral center into the product, provided that $R_2$ and $R_3$ are not the same.

The (S)-protected compound (III) is then reduced by means well known to those skilled in the art for reduction of a ketone to the corresponding secondary alcohol affording the corresponding alcohol (IV). The means and reaction conditions for reducing the (S)-protected compound (III) to the corresponding alcohol (IV) include, for example, sodium borohydride, lithium borohydride, borane, diisobutylaluminum hydride, and lithium aluminium hydride. Sodium borohydride is the preferred reducing agent. The reductions are carried out for a period of time between 1 hour and 3 days at temperatures ranging from −78 degrees C. to elevated temperature up to the reflux point of the solvent employed. It is preferred to conduct the reduction between −78 degrees C. and 0 degrees C. If borane is used, it may be employed as a complex, for example, borane-methyl sulfide complex, borane-piperidine complex, or borane-tetrahydrofuran complex. The preferred combination of reducing agents and reaction conditions needed are known to those skilled in the art, see for example, Larock, R. C. in Comprehensive Organic Transformations, VCH Publishers, 1989. The reduction of the (S)-protected compound (III) to the corresponding alcohol (IV) produces the second chiral center (third chiral center if $R_2$ and $R_3$ are not the same). The reduction of the (S)-protected compound (III) produces a mixture of enantiomers at the second center, (S,R/S)-alcohol (IV). This enantiomeric mixture is then separated by means known to those skilled in the art such as selective low-temperature recrystallization or chromatographic separation, for example by HPLC, employing commercially available chiral columns. The preferred enantiomer that is used in the remainder of the process of CHART A is the (S,S)-alcohol (IV).

The (S,S)-alcohol (IV) is transformed to the corresponding epoxide (V) by means known to those skilled in the art. The stereochemistry of the (S)-(IV) center is maintained in forming the epoxide (V). A preferred means is by reaction with base, for example, but not limited to, hydroxide ion generated from sodium hydroxide, potassium hydroxide, lithium hydroxide and the like. Reaction conditions include the use of $C_1$-$C_6$ alcohol solvents; ethanol is preferred. A common co-solvent, such as for example, ethyl acetate may also be employed. Reactions are conducted at temperatures ranging from −45 degrees C. up to the reflux temperature of the alcohol employed; preferred temperature ranges are between −20 degrees C. and 20-25 degrees C.

The epoxide (V) is then reacted with the appropriately substituted C-terminal secondary amine $(R_{C-A})(R_C\text{-}Z)$ NH including N-ring heterocycles, or primary amine $R_C$—$NH_2$ (VI) by means known to those skilled in the art which opens the epoxide to produce the desired corresponding enantiomerically pure (S,R)-protected alcohol (VI). The substituted C-terminal secondary amine $(R_{C-A})(R_C\text{-}Z)$ NH or primary amine $R_C$—$NH_2$ (VI) of this invention are commercially available or are known to those skilled in the art and can be readily prepared from known compounds. $R_C$ includes:

(I) —$C_1$-$C_{10}$ alkyl optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, —$NR_{1-a}R_{1-b}$ where $R_{1-a}$ and $R_{1-b}$ are as defined above, —OC═O $NR_{1-a}R_{1-b}$ where $R_{1-a}$ and $R_{1-b}$ are as defined above, —$S(═O)_{0-2}R_{1-a}$ where $R_{1-a}$ is as defined above, —$NR_{1-a}$ C═O $NR_{1-a}R_{1-b}$ where $R_{1-a}$ and $R_{1-b}$ are as defined above, —C═O $NR_{1-a}R_{1-b}$ where $R_{1-a}$ and $R_{1-b}$ are as defined above, and —$S(═O)_2NR_{1-a}R_{1-b}$ where $R_{1-a}$ and $R_{1-b}$ are as defined above, (II) —$(CH_2)_{0-3}$—$(C_3$-$C_8)$cycloalkyl where cycloalkyl can be optionally substituted with one, two, or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, —CO—OH, —CO—O—($C_1$-$C_4$ alkyl), and —$NR_{1-a}R_{1-b}$ where $R_{1-a}$ and $R_{1-b}$ are as defined above, (III) —$(CR_{C-x}R_{C-y})_{0-4}$—$R_{C-aryl}$ where $R_{C-x}$ and $R_{C-y}$ are
  (A) —H,
  (B) $C_1$-$C_4$ alkyl optionally substituted with one or two —OH,
  (C) $C_1$-$C_4$ alkoxy optionally substituted with one, two, or three —F,
  (D) —$(CH_2)_{0-4}$—$C_3$-$C_7$ cycloalkyl,
  (E) $C_2$-$C_6$ alkenyl containing one or two double bonds,
  (F) $C_2$-$C_6$ alkynyl containing one or two triple bonds,
  (G) phenyl-,
  (H) $C_0$-$C_4$ alkylC(O)$NR_{1-a}R_{1-b}$ where $R_{1-a}$ and $R_{1-b}$ are as defined above, and where $R_{C-x}$ and $R_{C-y}$ are taken together with the carbon to which they are attached to form a carbocycle of three, four, five, six, or seven carbon atoms, optionally where one carbon atom is replaced by a heteroatom selected from the group consisting of —O—, —S—, —$SO_2$—, —$NR_{N-2}$— and $R_{C-aryl}$ is the same as $R_{N-aryl}$ and where $R_{C-aryl}$ may optionally be substituted with —$C_0$-$C_4$ alkyl-C(O)$NR_{1-a}R_{1-b}$, $C_0$-$C_4$ alkylC(O)$OR_{1-a}$ where $R_{1-a}$ and $R_{1-b}$ are as defined above, (IV) —$(CR_{C-x}R_{C-y})_{0-4}$—$R_{C\text{-}heteroaryl}$ where $R_{C\text{-}heteroaryl}$ is the same as $R_{N\text{-}heteroaryl}$ and $R_{C-x}$ and $R_{C-y}$ are as defined above, (V) —$(CR_{C-x}R_{C-y})_{0-4}$—$R_{C-aryl}$—$R_{C-aryl}$ where $R_{C-aryl}$, $R_{C-x}$ and $R_{C-y}$ are as defined above, (VI) —$(CR_{C-x}R_{C-y})_{0-4}$—$R_{C-aryl}$—$R_{C\text{-}heteroaryl}$ where $R_{C-aryl}$, $R_{C\text{-}heteroaryl}$, $R_{C-x}$ and $R_{C-y}$ are as defined above, (VII) —$(CR_{C-x}R_{C-y})_{0-4}$—$R_{C\text{-}heteroaryl}$—$R_{C-aryl}$ where $R_{C\text{-}heteroaryl}$, $R_{C-aryl}$, $R_{C-x}$ and $R_{C-y}$ are as defined above, (VIII) —$(CR_{C-x}R_{C-y})_{0-4}$—$R_{C\text{-}heteroaryl}$—$R_{C\text{-}heteroaryl}$ where $R_{C\text{-}heteroaryl}$, $R_{C-x}$ and $R_{C-y}$ are as defined above, (IX) —$(CR_{C-x}R_{C-y})_{0-4}$—$R_{C-aryl}$—$R_{C\text{-}heterocycle}$ where $R_{C\text{-}heterocycle}$ is the same as $R_{1\text{-}heterocycle}$, and $R_{C-aryl}$, $R_{C-x}$ and $R_{C-y}$ are as defined above, (X) —$(CR_{C-x}R_{C-y})_{0-4}$—$R_{C\text{-}heteroaryl}$—$R_{C\text{-}heterocycle}$ where $R_{C\text{-}heteroaryl}$, $R_{C\text{-}heterocycle}$, $R_{C-x}$ and $R_{C-y}$ are as defined above, (XI) —$(CR_{C-x}R_{C-y})_{0-4}$—$R_{C\text{-}heterocycle}$—$R_{C\text{-}aryl}$ where $R_{C\text{-}heterocycle}$, $R_{C\text{-}aryl}$, $R_{C-x}$ and $R_{C-y}$ are as defined above, (XII) —$(CR_{C-x}R_{C-y})_{0-4}$—$R_{C\text{-}heterocycle}$—$R_{C\text{-}heteroaryl}$ where $R_{C\text{-}heterocycle}$, $R_{C\text{-}heteroaryl}$, $R_{C-x}$ and $R_{C-y}$ are as defined above, (XIII) —$(CR_{C-x}R_{C-y})_{0-4}$—$R_{C\text{-}heterocycle}$—$R_{C\text{-}heterocycle}$ where $R_{C\text{-}heterocycle}$, $R_{C-x}$ and $R_{C-y}$ are as defined above, (XIV) —$(CR_{C-x}R_{C-y})_{0-4}$—$R_{C\text{-}heterocycle}$ where $R_{C\text{-}heterocycle}$, $R_{C-x}$, and $R_{C-y}$ are as defined above, (XV) —$[C(R_{C-1})(R_{C-2})]_{1-3}$—CO—N—$(R_{C-3})_2$ where $R_{C-3}$ is as defined below and $R_{C-1}$, $R_{C-2}$ are the same or different and are selected from the group consisting of:

(A) —H, (B) —$C_1$-$C_6$ alkyl, optionally substituted with one, two, or three substituents independently selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above, (D) $C_2$-$C_6$ alkenyl with one, or two double bonds, optionally substituted with one, two, or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above, (E) $C_2$-$C_6$ alkynyl with one or two triple bonds, optionally substituted with one, two, or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above, (F) —$(CH_2)_{1-2}$—$S(O)_{0-2}$—($C_1$-$C_6$ alkyl), (F) —$(CH_2)_{0-4}$-$C_3$-$C_7$ cycloalkyl, optionally substituted with one, two, or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above, (G) —($C_1$-$C_4$ alkyl)-$R_{C'\text{-}aryl}$ where $R_{C'\text{-}aryl}$ is as defined for $R_{1\text{-}aryl}$, (H) —($C_1$-$C_4$ alkyl)-$R_{C\text{-}heteroaryl}$ where $R_{C\text{-}heteroaryl}$ is as defined above, (I) —($C_1$-$C_4$ alkyl)-$R_{C\text{-}heterocycle}$ where $R_{C\text{-}heterocycle}$ is as defined above, (J) —$R_{C\text{-}heteroaryl}$ where $R_{C\text{-}heteroaryl}$ is as defined above, (K) —$R_{C\text{-}heterocycle}$ where $R_{C\text{-}heterocycle}$ is as defined above, (M) —$(CH_2)_{1-4}$—$R_{C-4}$—$(CH_2)_{0-4}$—$R_{C'\text{-}aryl}$ where $R_{C-4}$ is —O—, —S— or —$NR_{C-5}$— where $R_{C-5}$ is $C_1$-$C_6$ alkyl, and where $R_{C'\text{-}aryl}$ is defined above, (N) —$(CH_2)_{1-4}$—$R_{C-4}$—$(CH_2)_{0-4}$—$R_{C\text{-}heteroaryl}$ where $R_{C-4}$ and $R_{C\text{-}heteroaryl}$ are as defined above, and (O) —$R_{C'\text{-}aryl}$ where $R_{C'\text{-}aryl}$ is as defined above, and where $R_{C-3}$ is the same or different and is:

(a) —H, (b) —$C_1$-$C_6$ alkyl optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and $NR_{1-a}R_{1-b}$ where $R_{1-a}$ and $R_{1-b}$ are as defined above, (c) $C_2$-$C_6$ alkenyl with one or two double bonds, optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above, (d) $C_2$-$C_6$ alkynyl with one, or two triple bonds, optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above, (e) —$(CH_2)_{0-4}$—$C_3$-$C_7$ cycloalkyl, optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above, (f) —$R_{C'\text{-}aryl}$ where $R_{C'\text{-}aryl}$ is as defined above, (g) —$R_{C\text{-}heteroaryl}$ where $R_{C\text{-}heteroaryl}$ is as defined above, (h) —$R_{C\text{-}heterocycle}$ where $R_{C\text{-}heterocycle}$ is as defined above, (i) —($C_1$-$C_4$ alkyl)-$R_{C'\text{-}aryl}$ where $R_{C'\text{-}aryl}$ is as defined above, (j) —($C_1$-$C_4$ alkyl)-$R_{C\text{-}heteroaryl}$ where $R_{C\text{-}heteroaryl}$ is as defined above, (k) —($C_1$-$C_4$ alkyl)-$R_{C\text{-}heterocycle}$ where $R_{C\text{-}heterocycle}$ is as defined above, (XVI) —$CH(R_{C\text{-}aryl})_2$ where $R_{C\text{-}aryl}$ are the same or different and are as defined above, (XVII) —$CH(R_{C\text{-}heteroaryl})_2$ where $R_{C\text{-}heteroaryl}$ are the same or different and are as defined above, (XVIII) —$CH(R_{C\text{-}aryl})(R_{C\text{-}heteroaryl})$ where $R_{C\text{-}aryl}$ and $R_{C\text{-}heteroaryl}$ are as defined above, (XIX) -cyclopentyl, -cyclohexyl, or -cycloheptyl ring fused to $R_{C\text{-}aryl}$ or $R_{C\text{-}heteroaryl}$ or $R_{C\text{-}heterocycle}$ where $R_{C\text{-}aryl}$ or $R_{C\text{-}heteroaryl}$ or $R_{C\text{-}heterocycle}$ are as defined above where one carbon of cyclopentyl, cyclohexyl, or cycloheptyl is optionally replaced with NH, $NR_{N-5}$, O, or $S(=O)_{0-2}$, and where cyclopentyl, cyclohexyl, or cycloheptyl can be optionally substituted with one, or two —$C_1$-$C_3$ alkyl, —F, —OH, —SH, —C≡N, —$CF_3$, $C_1$-$C_6$ alkoxy, =O, or —$NR_{1-a}R_{1-b}$ where $R_{1-a}$ and $R_{1-b}$ are as defined above, (XX) $C_2$-$C_{10}$ alkenyl containing one or two double bonds optionally substituted with one, two, or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above, (XXI) $C_2$-$C_{10}$ alkynyl containing one, or two triple bonds optionally substituted with one, two, or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above, (XXI) —$(CH_2)_{0-1}$—$CHR_{C-6}$—$(CH_2)_{0-1}$—$R_{C\text{-}aryl}$ where $R_{C\text{-}aryl}$ is as defined above and $R_{C-6}$ is —$(CH_2)_{0-6}$—OH, (XXII) —$(CH_2)_{0-1}$—$CHR_{C-6}$—$(CH_2)_{0-1}$—$R_{C\text{-}heteroaryl}$ where $R_{C\text{-}heteroaryl}$ and $R_{C-6}$ is as defined above, (XXII) —CH(—$R_{C\text{-}aryl}$ or $R_{C\text{-}heteroaryl}$)—CO—O($C_1$-$C_4$ alkyl) where $R_{C\text{-}aryl}$ and $R_{C\text{-}heteroaryl}$ are as defined above, (XXIV) —CH(—$CH_2$—OH)—CH(—OH)-phenyl-$NO_2$, (XXV) ($C_1$-$C_6$ alkyl)-O—($C_1$-$C_6$ alkyl)-OH, (XXVII) —$CH_2$—NH—$CH_2$—CH(—O—$CH_2$—$CH_3$)$_2$, or (XXVIII) —$(CH_2)_{0-6}$—C(=$NR_{1-a}$)($NR_{1-a}R_{1-b}$) where $R_{1-a}$ and $R_{1-b}$ are as defined above.

It is preferred that $R_C$ is:

—$C_1$-$C_8$ alkyl,
—$(CH_2)_{0-3}$—$(C_3$-$C_7)$cycloalkyl,
—$(CR_{C-x}R_{C-y})_{0-4}$—$R_{C-aryl}$,
—$(CR_{C-x}R_{C-y})_{0-4}$—$R_{C-heteroaryl}$,
—$(CR_{C-x}R_{C-y})_{0-4}$—$R_{C-heterocycle}$,
-cyclopentyl or -cyclohexyl ring fused to $R_{C-aryl}$ or $R_{C-heteroaryl}$ or $R_{C-heterocycle}$.

It is more preferred that $R_C$ is:
—$(CH_2)_{0-3}$—$(C_3$-$C_7)$cycloalkyl,
—$(CR_{C-x}R_{C-y})_{0-4}$—$R_{C-aryl}$,
—$(CR_{C-x}R_{C-y})_{0-4}$—$R_{C-heteroaryl}$,
—$(CR_{C-x}R_{C-y})_{0-4}$—$R_{C-heterocycle}$,
-cyclopentyl or -cyclohexyl ring fused to a $R_{C-aryl}$ or $R_{C-heteroaryl}$ or $R_{C-heterocycle}$.

It is even more preferred that $R_C$ is:
—$(CR_{C-x}R_{C-y})_{0-4}$—$R_{C-aryl}$,
—$(CR_{C-x}R_{C-y})_{0-4}$—$R_{C-heteroaryl}$,
-cyclopentyl or -cyclohexyl ring fused to a $R_{C-aryl}$ or $R_{C-heteroaryl}$ or $R_{C-heterocycle}$.

It is still more preferred that $R_C$ is selected from the group consisting of:
—$(CR_{C-x}R_{C-y})_{0-4}$—$R_{C-aryl}$ where $R_{C-aryl}$ is phenyl,
—$(CR_{C-x}R_{C-y})_{0-4}$—$R_{C-heteroaryl}$,
-cyclopentyl or -cyclohexyl ring fused to a $R_{C-aryl}$ or $R_{C-heteroaryl}$ or $R_{C-heterocycle}$. Further, it is preferred that when $R_C$ is phenyl, it is substituted in the 3-position or 3,5-positions.

$R_{C-A}$ includes H, $C_1$-$C_{10}$ alkyl, $C_2$-$C_{10}$alkenyl and alkynyl, phenyl, $C_1$-$C_4$ alkyl-$R_{N-aryl}$, $C_1$-$C_4$ alkyl-$R_{N-heteroaryl}$, $C_1$-$C_4$ alkyl-$C_3$-$C_7$ cycloalkyl, or $C_1$-$C_4$ alkyl-$R_{1-heterocycle}$, wherein each multi-atom group may be optionally substituted with one, two, or three substituents independently selected from the group consisting of —F, —Cl, —OH, —SH, —C≡N, —$CF_3$, $C_1$-$C_3$ alkoxy, —C(O)O—$R_{1-a}$, and —$NR_{1-a}R_{1-b}$ where $R_{1-a}$ and $R_{1-b}$ are —H, $C_1$-$C_6$ alkyl or phenyl, with the proviso that when $R_{N-A}$ is H, then $R_{C-A}$ may not be H. Preferred $R_{C-A}$ groups are methyl and ethyl.

Additionally the epoxide-opening amine (VI) may be a cyclic amine such as piperidine or morpholine with appropriately substitution.

Z includes:
(A) —C(O)—,
(B) —$S(O)_{1-2}$—,
(C) —C(O)—$X_{N-1}$— where $X_{N-1}$ is selected from the group consisting of —O—, —S— and —NR'— and where R' is as defined above; and
(D) a single bond.

One of ordinary skill in the art will readily appreciate that the disubstituted amines may be obtained by reacting, for example the primary amine $R_C$—$NH_2$ with $R_{C-A}$ possessing an appropriate leaving group with, by way of a non-limiting example, a chloro or bromo group or a tosylate or triflate group or another group that may be displaced by a nucleophile via a nucleophilic substitution.

Suitable reaction conditions for opening the epoxide (V) include running the reaction in a wide range of common and inert solvents. $C_1$-$C_6$ alcohol solvents are preferred and isopropyl alcohol is most preferred. The reactions can be run at temperatures ranging from 20-25 degrees C. up to the reflux temperature of the alcohol employed. The preferred temperature range for conducting the reaction is between 50 degrees C. up to the reflux temperature of the alcohol employed. When the substituted C-terminal amine (VI) is a 1-amino-3,5-cis-dimethyl cyclohexyldicarboxylate it is preferably prepared as follows. To dimethyl-5-aminoisophthalate in acetic acid and methanol, is added rhodium in alumina in a high-pressure bottle. The bottle is saturated with hydrogen at 55 psi and shaken for one week of time. The mixture is then filtered through a layer of diatomaceous earth and rinsed with methanol three times, the solvents are removed under reduced pressure (with heat) to give a concentrate. The concentrate is triturated with ether and filtered again to give the desired C-terminal amine (VI). When the substituted C-terminal amine (VI) is 1-amino-3,5-cis-dimethoxy cyclohexane it is preferably prepared by following the general procedure above and making non-critical variations but starting with 3,5-dimethoxyaniline. When the substituted C-terminal amine (VI) is an aminomethyl group where the substituent on the methyl group is an aryl group, for example $NH_2$—$CH_2$—$R_{C-aryl}$, and $NH_2$—$CH_2$—$R_{C-aryl}$ is not commercially available it is preferably prepared as follows. A suitable starting material is the (appropriately substituted) aralkyl compound. The first step is bromination of the alkyl substituent via methods known to those skilled in the art, see for example R. C. Larock in Comprehensive Organic Transformations, VCH Publishers, 1989, p. 313. Next the alkyl halide is reacted with azide to produce the aryl-(alkyl)-azide. Last the azide is reduced to the corresponding amine by hydrogen/catalyst to give the C-terminal amine (VI) of formula $NH_2$—$CH_2$—$R_{C-aryl}$. The suitably functionalized C-terminal amines (VI) may readily be prepared by one skilled in the art via known methods in the literature, making non-significant modifications. Select literature references include 1) Calderwood, et al., *Tet. Lett.*, 1997, 38, 1241, 2) Ciganek, *J. Org. Chem.*, 1992, 57, 4521, 3) Thurkauf, et al., *J. Med. Chem.*, 1990, 33, 1452, 4) Werner, et al., *Org. Syn., Coll. Vol.* 5, 273, 5) *J. Med. Chem.*, 1999, 42, 4193, 6) *Chem. Rev.* 1995, 95, 2457, 7) *J. Am. Chem. Soc.*, 1986, 3150, 8) Felman et al., *J. Med. Chem.*, 1992, 35, 1183, 9) *J. Am. Chem. Soc.* 1970, 92, 3700, 10) *J. Med. Chem.*, 1997, 40, 2323.

The (S,R)-amine (VIII) is then reacted with an appropriately substituted amide forming agent (IX) such as anhydride, acyl halide, or acid of the formula $(R_{N-1}$—$X_N)_2$O or $R_{N-1}$—$X_N$—$X_2$ or $R_{N-1}$—$X_N$—OH (IX) by nitrogen-acylation means known to those skilled in the art to produce the corresponding (S,R)-substituted amine (X). Nitrogen acylation conditions for reaction of the (S,R)-amine (VIII) with an amide forming agent (IX) to produce the corresponding (S,R)-substituted amine (X) are known to those skilled in the art and can be found in R. C. Larock in Comprehensive Organic Transformations, VCH Publishers, 1989, p. 981, 979, and 972. $R_N$ includes:
(I) $R_{N-1}$—$X_N$— where $X_N$ is selected from the group consisting of:
(A) —CO—,
(B) —$SO_2$—,
(C) —$(CR'R'')_{1-6}$ where R' and R" are the same or different and are —H or $C_1$-$C_4$ alkyl,
(D) —CO—$(CR'R'')_{1-6}$—$X_{N-1}$ where $X_{N-1}$ is selected from the group consisting of —O—, —S— and —NR'— and where R' and R" are as defined above, and
(E) a single bond;
where $R_{N-1}$ is selected from the group consisting of:
(A) $R_{N-aryl}$ where $R_{N-aryl}$ is phenyl, 1-naphthyl, 2-naphthyl, tetralinyl, indanyl, or 6,7,8,9-tetrahydro-5H-benzo[a]cycloheptenyl, or dihydronaphthyl optionally substituted with one, two or three of the following substituents which can be the same or different and are:
(1) $C_1$-$C_6$ alkyl, optionally substituted with one, two or three substituents selected from the group consisting of $C_1$-$C_3$ alkyl, —F, —Cl, —Br, —I, —OH, —SH, —C≡N, —CF$_3$, $C_1$-$C_3$ alkoxy, and —NR$_{1-a}$R$_{1-b}$ where R$_{1-a}$ and R$_{1-b}$ are as defined above,
(2) —OH,
(3) —NO$_2$,
(4) —F, —Cl, —Br, or —I,
(5) —CO—OH,
(6) —C≡N,
(7) —(CH$_2$)$_{0-4}$—CO—NR$_{N-2}$R$_{N-3}$ where R$_{N-2}$ and R$_{N-3}$ are the same or different and are selected from the group consisting of:
  (a) —H,
  (b) —$C_1$-$C_6$ alkyl optionally substituted with one substituent selected from the group consisting of:
    (i) —OH, and
    (ii) —NH$_2$,
  (c) —$C_1$-$C_6$ alkyl optionally substituted with one to three —F, —Cl, —Br, or —I,
  (d) —$C_3$-$C_7$ cycloalkyl,
  (e) —($C_1$-$C_2$ alkyl)-($C_3$-$C_7$ cycloalkyl),
  (f) —($C_1$-$C_6$ alkyl)-O—($C_1$-$C_3$ alkyl),
  (g) —$C_2$-$C_6$ alkenyl with one or two double bonds,
  (h) —$C_2$-$C_6$ alkynyl with one or two triple bonds,
  (i) —$C_1$-$C_6$ alkyl chain with one double bond and one triple bond,
  (j) —R$_{1-aryl}$ where R$_{1-aryl}$ is as defined above, and
  (k) —R$_{1-heteroaryl}$ where R$_{1-heteroaryl}$ is as defined above,
(8) —(CH$_2$)$_{0-4}$—CO—($C_1$-$C_{12}$ alkyl),
(9) —(CH$_2$)$_{0-4}$—CO—($C_2$-$C_{12}$ alkenyl with one, two or three double bonds),
(10) —(CH$_2$)$_{0-4}$—CO—($C_2$-$C_{12}$ alkynyl with one, two or three triple bonds),
(11) —(CH$_2$)$_{0-4}$—CO—($C_3$-$C_7$ cycloalkyl),
(12) —(CH$_2$)$_{0-4}$—CO—R$_{1-aryl}$ where R$_{1-aryl}$ is as defined above,
(13) —(CH$_2$)$_{0-4}$—CO—R$_{1-heteroaryl}$ where R$_{1-heteroaryl}$ is as defined above,
(14) —(CH$_2$)$_{0-4}$—CO—R$_{1-heterocycle}$ where R$_{1-heterocycle}$ is as defined above,
(15) —(CH$_2$)$_{0-4}$—CO—R$_{N-4}$ where R$_{N-4}$ is selected from the group consisting of morpholinyl, thiomorpholinyl, piperazinyl, piperidinyl, homomorpholinyl, homothiomorpholinyl, homothiomorpholinyl S-oxide, homothiomorpholinyl S,S-dioxide, pyrrolinyl and pyrrolidinyl where each group is optionally substituted with one, two, three, or four of: $C_1$-$C_6$ alkyl,
(16) —(CH$_2$)$_{0-4}$—CO—O—R$_{N-5}$ where R$_{N-5}$ is selected from the group consisting of:
  (a) $C_1$-$C_6$ alkyl,
  (b) —(CH$_2$)$_{0-2}$—(R$_{1-aryl}$) where R$_{1-aryl}$ is as defined above,
  (c) $C_2$-$C_6$ alkenyl containing one or two double bonds,
  (d) $C_2$-$C_6$ alkynyl containing one or two triple bonds,
  (e) $C_3$-$C_7$ cycloalkyl,
  (f) —(CH$_2$)$_{0-2}$—(R$_{1-heteroaryl}$) where R$_{1-heteroaryl}$ is as defined above,
(17) —(CH$_2$)$_{0-4}$—SO$_2$—NR$_{N-2}$R$_{N-3}$ where R$_{N-2}$ and R$_{N-3}$ are as defined above,
(18) —(CH$_2$)$_{0-4}$—SO—($C_1$-$C_8$ alkyl),
(19) —(CH$_2$)$_{0-4}$—SO$_2$—($C_1$-$C_{12}$ alkyl),
(20) —(CH$_2$)$_{0-4}$—SO$_2$—($C_3$-$C_7$ cycloalkyl),
(21) —(CH$_2$)$_{0-4}$—N(H or R$_{N-5}$)—CO—O—R$_{N-5}$ where R$_{N-5}$ can be the same or different and is as defined above,
(22) —(CH$_2$)$_{0-4}$—N(H or R$_{N-5}$)—CO—N(R$_{N-5}$)$_2$, where R$_{N-5}$ can be the same or different and is as defined above,
(23) —(CH$_2$)$_{0-4}$—N—CS—N(R$_{N-5}$)$_2$, where R$_{N-5}$ can be the same or different and is as defined above,
(24) —(CH$_2$)$_{0-4}$—N(—H or R$_{N-5}$)—CO—R$_{N-2}$ where R$_{N-5}$ and R$_{N-2}$ can be the same or different and are as defined above,
(25) —(CH$_2$)$_{0-4}$—NR$_{N-2}$R$_{N-3}$ where R$_{N-2}$ and R$_{N-3}$ can be the same or different and are as defined above,
(26) —(CH$_2$)$_{0-4}$—R$_{N-4}$ where R$_{N-4}$ is as defined above,
(27) —(CH$_2$)$_{0-4}$—O—CO—($C_1$-$C_6$ alkyl),
(28) —(CH$_2$)$_{0-4}$—O—P(O)—(OR$_{N-aryl-1}$)$_2$ where R$_{N-aryl-1}$ is —H or $C_1$-$C_4$ alkyl,
(29) —(CH$_2$)$_{0-4}$—O—CO—N(R$_{N-5}$)$_2$ where R$_{N-5}$ is as defined above,
(30) —(CH$_2$)$_{0-4}$—O—CS—N(R$_{N-5}$)$_2$ where R$_{N-5}$ is as defined above,
(31) —(CH$_2$)$_{0-4}$—O—(R$_{N-5}$)$_2$ where R$_{N-5}$ is as defined above,
(32) —(CH$_2$)$_{0-4}$—O—(R$_{N-5}$)$_2$—COOH where R$_{N-5}$ is as defined above,
(33) —(CH$_2$)$_{0-4}$—S—(R$_{N-5}$)$_2$ where R$_{N-5}$ is as defined above,
(34) —(CH$_2$)$_{0-4}$—O—($C_1$-$C_6$ alkyl optionally substituted with one, two, three, four, or five —F),
(35) $C_3$-$C_7$ cycloalkyl,
(36) $C_2$-$C_6$ alkenyl with one or two double bonds optionally substituted with $C_1$-$C_3$ alkyl, —F, —Cl, —Br, —I, —OH, —SH, —C≡N, —CF$_3$, $C_1$-$C_3$ alkoxy, or —NR$_{1-a}$R$_{1-b}$ where R$_{1-a}$ and R$_{1-b}$ are as defined above,
(37) $C_2$-$C_6$ alkynyl with one or two triple bonds optionally substituted with $C_1$-$C_3$ alkyl, —F, —Cl, —Br, —I, —OH, —SH, —C≡N, —CF$_3$, $C_1$-$C_3$ alkoxy, or —NR$_{1-a}$R$_{1-b}$ where R$_{1-a}$ and R$_{1-b}$ are as defined above,
(38) —(CH$_2$)$_{0-4}$—N(—H or R$_{N-5}$)—SO$_2$—R$_{N-2}$ where R$_{N-5}$ and R$_{N-2}$ can be the same of different and are as described above, or
(39) —(CH$_2$)$_{0-4}$—$C_3$-$C_7$ cycloalkyl,
(B) —R$_{N-heteroaryl}$, where R$_{N-heteroaryl}$ is selected from the group as defined above in R$_1$ heteroaryl and where the R$_{N-heteroaryl}$ group is bonded by any atom of the parent R$_{N-heteroaryl}$ group substituted by hydrogen such that the new bond to the R$_{N-heteroaryl}$ group replaces the hydrogen atom and its bond, where heteroaryl is optionally substituted with one, two, three, or four of:
(1) $C_1$-$C_6$ alkyl, optionally substituted with one, two or three substituents selected from the group consisting of $C_1$-$C_3$ alkyl, —F, —Cl, —Br, —I, —OH, —SH, —C≡N, —CF$_3$, $C_1$-$C_3$ alkoxy, and —NR$_{1-a}$R$_{1-b}$ where R$_{1-a}$ and R$_{1-b}$ are as defined above,
(2) —OH,
(3) —NO$_2$,
(4) —F, —Cl, —Br, or —I,
(5) —CO—OH,
(6) —C≡N,
(7) —(CH$_2$)$_{0-4}$—CO—NR$_{N-2}$R$_{N-3}$ where R$_{N-2}$ and R$_{N-3}$ are the same or different and are selected from the group consisting of:

(a) —H,
(b) —$C_1$-$C_6$ alkyl optionally substituted with one substituent selected from the group consisting of:
  (i) —OH, and
  (ii) —$NH_2$,
(c) —$C_1$-$C_6$ alkyl optionally substituted with one to three —F, —Cl, —Br, or —I,
(d) —$C_3$-$C_7$ cycloalkyl,
(e) —($C_1$-$C_2$ alkyl)-($C_3$-$C_7$ cycloalkyl),
(f) —($C_1$-$C_6$ alkyl)-O—($C_1$-$C_3$ alkyl),
(g) —$C_2$-$C_6$ alkenyl with one or two double bonds,
(h) —$C_2$-$C_6$ alkynyl with one or two triple bonds,
(i) —$C_1$-$C_6$ alkyl chain with one double bond and one triple bond,
(j) —$R_{1\text{-}aryl}$ where $R_{1\text{-}aryl}$ is as defined above, and
(k) —$R_{1\text{-}heteroaryl}$ where $R_{1\text{-}heteroaryl}$ is as defined above,
(8) —$(CH_2)_{0\text{-}4}$—CO—($C_1$-$C_{12}$ alkyl),
(9) —$(CH_2)_{0\text{-}4}$—CO—($C_2$-$C_{12}$ alkenyl with one, two, or three double bonds),
(10) —$(CH_2)_{0\text{-}4}$—CO—($C_2$-$C_{12}$ alkynyl with one, two, or three triple bonds),
(11) —$(CH_2)_{0\text{-}4}$—CO—($C_3$-$C_7$ cycloalkyl),
(12) —$(CH_2)_{0\text{-}4}$—CO—$R_{1\text{-}aryl}$ where $R_{1\text{-}aryl}$ is as defined above,
(13) —$(CH_2)_{0\text{-}4}$—CO—$R_{1\text{-}heteroaryl}$ where $R_{1\text{-}heteroaryl}$ is as defined above,
(14) —$(CH_2)_{0\text{-}4}$—CO—$R_{1\text{-}heterocycle}$ where $R_{1\text{-}heterocycle}$ is as defined above,
(15) —$(CH_2)_{0\text{-}4}$—CO—$R_{N\text{-}4}$ where $R_{N\text{-}4}$ is selected from the group consisting of morpholinyl, thiomorpholinyl, piperazinyl, piperidinyl, homomorpholinyl, homothiomorpholinyl, homothiomorpholinyl S-oxide, homothiomorpholinyl S,S-dioxide, pyrrolinyl and pyrrolidinyl where each group is optionally substituted with one, two, three, or four of: $C_1$-$C_6$ alkyl,
(16) —$(CH_2)_{0\text{-}4}$—CO—O—$R_{N\text{-}5}$ where $R_{N\text{-}5}$ is selected from the group consisting of:
  (a) $C_1$-$C_6$ alkyl,
  (b) —$(CH_2)_{0\text{-}2}$—($R_{1\text{-}aryl}$) where $R_{1\text{-}aryl}$ is as defined above,
  (c) $C_2$-$C_6$ alkenyl containing one or two double bonds,
  (d) $C_2$-$C_6$ alkynyl containing one or two triple bonds,
  (e) $C_3$-$C_7$ cycloalkyl, and
  (f) —$(CH_2)_{0\text{-}2}$—($R_{1\text{-}heteroaryl}$) where $R_{1\text{-}heteroaryl}$ is as defined above,
(17) —$(CH_2)_{0\text{-}4}$—$SO_2$—$NR_{N\text{-}2}R_{N\text{-}3}$ where $R_{N\text{-}2}$ and $R_{N\text{-}3}$ are as defined above,
(18) —$(CH_2)_{0\text{-}4}$—SO—($C_1$-$C_8$ alkyl),
(19) —$(CH_2)_{0\text{-}4}$—$SO_2$—($C_1$-$C_{12}$ alkyl),
(20) —$(CH_2)_{0\text{-}4}$—$SO_2$—($C_3$-$C_7$ cycloalkyl),
(21) —$(CH_2)_{0\text{-}4}$—N(H or $R_{N\text{-}5}$)—CO—O—$R_{N\text{-}5}$ where $R_{N\text{-}5}$ can be the same or different and is as defined above,
(22) —$(CH_2)_{0\text{-}4}$—N(H or $R_{N\text{-}5}$)—CO—N($R_{N\text{-}5}$)$_2$, where $R_{N\text{-}5}$ can be the same or different and is as defined above,
(23) —$(CH_2)_{0\text{-}4}$—N—CS—N($R_{N\text{-}5}$)$_2$, where $R_{N\text{-}5}$ can be the same or different and is as defined above,
(24) —$(CH_2)_{0\text{-}4}$—N(—H or $R_{N\text{-}5}$)—CO—$R_{N\text{-}2}$ where $R_{N\text{-}5}$ and $R_{N\text{-}2}$ can be the same or different and are as defined above,
(25) —$(CH_2)_{0\text{-}4}$—$NR_{N\text{-}2}R_{N\text{-}3}$ where $R_{N\text{-}2}$ and $R_{N\text{-}3}$ can be the same or different and are as defined above,
(26) —$(CH_2)_{0\text{-}4}$—$R_{N\text{-}4}$ where $R_{N\text{-}4}$ is as defined above,
(27) —$(CH_2)_{0\text{-}4}$—O—CO—($C_1$-$C_6$ alkyl),
(28) —$(CH_2)_{0\text{-}4}$—O—P(O)—(O$R_{N\text{-}aryl\text{-}1}$)$_2$ where $R_{N\text{-}aryl\text{-}1}$ is —H or $C_1$-$C_4$ alkyl,
(29) —$(CH_2)_{0\text{-}4}$—O—CO—N($R_{N\text{-}5}$)$_2$ where $R_{N\text{-}5}$ is as defined above,
(30) —$(CH_2)_{0\text{-}4}$—O—CS—N($R_{N\text{-}5}$)$_2$ where $R_{N\text{-}5}$ is as defined above,
(31) —$(CH_2)_{0\text{-}4}$—O—($R_{N\text{-}5}$)$_2$ where $R_{N\text{-}5}$ is as defined above,
(32) —$(CH_2)_{0\text{-}4}$—O—($R_{N\text{-}5}$)$_2$—COOH where $R_{N\text{-}5}$ is as defined above,
(33) —$(CH_2)_{0\text{-}4}$—S—($R_{N\text{-}5}$)$_2$ where $R_{N\text{-}5}$ is as defined above,
(34) —$(CH_2)_{0\text{-}4}$—O—($C_1$-$C_6$ alkyl optionally substituted with one, two, three, four, or five of —F),
(35) $C_3$-$C_7$ cycloalkyl,
(36) $C_2$-$C_6$ alkenyl with one or two double bonds optionally substituted with $C_1$-$C_3$ alkyl, —F, —Cl, —Br, —I, —OH, —SH, —C≡N, —$CF_3$, $C_1$-$C_3$ alkoxy, or —$NR_{1\text{-}a}R_{1\text{-}b}$ where $R_{1\text{-}a}$ and $R_{1\text{-}b}$ are as defined above,
(37) $C_2$-$C_6$ alkynyl with one or two triple bonds optionally substituted with $C_1$-$C_3$ alkyl, —F, —Cl, —Br, —I, —OH, —SH, —C≡N, —$CF_3$, $C_1$-$C_3$ alkoxy, or —$NR_{1\text{-}a}R_{1\text{-}b}$ where $R_{1\text{-}a}$ and $R_{1\text{-}b}$ are as defined above, or
(38) —$(CH_2)_{0\text{-}4}$—N(—H or $R_{N\text{-}5}$)—$SO_2$—$R_{N\text{-}2}$ where $R_{N\text{-}5}$ and $R_{N\text{-}2}$ can be the same of different and are as described above,
(39) —$(CH_2)_{0\text{-}4}$—$C_3$-$C_7$ cycloalkyl,
(C) $R_{N\text{-}aryl}$—W—$R_{N\text{-}aryl}$,
(D) $R_{N\text{-}aryl}$—W—$R_{N\text{-}heteroaryl}$,
(E) $R_{N\text{-}aryl}$—W—$R_{N\text{-}1\text{-}heterocycle}$, where $R_{n\text{-}1\text{-}heterocycle}$ is the same as $R_{1\text{-}heterocycle}$, as defined above,
(F) $R_{N\text{-}heteroaryl}$—W—$R_{N\text{-}aryl}$,
(G) $R_{N\text{-}heteroaryl}$—W—$R_{N\text{-}heteroaryl}$,
(H) $R_{N\text{-}heteroaryl}$—W—$R_{1\text{-}heterocycle}$,
(I) $R_{1\text{-}heterocycle}$—W—$R_{N\text{-}aryl}$,
(J) $R_{1\text{-}heterocycle}$—W—$R_{N\text{-}heteroaryl}$, and
(K) $R_{1\text{-}heterocycle}$—W—$R_{1\text{-}heterocycle}$,
where W is
  (1) —$(CH_2)_{0\text{-}4}$—,
  (2) —O—,
  (3) —S(O)$_{0\text{-}2}$—,
  (4) —N($R_{N\text{-}5}$)— where $R_{N\text{-}5}$ is as defined above, or
  (5) —CO—;
(II) —CO—($C_1$-$C_{10}$ alkyl) where alkyl is optionally substituted with one, two, or three substituents selected from the group consisting of:
(A) —OH,
(B) —$C_1$-$C_6$ alkoxy,
(C) —$C_1$-$C_6$ thioalkoxy,
(D) —CO—O—$R_{N\text{-}8}$ where $R_{N\text{-}8}$ is —H, $C_1$-$C_6$ alkyl or -phenyl,
(E) —CO—$NR_{N\text{-}2}R_{N\text{-}3}$ where $R_{N\text{-}2}$ and $R_{N\text{-}3}$ are the same or different and are as defined above,
(F) —CO—$R_{N\text{-}4}$ where $R_{N\text{-}4}$ is as defined above,
(G) —$SO_2$—($C_1$-$C_8$ alkyl),
(H) —$SO_2$—$NR_{N\text{-}2}R_{N\text{-}3}$ where $R_{N\text{-}2}$ and $R_{N\text{-}3}$ are the same or different and are as defined above,
(I) —NH—CO—($C_1$-$C_6$ alkyl), (J) —NH—CO—O—$R_{N-8}$ where $R_{N-8}$ is as defined above,
(K) —$NR_{N-2}R_{N-3}$ where $R_{N-2}$ and $R_{N-3}$ are the same or different and are as defined above,
(L) —$R_{N-4}$ where $R_{N-4}$ is as defined above,
(M) —O—CO—($C_1$-$C_6$ alkyl),
(N) —O—CO—$NR_{N-8}R_{N-8}$ where $R_{N-8}$ are the same or different and are as defined above,
(O) —O—($C_1$-$C_5$ alkyl)-COOH,
(P) —O—($C_1$-$C_6$ alkyl optionally substituted with one, two, or three —F, —Cl, —Br, or —I),
(Q) —NH—$SO_2$—($C_1$-$C_6$ alkyl), and
(R) —F, or —Cl,
(III) —CO—($C_1$-$C_6$ alkyl)-O—($C_1$-$C_6$ alkyl) where alkyl is optionally substituted with one, two, or three substituents selected from the group consisting of:
(A) —OH,
(B) —$C_1$-$C_6$ alkoxy,
(C) —$C_1$-$C_6$ thioalkoxy,
(D) —CO—O—$R_{N-8}$ where $R_{N-8}$ is —H, $C_1$-$C_6$ alkyl or, -phenyl,
(E) —CO—$NR_{N-2}R_{N-3}$ where $R_{N-2}$ and $R_{N-3}$ are the same or different and are as defined above,
(F) —CO—$R_{N-4}$ where $R_{N-4}$ is as defined above,
(G) —$SO_2$—($C_1$-$C_8$ alkyl),
(H) —$SO_2$—$NR_{N-2}R_{N-3}$ where $R_{N-2}$ and $R_{N-3}$ are the same or different and are as defined above,
(I) —NH—CO—($C_1$-$C_6$ alkyl),
(J) —NH—CO—O—$R_{N-8}$ where $R_{N-8}$ is as defined above,
(K) —$NR_{N-2}R_{N-3}$ where $R_{N-2}$ and $R_{N-3}$ are the same or different and are as defined above,
(L) —$R_{N-4}$ where $R_{N-4}$ is as defined above,
(M) —O—CO—($C_1$-$C_6$ alkyl),
(N) —O—CO—$NR_{N-8}R_{N-8}$ where the $R_{N-8}$s are the same or different and are as defined above,
(O) —O—($C_1$-$C_5$ alkyl)-COOH,
(P) —O—($C_1$-$C_6$ alkyl optionally substituted with one, two, or three —F, —Cl, —Br, or —I),
(Q) —NH—$SO_2$—($C_1$-$C_6$ alkyl), and
(R) —F, or —Cl,
(IV) —CO—($C_1$-$C_6$ alkyl)-S—($C_1$-$C_6$ alkyl) where alkyl is optionally substituted with one, two, or three substituents selected from the group consisting of:
(A) —OH,
(B) —$C_1$-$C_6$ alkoxy,
(C) —$C_1$-$C_6$ thioalkoxy,
(D) —CO—O—$R_{N-8}$ where $R_{N-8}$ is as defined above,
(E) —CO—$NR_{N-2}R_{N-3}$ where $R_{N-2}$ and $R_{N-3}$ are the same or different and are as defined above,
(F) —CO—$R_{N-4}$ where $R_{N-4}$ is as defined above,
(G) —$SO_2$—($C_1$-$C_8$ alkyl),
(H) —$SO_2$—$NR_{N-2}R_{N-3}$ where $R_{N-2}$ and $R_{N-3}$ are the same or different and are as defined above,
(I) —NH—CO—($C_1$-$C_6$ alkyl),
(J) —NH—CO—O—$R_{N-8}$ where $R_{N-8}$ is as defined above,
(K) —$NR_{N-2}R_{N-3}$ where $R_{N-2}$ and $R_{N-3}$ are the same or different and are as defined above,
(L) —$R_{N-4}$ where $R_{N-4}$A is as defined above,
(M) —O—CO—($C_1$-$C_6$ alkyl),
(N) —O—CO—$NR_{N-8}R_{N-8}$ where $R_{N-8}$ are the same or different and are as defined above,
(O) —O—($C_1$-$C_5$ alkyl)-COOH,
(P) —O—($C_1$-$C_6$ alkyl optionally substituted with one, two, or three —F, —Cl, —Br, or —I),
(Q) —NH—$SO_2$—($C_1$-$C_6$ alkyl), and
(R) —F, or —Cl,
(V) —CO—CH(—($CH_2$)$_{0-2}$—O—$R_{N-10}$) —($CH_2$)$_{0-2}$—$R_{N-aryl}$/$R_{N-heteroaryl}$) where $R_{N-aryl}$ and $R_{N-heteroaryl}$ are as defined above, where $R_{N-10}$ is selected from the group consisting of:
(A) —H,
(B) $C_1$-$C_6$ alkyl,
(C) $C_3$-$C_7$ cycloalkyl,
(D) $C_2$-$C_6$ alkenyl with one double bond,
(E) $C_2$-$C_6$ alkynyl with one triple bond,
(F) $R_{1-aryl}$ where $R_{1-aryl}$ is as defined above, and
(G) $R_{N-heteroaryl}$ where $R_{N-heteroaryl}$ is as defined above, or
(VI) —CO—($C_3$-$C_8$ cycloalkyl) where alkyl is optionally substituted with one or two substituents selected from the group consisting of:
(A) —($CH_2$)$_{0-4}$—OH,
(B) —($CH_2$)$_{0-4}$—$C_1$-$C_6$ alkoxy,
(C) —($CH_2$)$_{0-4}$—$C_1$-$C_6$ thioalkoxy,
(D) —($CH_2$)$_{0-4}$—CO—O—$R_{N-8}$ where $R_{N-8}$ is —H, $C_1$-$C_6$ alkyl or -phenyl,
(E) —($CH_2$)$_{0-4}$—CO—$NR_{N-2}R_{N-3}$ where $R_{N-2}$ and $R_{N-3}$ are the same or different and are as defined above,
(F) —($CH_2$)$_{0-4}$—CO—$R_{N-4}$ where $R_{N-4}$ is as defined above,
(G) —($CH_2$)$_{0-4}$—$SO_2$—($C_1$-$C_8$ alkyl),
(H) —($CH_2$)$_{0-4}$—$SO_2$—$NR_{N-2}R_{N-3}$ where $R_{N-2}$ and $R_{N-3}$ are the same or different and are as defined above,
(I) —($CH_2$)$_{0-4}$—NH—CO—($C_1$-$C_6$ alkyl),
(J) —NH—CO—O—$R_{N-8}$ where $R_{N-8}$ is as defined above,
(K) —($CH_2$)$_{0-4}$—$NR_{N-2}R_{N-3}$ where $R_{N-2}$ and $R_{N-3}$ are the same or different and are as defined above,
(L) —($CH_2$)$_{0-4}$—$R_{N-4}$ where $R_{N-4}$ is as defined above,
(M) —O—CO—($C_1$-$C_6$ alkyl),
(N) —O—CO—$NR_{N-8}R_{N-8}$ where $R_{N-8}$ are the same or different and are as defined above,
(O) —O—($C_1$-$C_5$ alkyl)-COOH,
(P) —O—($C_1$-$C_6$ alkyl optionally substituted with one, two, or three —F, —Cl, —Br, or —I),
(Q) —NH—$SO_2$—($C_1$-$C_6$ alkyl), and
(R) —F, or —Cl.

It is preferred that $R_N$ is selected from the group consisting of:

$R_{N-1}X_N$— where $X_N$ is —CO—, where $R_{N-1}$ is $R_{N-aryl}$ or $R_{N-heteroaryl}$ where $R_{N-aryl}$ is phenyl where the substitution on phenyl is 1,3-, and where $R_{N-aryl}$ or $R_{N-heteroaryl}$ are substituted with one —CO—$NR_{N-2}R_{N-3}$, $R_{N-1}X_N$— where $X_N$ is —CO—, where $R_{N-1}$ is $R_{N-aryl}$ or $R_{N-heteroaryl}$ where $R_{N-aryl}$ is phenyl substituted with one $C_1$ alkyl where the substitution on the phenyl is 1,3,5-, and where $R_{N-aryl}$ or $R_{N-heteroaryl}$ are substituted with one —CO—$NR_{N-2}R_{N-3}$, $R_{N-1}$—$X_N$— where $X_N$ is —CO—, where $R_{N-1}$ is $R_{N-heteroaryl}$ where $R_{N-heteroaryl}$ is substituted with one —CO—$NR_{N-2}R_{N-3}$. It is further preferred that $R_{N-2}$ and $R_{N-3}$ are the same and are $C_3$ alkyl. It is further preferred that:

$R_{N-1}$—$X_N$— where $X_N$ is —CO—, where $R_{N-1}$ is $R_{N-aryl}$ where $R_{N-aryl}$ is phenyl substituted with one —CO—$NR_{N-2}R_{N-3}$ where the substitution on phenyl is 1,3-, $R_{N-1}$—$X_N$— where $X_N$ is —CO—, where $R_{N-1}$ is $R_{N-aryl}$ where $R_{N-aryl}$ is phenyl substituted with one $C_1$ alkyl and with one —CO—$NR_{N-2}R_{N-3}$ where the substitution on the phenyl is 1,3,5-.

It is also preferred that $X_N$ is (A) —CO— and (B) —SO$_2$—, and it is more preferred that $X_N$ be —CO—.

$X_2$ includes —Cl, —Br, and it is preferred that $X_2$ is —Cl.

The nitrogen-acylation of primary amines to produce secondary amides is one of the oldest known reactions. The amide forming agents, $(R_{N-1}—X_N)_2O$ or $R_{N-1}—X_N—X_2$ or $R_{N-1}—X_N—OH$ (IX) are known to those skilled in the art and are commercially available or can be readily prepared from known starting materials by methods known in the literature. It is preferred to use an isophthalic acid acylating agent (IX) of the formula $R_{N-2}R_{N-3}N$—CO-phenyl-CO— or a methyl-isophthalic acid acylating agent (IX).

CHART B discloses an process for production of disubstituted N terminus amines, e.g. those having the formula $(R_{N-A})(R_{N-1}—X_N)N$— on the N-terminus. These compounds are advantageously prepared by adding a protecting group to the C-terminal amine after ring opening of the epoxide (V) and subsequent addition of a $R_{N\_A}$ substituent by, for example, reductive amination, followed by coupling of an acid $R_{N-1}—X_N$ component by EDC coupling or other activated amide bond formation techniques.

$R_{N-2}R_{N-3}N$—CO—(CH$_3$-)phenyl-CO— includes compounds such as is 5-methyl-1,3-isophthalic acid. A more preferred 5-methyl-1,3-isophthalic acid is 3-[(N,N-dipropylamino)carbonyl]-5-methylbenzoic acid (IX). These compounds are preferably prepared as set forth as follows. An ester, preferably the monomethyl ester of isophthalic acid or methyl 5-methyl-1,3-isophthalate is dissolved in a THF/DMF mixture. 1,1'-Carbonyldiimidazole is added at 20-25 degrees C. Next the desired amine (H—NR$_{N-2}$R$_{N-3}$) is added. After 3-24 hr of stirring at 20 degrees C. to the reflux temperature of the solvent, the reaction mixture is partitioned between saturated aqueous ammonium chloride and a water immiscible organic solvent such as ethyl acetate. The aqueous layer is separated and extracted twice more with the organic solvent (ethyl acetate). The organic extracts are combined and then washed with saturated aqueous solutions of bicarbonate and saline and dried over anhydrous sodium sulfate or magnesium sulfate. Filtration of the drying agent and removal of solvents by reduced pressure gives the methyl ester of the desired $R_{N-2}R_{N-3}N$—CO-phenyl-CO—O—CH$_3$ or a methylisophthalic acid acylating agent (IX) $R_{N-2}R_{N-3}N$—CO—(CH$_3$—)phenyl-CO—O—CH$_3$. Purification of the (methyl) ester can be achieved via chromatography on silica gel eluting with ethyl acetate in hexanes. The isophthalate ester or methylisophthalate ester of the mono-alkyl or di-alkyl amide is then treated with an aqueous solution of base such as lithium hydroxide in a minimum amount of THF/methanol/water and stirred 3-24 hours at 20 degrees C. to the reflux temperature of the solvent. The solvents are then removed under reduced pressure and subsequently partitioned between water and a water immiscible solvent such as ethyl acetate, for example. If emulsions prohibit separation of the two phases, a small amount of saline is added to aid in separation. The aqueous phase is separated and extracted once more with a water immiscible solvent such as ethyl acetate, for example. The aqueous phase is then acidified with concentrated acid, preferably hydrochloric until pH$\leq$3. The mixture obtained is then extracted three times with a water immiscible solvent such as ethyl acetate, for example. These combined organic extracts are dried over anhydrous sodium or magnesium sulfate. The drying agent is removed by filtration and the organic solvent is removed under reduced pressure to give product. The mono- or di-alkyl amide isophthalate/methylisophthalate is used as such in the next reaction with the (S,R)-amine (VIII) to produce the (S,R)-substituted amine (X).

When it is desired that the amine be cyclized to be a group such as morpholinyl, piperazinyl, piperidinyl and pyrrolidinyl, etc the following procedure is followed. An ester, preferably the methyl ester of isophthalic acid or methyl 5-methyl-1,3-isophthalate is dissolved in dry methylene chloride and three drops of DMF are added. The mixture is cooled to 0 degrees C. and then oxalyl chloride is added. The mixture is stirred at 0 degrees C. for 30 minutes to two hours after which the solvents are removed under reduced pressure. The acid chloride is left under vacuum overnight. The crude acid chloride is dissolved in dry methylene and cooled to 0 degrees C. before the addition of the cyclic amine and a tertiary amine base such as N-methyl piperidine, for example. The reaction mixture is stirred at 0 degrees C. for 1 to 6 hr before the solvents are removed under reduced pressure. The residue is diluted with water and a water immiscible solvent such as ethyl acetate, for example, and the phases are separated. The aqueous phase is extracted twice more with a water immiscible solvent such as ethyl acetate, for example, and the combined organic extracts are washed with saturated aqueous bicarbonate and dried over anhydrous sodium or magnesium sulfate. Filtration of the drying agent and removal of solvents under reduced pressure gives the product cyclic amide. The cyclic amide is then treated with an aqueous base such as lithium hydroxide in a minimum amount of THF/methanol/water and stirred overnight at 20-25 degrees C., after which time the solvents are removed under reduced pressure and the residue is subsequently partitioned between water and a water immiscible solvent such as ethyl acetate, for example. The aqueous phase is extracted once more with ethyl acetate. Removal of water from the aqueous phase under reduced pressure gives the desired cyclic amide product (I).

CHART C illustrates sythesis of sulfonamido tertiary C-terminus amine derivatives by reaction of an amine with an appropriately substituted sulfonyl chloride to produce the sulfonamide which is used to effect ring opening of the epoxide (V) with subsequent standard removal of the N-terminal protecting group and coupling with an $R_N$ group.

In a smilar vein, CHART D shows a synthetic approach to C-terminal lactans, wherein the lactam nitrogen is provided by the C-terminal amine. The epoxide (V) is treated with the lithium amide anion at low temperature to accomplish a ring opening addition. Deprotection and coupling of the N-terminus nitrogen is accomplished as previously described. Hydrogenation removes the carboxybenzoyl group to provide a free amine that is alkylated with isopropylamine.

CHART E outlines the preparation of an N-substituted amino acid carboxamide, coupling of the amide to the hydroxyethylamine backbone via ring-opening addition to the epoxide (V) and then deprotection and coupling of the C-terminus group through standard procedures.

CHART F discloses a method to produce the $R_C$ portion of the di substituted amine (I) or (II) where $R_C$ is a cycle encompassing the C-terminal nitrogen.

CHART G discloses a method for converting the diacid to the cyclic anhydride using standard coupling reagents such as DCC under high dilution conditions. The anhydride thus formed is used to protect the NH2 group of a primary amine under refluxing conditions. This procedure is described in *Protecting groups* by T. W. Green and P. G. M. Wuts pg. no. 564-565 (1999). The phthalimide thus formed can be selectivity reduced to yield the oxindole using lithium aluminum hydride under controlled conditions. All the reactions described in Chart G can be performed by one skilled in the art.

CHARTS H through P illustrate various methods to produce the $R_N$ portion of the disubstituted amines (I) and (II)

where the phenyl ring of the $R_N$ 1,3-disubstituted moiety, —CO-phenyl-CO—, is further substituted in the 5-position with various groups such as amides, nitriles, halides, and amines. These compounds are prepared by methods known to those skilled in the art. The process chemistry of each reaction is known to those skilled in the art. What is novel here is the order of each process step and/or the specific reactants used. One skilled in the art knowing the desired product would know at least one method to prepare the desired product by using known starting materials. Hence, the following discussion is not necessary but is set forth to further aid those interested in preparing the compounds of the invention.

CHART H discloses alternate processes for the transformation of the aniline (XVII) or acid ester (XVIII) to the corresponding acid (IX-XXIII). One process begins with the commercially available aniline (XVII) where $R_{N-a}$ is preferably —H, $C_1$-$C_4$ alkyl or benzyl. The aniline (XVII) is treated with a diazotizing reagent such as sodium or potassium nitrite in mineral acid, followed by a halogen source such as copper (II) halide or alkali metal halide, or by an organic diazotizing reagent such as an alkyl nitrite in a strong acid such as acetic acid or trifluoroacetic acid, followed by a halide source such as copper (II) halide or alkali metal halide to give the halo acid ester (XIX) where $R_{N-b}$ is —Cl, —Br or —I. Alternatively, the acid ester (XVIII) is treated with N-halosuccinimide and trifluoromethanesulfonic acid to give the halo acid ester (XIX). The halo acid ester (XIX) is then converted to the ester amide (XXI) using a primary or secondary amine of the formula H—$NR_{Nalpha}R_{Nbeta}$ (AMINE) where $R_{Nalpha}$ and $R_{Nbeta}$ are the same or different or can be cyclized. These groups, $R_{Nalpha}$ and $R_{Nbeta}$, become part of the substituted amine (X) and are included in the definition of $R_N$. $R_N$ includes $R_{N-1}$—$X_N$— where the linker, —$X_N$—, includes (A) —CO— and $R_{N-1}$ includes $R_{N-aryl}$. $R_{N-aryl}$ is defined to include phenyl (-phenyl) optionally substituted with two amides:

—CO—$NR_{N-2}R_{N-3}$ and
—CO—$R_{N-4}$. $R_{Nalpha}$ and $R_{Nbeta}$ include both the non-cyclic amides, —CO—$NR_{N-2}$—$R_{N-3}$ and the cyclic amides-CO—$R_{N-4}$ where $R_{N-2}$, $R_{N-3}$ and $R_{N-4}$ are as defined in the claims. Alternatively, the halo acid ester (XIX) is converted to the dihalo ester (XX) by methods known to those skilled in the art. $R_{N-c}$ includes —Cl and —F. The dihalo ester (XX) is treated with a primary or secondary amine of the formula H—$NR_{Nalpha}R_{Nbeta}$ (AMINE) to give the ester amide (XXI). The ester amide (XXI) is then reacted with an AMINE in a carbon monoxide atmosphere in the presence of a palladium catalyst using methods such as those reviewed by Heck, (Palladium Reagents in Organic Synthesis, 1985 pp. 342-365). to give the diamide (XXII). Hydrolysis of the ester portion of the diamide (XXII) using methods well known to those skilled in the art gives the diamide acid (XXIII).

In CHART I, an alternate route to intermediate diamide (XXII) is shown starting from commercially available phenol (XXIV). The phenol (XXIV) is treated with a trifluoromethanesulfonating reagent such as trifluoromethanesulfonic anhydride to give triflate (XXV). The triflate (XXV) is reacted under the conditions of palladium catalysis in the presence of carbon monoxide and an amine of the formula H—$NR_{Nalpha}R_{Nbeta}$ (AMINE) as for the conversion of the ester amide (XXI) to the corresponding diamide (XXII) in Chart E to give the diester (XXVI). The diester (XXVI) is hydrolyzed using methods known to those skilled in the art to give the monoacid (XXVII). The monoacid (XXVII) is converted to the diamide (XXII) using conditions such as for the conversion of the halo acid ester (XIX) to the ester amide (XXI) in Chart E.

Chart J discloses another route to prepare the ester amide (XXI). The reaction starts with commercially available nitro compound (XXVIII) which is condensed with an (AMINE) using coupling methods known to those skilled in the art to give the nitro amide (XXX). The nitro amide (XXX) can also be prepared by first treating the nitro compound (XXVIII) with reagents such as thionyl chloride, or DMF and oxalyl chloride, or other methods known to those skilled in the art to give the acid chloride (XXIX), which upon treatment with the (AMINE) gives the nitro amide (XXX). Reduction of the nitro amide (XXX) using methods known to those skilled in the art (see, for example, Smith and March, Advanced Organic Chemistry, $5^{th}$ ed.) gives amide aniline (XXXI). The amide aniline (XXXI) is then treated with diazotizing reagents such as sodium or potassium nitrite in mineral acid, followed by a halogen source such as copper (II) halide or alkali metal halide, or by an organic diazotizing reagent such as an alkyl nitrite in a strong acid such as acetic acid or trifluoroacetic acid, followed by a halide source such as copper (II) halide or alkali metal halide to give the ester amide (XXI).

Chart K discloses a process to prepare the diamide acid (IX-XXIII) from the ester amide (XXI), where one of the amides is unsubstituted and is —CO—$NH_2$. This process starts from either the ester or the acid, for example the ester amide (XXI) is treated with copper (I) cyanide (CuCN) in N-methylpyrrolidinone or DMF, preferably N-methylpyrrolidinone, to give the nitrile (XXXII). The nitrile (XXXII) is converted to the primary amide (XXXIII) using urea-hydrogen peroxide complex (see *Synth. Commun*. (1993) 3149) or the methods of Synth. Commun. (1990) 1445, *Synth. Commun*. (1997) 3119, *J. Org. Chem*. (1992) 2521, *Tet. Lett*. (1996) 6555, *Ind. J. Chem*., Sect. B, (1999) 974, *Tet. Lett*. (1995) 3469, *Tet. Lett*. (1998) 3005, or others. When the ester amide (XXI) is in the form of an ester, an additional hydrolysis step using lithium hydroxide, sodium hydroxide, potassium hydroxide, barium hydroxide, or other hydrolysis methods known to those skilled in the art is used to convert the diamide ester (XXXIII) to the diamide acid (IX-XXIII).

CHART L discloses a process to prepare compounds where the phenyl ring of the $R_N$ substituent of —CO-phenyl-CO— is substituted with a sulfonamide group in the 5-position. The process starts with the halo amide ester, which is reacted with sodium nitrite, sulfur dioxide, copper chloride (II) and acetic acid by the method disclosed in *J. Med. Chem.,* 42, 3797 (1999) to prepare the sulfonyl chloride (XXXVII). The sulfonyl chloride (XXXVII) is then reacted with AMINE, as defined above, by methods known to those skilled in the art to produce the corresponding sulfonamide (XXXVIII). Last the sulfonamide (XXXVIII) is transformed to the corresponding sulfonamide acid (XXXIX) by methods known to those skilled in the art such as using lithium hydroxide, sodium hydroxide, potassium hydroxide, barium hydroxide, or other hydrolysis methods known to those skilled in the art.

CHART M discloses how to prepare the $R_N$ substituents where $R_N$ is $R_{N-1}$—$X_N$—, where $X_N$ is —CO— and $R_{N-1}$ is $R_{N-aryl}$ where $R_N$ aryl is phenyl substituted with one alkyl group and one —CO—$NR_{N-2}R_{N-3}$ or —CO—$R_{N-4}$. See the discussion above for CHART E regarding the amine, H—$NR_{Nalpha}R_{Nbeta}$ (AMINE), used to form the amide $R_N$ substituents. The process starts with the halo amide ester (XXI) which is then reacted with an alkyl boronic acid having the desired alkyl group in the presence of a palladium catalyst such as $Pd(PPh_3)Cl_2$ using the general method described in *J. Med. Chem.,* 4288 (2000). The alkyl boronic acids are commercially available or can be prepared by the process described in *J. Am. Chem. Soc.*, 60, 105 (1938). It is preferred that $R_{N-b}$ is bromo. This step produces the alkyl ester (XL) which is then hydrolyzed by means known to those skilled in the art to produce the desired alkyl acid (XLI).

CHART N discloses a process to prepare the amide forming agent (IX-XLVII) where the $R_N$ substituent is $R_{N-1}$—$X_N$—, where the linker, —$X_N$— is —CO—, where $R_{N-1}$ is $R_{N-aryl}$ and where $R_{N-aryl}$ is phenyl (-phenyl) substituted with groups:

$C_1$-$C_6$ alkyl, optionally substituted with one, two or three substituents selected from the group consisting of $C_1$-$C_3$ alkyl, —F, —Cl, —Br, —I, —OH, —SH, —C≡N, —$CF_3$, $C_1$-$C_3$ alkoxy, —$NR_{1-a}R_{1-b}$ where $R_{1-a}$ and $R_{1-b}$ are as defined above, and —N(—H and $C_1$-$C_3$ alkyl)-CO—$R_{N-5}$. This specific amide forming agent, (IX-XLVII) is prepared by starting with the phenyl nitro compound (XLII) which is reduced to the corresponding phenyl nitro hydroxy compound (XLIII) using borane-methyl sulfide or borane in THF. The phenyl nitro hydroxy compound (XLIII) is reduced to the corresponding phenyl amino hydroxy compound (XLIV) using hydrogen and palladium catalyst as is known to those skilled in the art. The phenyl amino hydroxy compound (XLIV) is reacted with an aldehyde in the presence of a reducing agent such as sodium cyanoborohydride or sodium triacetoxyborohydride to give the phenyl substituted amino hydroxy compound (XLV). The phenyl substituted amino hydroxy compound (XLV) is acylated with an acid chloride or acid anhydride by methods known to those skilled in the art to give the phenyl disubstituted amino hydroxy compound (XLVI). The phenyl disubstituted amino hydroxy compound (XLVI) is hydrolyzed using an alkali hydroxide, followed by acidification, to give the amide forming agent (IX-XLVII). The amide forming agent (XLVII) is then coupled with amine (VIII) using methods known to those skilled in the art and methods previously discussed, such as with diethyl cyanophosphonate, to give the substituted amine (X). Further treatment of the substituted amine (X) with diethyl cyanophosphonate gives the substituted amine where the hydroxyalkyl substitutent on the phenyl ring has a phosphate substituent.

CHART O discloses a process to prepare amide forming agents (IX-L) where the where the $R_N$ substituent is $R_{N-1}$—$X_N$—, where the linker, —$X_N$— is —CO—, where $R_{N-1}$ is $R_{N-aryl}$ and where $R_{N-aryl}$ is phenyl (-phenyl) substituted with two groups. The first substituent at what is usually identified as position "5-" can be either:

—$R_{N-aryl}$ or
—$R_{N-heteroaryl}$. The second substituent at what is usually identified as postion "3-" can be either:
—CO—$NR_{N-2}R_{N-3}$ or
—CO—$R_{N-4}$. $R_{N alpha}$ and $R_{N beta}$ include both the non-cyclic amides, —CO—$NR_{N-2}$—$R_{N-3}$ and the cyclic amides —CO—$R_{N-4}$ where $R_{N-2}$, $R_{N-3}$ and $R_{N-4}$ are as defined in the claims. The process starts with the trisubstituted phenyl compound (XLVIII) where $R_{N-d}$ is —Cl, —Br, —I or —O-triflate. Treatment with an aryl or heteroaryl boronic acid or heteroaryl or aryl boronic acid ester such as (aryl or heteroaryl)-$B(OH)_2$ or (aryl or heteroaryl)-$B(OR^a)(OR^b)$ (where $R^a$ and $R^b$ are lower alkyl, ie. $C_1$-$C_6$, or taken together, $R^a$ and $R^b$ are lower alkylene, ie. $C_2$-$C_{12}$) in the presence of a metal catalyst with or without a base in an inert solvent yields (XLIX). Metal catalysts in these transformations include, but are not limited to, salts or phosphine complexes of Cu, Pd, or Ni (eg. $Cu(OAc)_2$, $PdCl_2(PPh_3)_2$, $NiCl_2(PPh_3)_2$). Bases may include, but are not limited to, alkaline earth metal carbonates, alkaline earth metal bicarbonates, alkaline earth metal hydroxides, alkali metal carbonates, alkali metal bicarbonates, alkali metal hydroxides, alkali metal hydrides (preferably sodium hydride), alkali metal alkoxides (preferably sodium methoxide or sodium ethoxide), alkaline earth metal hydrides, alkali metal dialkylamides (preferably lithium diisopropylamide), alkali metal bis(trialkylsilyl)amides (preferably sodium bis (trimethylsilyl)amide), trialkyl amines (preferably diisopropylethylamine or triethylamine) or aromatic amines (preferably pyridine). Inert solvents may include, but are not limited to, acetonitrile, dialkyl ethers (preferably diethyl ether), cyclic ethers (preferably tetrahydrofuran or 1,4-dioxane), N,N-dialkylacetamides (preferably dimethylacetamide), N,N-dialkylformamides (preferably dimethylformamide), dialkylsulfoxides (preferably dimethylsulfoxide), aromatic hydrocarbons (preferably benzene or toluene) or haloalkanes (preferably methylene chloride). Preferred reaction temperatures range from room temperature up to the boiling point of the solvent employed. The reactions may be run in conventional glassware or in one of many commercially available parallel synthesizer units. Non-commercially available boronic acids or boronic acid esters may be obtained from the corresponding optionally substituted aryl halide as described in *Tetrahedron*, 50, 979-988 (1994). Intermediate (XLIX) is then hydrolyzed using alkali metal hydroxide, for example lithium, sodium or potassium hydroxide, followed by acidification, to give aryl or heteroaryl coupled acids (IX-L). Alternatively, as described in *Tetrahedron*, 50, 979-988 (1994), one may convert the $R_{N-d}$ to the corresponding boronic acid or boronic acid ester $(OH)_2B$— or $(OR^a)(OR^b)B$— and obtain the same products set forth above by treating with a suitable aryl or heteroaryl halide or triflate.

CHART P discloses a process to prepare amide forming agents (IX-LII) where the where the $R_N$ substituent is $R_{N-1}$—$X_N$— where the linker, —$X_N$— is —CO—, where $R_{N-1}$ is $R_{N-aryl}$ and where $R_{N-aryl}$ is phenyl (-phenyl) substituted with two groups. The first substituent at what is usually identified as postion "5-" is —C≡C—R. The second substituent at what is usually identified as postion "3-" can be either —CO—$NR_{N-2}R_{N-3}$ or —CO—$R_{N-4}$. The halo ester (XXI) is treated with a mixture of $PdCl_2(Pphenyl_3)_2$ and trimethylsilyl acetylene, using methods known to those skilled in the art, to give acetylene ester (LI). Acetylene ester (LI) is then hydrolyzed using alkali metal hydroxide, followed by acidification, to give acetylene acid (IX-LII).

CHART U discloses a general method for preparing various C-terminal amines (VI) as represented by the preparation of C-terminal amine (LXXXIV). Methods to prepare amines of this type are well understood using methods known to those skilled in the art, or one may consult the references: 1) *JACS*, 1970, 92, 3700, and 2) U.S. Pat. No. 4,351,842.

CHART V further discloses general methods for preparing various C-terminal amines (VI) as represented by the preparation of C-terminal amines (LXXXIX). Multiple examples of the heterocyclic carboxylic acids or acid chlorides are commercially available. Optionally, the carboxylic acid (LXXXV) may be converted to the acid chloride (LXXXVI) with reagents such as, but not limited to, thionyl chloride. Displacement with ammonia generates the common intermediate amides (LXXXVII) which are readily reduced to amines (VI-LXXXIX) using a variety of methods detailed previously. Alternatively, other heteroaryls are commecially available as the methyl halide (LXXXVIII) which are treated with ammonia to yield the title C-terminal amines (VI-LXXXVIII).

CHART W discloses general methods for preparing thiazolyl containing C-terminal amines as represented by the preparation of C-terminal amines (LXXXXI). The synthesis of the thiazoles is outlined in CHART W; these procedures are amply taught in the literature and are modified from the procedures outlined in: Mashraqui, S H; Keehn, P M. *J. Am. Chem. Soc.* 1982, 104, 4461-4465. The synthesis of substituted 5-aminomethylthiazoles (XCI) was achieved from 5-hydroxymethylthiazole (XC) by the procedure described in: Alterman et al. *J. Med. Chem.* 1998, 41, 3782-3792. All other thiazole analogs were transformed to the hydroxymethyl derivative using CHART W, and converted to the aminomethyl derivative by the Alterman procedure without notable changes.

CHART X discloses general methods for preparing isoxazolyl containing C-terminal amines as represented by the preparation of C-terminal amines (XCII). The synthesis of isoxazole derivatives was modified from the procedure in: Felman, S W et al. *J. Med. Chem.* 1992, 35, 1183-1190 and is readily understood by those skilled in the art making non-notable changes to achieve the title compounds. The substituted hydroxylamine precursors were synthesized using the procedure taught by Bousquet, E W. *Org. Synth. Coll. Vol II,* 313-315. Commercially available propargylamine may be protected using any number of methods known in the art (see: Greene, T W; Wuts, P G M. *Protective Groups in Organic Synthesis,* 3$^{rd}$ Ed. New York: John Wiley, 1999. Chapter 7.), prefered is a BOC protecting group. Substituted propargyl amines may be obtained by a number of methods commonly known in the art.

CHART Y discloses a general route to prepare hydroxyethylamines where one carbon atom of the peptide backbone, along with $R_2$ and $R_3$ form a ring. It is understood the present invention also allows for a heteroatom to be incorporated into the ring. In summary, the synthesis of compounds where $R_2$ and $R_3$ may form a ring proceeds from a suitably protected amino acid aldehyde and cycloalkyllithium species, both of which are commercially available or where known procedures for making such compounds are known in the art. The general procedure involved is also precedent in the literature, for example, see Klumpp, et al., *J. Am. Chem. Soc.,* 1979, 101, 7065, and it is intended that making non-critical variations, one may obtain the title compounds provided for by CHART Y. Treatment of a suitably protected amino acid aldehyde and cycloalkyllithium species affords alcohol (XCIII). These reactions are carried out in an inert solvent such as, for example, tetrahydrofuran or diethyl ether. Optimally the reactions are conducted at low temperatures, for example below 0° C. Carbonylation via the Klumpp procedure yields the acid (XCIV) which when exposed to Curtius or related procedures well known to those skilled in the art generates the primary amine (XCV). The primary amines (XCV) may be capped C-terminally via the conditions set forth in CHART C & D followed by nitrogen deprotection and capping N-terminally via the conditions set forth in CHART A.

The compounds of the invention may contain geometric or optical isomers as well as tautomers. Thus, the invention includes all tautomers and pure geometric isomers, such as the E and Z geometric isomers, as well as mixtures thereof. Futhermore, the invention includes pure enantiomers and diasteriomers as well as mixtures thereof, including racemic mixtures. The individual geometric isomers, enantiomers, or diasteriomers may be prepared or isolated by methods known in the art.

Compounds of the invention with the stereochemistry designated in formula X may be included in mixtures, including racemic mixtures, with other enantiomers, diasteriomers, geometric isomers or tautomers. Compounds of the invention with the stereochemistry designated in formula X are typically present in these mixtures in excess of 50 percent. Preferably, compounds of the invention with the stereochemistry designated in formula X are present in these mixtures in excess of 80 percent. Most preferably, compounds of the invention with the stereochemistry designated in formula X are present in these mixtures in excess of 90 percent.

The (S,R)-disubstituted amine (I) and and the substituted amine with RN cyclized (II) are amines and as such form salts when reacted with acids. Pharmaceutically acceptable salts are preferred over the corresponding (S,R)-disubstituted amines (I) and the substituted amines with $R_N$ cyclized (II) since they produce compounds which are more water soluble, stable and/or more crystalline.

Pharmaceutically acceptable salts are any salt which retains the activity of the parent compound and does not impart any deleterious or undesirable effect on the subject to whom it is administered and in the context in which it is administered. Pharmaceutically acceptable salts include salts of both inorganic and organic acids. The preferred pharmaceutically acceptable salts include salts of the following acids acetic, aspartic, benzenesulfonic, benzoic, bicarbonic, bisulfuric, bitartaric, butyric, calcium edetate, camsylic, carbonic, chlorobenzoic, citric, edetic, edisylic, estolic, esyl, esylic, formic, fumaric, gluceptic, gluconic, glutamic, glycollylarsanilic, hexamic, hexylresorcinoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalactouronic, propionic, salicylic, stearic, succinic, succinic, sulfamic, sulfanilic, sulfonic, sulfuric, tannic, tartaric, teoclic and toluenesulfonic. For other acceptable salts, see *Int. J. Pharm.,* 33, 201-217 (1986) and *J. Pharm. Sci.,* 66(1), 1, (1977).

The present invention provides compounds, compositions, kits, and methods for inhibiting beta-secretase enzyme activity and A beta peptide production. Inhibition of beta-secretase enzyme activity halts or reduces the production of A beta from APP and reduces or eliminates the formation of beta-amyloid deposits in the brain.

Methods of the Invention

The compounds of the invention, and pharmaceutically acceptable salts thereof, are useful for treating humans or animals suffering from a condition characterized by a pathological form of beta-amyloid peptide, such as beta-amyloid plaques, and for helping to prevent or delay the onset of such a condition. For example, the compounds are useful for treating Alzheimer's disease, for helping prevent or delay the onset of Alzheimer's disease, for treating patients with MCI (mild cognitive impairment) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobal hemorrhages, for treating other degenerative dementias, including dementias of mixed vascular and degenerative origin, dementia associated with Parkinson's disease, dementia associated with progressive supranuclear palsy, dementia associated with cortical basal degeneration, and diffuse Lewy body type Alzheimer's disease. The compounds and compositions of the invention are particularly useful for treating or preventing Alzheimer's disease. When treating or preventing these diseases, the compounds of the invention can either be used individually or in combination, as is best for the patient.

As used herein, the term "treating" means that the compounds of the invention can be used in humans with at least a tentative diagnosis of disease. The compounds of the invention will delay or slow the progression of the disease thereby giving the individual a more useful life span.

The term "preventing" means that the compounds of the present invention are useful when administered to a patient who has not been diagnosed as possibly having the disease at the time of administration, but who would normally be expected to develop the disease or be at increased risk for the disease. The compounds of the invention will slow the development of disease symptoms, delay the onset of the disease, or prevent the individual from developing the disease at all. Preventing also includes administration of the compounds of the invention to those individuals thought to be predisposed to the disease due to age, familial history, genetic or chromosomal abnormalities, and/or due to the presence of one or more biological markers for the disease, such as a known genetic mutation of APP or APP cleavage products in brain tissues or fluids.

In treating or preventing the above diseases, the compounds of the invention are administered in a therapeutically effective amount. The therapeutically effective amount will vary depending on the particular compound used and the route of administration, as is known to those skilled in the art.

In treating a patient displaying any of the diagnosed above conditions a physician may administer a compound of the invention immediately and continue administration indefinitely, as needed. In treating patients who are not diagnosed as having Alzheimer's disease, but who are believed to be at substantial risk for Alzheimer's disease, the physician should preferably start treatment when the patient first experiences early pre-Alzheimer's symptoms such as, memory or cognitive problems associated with aging. In addition, there are some patients who may be determined to be at risk for developing Alzheimer's through the detection of a genetic marker such as APOE4 or other biological indicators that are predictive for Alzheimer's disease. In these situations, even though the patient does not have symptoms of the disease, administration of the compounds of the invention may be started before symptoms appear, and treatment may be continued indefinitely to prevent or delay the outset of the disease.

Dosage Forms and Amounts

The compounds of the invention can be administered orally, parenterally, (IV, IM, depo-IM, SQ, and depo SQ), sublingually, intranasally (inhalation), intrathecally, topically, or rectally. Dosage forms known to those of skill in the art are suitable for delivery of the compounds of the invention.

Compositions are provided that contain therapeutically effective amounts of the compounds of the invention. The compounds are preferably formulated into suitable pharmaceutical preparations such as tablets, capsules, or elixirs for oral administration or in sterile solutions or suspensions for parenternal administration. Typically the compounds described above are formulated into pharmaceutical compositions using techniques and procedures well known in the art.

About 1 to 500 mg of a compound or mixture of compounds of the invention or a physiologically acceptable salt or ester is compounded with a physiologically acceptable vehicle, carrier, excipient, binder, preservative, stabilizer, flavor, etc., in a unit dosage form as called for by accepted pharmaceutical practice. The amount of active substance in those compositions or preparations is such that a suitable dosage in the range indicated is obtained. The compositions are preferably formulated in a unit dosage form, each dosage containing from about 2 to about 100 mg, more preferably about 10 to about 30 mg of the active ingredient. The term "unit dosage from" refers to physically discrete units suitable as unitary dosages for human subjects and other mammals, each unit containing a predetermined quantity of active material calculated to produce the desired therapeutic effect, in association with a suitable pharmaceutical excipient.

To prepare compositions, one or more compounds of the invention are mixed with a suitable pharmaceutically acceptable carrier. Upon mixing or addition of the compound(s), the resulting mixture may be a solution, suspension, emulsion, or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the compound in the selected carrier or vehicle. The effective concentration is sufficient for lessening or ameliorating at least one symptom of the disease, disorder, or condition treated and may be empirically determined.

Pharmaceutical carriers or vehicles suitable for administration of the compounds provided herein include any such carriers known to those skilled in the art to be suitable for the particular mode of administration. In addition, the active materials can also be mixed with other active materials that do not impair the desired action, or with materials that supplement the desired action, or have another action. The compounds may be formulated as the sole pharmaceutically active ingredient in the composition or may be combined with other active ingredients.

Where the compounds exhibit insufficient solubility, methods for solubilizing may be used. Such methods are known and include, but are not limited to, using cosolvents such as dimethylsulfoxide (DMSO), using surfactants such as Tween®, and dissolution in aqueous sodium bicarbonate. Derivatives of the compounds, such as salts or prodrugs may also be used in formulating effective pharmaceutical compositions.

The concentration of the compound is effective for delivery of an amount upon administration that lessens or ameliorates at least one symptom of the disorder for which the compound is administered. Typically, the compositions are formulated for single dosage administration.

The compounds of the invention may be prepared with carriers that protect them against rapid elimination from the body, such as time-release formulations or coatings. Such carriers include controlled release formulations, such as, but not limited to, microencapsulated delivery systems. The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder.

The compounds and compositions of the invention can be enclosed in multiple or single dose containers. The enclosed compounds and compositions can be provided in kits, for example, including component parts that can be assembled for use. For example, a compound inhibitor in lyophilized form and a suitable diluent may be provided as separated components for combination prior to use. A kit may include a compound inhibitor and a second therapeutic agent for co-administration. The inhibitor and second therapeutic agent may be provided as separate component parts. A kit may include a plurality of containers, each container holding one or more unit dose of the compound of the invention. The containers are preferably adapted for the desired mode of administration, including, but not limited to tablets, gel capsules, sustained-release capsules, and the like for oral administration; depot products, pre-filled syringes, ampules, vials, and the like for parenternal administration; and patches, medipads, creams, and the like for topical administration.

The concentration of active compound in the drug composition will depend on absorption, inactivation, and excretion rates of the active compound, the dosage schedule, and amount administered as well as other factors known to those of skill in the art.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound should be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

The active materials can also be mixed with other active materials that do not impair the desired action, or with materials that supplement the desired action.

Solutions or suspensions used for parenternal, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers. These may be prepared according to methods known for example, as described in U.S. Pat. No. 4,522,811.

The active compounds may be prepared with carriers that protect the compound against rapid elimination from the body, such as time-release formulations or coatings. Such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, and the like. Methods for preparation of such formulations are known to those skilled in the art.

The compounds of the invention can be administered orally, parenternally (IV, IM, depo-IM, SQ, and depo-SQ), sublingually, intranasally (inhalation), intrathecally, topically, or rectally. Dosage forms known to those skilled in the art are suitable for delivery of the compounds of the invention.

Compounds of the invention may be administered enterally or parenterally. When administered orally, compounds of the invention can be administered in usual dosage forms for oral administration as is well known to those skilled in the art. These dosage forms include the usual solid unit dosage forms of tablets and capsules as well as liquid dosage forms such as solutions, suspensions, and elixirs. When the solid dosage forms are used, it is preferred that they be of the sustained release type so that the compounds of the invention need to be administered only once or twice daily.

The oral dosage forms are administered to the patient 1, 2, 3, or 4 times daily. It is preferred that the compounds of the invention be administered either three or fewer times, more preferably once or twice daily. Hence, it is preferred that the compounds of the invention be administered in oral dosage form. It is preferred that whatever oral dosage form is used, that it be designed so as to protect the compounds of the invention from the acidic environment of the stomach. Enteric coated tablets are well known to those skilled in the art. In addition, capsules filled with small spheres each coated to protect from the acidic stomach, are also well known to those skilled in the art.

When administered orally, an administered amount therapeutically effective to inhibit beta-secretase activity, to inhibit A beta production, to inhibit A beta deposition, or to treat or prevent AD is from about 0.1 mg/day to about 1,000 mg/day. It is preferred that the oral dosage is from about 1 mg/day to about 100 mg/day. It is more preferred that the oral dosage is from about 5 mg/day to about 50 mg/day. It is understood that while a patient may be started at one dose, that dose may be varied over time as the patient's condition changes.

Compounds of the invention may also be advantageously delivered in a nano crystal dispersion formulation. Preparation of such formulations is described, for example, in U.S. Pat. No. 5,145,684. Nano crystalline dispersions of HIV protease inhibitors and their method of use are described in U.S. Pat. No. 6,045,829. The nano crystalline formulations typically afford greater bioavailability of drug compounds.

The compounds of the invention can be administered parenterally, for example, by IV, IM, depo-IM, SC, or depo-SC. When administered parenterally, a therapeutically effective amount of about 0.5 to about 100 mg/day, preferably from about 5 to about 50 mg daily should be delivered. When a depot formulation is used for injection once a month or once every two weeks, the dose should be about 0.5 mg/day to about 50 mg/day, or a monthly dose of from about 15 mg to about 1,500 mg. In part because of the forgetfulness of the patients with Alzheimer's disease, it is preferred that the parenteral dosage form be a depo formulation.

The compounds of the invention can be administered sublingually. When given sublingually, the compounds of the invention should be given one to four times daily in the amounts described above for IM administration.

The compounds of the invention can be administered intranasally. When given by this route, the appropriate dosage forms are a nasal spray or dry powder, as is known to those skilled in the art. The dosage of the compounds of the invention for intranasal administration is the amount described above for IM administration.

The compounds of the invention can be administered intrathecally. When given by this route the appropriate dosage form can be a parenternal dosage form as is known to those skilled in the art. The dosage of the compounds of the invention for intrathecal administration is the amount described above for IM administration.

The compounds of the invention can be administered topically. When given by this route, the appropriate dosage form is a cream, ointment, or patch. Because of the amount of the compounds of the invention to be administered, the patch is preferred. When administered topically, the dosage is from about 0.5 mg/day to about 200 mg/day. Because the amount that can be delivered by a patch is limited, two or more patches may be used. The number and size of the patch is not important, what is important is that a therapeutically effective amount of the compounds of the invention be delivered as is known to those skilled in the art. The compounds of the invention can be administered rectally by suppository as is known to those skilled in the art. When administered by suppository, the therapeutically effective amount is from about 0.5 mg to about 500 mg.

The compounds of the invention can be administered by implants as is known to those skilled in the art. When administering a compound of the invention by implant, the therapeutically effective amount is the amount described above for depot administration.

The invention here is the new compounds of the invention and new methods of using the compounds of the invention. Given a particular compound of the invention and a desired dosage form, one skilled in the art would know how to prepare and administer the appropriate dosage form.

The compounds of the invention are used in the same manner, by the same routes of administration, using the same pharmaceutical dosage forms, and at the same dosing schedule as described above, for preventing disease or treating patients with MCI (mild cognitive impairment) and preventing or delaying the onset of Alzheimer's disease in those who would progress from MCI to AD, for treating or preventing Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, and diffuse Lewy body type of Alzheimer's disease.

The compounds of the invention can be used in combination, with each other or with other therapeutic agents or approaches used to treat or prevent the conditions listed above. Such agents or approaches include: acetylcholine esterase inhibitors such as tacrine (tetrahydroaminoacridine, marketed as COGNEX®), donepezil hydrochloride, (marketed as Aricept® and rivastigmine (marketed as Exelon®); gamma-secretase inhibitors; anti-inflammatory agents such as cyclooxygenase II inhibitors; anti-oxidants such as Vitamin E and ginkolides; immunological approaches, such as, for example, immunization with A beta peptide or administration of anti-A beta peptide antibodies; statins; and direct or indirect neurotropic agents such as Cerebrolysin®, AIT-082 (Emilieu, 2000, *Arch. Neurol.* 57:454), and other neurotropic agents of the future.

It should be apparent to one skilled in the art that the exact dosage and frequency of administration will depend on the particular compounds of the invention administered, the particular condition being treated, the severity of the condition being treated, the age, weight, general physical condition of the particular patient, and other medication the individual may be taking as is well known to administering physicians who are skilled in this art.

Inhibition of APP Cleavage

The compounds of the invention inhibit cleavage of APP between Met595 and Asp596 numbered for the APP695 isoform, or a mutant thereof, or at a corresponding site of a different isoform, such as APP751 or APP770, or a mutant thereof (sometimes referred to as the "beta secretase site"). While not wishing to be bound by a particular theory, inhibition of beta-secretase activity is thought to inhibit production of beta amyloid peptide (A beta). Inhibitory activity is demonstrated in one of a variety of inhibition assays, whereby cleavage of an APP substrate in the presence of a beta-secretase enzyme is analyzed in the presence of the inhibitory compound, under conditions normally sufficient to result in cleavage at the beta-secretase cleavage site. Reduction of APP cleavage at the beta-secretase cleavage site compared with an untreated or inactive control is correlated with inhibitory activity. Assay systems that can be used to demonstrate efficacy of the compound inhibitors of the invention are known. Representative assay systems are described, for example, in U.S. Pat. Nos. 5,942,400, 5,744,346, as well as in the Examples below.

The enzymatic activity of beta-secretase and the production of A beta can be analyzed in vitro or in vivo, using natural, mutated, and/or synthetic APP substrates, natural, mutated, and/or synthetic enzyme, and the test compound. The analysis may involve primary or secondary cells expressing native, mutant, and/or synthetic APP and enzyme, animal models expressing native APP and enzyme, or may utilize transgenic animal models expressing the substrate and enzyme. Detection of enzymatic activity can be by analysis of one or more of the cleavage products, for example, by immunoassay, flurometric or chromogenic assay, HPLC, or other means of detection. Inhibitory compounds are determined as those having the ability to decrease the amount of beta-secretase cleavage product produced in comparison to a control, where beta-secretase mediated cleavage in the reaction system is observed and measured in the absence of inhibitory compounds.

Beta-Secretase

Various forms of beta-secretase enzyme are known, and are available and useful for assay of enzyme activity and inhibition of enzyme activity. These include native, recombinant, and synthetic forms of the enzyme. Human beta-secretase is known as Beta Site APP Cleaving Enzyme (BACE), Asp2, and memapsin 2, and has been characterized, for example, in U.S. Pat. No. 5,744,346 and published PCT patent applications WO98/22597, WO00/03819, WO01/23533, and WO00/17369, as well as in literature publications (Hussain et. al., 1999, *Mol. Cell. Neurosci.* 14:419-427; Vassar et. al., 1999, *Science* 286:735-741; Yan et. al., 1999, *Nature* 402: 533-537; Sinha et. al., 1999, *Nature* 40:537-540; and Lin et. al., 2000, *PNAS USA* 97:1456-1460). Synthetic forms of the enzyme have also been described (WO98/22597 and WO00/17369). Beta-secretase can be extracted and purified from human brain tissue and can be produced in cells, for example mammalian cells expressing recombinant enzyme.

Useful inhibitory compounds are effective to inhibit 50% of beta-secretase enzymatic activity at a concentration of less than 50 micromolar, preferably at a concentration of 10 micromolar or less, more preferably 1 micromolar or less, and most preferably 10 nanomolar or less.

APP Substrate

Assays that demonstrate inhibition of beta-secretase-mediated cleavage of APP can utilize any of the known forms of APP, including the 695 amino acid "normal" isotype described by Kang et. al., 1987, *Nature* 325:733-6, the 770 amino acid isotype described by Kitaguchi et. al., 1981, *Nature* 331:530-532, and variants such as the Swedish Mutation (KM670-1NL) (APP-SW), the London Mutation (V7176F), and others. See, for example, U.S. Pat. No. 5,766, 846 and also Hardy, 1992, *Nature Genet.* 1:233-234, for a review of known variant mutations. Additional useful substrates include the dibasic amino acid modification, APP-KK disclosed, for example, in WO 00/17369, fragments of APP, and synthetic peptides containing the beta-secretase cleavage site, wild type (WT) or mutated form, e.g., SW, as described, for example, in U.S. Pat. No. 5,942,400 and WO00/03819.

The APP substrate contains the beta-secretase cleavage site of APP (KM-DA or NL-DA) for example, a complete APP peptide or variant, an APP fragment, a recombinant or synthetic APP, or a fusion peptide. Preferably, the fusion peptide includes the beta-secretase cleavage site fused to a peptide having a moiety useful for enzymatic assay, for example, having isolation and/or detection properties. A useful moiety may be an antigenic epitope for antibody binding, a label or other detection moiety, a binding substrate, and the like.

Antibodies

Products characteristic of APP cleavage can be measured by immunoassay using various antibodies, as described, for example, in Pirttila et. al., 1999, *Neuro. Lett.* 249:21-4, and in U.S. Pat. No. 5,612,486. Useful antibodies to detect A beta include, for example, the monoclonal antibody 6E10 (Senetek, St. Louis, Mo.) that specifically recognizes an epitope on amino acids 1-16 of the A beta peptide; antibodies 162 and 164 (New York State Institute for Basic Research, Staten Island, N.Y.) that are specific for human A beta 140 and 142, respectively; and antibodies that recognize the junction region of beta-amyloid peptide, the site between residues 16 and 17, as described in U.S. Pat. No. 5,593,846. Antibodies raised against a synthetic peptide of residues 591 to 596 of APP and SW192 antibody raised against 590-596 of the Swedish mutation are also useful in immunoassay of APP and its cleavage products, as described in U.S. Pat. Nos. 5,604, 102 and 5,721,130.

Assay Systems

Assays for determining APP cleavage at the beta-secretase cleavage site are well known in the art. Exemplary assays, are described, for example, in U.S. Pat. Nos. 5,744,346 and 5,942,400, and described in the Examples below.

Cell Free Assays

Exemplary assays that can be used to demonstrate the inhibitory activity of the compounds of the invention are described, for example, in WO00/17369, WO 00/03819, and U.S. Pat. Nos. 5,942,400 and 5,744,346. Such assays can be performed in cell-free incubations or in cellular incubations using cells expressing a beta-secretase and an APP substrate having a beta-secretase cleavage site.

An APP substrate containing the beat-secretase cleavage site of APP, for example, a complete APP or variant, an APP fragment, or a recombinant or synthetic APP substrate containing the amino acid sequence: KM-DA or NL-DA, is incubated in the presence of beta-secretase enzyme, a fragment thereof, or a synthetic or recombinant polypeptide variant having beta-secretase activity and effective to cleave the beta-secretase cleavage site of APP, under incubation conditions suitable for the cleavage activity of the enzyme. Suitable substrates optionally include derivatives that may be fusion proteins or peptides that contain the substrate peptide and a modification useful to facilitate the purification or detection of the peptide or its beta-secretase cleavage products. Useful modifications include the insertion of a known antigenic epitope for antibody binding; the linking of a label or detectable moiety, the linking of a binding substrate, and the like.

Suitable incubation conditions for a cell-free in vitro assay include, for example: approximately 200 nanomolar to 10 micromolar substrate, approximately 10 to 200 picomolar enzyme, and approximately 0.1 nanomolar to 10 micromolar inhibitor compound, in aqueous solution, at an approximate pH of 4-7, at approximately 37 degrees C., for a time period of approximately 10 minutes to 3 hours. These incubation conditions are exemplary only, and can be varied as required for the particular assay components and/or desired measurement system. Optimization of the incubation conditions for the particular assay components should account for the specific beta-secretase enzyme used and its pH optimum, any additional enzymes and/or markers that might be used in the assay, and the like. Such optimization is routine and will not require undue experimentation.

One useful assay utilizes a fusion peptide having maltose binding protein (MBP) fused to the C-terminal 125 amino acids of APP-SW. The MBP portion is captured on an assay substrate by anti-MBP capture antibody. Incubation of the captured fusion protein in the presence of beta-secretase results in cleavage of the substrate at the beta-secretase cleavage site. Analysis of the cleavage activity can be, for example, by immunoassay of cleavage products. One such immunoassay detects a unique epitope exposed at the carboxy terminus of the cleaved fusion protein, for example, using the antibody SW192. This assay is described, for example, in U.S. Pat. No. 5,942,400.

Cellular Assay

Numerous cell-based assays can be used to analyze beta-secretase activity and/or processing of APP to release A beta. Contact of an APP substrate with a beta-secretase enzyme within the cell and in the presence or absence of a compound inhibitor of the invention can be used to demonstrate beta-secretase inhibitory activity of the compound. Preferably, assay in the presence of a useful inhibitory compound provides at least about 30%, most preferably at least about 50% inhibition of the enzymatic activity, as compared with a non-inhibited control.

In one embodiment, cells that naturally express beta-secretase are used. Alternatively, cells are modified to express a recombinant beta-secretase or synthetic variant enzyme as discussed above. The APP substrate may be added to the culture medium and is preferably expressed in the cells. Cells that naturally express APP, variant or mutant forms of APP, or cells transformed to express an isoform of APP, mutant or variant APP, recombinant or synthetic APP, APP fragment, or synthetic APP peptide or fusion protein containing the beta-secretase APP cleavage site can be used, provided that the expressed APP is permitted to contact the enzyme and enzymatic cleavage activity can be analyzed.

Human cell lines that normally process A beta from APP provide a useful means to assay inhibitory activities of the compounds of the invention. Production and release of A beta and/or other cleavage products into the culture medium can be measured, for example by immunoassay, such as Western blot or enzyme-linked immunoassay (EIA) such as by ELISA.

Cells expressing an APP substrate and an active beta-secretase can be incubated in the presence of a compound inhibitor to demonstrate inhibition of enzymatic activity as compared with a control. Activity of beta-secretase can be measured by analysis of one or more cleavage products of the APP substrate. For example, inhibition of beta-secretase activity against the substrate APP would be expected to decrease release of specific beta-secretase induced APP cleavage products such as A beta.

Although both neural and non-neural cells process and release A beta, levels of endogenous beta-secretase activity are low and often difficult to detect by EIA. The use of cell types known to have enhanced beta-secretase activity, enhanced processing of APP to A beta, and/or enhanced production of A beta are therefore preferred. For example, transfection of cells with the Swedish Mutant form of APP (APP-SW); with APP-KK; or with APP-SW-KK provides cells having enhanced beta-secretase activity and producing amounts of A beta that can be readily measured.

In such assays, for example, the cells expressing APP and beta-secretase are incubated in a culture medium under conditions suitable for beta-secretase enzymatic activity at its cleavage site on the APP substrate. On exposure of the cells to the compound inhibitor, the amount of A beta released into the medium and/or the amount of CTF99 fragments of APP in the cell lysates is reduced as compared with the control. The cleavage products of APP can be analyzed, for example, by immune reactions with specific antibodies, as discussed above.

Preferred cells for analysis of beta-secretase activity include primary human neuronal cells, primary transgenic animal neuronal cells where the transgene is APP, and other cells such as those of a stable 293 cell line expressing APP, for example, APP-SW.

In Vivo Assays: Animal Models

Various animal models can be used to analyze beta-secretase activity and/or processing of APP to release A beta, as described above. For example, transgenic animals expressing APP substrate and beta-secretase enzyme can be used to demonstrate inhibitory activity of the compounds of the invention. Certain transgenic animal models have been described, for example, in U.S. Pat. Nos. 5,877,399; 5,612,486; 5,387,742; 5,720,936; 5,850,003; 5,877,015, and 5,811,633, and in Ganes et. al., 1995, *Nature* 373:523. Preferred are animals that exhibit characteristics associated with the pathophysiology of AD. Administration of the compound inhibitors of the invention to the transgenic mice described herein provides an alternative method for demonstrating the inhibitory activity of the compounds. Administration of the compounds in a pharmaceutically effective carrier and via an administrative route that reaches the target tissue in an appropriate therapeutic amount is also preferred.

Inhibition of beta-secretase mediated cleavage of APP at the beta-secretase cleavage site and of A beta release can be analyzed in these animals by measure of cleavage fragments in the animal's body fluids such as cerebral fluid or tissues. Analysis of brain tissues for A beta deposits or plaques is preferred.

On contacting an APP substrate with a beta-secretase enzyme in the presence of an inhibitory compound of the invention and under conditions sufficient to permit enzymatic mediated cleavage of APP and/or release of A beta from the substrate, the compounds of the invention are effective to reduce beta-secretase-mediated cleavage of APP at the beta-secretase cleavage site and/or effective to reduce released amounts of A beta. Where such contacting is the administration of the inhibitory compounds of the invention to an animal model, for example, as described above, the compounds are effective to reduce A beta deposition in brain tissues of the animal, and to reduce the number and/or size of beta amyloid plaques. Where such administration is to a human subject, the compounds are effective to inhibit or slow the progression of disease characterized by enhanced amounts of A beta, to slow the progression of AD in the, and/or to prevent onset or development of AD in a patient at risk for the disease.

Unless defined otherwise, all scientific and technical terms used herein have the same meaning as commonly understood by one of skill in the art to which this invention belongs. All patents and publications referred to herein are hereby incorporated by reference for all purposes.

Definitions and Conventions

The definitions and explanations below are for the terms as used throughout this entire document including both the specification and the claims.

I. Conventions for Formulas and Definitions of Variables

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$," where "i" is an integer. These variable substituents are either monovalent or bivalent, that is, they represent a group attached to the formula by one or two chemical bonds. For example, a group $Z_1$ would represent a bivalent variable if attached to the formula $CH_3-C(=Z_1)H$. Groups $R_i$ and $R_j$ would represent monovalent variable substituents if attached to the formula $CH_3—CH_2—C(R_i)(R_j)H_2$. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom. Also, for any molecule with an established system of carbon atom numbering, such as steroids, these carbon atoms are designated as $C_i$, where "i" is the integer corresponding to the carbon atom number. For example, $C_6$ represents the 6 position or carbon atom number in the steroid nucleus as traditionally designated by those skilled in the art of steroid chemistry. Likewise the term "$R_6$" represents a variable substituent (either monovalent or bivalent) at the $C_6$ position.

Chemical formulas or portions thereof drawn in a linear fashion represent atoms in a linear chain. The symbol "—" in general represents a bond between two atoms in the chain. Thus $CH_3—O—CH_2—CH(R_i)—CH_3$ represents a 2-substituted-1-methoxypropane compound. In a similar fashion, the symbol "=" represents a double bond, e.g., $CH_2=C(R_i)—O—CH_3$, and the symbol "≡" represents a triple bond, e.g., $HC\equiv C—CH(R_i)—CH_2—CH_3$. Carbonyl groups are represented in either one of two ways: —CO—, —C(O)— or —C(=O)—, with the former two representations being preferred for simplicity.

Chemical formulas of cyclic (ring) compounds or molecular fragments can be represented in a linear fashion. Thus, the compound 4-chloro-2-methylpyridine can be represented in linear fashion by $N^*=C(CH_3)—CH=CCl—CH=C^*H$ with the convention that the atoms marked with an asterisk (*) are bonded to each other resulting in the formation of a ring. Likewise, the cyclic molecular fragment, 4-(ethyl)-1-piperazinyl can be represented by $—N^*—(CH_2)_2—N(C_2H_5)—CH_2—C^*H_2$.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system, $—C(X_1)(X_2)—$ the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other. In chemical structural formulas depicting such compounds, a substituent ($X_1$) which is "below" another substituent ($X_2$) will be identified as being in the alpha configuration and is identified by a broken, dashed or dotted line attachment to the carbon atom, i.e., by the symbol " - - - " or " . . . ". The corresponding substituent attached "above" ($X_2$) the other ($X_1$) is identified as being in the beta configuration and is indicated by an unbroken line attachment to the carbon atom.

When a variable substituent is bivalent, the valences may be taken together or separately or both in the definition of the variable. For example, a variable $R_i$ attached to a carbon atom as $—C(=R_i)—$ might be bivalent and be defined as oxo or keto (thus forming a carbonyl group (—CO—) or as two separately attached monovalent variable substituents alpha-$R_{i-j}$ and beta-$R_{i-k}$. When a bivalent variable, $R_i$, is defined to consist of two monovalent variable substituents, the convention used to define the bivalent variable is of the form "alpha-$R_{i-j}$:beta-$R_{i-k}$" or some variant thereof. In such a case both alpha-$R_{i-j}$ and beta-$R_{i-k}$ are attached to the carbon atom to give $—C(alpha-R_{i-j})(beta-R_{i-k})—$. For example, when the bivalent variable $R_6$, $—C(=R_6)—$ is defined to consist of two monovalent variable substituents, the two monovalent variable substituents are alpha-$R_{6-1}$:beta-$R_{6-2}$, . . . alpha-$_{6-9}$:beta-$R_{6-10}$, etc, giving $—C(alpha-R_{6-1})(beta-R_{6-2})—$, . . . $—C(alpha-R_{6-9})(beta-R_{6-10})—$, etc. Likewise, for the bivalent variable $R_{11}$, $—C(=R_{11})—$, two monovalent variable substituents are alpha-$R_{11-1}$:beta-$R_{11-2}$. For a ring substituent for which separate alpha and beta orientations do not exist (e.g. due to the presence of a carbon carbon double bond in the ring), and for a substituent bonded to a carbon atom which is not part of a ring the above convention is still used, but the alpha and beta designations are omitted.

Just as a bivalent variable may be defined as two separate monovalent variable substituents, two separate monovalent variable substituents may be defined to be taken together to form a bivalent variable. For example, in the formula $—C_1(R_i)H—C_2(R_j)H—$ ($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group —X—Y—, then the orientation of the entity is such that C, in the above formula is bonded to X and $C_2$ is bonded to Y. Thus, by convention the designation ". . . $R_i$ and $R_j$ are taken together to form $—CH_2—CH_2—O—CO—$ . . ." means a lactone in which the carbonyl is bonded to $C_2$. However, when designated ". . . $R_j$ and $R_i$ are taken together to form $—CO—O—CH_2—CH_2—$ the convention means a lactone in which the carbonyl is bonded to $C_1$.

The carbon atom content of variable substituents is indicated in one of two ways. The first method uses a prefix to the entire name of the variable such as "$C_1$-$C_4$", where both "1" and "4" are integers representing the minimum and maximum number of carbon atoms in the variable. The prefix is separated from the variable by a space. For example, "$C_1$-$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$-$C_4$ alkoxycarbonyl describes a group $CH_3—(CH_2)_n—O—CO—$ where n is zero, one or two. By the second method the carbon atom content of only each portion of the definition is indicated separately by enclosing the "$C_i$-$C_j$" designation in parentheses and placing it immediately (no intervening space) before the portion of the definition being defined. By this optional convention ($C_1$-$C_3$)alkoxycarbonyl has the same meaning as $C_2$-$C_4$ alkoxycarbonyl because the "$C_1$-$C_3$" refers only to the carbon atom content of the alkoxy group. Similarly while both $C_2$-$C_6$ alkoxyalkyl and ($C_1$-$C_3$)alkoxy($C_1$-$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

When the claims contain a fairly complex (cyclic) substituent, at the end of the phrase naming/designating that particular substituent will be a notation in (parentheses) which will correspond to the same name/designation in one of the CHARTS which will also set forth the chemical structural formula of that particular substituent.

II. Definitions

All temperatures are in degrees Celsius.
TLC refers to thin-layer chromatography.
psi refers to pounds/in$^2$.
rt or R.T. refers to room temperature and is defined to be between about 20 to 25 degrees C.
HPLC refers to high pressure liquid chromatography.
THF refers to tetrahydrofuran.
DMF refers to dimethylformamide.
DCM refers to dichloromethane, also called methylene chloride.
EDC refers to ethyl-1-(3-dimethylaminopropyl)carbodiimide or 1-(3-dimethylaminopropyl)-3-ethylcarbodiimide hydrochloride.
HOBt refers to 1-hydroxy benzotriazole hydrate.
NMM refers to N-methylmorpholine.
NBS refers to N-bromosuccinimide.
TEA refers to triethylamine.
BOC refers to 1,1-dimethylethoxy carbonyl or t-butoxycarbonyl, —CO—O—C(CH$_3$)$_3$.
CBZ refers to benzyloxycarbonyl, —CO—O—CH$_2$-phenyl.
FMOC refers to 9-fluorenylmethyl carbonate.
TFA refers to trifluoracetic acid, CF$_3$—COOH.
CDI refers to 1,1'-carbonyldiimidazole.
Saline refers to an aqueous saturated sodium chloride solution.
Chromatography (column and flash chromatography) refers to purification/separation of compounds expressed as (support, eluent). It is understood that the appropriate fractions are pooled and concentrated to give the desired compound(s).
CMR refers to C-13 magnetic resonance spectroscopy, chemical shifts are reported in ppm (δ) downfield from TMS.
NMR refers to nuclear (proton) magnetic resonance spectroscopy, chemical shifts are reported in ppm (d) downfield from TMS.
IR refers to infrared spectroscopy.
MS refers to mass spectrometry expressed as m/e, m/z or mass/charge unit. MH$^+$ refers to the positive ion of a parent plus a hydrogen atom. EI refers to electron impact. CI refers to chemical ionization. FAB refers to fast atom bombardment.
HRMS refers to high resolution mass spectrometry.
Ether refers to diethyl ether.
Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.
When solvent pairs are used, the ratios of solvents used are volume/volume (v/v).
When the solubility of a solid in a solvent is used the ratio of the solid to the solvent is weight/volume (wt/v).
BOP refers to benzotriazol-1-yloxy-tris(dimethylamino) phosphonium hexafluorophosphate.
TBDMSCl refers to t-butyldimethylsilyl chloride.
TBDMSOTf refers to t-butyldimethylsilyl trifluosulfonic acid ester.
Trisomy 21 refers to Down's Syndrome.
The following terms are used (in EXAMPLEs 321 and above) for the amide forming agent (IX):

"PHTH" refers to (CH$_3$—CH$_2$—CH$_2$—)$_2$N—CO-phenyl-CO—OH where the attachment to the -phenyl-ring is 1,3-;
"5-Me-PHTH" refers to (CH$_3$—CH$_2$—CH$_2$—)$_2$N—CO—(CH$_3$—)phenyl-CO—OH where the attachment to the -phenyl-ring is 1,3- for the carbonyl groups and 5- for the methyl group;
"3,5-pyridinyl" refers to (CH$_3$—CH$_2$—CH$_2$—)$_2$N—CO-(pyridinyl)-CO—OH where the attachment to the -pyridinyl-ring is 3,5- for the carbonyl groups;
"—SO$_2$-" refers to (CH$_3$—CH$_2$—CH$_2$—)$_2$CH—SO$_2$—phenyl —CO—OH where the attachment to the -phenyl-ring is 1,3-;
"5-OMe-PHTH" refers to (CH$_3$—CH$_2$—CH$_2$—)$_2$N—CO—(CH$_3$—O—)phenyl-CO—OH where the attachment to the -phenyl-ring is 1,3- for the carbonyl groups and 5- for the methoxy group;
"5-Cl-PHTH" refers to (CH$_3$—CH$_2$—CH$_2$—)$_2$N—CO—(Cl-)phenyl-CO—OH where the attachment to the -phenyl-ring is 1,3- for the carbonyl groups and 5- for the chlorine atom;
"5-F-PHTH" refers to (CH$_3$—CH$_2$—CH$_2$—)$_2$N—CO—(F-)phenyl-CO—OH where the attachment to the -phenyl-ring is 1,3- for the carbonyl groups and 5- for the fluorine atom;
"thienyl" refers to (CH$_3$—CH$_2$—CH$_2$—)$_2$N—CO-thienyl-CO—OH where the attachment to the thiophene ring is -2,5;
"2,4-pyridinyl" refers to (CH$_3$—CH$_2$—CH$_2$—)$_2$N—CO-(pyridinyl)-CO—OH where the attachment to the -pyridinyl-ring is 2,4- for the carbonyl groups;
"4,6-pyrimidinyl" refers to (CH$_3$—CH$_2$—CH$_2$—)$_2$N—CO-(pyrimidinyl-)phenyl-CO—OH where the attachment to the -pyrimidiny-1 ring is 4,6- for the carbonyl groups;
"morpholinyl" refers to morpholinyl-CO-phenyl-CO—OH where the attachment to the -phenyl-ring is 1,3 for the carbonyl groups.

APP, amyloid precursor protein, is defined as any APP polypeptide, including APP variants, mutations, and isoforms, for example, as disclosed in U.S. Pat. No. 5,766,846.

A beta, amyloid beta peptide, is defined as any peptide resulting from beta-secretase mediated cleavage of APP, including peptides of 39, 40, 41, 42, and 43 amino acids, and extending from the beta-secretase cleavage site to amino acids 39, 40, 41, 42, or 43.

Beta-secretase (BACE1, Asp2, Memapsin 2) is an aspartyl protease that mediates cleavage of APP at the amino-terminal edge of A beta. Human beta-secretase is described, for example, in WO00/17369.

A therapeutically effective amount is defined as an amount effective to reduce or lessen at least one symptom of the disease being treated or to reduce or delay onset of one or more clinical markers or symptoms of the disease.

The present invention provides compounds, compositions, and methods for inhibiting beta-secretase enzyme activity and A beta peptide production. Inhibition of beta-secretase enzyme activity halts or reduces the production of A beta from APP and reduces or eliminates the formation of beta-amyloid deposits in the brain.

EXAMPLES

Without further elaboration, it is believed that one skilled in the art can, using the preceding description, practice the present invention to its fullest extent. The following detailed examples describe how to prepare the various compounds and/or perform the various syntheses of the invention and are to be construed as merely illustrative, and not limitations of the preceding disclosure in any way whatsoever. Those skilled in the art will promptly recognize appropriate variations from the procedures both as to reactants and as to reaction conditions and techniques.

Preparation 1 3-Amino-5-(methoxycarbonyl)benzoic acid (XVII)

A suspension of mono-methyl 5-nitro-isophthalate (22.5 g, 100 mmol) and palladium on carbon (5%, 2.00 g) in methanol (100 mL) is shaken in a hydrogenation apparatus under hydrogen (50 psi) for 3 hours. The mixture is then filtered through diatomaceous earth and concentrated to give the title compound, NMR (300 MHz, CDCl$_3$) beta 7.67, 7.41, 7.40 and 3.83; MS (ESI−) for C$_9$H$_9$NO$_4$ m/z (M−H)$^-$=194.

Preparation 2 3-Bromo-5-(methoxycarbonyl)benzoic acid (XIX)

A mixture of copper (II) bromide (1.85 g, 8.30 mmol), n-butyl nitrite (1.07 g, 10.4 mmol), and acetonitrile (30 mL) is stirred in a round bottomed flask in a water bath to which a few chunks of ice has been added. 3-Amino-5-(methoxycarbonyl)benzoic acid (XVII, PREPARATION 1, 1.35 g, 6.92 mmol) is added as a slurry in warm acetonitrile (70 mL) over 15 min and the mixture is stirred at 20-25 degrees C. for an additional 2 hour, at which time the mixture is partitioned between dichloromethane and hydrochloric acid (3N). The organic phase is separated and dried over sodium sulfate and concentrated to dryness. Chromatography (silica gel, 125 mL; methanol/dichloromethane, 15/85) and concentration of the appropriate fractions gives a solid which is crytallized from methanol to give the title compound in two crops, NMR (DMSO-d$_6$) delta 3.90, 8.26 and 8.65.

Preparation 3 Methyl 3-bromo-5-[(dipropylamino)carbonyl]benzoate (XXI)

Carbonyl diimidazole (3.0 g, 18 mmol) is added to a solution of 3-bromo-5-(methoxycarbonyl)benzoic acid (XIX, PREPARATION 2, 3.9 g, 15 mmol) in THF (30 mL). The mixture is stirred for 0.5 hours. Dipropylamine (AMINE, 4.2 mL, 30 mmol) is added to the mixture, which is then stirred for 24 hours. The solvent is then removed under reduced pressure and the mixture is partitioned between ethyl acetate and water. The organic phase is then washed with saline, dried over anhydrous magnesium sulfate, filtered, and concentrated. Column chromatography (silica gel; ethyl acetate/hexanes, 15/85) gives the title compound, IR (diffuse reflectance) 2968, 2958, 1714, 1637, 1479, 1440, 1422, 1321, 1310, 1288, 1273, 1252, 889, 772 and 718 cm$^{-1}$; NMR (300 MHz, CDCl$_3$) δ 8.21, 7.96, 7.70, 3.95, 3.46, 3.15, 1.69, 1.57, 1.00 and 0.78; MS (ESI+) for C$_{15}$H$_{20}$BrNO$_3$ m/z (M+H)$^+$=344.1.

Preparation 4 3-Bromo-5-[(dipropylamino)carbonyl]benzoic acid

To a solution of methyl 3-bromo-5-[(dipropylamino)carbonyl]benzoate (XXI, PREPARATION 3, 1.4 g, 4.1 mmol) in THF/water/methanol (4/2/2, 8 mL) is added to lithium hydroxide monohydrate (0.17 g, 4.05 mmol). The mixture is stirred at 20 degrees −25 degrees C. for 1 hour and then solvent is removed under reduced pressure. The residue is dissolved in water (50 mL) and hydrochloric acid (1 N) is added to adjust the pH to about 3. The aqueous mixture is extracted with ethyl acetate and the organic phase is separated and dried over magnesium sulfate to give the title compound. Analytical calculated for C$_{14}$H$_{18}$BrNO$_3$: C, 51.23; H, 5.53; N, 4.27; Br, 24.35. Found: C, 51.37; H, 5.56; N, 4.28.

Preparation 5 Methyl 3-(aminocarbonyl)-5-[(dipropylamino)carbonyl]-benzoate (XXII)

To a mixture of methyl 3-bromo-5-[(dipropylamino)carbonyl]benzoate (XXI, PREPARATION 3, 0.5 g, 1.47 mmol) in dry N-methylpyrrolidinone under a carbon monoxide atmosphere is added palladium (II) acetate (0.017 g, 0.074 mmol), 1,3-bis(diphenylphosphino)propane (0.045 g, 0.11 mmol), hexamethyldisilazane (1.0 mL, 4.7 mmol), and diisopropylethylamine (0.38 g, 2.94 mmol). The mixture is heated at 100 degrees C. for 24 hours. The mixture is cooled to 20-25 degrees C. and partitioned between water and ethyl acetate. The layers are separated and the aqueous phase is backwashed with ethyl acetate. The organic phases are combined and washed three times with saline, dried over anhydrous magnesium sulfate, filtered and concentrated. Column chromatography (silica gel, 75 mL; methanol/methylene chloride, 2.5/97.5) gives the title compound, NMR (CDCl$_3$) delta 0.77, 1.02, 1.57, 1.71, 3.17, 3.49, 3.98, 5.78, 6.34, 8.07, 8.20 and 8.48.

Preparation 6 3-(Aminocarbonyl)-5-[(dipropylamino)carbonyl]benzoic acid (XXIII)

To a mixture of methyl 3-(aminocarbonyl)-5-[(dipropylamino)carbonyl]benzoate (XXII, PREPARATION 5, 0.197 g, 0.64 mmol) in methanol (5.0 mL) is added sodium hydroxide (1N, 3.0 mL). The mixture is stirred at 20-25 degrees C. for 24 hours. The mixture is acidified to about pH 5 with hydrochloric acid (10%). Water (50 mL) is added and the mixture is washed twice with ethyl acetate (2×50 mL). The organic extracts are combined and dried over anhydrous magnesium sulfate and concentrated to give the title compound, NMR (DMSO-d$_6$) delta 0.66, 0.930, 1.48, 1.62, 3.12, 3.35, 7.54, 7.98, 8.22 and 8.51.

Preparation 7 3-Cyano-5-[(dipropylamino)carbonyl]benzoic acid (IX/XXXII)

A mixture of 3-bromo-5-[(dipropylamino)carbonyl]benzoic acid (PREPARATION 4, 0.596 g, 1.82 mmol) and copper nitrile (0.325 g, 3.63 mmol) in N-methylpyrrolidinone (1.5 mL) is stirred at 175 degrees C. for 2.5 hour, at which time the mixture is cooled and partitioned between ethyl acetate and hydrochloric acid (3N). The organic layer is washed twice more with hydrochloric acid (3N) and then twice more with saline which had been acidified with a small amount of hydrochloric acid (3N). The organic layer is dried over magnesium sulfate and concentrated under high vacuum to give the title compound, NMR (CDCl$_3$) delta 0.80, 1.02, 1.60, 1.73, 3.17, 3.51, 7.90, 8.31 and 8.41; an aliquot is crystallized from ethyl ether/dichloromethane/hexane—IR (diffuse reflectance) 3017, 2970, 2937, 2898, 2877, 2473, 2432, 2350, 2318, 2236, 1721, 1608, 1588, 1206 and 1196 cm$^{-1}$.

Preparation 8 3-(Aminocarbonyl)-5-[(dipropylamino)carbonyl]benzoic acid (XXXIII)

A mixture of 3-cyano-5-[(dipropylamino)carbonyl]benzoic acid (IX/XXXII, PREPARATION 7, 0.602 g, 2.19 mmol), potassium carbonate (0.212 g, 1.53 mmol), and acetone (2.5 mL) is stirred at 20-25 degrees C. Water (2.5 mL) and urea-hydrogen peroxide adduct (0.825 g, 8.78 mmol) are added and the mixture is stirred for 15 hours at 20-25 degrees C., at which time additional urea-hydrogen peroxide adduct (0.204 g) is added; after stirring for another 3 hours, an additional 0.205 g of urea-hydrogen peroxide is added. After a total of 39 hours has elapsed, the acetone is removed under reduced pressure and the residue is acidified with hydrochloric acid (3N) to pH=2-4. The mixture is extracted with dichloromethane, the organic layer is separated and washed with hydrochloric acid (0.5 N), and the organic phase is dried with anhydrous magnesium sulfate to a solid. The solid is crystallized from dichloromethane/hexane/methanol to give the title compound, MS (ESI+) for $C_{15}H_{20}N_2O_4$ m/z (M+H)$^+$=293.2.

PREPARATION 9 Methyl 3-[(dipropylamino)carbonyl]-5-nitrobenzoate (XXX)

Carbonyl diimidazole (3.90 g, 24.0 mmol) is added to a mixture of mono-methyl 5-nitro-isophthalate (XXVIII, 4.50 g, 20.0 mmol) in dry THF (50 mL). The mixture is stirred for 0.5 hours. Dipropylamine (3.28 mL, 24.0 mmol) is added slowly to the mixture. The reaction mixture is then stirred for 4 hours. The solvent is removed under reduced pressure and the mixture is partitioned between ethyl acetate and water. The organic phase is separated and washed with saline, dried over anhydrous sodium sulfate, filtered, and concentrated. Column chromatography (silica gel; ethyl acetate/hexanes, 15/85) gives the title compound, NMR (300 MHz, CDCl$_3$) delta 8.88, 8.41, 8.35, 4.00, 3.48, 3.15, 1.72, 1.57, 1.00 and 0.77; MS (ESI+) for $C_{15}H_{20}N_2O_5$ m/z (M+H)$^+$=309.2.

Preparation 10 Methyl 3-amino-5-[(dipropylamino)carbonyl]benzoate (XXXI)

A suspension of methyl 3-[(dipropylamino)carbonyl]-5-nitrobenzoate (XXX, PREPARATION 9, 6.00 g, 20.0 mmol) and palladium on carbon (5%, 0.600 g) in methanol (40 mL) is shaken in a hydrogenation apparatus under hydrogen (45 psi) for 3 hours. The mixture is then filtered through diatomaceous earth and concentrated to give the title compound, NMR (300 MHz, CDCl$_3$) delta 7.27, 6.77, 4.10, 3.82, 3.38, 3.10, 1.62, 1.46, 0.91 and 0.68.

Preparation 11 Methyl 3-(chlorosulfonyl)-5-[(dipropylamino)carbonyl]-benzoate (XXXVII)

Methyl 3-amino-5-[(dipropylamino)carbonyl]benzoate (XXXI, PREPARATION 10, 1.11 g, 4 mmol) is added to a mixture of water (5 mL) and concentrated hydrochloric acid (1 mL). Sodium nitrite (0.276 g, 4 mmol) is added to the mixture slowly at 0 degrees C. The mixture is then added to an acetic acid solution (5 mL) of CuCl$_2$.2H$_2$O saturated with sulfur dioxide. The mixture is stirred for 0.5 hours and poured into ice water. The mixture is extracted with ethyl acetate. The organic phase is separated and washed with saturated sodium bicarbonate, water, and saline and dried over anhydrous sodium sulfate, filtered, and concentrated to give the title compound, NMR (300 MHz, CDCl$_3$) delta 8.69, 8.38, 8.20, 4.01, 3.49, 3.14, 1.72, 1.59, 1.01 and 0.79; MS (ESI+) for $C_{15}H_{20}ClNO_5S$ m/z (M+H)$^+$=362.2.

Preparation 12 Methyl 3-(aminosulfonyl)-5-[(dipropylamino)carbonyl]-benzoate (XXXVIII)

To a solution of methyl 3-(chlorosulfonyl)-5-[(dipropylamino)carbonyl]benzoate (XXXVII, PREPARATION 11, 0.100 g, 0.300 mmol) in dry THF (3 mL) is added ammonia (7 N solution in methanol, 0.214 mL, 1.50 mmol). The mixture is stirred for 18 hours and solvent is then removed. The residue is partitioned between ethyl acetate and water. The organic phase is separate and washed with saline, dried over anhydrous sodium sulfate, filtered, and concentrated to give the title compound, NMR (300 MHz, CDCl$_3$) delta 8.45, 8.07, 8.01, 6.05, 3.93, 3.44, 3.09, 1.67, 1.52, 0.96 and 0.73; MS (ESI+) for $C_{12}H_{22}N_2O_5S$ m/z (M+H)$^+$=343.3.

Preparation 13 3-(Aminosulfonyl)-5-[(dipropylamino)carbonyl]benzoic acid (XXXVIII)

Lithium hydroxide monohydrate (0.011 g, 0.263 mmol) is added to a solution of methyl 3-(aminosulfonyl)-5-[(dipropylamino)carbonyl]benzoate (XXXVIII, PREPARATION 12, 0.090 g, 0.263 mmol) in a mixture of THF/methanol/water (2/1/1, 2 mL). The mixture is stirred at 20-25 degrees C. for 3 hours. The mixture is then diluted with water and hydrochloric acid (1 N) is added to bring the pH to less than 3. The aqueous solution is extracted with ethyl acetate. The organic phase is separated and washed with saline, dried over anhydrous sodium sulfate, filtered and concentrated to give the title compound. $^1$H NMR (300 MHz, CDCl$_3$) delta 10.36 (s, 1H), 8.39 (s, 1H), 8.09 (s, 2H), 6.06 (s, 2H), 3.48 (t, J=7 Hz, 2H), 3.15 (t, J=7 Hz, 2H), 1.71 (m, 2H), 1.55 (m, 2H), 0.97 (t, J=7 Hz, 3H), 0.74 (t, J=7 Hz, 3H). MS (ESI+) for $C_{11}H_{20}N_2O_5S$ 329.2 (M+H)$^+$.

Preparation 14 Methyl 3-[(dipropylamino)carbonyl]-5-(1-pyrrolidinylsulfonyl)-benzoate (XXXVIII)

Following the general procedure of PREPARATION 12 and making non-critical variations but using pyrrolidine (0.347 mL, 4.16 mmol), the title compound is obtained, MS (ESI+) for $C_{19}H_{28}N_2O_5S$ m/z (M+H)$^+$=397.1.

Preparation 15 3-[(Dipropylamino)carbonyl]-5-(1-pyrrolidinylsulfonyl)benzoic acid (XXXIX)

Following the general procedure of PREPARATION 13 and making non-critical variations, the title compound is obtained, MS (ESI+) for $C_{18}H_{26}N_2O_5S$ m/z (M+H)$^+$=383.3.

Preparation 16 Methyl 3-[(dipropylamino)carbonyl]-5-[(methylamino)-sulfonyl]benzoate (XXXVIII)

Following the general procedure of PREPARATION 12 and making non-critical variations but using methyl amine (2 N solution in THF, 0.692 mL, 1.38 mmol), the title compound is obtained, MS (ESI+) for $C_{16}H_{24}N_2O_5S$ m/z (M+H)$^+$=357.1.

Preparation 17 3-[(Dipropylamino)carbonyl]-5-[(methylamino)-sulfonyl]benzoic acid (XXXIX)

Following the general procedure of PREPARATION 13 and making non-critical variations, the title compound is obtained, MS (ESI+) for $C_{15}H_{22}N_2O_5S$ m/z (M+H)$^+$=343.1.

Preparation 18 Methyl 3-[(dimethylamino)sulfonyl]-5-[(dipropylamino)-carbonyl]benzoate (XXXVIII)

Following the general procedure of PREPARATION 12 and making non-critical variations but using dimethylamine (2 N solution in THF, 0.692 mL, 1.38 mmol), the title compound is obtained, MS (ESI+) for $C_{17}H_{26}N_2O_5S$ m/z $(M+H)^+= 371.1$.

Preparation 19 3-[(Dimethylamino)sulfonyl]-5-[(dipropylamino)carbonyl]-benzoic acid (XXXIX)

Following the general procedure of PREPARATION 13 and making non-critical variations, the title compound is obtained, MS (ESI+) for $C_{16}H_{24}N_2O_5S$ m/z $(M+H)^+=357.1$.

Preparation 20 Methyl 3-[(dipropylamino)carbonyl]-5-ethylbenzoate (IX)

Ethylboronic acid (0.800 g, 10.8 mmol), dichlorobis(triphenylphosphine)-palladium(II) (0.252 g, 0.360 mmol), potassium carbonate (2.50 g, 18.0 mmol) and lithium chloride (0.151 g, 3.60 mmol) are added to a mixture of methyl 3-bromo-5-[(dipropylamino)carbonyl]benzoate (1.23 g, 3.60 mmol) in dry DMF (20 mL). The mixture is heated at 100 degrees C. for 18 hours. The mixture is then partitioned between ethyl acetate and water. The phases are separated and the ethyl acetate phase is washed with saline, dried over sodium sulfate and concentrated. The concentrate is column chromatographed (silica gel; ethyl acetate/hexanes, 15/85) to give the title compound, MS (ESI+) for $C_{17}H_{25}NO_3$ m/z $(M+H)^+=292.2$.

Preparation 21 3-[(Dipropylamino)carbonyl]-5-ethylbenzoic acid (IX)

Lithium hydroxide monohydrate (0.0680 g, 1.6 mmol) is added to a mixture of methyl 3-[(dipropylamino)carbonyl]-5-ethylbenzoate (PREPARATION 20, 0.450 g, 1.6 mmol) in a mixture of THF/methanol/water (2/1/1, 8 mL). The mixture is stirred at 20-25 degrees C. for 3 hours. The mixture is then diluted with water (20 mL) and hydrochloric acid (1 N) is added to bring the pH to less than 3. The aqueous mixture is extracted with ethyl acetate. The organic phase is separated and washed with saline, dried over anhydrous magnesium sulfate, filtered and concentrated to give the title compound, MS (ESI+) for $C_{16}H_{23}NO_3$ m/z $(M+H)^+=278.2$.

Preparation 22 Piperidine-2-(N-isobutyl)carboxamide

Boc-piperidine-carboxamide (95 mg, 0.28 mmol, Aldrich) was dissolved in dry $CH_2Cl_2$ (2 mL) at room temperature, and EDC was added followed by 50 mg of the isobutyl amine. The reaction was run at room temperature for 6 h. The solvent was removed and the residue was chromatographed to obtain desired Boc-piperidine-carboxamide which was deprotected using 50% TFA/$CH_2Cl_2$. The residue was purified by flash chromatography (10% MeOH/$CH_2Cl_2$) to give desired amide Rf=0.4 (10% MeOH/$CH_2Cl_2$) in 80% yield. The amide thus obtained was used in CHART D for the opening of the epoxide. Thus, to the piperidine-carboxamide (1.5 eq.) in isopropanol (about 5 mL) lithium perchlorate was added (1.2 eq) followed by epoxide (1 eq). The mixture was stirred at 800 degrees C. in a sealed tube for 15 hours. The product was worked up using organic and aqueous sodium carbonate, brine and dried with magnesium sulfate. The solvent was removed under pressure and resulted in a crude mixture that was purified by column chromatography to yield the desired product in 60%. MH+ 629.9.

Preparation 23 N1-[(1S,2R)-1-(3,5-difluorobenzyl)-2-hydroxy-3-(4-methyl-1-piperazinyl)propyl]-5-methyl-N3,N3-dipropylisophthalamide Following the general procedure of PREPARATION 22 and making non-critical variations, the title compound was similarly prepared from comercially available N-methyl-piperazine in 75% yield after chromatography. MH+ 545.4.

Preparation 24 N1-{(1S,2R)-1-benzyl-3-[4-(4-fluorophenyl)-1-piperazinyl]-2-hydroxypropyl}-N3,N3-dipropylisophthalamide Following the general procedure of PREPARATION 22 and making non-critical variations, the title compound was similaly prepared from commercially available N-(4-fluorophenyl)-piperazine in 60% yield after chromatography. MH+ 800.8.

Preparation 25 N1-[(1S,2R)-1-benzyl-2-hydroxy-3-(1,3-thiazolidin-3-yl)propyl]-N3,N3-dipropylisophthalamide Following the general procedure of PREPARATION 22 and making non-critical variations, the title compound was similarly prepared from commercially available thiazolidine in 50% yield after chromatography. MH+ 597.6.

Example 1 tert-Butyl (1S)-3-bromo-1-(3,5-difluorobenzyl)-2-oxopropylcarbamate (III)

N-methyl-morpholine (5.83 Ml, 53 mmole, 1.05 eq.) is added to (2S)-2-[(tert-butoxycarbonyl)amino]-3-(3,5-difluorophenyl)propanoic acid (II, 15 g, 50 mmole) in THF (100 mL) and the reaction is cooled to −78 degrees C. Isobutyl chloroformate (6.87 mL, 53 mmole, 1.05 eq.) is added rapidly. The cold bath is then removed and the mixture stirred for 1 hour. The reaction is monitored by TLC to insure completion of the reaction and the mixture is then filtered and washed with dry THF (50 ml) and kept cold in the filtered flask at −20 degrees C.

In an ice-salt bath is placed a 500 ml graduate cylinder containing ether (200 mL) and aqueous potassium hydroxide (40%, 60 ml). 1-Methyl-3-nitro-1-nitrosoguanidine (5.6 g, 106 mmole, 2.1 eq.) is added slowly with stirring and temperature kept below 0 degrees C. The mixture turned yellow and the bubbling lasted for 10 minutes. The stirring is stopped and without mixing the layers, the top diazomethane ethereal layer is transferred with non-ground tip pipette into the stirred mixed anhydride mixture at −20 degrees C. The reaction is monitored by TLC (ethyl acetate/hexane, 50/50; $R_f$=0.69). After 1 hour nitrogen is then bubbled into the mixture. The solvent is removed under reduced pressure (with heat) and the mixture is partitioned between ether and water. The phases are separated, the organic phase is washed with bicarbonate, saline, dried over anhydrous sodium sulfate and solvent removed under reduced pressure (with heat). The residue is dissolved in ether (100 mL) and hydrobromic acid (48%, 15 mL, 135 mmole, 2.7 eq,) is added at −20 degrees C., the cold bath is removed and the mixture is stirred for another 0.5 hours. The reaction is monitored by TLC (ethyl acetate/hexane, 50/50; $R_f$=0.88). The mixture is partitioned between ether and water, washed with bicarbonate, saline, dried over anhydrous sodium sulfate and the solvent removed. The residue is recrystallized from ethanol to give the title compound, TLC (ethyl acetate/hexane, 50/50) $R_f$=0.88; MS (MH$^+$)= 379.3.

Example 2 tert-Butyl (1S,2S)-3-bromo-1-(3,5-difluorobenzyl)-2-hydroxypropylcarbamate (IV)

Sodium borohydride (1.32 g, 34.9 mmole, 1.1 eq.) is added to tert-Butyl (1S)-3-bromo-1-(3,5-difluorobenzyl)-2-oxo-propylcarbamate (III, EXAMPLE 1, 12 g, 31.75 mmole) dissolved in absolute alcohol (500 mL) at −78 degrees C. The reaction mixture is stirred for 0.5 hour and monitored by TLC (ethyl acetate/hexane, 20/80; $R_f$=0.2). The mixture is quenched with water (10 mL) and the solvent removed under reduced pressure with heat (not exceeding 30 degrees C.) to dryness. The solid is partitioned between dichloromethane and water, washed with saline, dried over anhydrous sodium sulfate. The solvent is removed under reduced pressure to give the title compound, TLC (ethyl acetate/hexane, 20/80) $R_f$=0.2; MS (MH$^+$)=381.2.

Example 3 tert-Butyl (1S)-2-(3,5-difluorophenyl)-1-[(2S)-oxiranyl]ethylcarbamate (V)

tert-Butyl (1S,2S)-3-bromo-1-(3,5-difluorobenzyl)-2-hydroxypropylcarbamate (IV, EXAMPLE 2) is dissolved in absolute alcohol (150 mL) and ethyl acetate (100 mL) and potassium hydroxide (2.3 g, 34.9 mmole, 1.1 eq.) in ethyl alcohol (85%, 5 mL) is added at −20 degrees C. The cold bath is then removed and the mixture stirred for 0.5 hour. The reaction is monitored by TLC (ethyl acetate/hexane, 20/80). When the reaction is complete, it is diluted with dichloromethane and extracted, washed with water, saline, dried over anhydrous sodium sulfate and the solvent removed under reduced pressure. The crude material is purified by flash chromatography on silica gel to give the title compound, TLC (ethyl acetate/hexane, 20/80) $R_f$=0.3; MS (MH$^+$)=300.4.

Example 4

6-({[[(2S,3S)-4-(3,5-difluorophenyl)-3-({3-[(dipropylamino) carbonyl]benzoyl}amino)-2-hydroxybutyl](ethyl)amino]carbonyl})hexanoic acid The compound XXX.1 of CHART A.1, where Protecting Group=tert-butoxy-carbonyl, $R_1$=CH$_2$-(3,5-diF phenyl), $R_{C-A}$=ethyl, (52 mg, 0.15 mmol) was combined with suberic acid monomethyl ester, HO$_2$C—(CH$_2$)$_5$CO$_2$Me, (Aldrich, 30 mg, 0.16 mmol) in dry DMF (2 mL) at 0 degrees C. Triethylamine (0.06 mL, 0.43 mmol), 1-hydroxybenzo-triazole hydrate (HOBt, 30 mg, 0.22 mmol), and 1-(3-dimethylamino-propyl)-3-ethylcarbodiimide hydrochloride (EDC, 44 mg, 0.23 mmol) were added in succession. This mixture was stirred at 0 degrees C. for 5 min, then allowed to warm to about 25 degrees C. over 22 hours, subsequently the reaction mixture was diluted with 10% aqueous citric acid. The mixture was extracted with EtOAc (3×). The combined organic extracts were washed (saturated NaHCO$_3$, saturated NaCl), dried (MgSO$_4$), filtered and concentrated under reduced pressure. The residue was purified by flash chromatography (EtOAc/hexanes elution) to give XXX.2 (where X=—C(O)— and $R_C$=—(CH$_2$)$_5$CO$_2$Me) MH+: 515.1.

This disubstituted amino alcohol (XXX.2, 63 mg, 0.12 mmol) was dissolved in trifluoroacetic acid (1 mL) at about 25 degrees C., and stirred for 1 hour, whereupon the mixture was concentrated under vacuum, and the residue was used without further purification.

N,N-Dipropylisophthalamic acid (39 mg, 0.16 mmol) was dissolved in dry DMF (1 mL) at 0 degrees C. A solution of the above deprotected amino alcohol (XXX.3) and triethylamine (0.07 mL, 0.50 mmol) in DMF (1 mL) was added, followed by HOBt (33 mg, 0.24 mmol) and EDC (48 mg, 0.25 mmol) in succession. This mixture was stirred at 0 degrees C. for 5 min, then allowed to warm to about 25 degrees C. over 1.25 hours, whereupon the reaction mixture was diluted with 10% aqueous citric acid. The mixture was extracted with EtOAc (3×). The combined organic extracts were washed (saturated NaHCO$_3$, saturated NaCl), dried (MgSO$_4$), filtered and concentrated under reduced pressure. The residue was purified by flash chromatography (MeOH/CH$_2$Cl$_2$ elution): MH+: 646.4.

The above ester alcohol (XXX.4, 52 mg, 0.081 mmol) was dissolved in THF/MeOH/H$_2$O (1:1:1, 3 mL total), and LiOH.H$_2$O (184 mg, 4.4 mmol) was added with stirring at about 25 degrees C. After 2 hours, the reaction mixture was cooled to 0 degrees C., and acidified to pH 2 using aqueous 1 N NaHSO$_4$. The aqueous mixture was diluted with water (10 mL), and extracted with 3:1 CHCl$_3$/iPrOH (3×). The combined organic layers were dried (MgSO$_4$), filtered and concentrated under reduced pressure. The residue was purified by flash chromatography (MeOH/CH$_2$Cl$_2$ elution) to provide 6-({[[(2S,3S)-4-(3,5-difluorophenyl)-3-({3-(dipropylamino)carbonyl]benzoyl}amino)-2-hydroxybutyl) (ethyl)amino]carbonyl}) hexanoic acid. MH+: 632.3.

Example 5

6-({[[(2S,3S)-4-(3,5-difluorophenyl)-3-({3-[(dipropylamino) carbonyl]benzoyl}amino)-2-hydroxybutyl](ethyl)amino]carbonyl}amino)hexanoic acid The compound XXX.1 as described above in Example 1 (95 mg, 0.28 mmol) was dissolved in dry CH$_2$Cl$_2$ (2 mL) at room temperature, and ethyl 6-isocyanatohexanoate (Lancaster, 0.06 mL, 0.33 mmol) was added dropwise by syringe. After 45 min, additional isocyanate (0.02 mL, 0.11 mmol) was added to the mixture. After 10 min, MeOH (1 mL) was added, and the reaction mixture was concentrated under vacuum. The residue was purified by flash chromatography (MeOH/CH$_2$Cl$_2$ elution) to give XXX.2 where X=—C(O)NH— and $R_C$=—(CH$_2$)$_5$CO$_2$Me.: $R_f$=0.38 (10% MeOH/CH$_2$Cl$_2$).

The subsequent deprotection and coupling procedures proceeded according to the analogous steps in Example 1 with non-critical variations. The product (XXX.5) was purified by flash chromatography (MeOH/CH$_2$Cl$_2$ elution) to provide 6-({[[(2S,3 S)-4-(3,5-difluorophenyl)-3-({3-[(dipropylamino)carbonyl]benzoyl}amino)-2-hydroxybutyl](ethyl)amino]carbonyl}amino)hexanoic acid: MH+: 633.5.

Example 6

N¹-[(1S,2S)-3-[(butylsulfonyl)(ethyl)amino]-1-(3,5-difluorobenzyl)-2-hydroxypropyl]-5-methyl-N³,N³-dipropylisophthalamide The epoxide of Example 3 was ring-opened by reactioni with N-ethyl butanesulfonamide as depicted in CHART C. The synthesis of N-ethyl butanesulfonamide was based on the literature procedure *Syn. Lett.* 1997, 4, 375-377, briefly it was prepared in a reaction between 1-butanesulfonyl chloride (1.57 g, 10 mM) and ethylamine (2M solution in THF, 15 mL, 30 mM) in 15 mL of dry ether and in the presence of Et3N at −50° C. After addition the temperature was increased slowly during one hour to about 25 degrees C. The crude product was dissolved in ice-cold water (100 mL) and neutralized by addition of 2N HCl. The water layer was extracted (5 times) with dichloromethane, washed with water, dried and concentrated. The reaction of epoxide (2) with sulfonamide (1) was carried out in isopropanol at 80 degrees C. for 15 hours in the presence of LiClO$_4$. Cleavage of the Boc protecting group and subsequent coupling of the 5-MePHTH acid was accomplished using standard methods as described above, to provide N'-[(1S,2S)-3-[(butylsulfonyl)(ethyl)amino]-1-(3,5-difluorobenzyl)-2-hydroxypropyl]-5-methyl-N³,N³-dipropylisophthalamide. MH+~610.3

CHART A

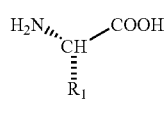

(1)

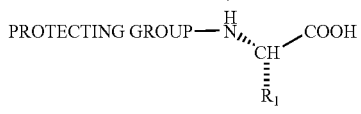

(2)

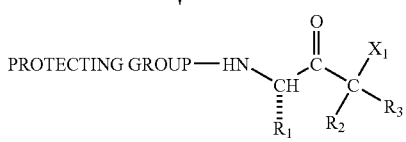

(III)

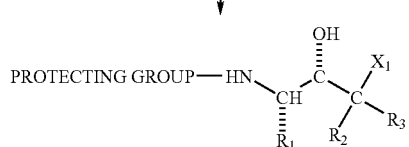

(IV)

-continued

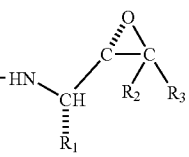

(V)

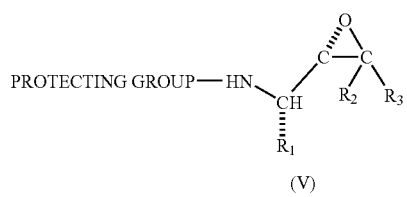

(V)

+

(R$_C$)(R$_{C-A}$)NH (including N-rings) or R$_C$—NH$_2$ (VI)

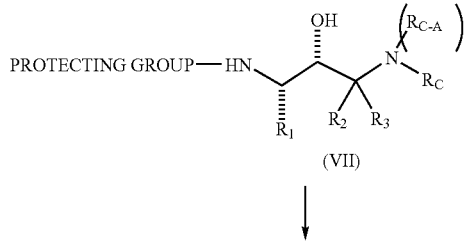

(VII)

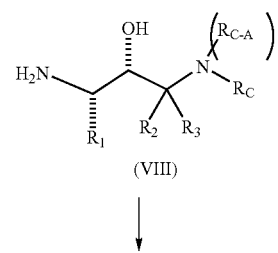

(VIII)

R$_N$X (X═Cl, Br, I) R$_{N-1}$CO$_2$H, R$_{N-1}$SO$_2$—X, R$_N$—OTs, etc.

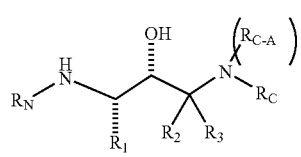

Ii

CHART A-1
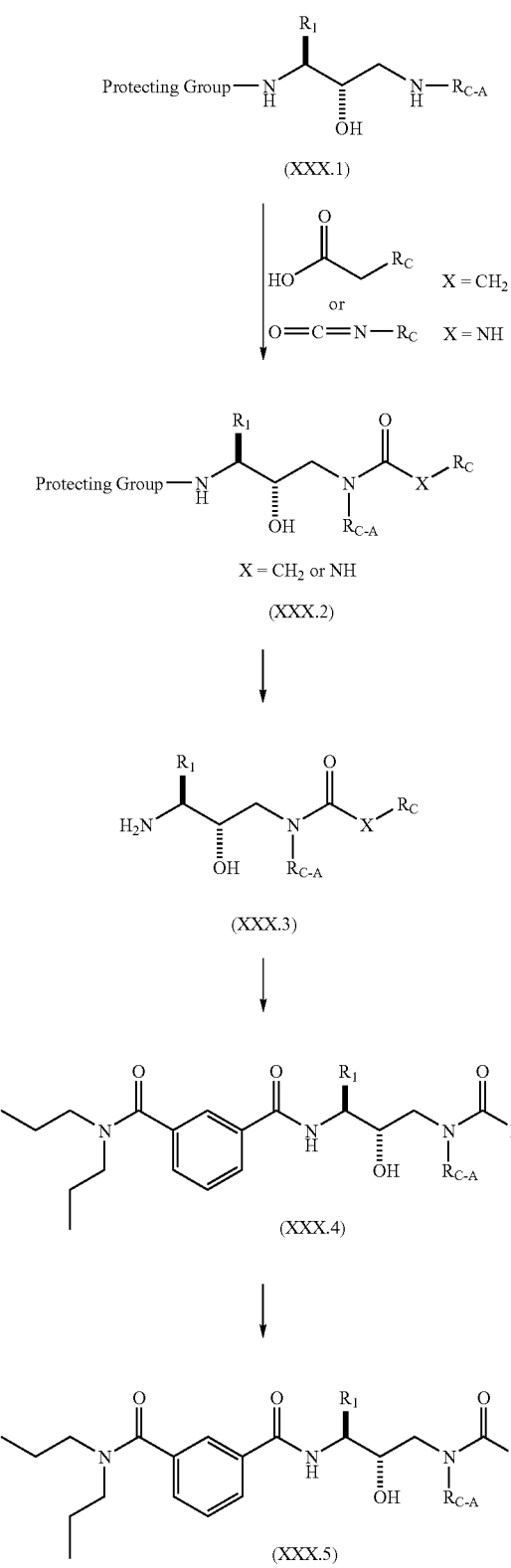
CHART B
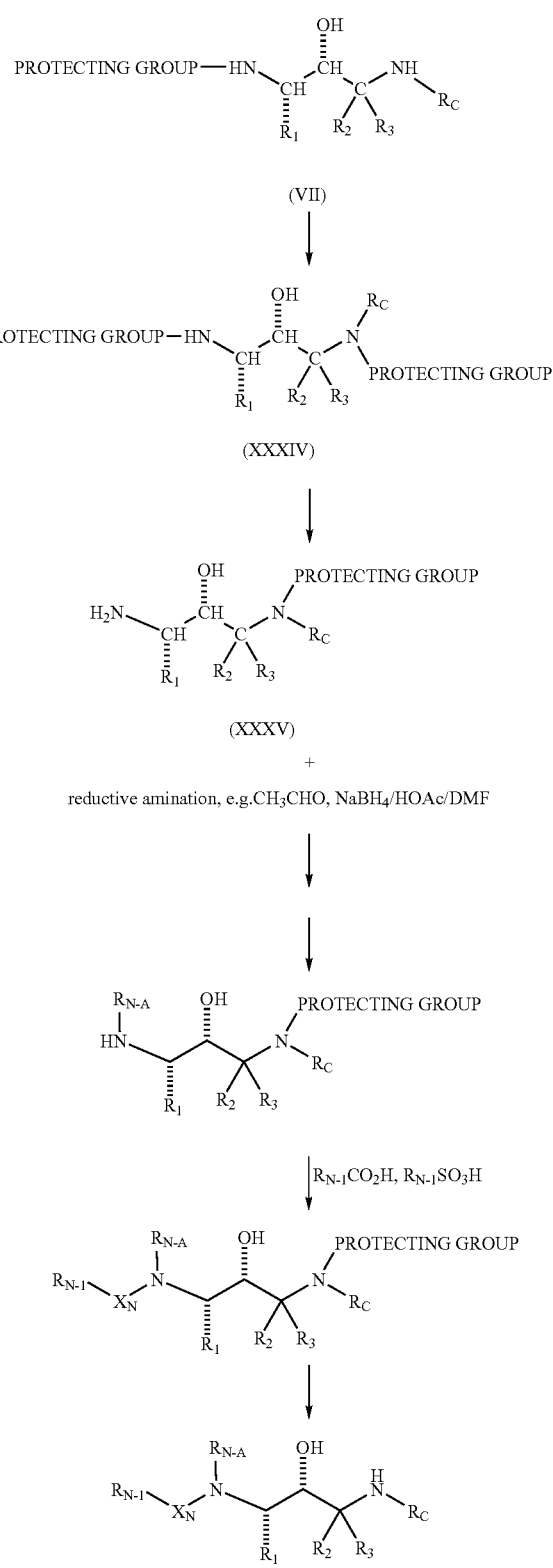

CHART C
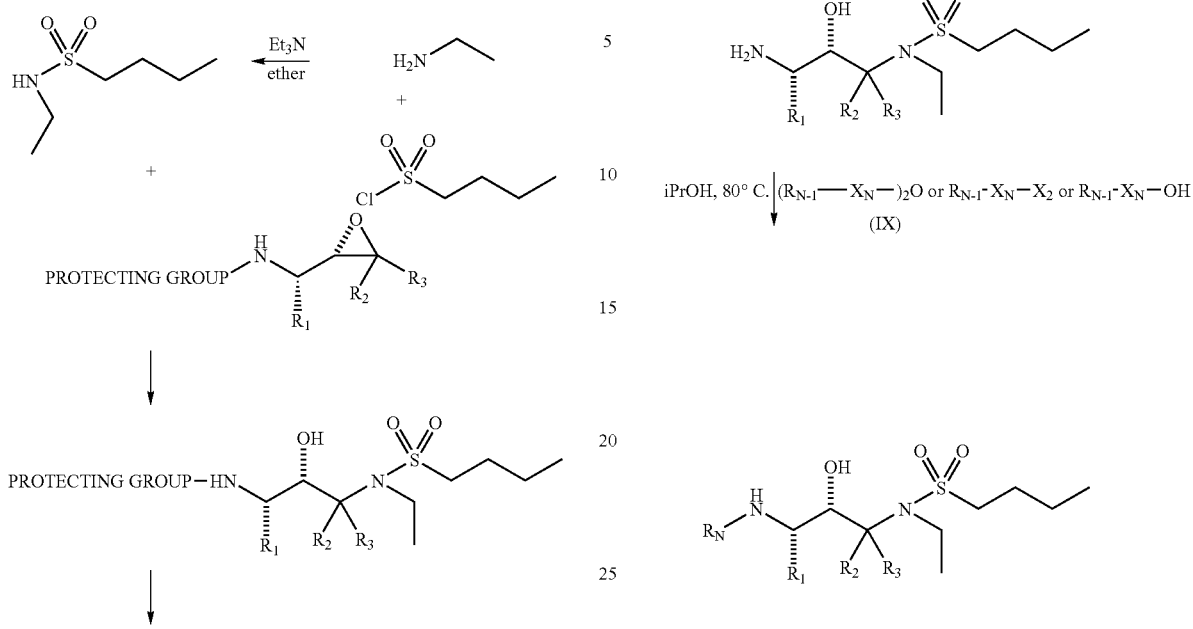
CHART D
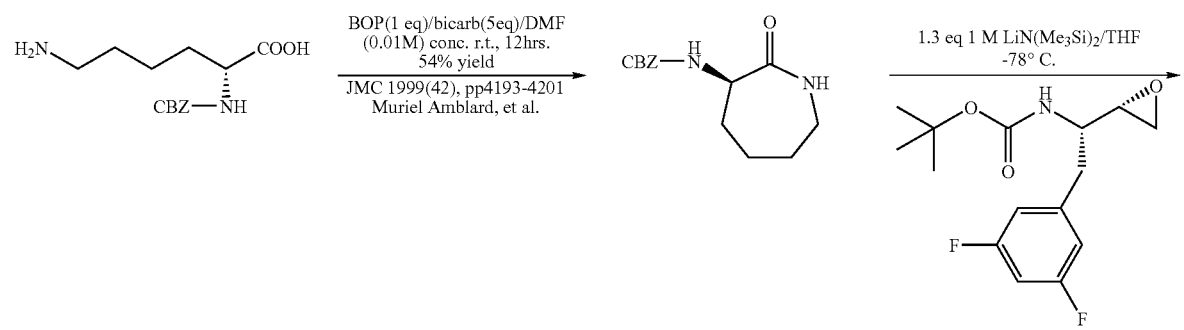
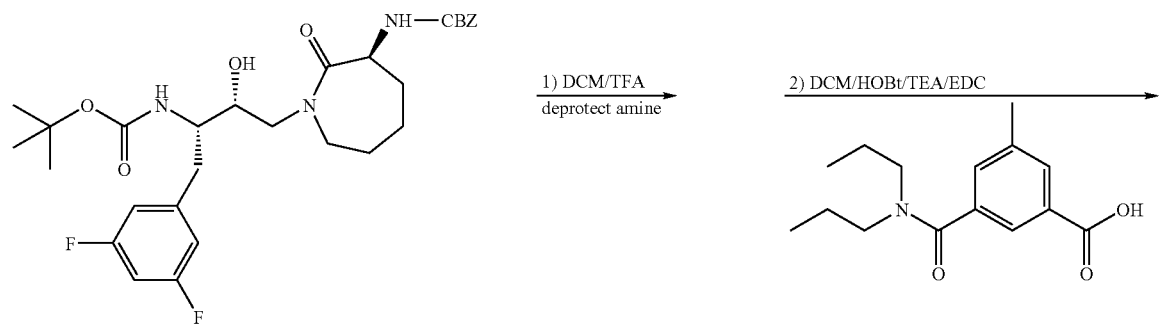

3) [H2]/Pd  4) n—propyl—Br / isopropylamine
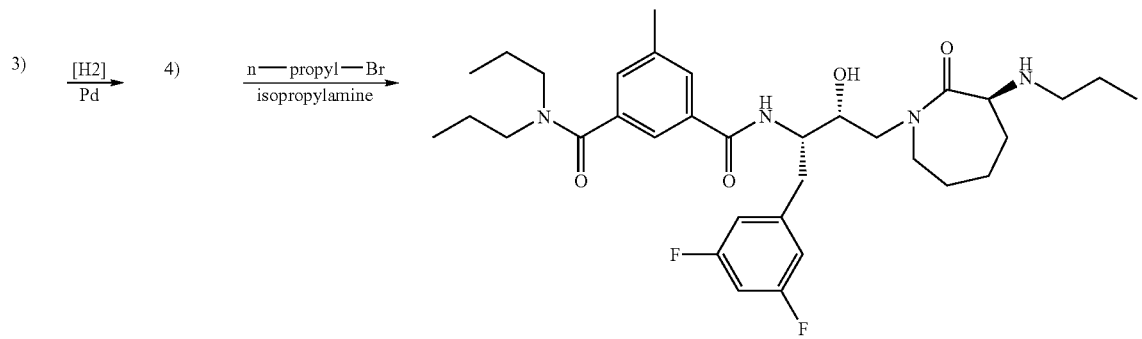
CHART E
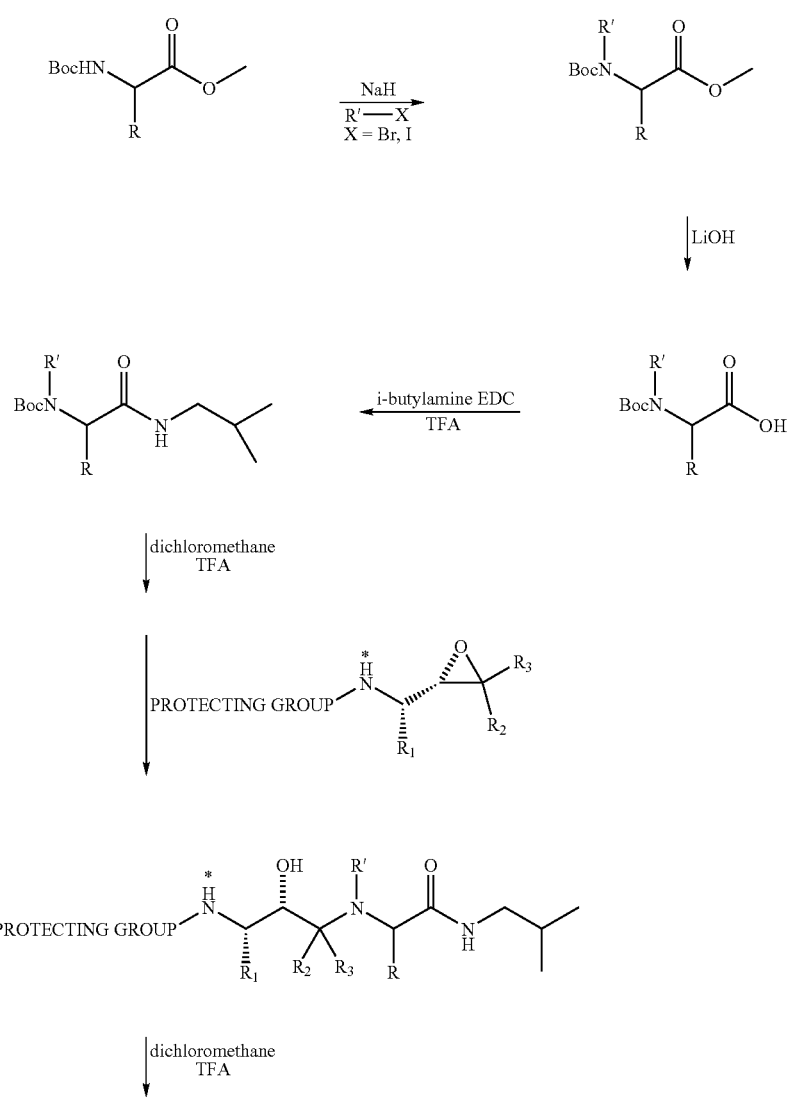

-continued
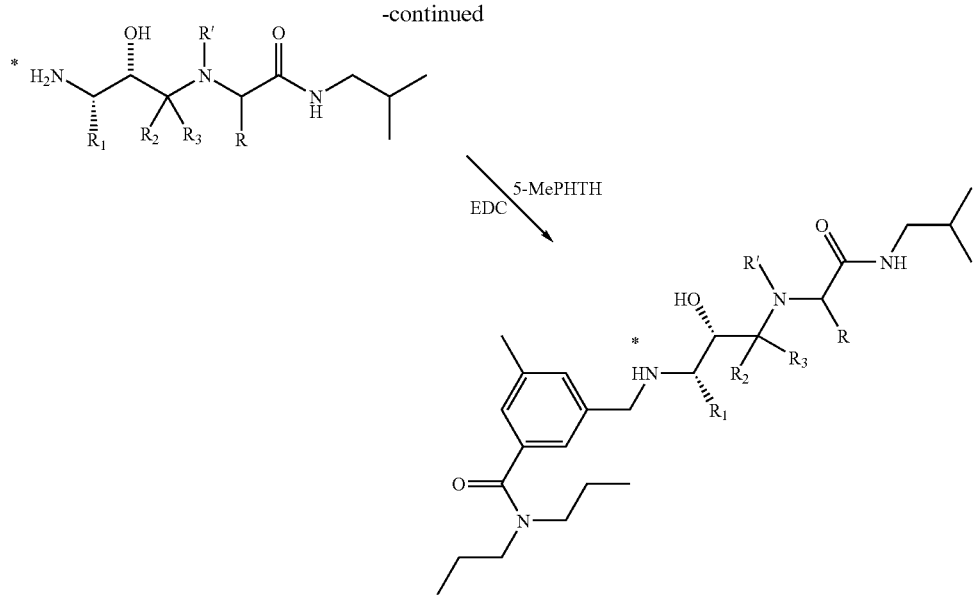
CHART F
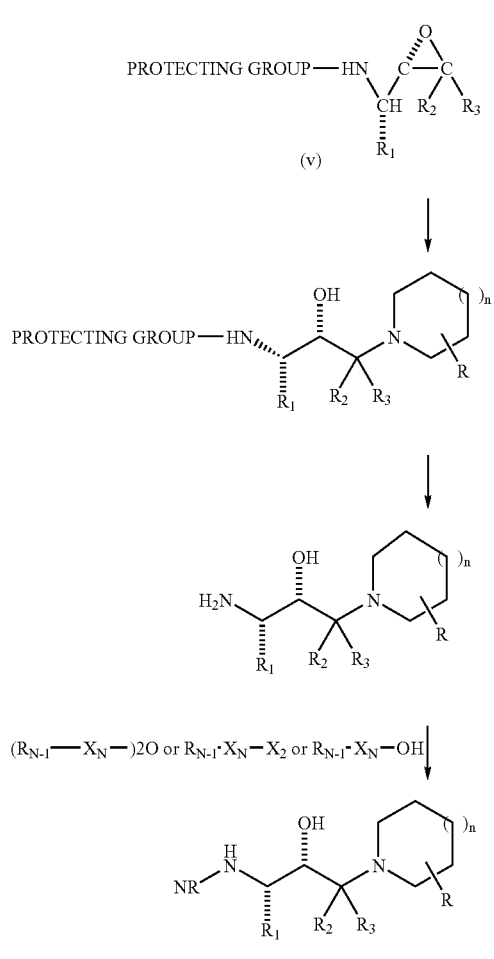
CHART G
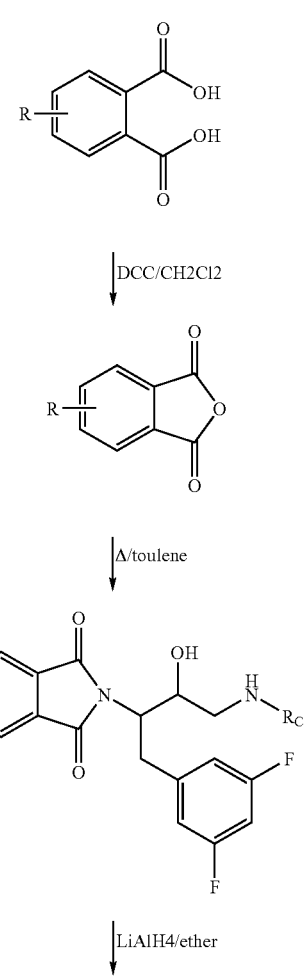

-continued
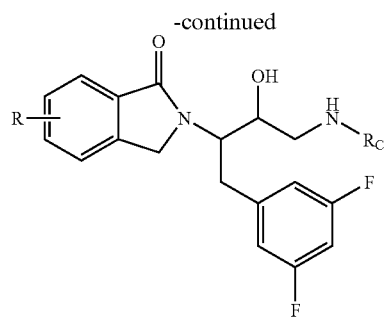
CHART H
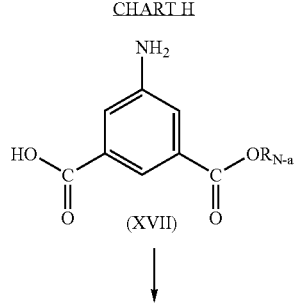
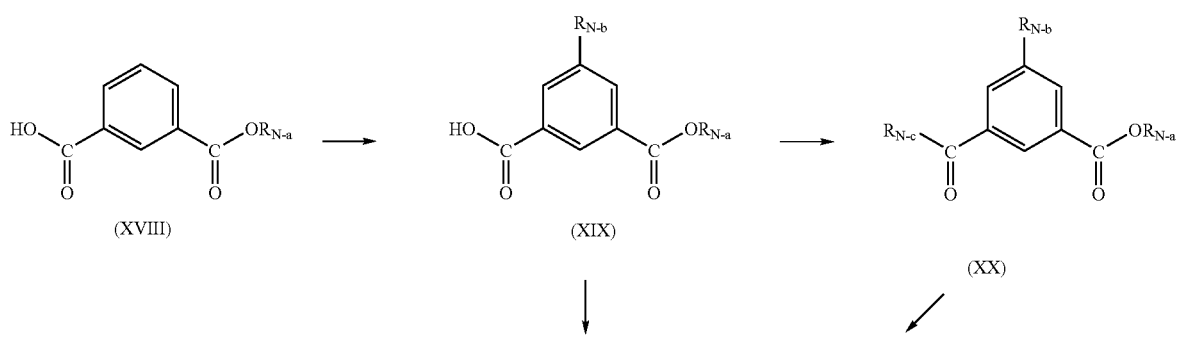
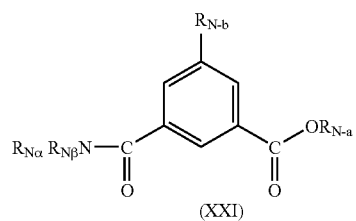

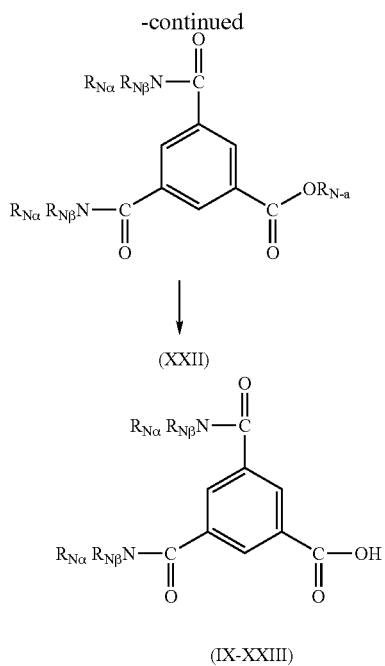
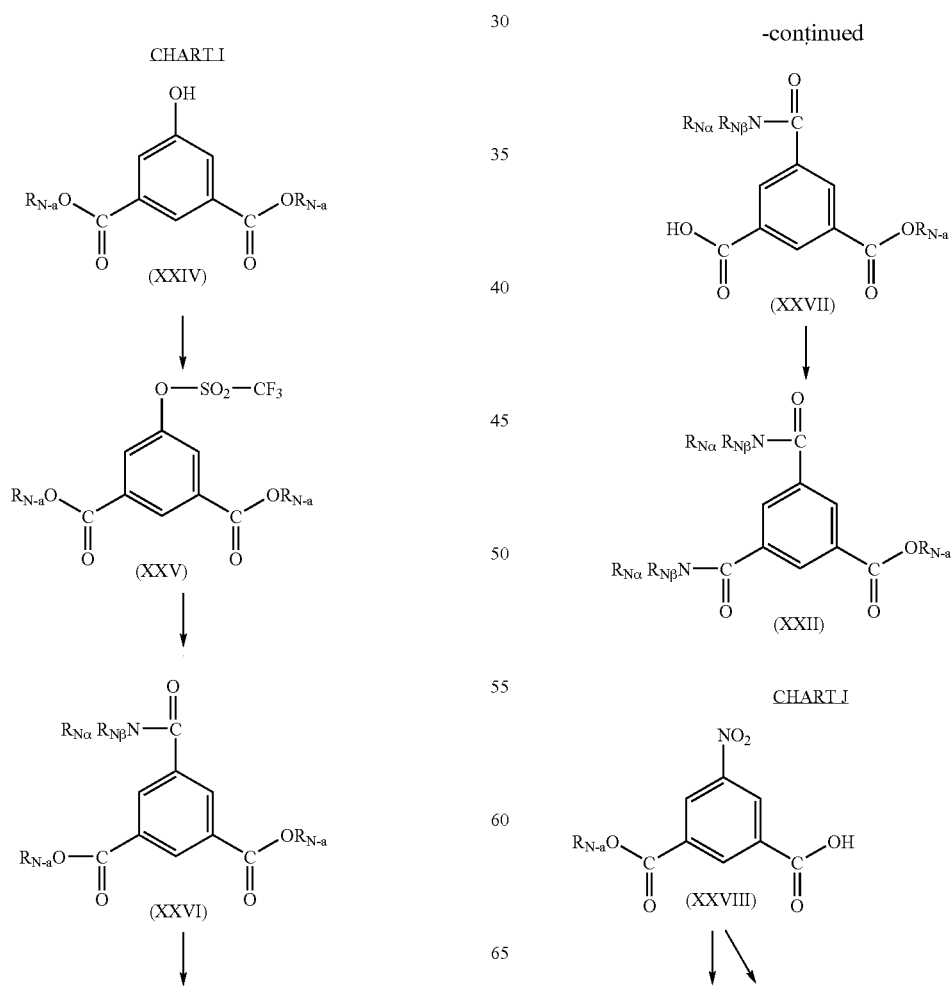
CHART I

-continued
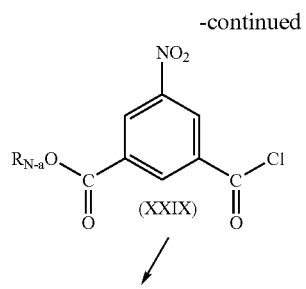
(XXIX)
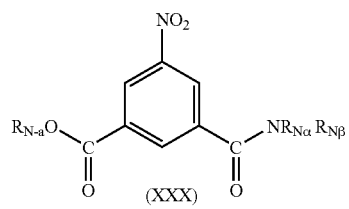
(XXX)
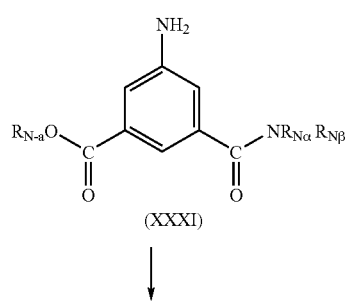
(XXXI)
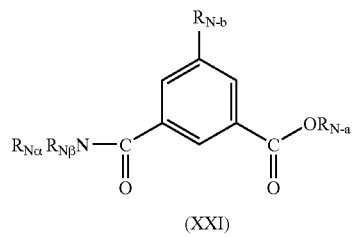
(XXI)
CHART K
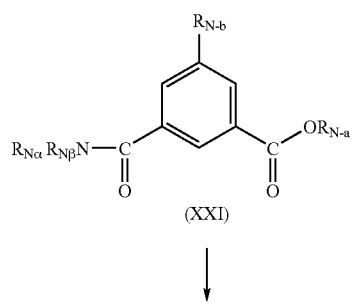
(XXI)
-continued
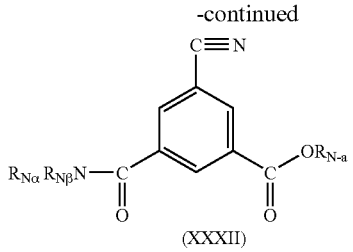
(XXXII)
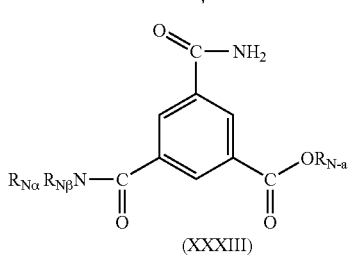
(XXXIII)
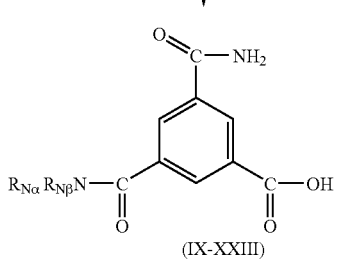
(IX-XXIII)
CHART L
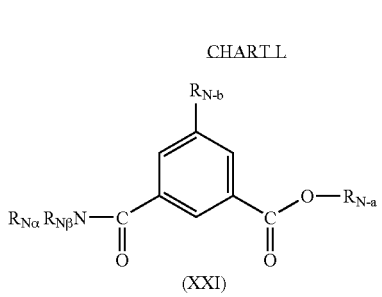
(XXI)
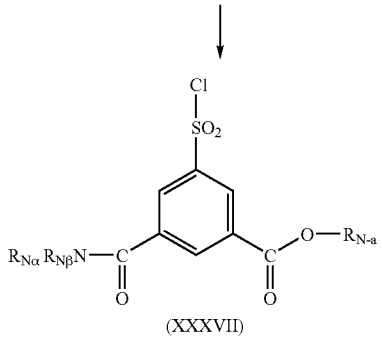
(XXXVII)

-continued
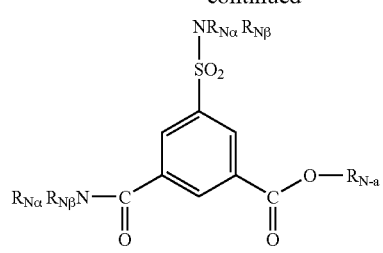
(XXXVIII)
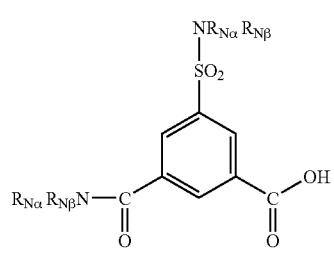
(IX-XXXIX)
CHART M
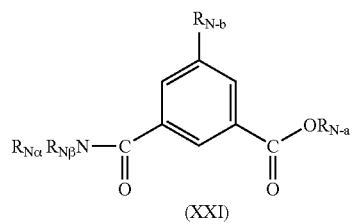
(XXI)
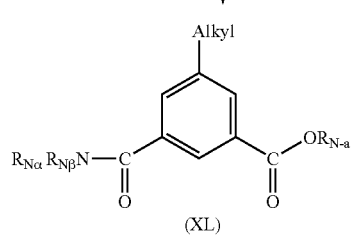
(XL)
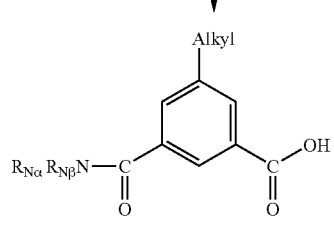
(IX-XLI)
CHART N
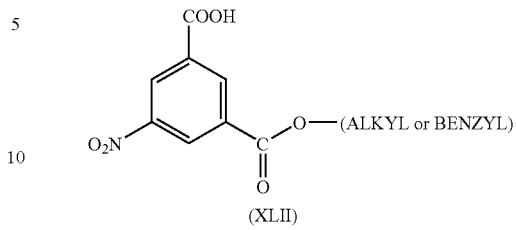
(XLII)
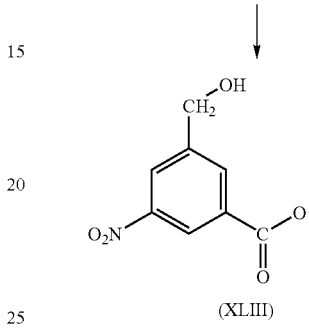
(XLIII)
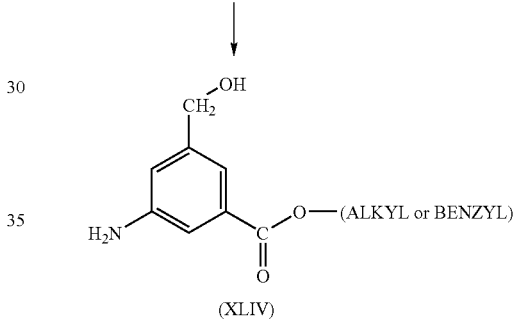
(XLIV)
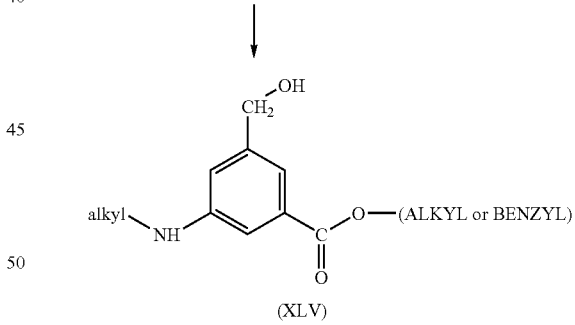
(XLV)
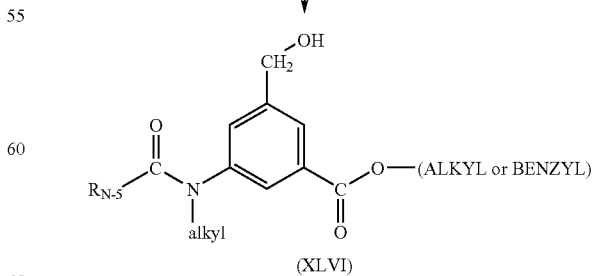
(XLVI)

CHART O
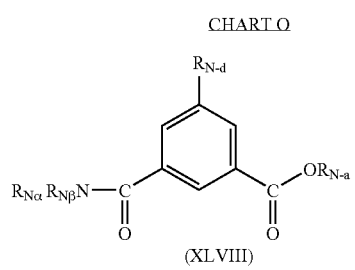
(XLVIII)
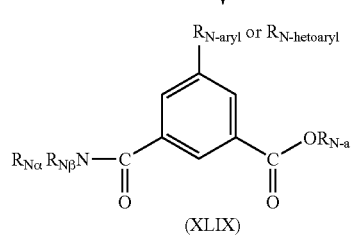
(XLIX)
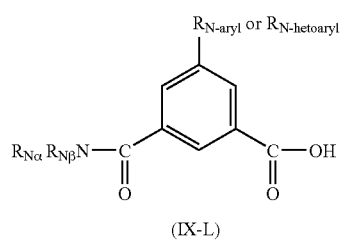
(IX-L)
CHART P
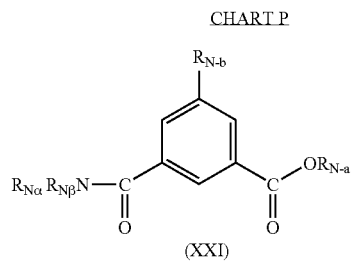
(XXI)
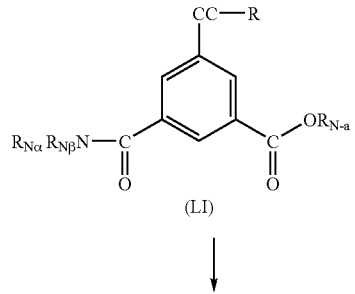
(LI)
-continued
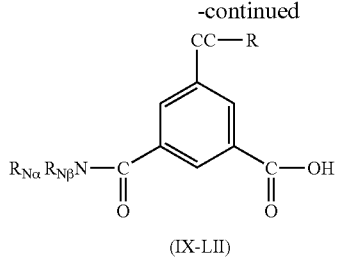
(IX-LII)
CHART U
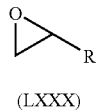
(LXXX)
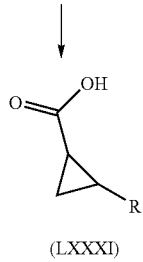
(LXXXI)
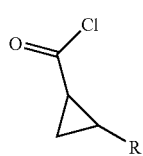
(LXXXII)
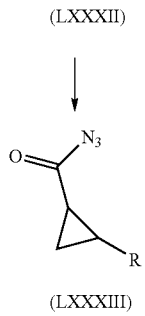
(LXXXIII)
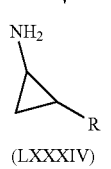
(LXXXIV)

CHART V

CHART W

CHART X

CHART Y

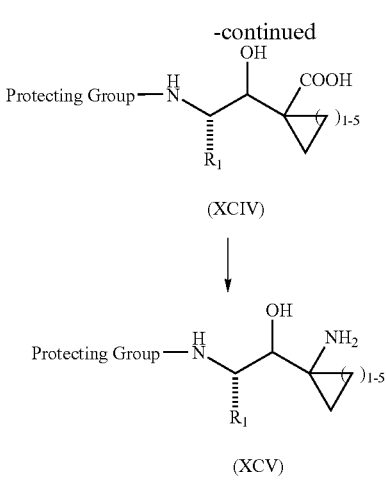

(XCIV)

↓

(XCV)

BIOLOGICAL EXAMPLES

Example A

Enzyme Inhibition Assay

The compounds of the invention are analyzed for inhibitory activity by use of the MBP-C125 assay. This assay determines the relative inhibition of beta-secretase cleavage of a model APP substrate, MBP-C125SW, by the compounds assayed as compared with an untreated control. A detailed description of the assay parameters can be found, for example, in U.S. Pat. No. 5,942,400. Briefly, the substrate is a fusion peptide formed of maltose binding protein (MBP) and the carboxy terminal 125 amino acids of APP-SW, the Swedish mutation. The beta-secretase enzyme is derived from human brain tissue as described in Sinha et. al, 1999, *Nature* 40:537-540) or recombinantly produced as the full-length enzyme (amino acids 1-501), and can be prepared, for example, from 293 cells expressing the recombinant cDNA, as described in WO00/47618.

Inhibition of the enzyme is analyzed, for example, by immunoassay of the enzyme's cleavage products. One exemplary ELISA uses an anti-MBP capture antibody that is deposited on precoated and blocked 96-well high binding plates, followed by incubation with diluted enzyme reaction supernatant, incubation with a specific reporter antibody, for example, biotinylated anti-SW192 reporter antibody, and further incubation with streptavidin/alkaline phosphatase. In the assay, cleavage of the intact MBP-C125SW fusion protein results in the generation of a truncated amino-terminal fragment, exposing a new SW-192 antibody-positive epitope at the carboxy terminus. Detection is effected by a fluorescent substrate signal on cleavage by the phosphatase. ELISA only detects cleavage following Leu 596 at the substrate's APP-SW 751 mutation site.

Specific Assay Procedure:

Compounds are diluted in a 1:1 dilution series to a six-point concentration curve (two wells per concentration) in one 96-plate row per compound tested. Each of the test compounds is prepared in DMSO to make up a 10 millimolar stock solution. The stock solution is serially diluted in DMSO to obtain a final compound concentration of 200 micromolar at the high point of a 6-point dilution curve. Ten (10) microliters of each dilution is added to each of two wells on row C of a corresponding V-bottom plate to which 190 microliters of 52 millimolar NaOAc, 7.9% DMSO, pH 4.5 are pre-added. The NaOAc diluted compound plate is spun down to pellet precipitant and 20 microliters/well is transferred to a corresponding flat-bottom plate to which 30 microliters of ice-cold enzyme-substrate mixture (2.5 microliters MBP-C125SW substrate, 0.03 microliters enzyme and 24.5 microliters ice cold 0.09% TX100 per 30 microliters) is added. The final reaction mixture of 200 micromolar compound at the highest curve point is in 5% DMSO, 20 millimolar NaAc, 0.06% TX100, at pH 4.5.

Warming the plates to 37 degrees C. starts the enzyme reaction. After 90 minutes at 37 degrees C., 200 microliters/well cold specimen diluent is added to stop the reaction and 20 microliters/well is transferred to a corresponding anti-MBP antibody coated ELISA plate for capture, containing 80 microliters/well specimen diluent. This reaction is incubated overnight at 4 degrees C. and the ELISA is developed the next day after a 2 hour incubation with anti-192SW antibody, followed by Streptavidin-AP conjugate and fluorescent substrate. The signal is read on a fluorescent plate reader.

Relative compound inhibition potency is determined by calculating the concentration of compound that showed a fifty percent reduction in detected signal ($IC_{50}$) compared to the enzyme reaction signal in the control wells with no added compound. In this assay, the compounds of the invention exhibited an $IC_{50}$ of less than 50 micromolar.

Example B

Cell Free Inhibition Assay Utilizing a Synthetic APP Substrate

A synthetic APP substrate that can be cleaved by beta-secretase and having N-terminal biotin and made fluorescent by the covalent attachment of Oregon green at the Cys residue is used to assay beta-secretase activity in the presence or absence of the inhibitory compounds of the invention. Useful substrates include the following:

```
                                              [SEQ ID NO: 1]
Biotin-SEVNL-DAEFRC[oregon green]KK

[SEQ ID NO: 2]
Biotin-SEVKM-DAEFRC[oregon green]KK

[SEQ ID NO: 3]
Biotin-GLNIKTEEISEISY-EVEFRC[oregon green]KK

[SEQ ID NO:4]
Biotin-ADRGLTTRPGSGLTNIKTEEISEVNL-DAEFRC
[oregon green]KK

[SEQ ID NO: 5]
Biotin-FVNQHLCoxGSHLVEALY-LVCoxGERGFFYTPKAC
[oregon green]KK
```

The enzyme (0.1 nanomolar) and test compounds (0.001-100 micromolar) are incubated in pre-blocked, low affinity, black plates (384 well) at 37 degrees C. for 30 minutes. The reaction is initiated by addition of 150 millimolar substrate to a final volume of 30 microliter per well. The final assay conditions are: 0.001-100 micromolar compound inhibitor; 0.1 molar sodium acetate (pH 4.5); 150 nanomolar substrate; 0.1 nanomolar soluble beta-secretase; 0.001% Tween 20, and 2% DMSO. The assay mixture is incubated for 3 hours at 37° C., and the reaction is terminated by the addition of a saturating concentration of immunopure streptavidin. After incubation with streptavidin at room temperature for 15 minutes, fluorescence polarization is measured, for example, using a LJL Acqurest (Ex485 nm/Em530 nm). The activity of the beta-secretase enzyme is detected by changes in the fluorescence polarization that occur when the substrate is cleaved by the enzyme. Incubation in the presence or absence of compound inhibitor demonstrates specific inhibition of beta-secretase enzymatic cleavage of its synthetic APP substrate. In this assay, compounds of the invention exhibited an IC50 of less than 50 micromolar.

Example C

Beta-Secretase Inhibition: P26-P4'SW Assay

Synthetic substrates containing the beta-secretase cleavage site of APP are used to assay beta-secretase activity, using the methods described, for example, in published PCT application WO00/47618. The P26-P4'SW substrate is a peptide of the sequence:

```
                                        [SEQ ID NO: 6]
(biotin)CGGADRGLTTRPGSGLTNIKTEEISEVNLDAEF
```

The P26-P1 standard has the sequence:

```
                                        [SEQ ID NO: 7]
(biotin)CGGADRGLTTRPGSGLTNIKTEEISEVNL
```

Briefly, the biotin-coupled synthetic substrates are incubated at a concentration of from about 0 to about 200 micromolar in this assay. When testing inhibitory compounds, a substrate concentration of about 1.0 micromolar is preferred. Test compounds diluted in DMSO are added to the reaction mixture, with a final DMSO concentration of 5%. Controls also contain a final DMSO concentration of 5%. The concentration of beta secretase enzyme in the reaction is varied, to give product concentrations with the linear range of the ELISA assay, about 125 to 2000 picomolar, after dilution.

The reaction mixture also includes 20 millimolar sodium acetate, pH 4.5, 0.06% Triton X100, and is incubated at 37 degrees C. for about 1 to 3 hours. Samples are then diluted in assay buffer (for example, 145.4 nanomolar sodium chloride, 9.51 millimolar sodium phosphate, 7.7 millimolar sodium azide, 0.05% Triton X405, 6 g/liter bovine serum albumin, pH 7.4) to quench the reaction, then diluted further for immunoassay of the cleavage products.

Cleavage products can be assayed by ELISA. Diluted samples and standards are incubated in assay plates coated with capture antibody, for example, SW192, for about 24 hours at 4 degrees C. After washing in TTBS buffer (150 millimolar sodium chloride, 25 millimolar Tris, 0.05% Tween 20, pH 7.5), the samples are incubated with strepavidin-AP according to the manufacturer's instructions. After a one hour incubation at room temperature, the samples are washed in TTBS and incubated with fluorescent substrate solution A (31.2 g/liter 2-amino-2-methyl-1-propanol, 30 mg/liter, pH 9.5). Reaction with streptavidin-alkaline phosphate permits detection by fluorescence. Compounds that are effective inhibitors of beta-secretase activity demonstrate reduced cleavage of the substrate as compared to a control.

Example D

Assays Using Synthetic Oligopeptide-Substrates

Synthetic oligopeptides are prepared that incorporate the known cleavage site of beta-secretase, and optionally detectable tags, such as fluorescent or chouromogenic moieties. Examples of such peptides, as well as their production and detection methods are described in U.S. Pat. No. 5,942,400, herein incorporated by reference. Cleavage products can be detected using high performance liquid chouromatography, or fluorescent or chouromogenic detection methods appropriate to the peptide to be detected, according to methods well known in the art. By way of example, one such peptide has the sequence SEVNL-DAEF [SEQ ID NO: 8], and the cleavage site is between residues 5 and 6. Another preferred substrate has the sequence ADRGLTTRPGSGLTNIKTEEISEVNL-DAEF [SEQ ID NO: 9], and the cleavage site is between residues 26 and 27.

These synthetic APP substrates are incubated in the presence of beta-secretase under conditions sufficient to result in beta-secretase mediated cleavage of the substrate. Comparison of the cleavage results in the presence of the compound inhibitor to control results provides a measure of the compound's inhibitory activity.

Example E

Inhibition of Beta-Secretase Activity—Cellular Assay

An exemplary assay for the analysis of inhibition of beta-secretase activity utilizes the human embryonic kidney cell line HEKp293 (ATCC Accession No. CRL-1573) transfected with APP751 containing the naturally occurring double mutation Lys651Met52 to Asn651Leu652 (numbered for APP751), commonly called the Swedish mutation and shown to overproduce A beta (Citron et. al., 1992, Nature 360:672-674), as described in U.S. Pat. No. 5,604,102.

The cells are incubated in the presence/absence of the inhibitory compound (diluted in DMSO) at the desired concentration, generally up to 10 micrograms/ml. At the end of the treatment period, conditioned media is analyzed for beta-secretase activity, for example, by analysis of cleavage fragments. A beta can be analyzed by immunoassay, using specific detection antibodies. The enzymatic activity is measured in the presence and absence of the compound inhibitors to demonstrate specific inhibition of beta-secretase mediated cleavage of APP substrate.

Example F

Inhibition of Beta-Secretase in Animal Models of AD

Various animal models can be used to screen for inhibition of beta-secretase activity. Examples of animal models useful in the invention include, but are not limited to, mouse, guinea pig, dog, and the like. The animals used can be wild type, transgenic, or knockout models. In addition, mammalian models can express mutations in APP, such as APP695-SW and the like described herein. Examples of transgenic non-human mammalian models are described in U.S. Pat. Nos. 5,604,102, 5,912,410 and 5,811,633.

PDAPP mice, prepared as described in Games et. al., 1995, Nature 373:523-527 are useful to analyze in vivo suppression of A beta release in the presence of putative inhibitory compounds. As described in U.S. Pat. No. 6,191,166, 4 month old PDAPP mice are administered compound formulated in vehicle, such as corn oil. The mice are dosed with compound (1-30 mg/ml; preferably 1-10 mg/ml). After time, e.g., 3-10 hours, the animals are sacrificed, and brains removed for analysis.

Transgenic animals are administered an amount of the compound inhibitor formulated in a carrier suitable for the chosen mode of administration. Control animals are untreated, treated with vehicle, or treated with an inactive compound. Administration can be acute, i.e., single dose or multiple doses in one day, or can be chouronic, i.e., dosing is repeated daily for a period of days. Beginning at time 0, brain tissue or cerebral fluid is obtained from selected animals and analyzed for the presence of APP cleavage peptides, including A beta, for example, by immunoassay using specific antibodies for A beta detection. At the end of the test period, animals are sacrificed and brain tissue or cerebral fluid is analyzed for the presence of A beta and/or beta-amyloid plaques. The tissue is also analyzed for necrosis.

Animals administered the compound inhibitors of the invention are expected to demonstrate reduced A beta in brain tissues or cerebral fluids and reduced beta amyloid plaques in brain tissue, as compared with non-treated controls.

Example G

Inhibition of A Beta Production in Human Patients

Patients suffering from Alzheimer's Disease (AD) demonstrate an increased amount of A beta in the brain. AD patients are administered an amount of the compound inhibitor formulated in a carrier suitable for the chosen mode of administration. Administration is repeated daily for the duration of the test period. Beginning on day 0, cognitive and memory tests are performed, for example, once per month.

Patients administered the compound inhibitors are expected to demonstrate slowing or stabilization of disease progression as analyzed by changes in one or more of the following disease parameters: A beta present in CSF or plasma; brain or hippocampal volume; A beta deposits in the brain; amyloid plaque in the brain; and scores for cognitive and memory function, as compared with control, non-treated patients.

Example H

Prevention of A Beta Production in Patients at Risk for AD

Patients predisposed or at risk for developing AD are identified either by recognition of a familial inheritance pattern, for example, presence of the Swedish Mutation, and/or by monitoring diagnostic parameters. Patients identified as predisposed or at risk for developing AD are administered an amount of the compound inhibitor formulated in a carrier suitable for the chosen mode of administration. Administration is repeated daily for the duration of the test period. Beginning on day 0, cognitive and memory tests are performed, for exmple, once per month.

Patients administered the compound inhibitors are expected to demonstrate slowing or stabilization of disease progression as analyzed by changes in one or more of the following disease parameters: A beta present in CSF or plasma; brain or hippocampal volume; amyloid plaque in the brain; and scores for cognitive and memory function, as compared with control, non-treated patients.

While this invention has been described with respect to various specific examples and embodiments, it is to be understood that the invention is not limited thereby and should only be construed by interpretation of the scope of the appended claims.

We claim:

1. A compound of formula I

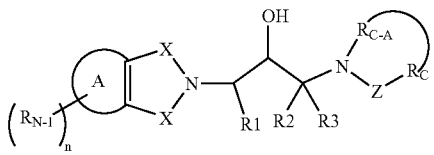

where $R_1$ is:
- (I) $C_1$-$C_6$ alkyl, optionally substituted with one, two or three substituents selected from the group consisting of $C_1$-$C_3$ alkyl, $C_1$-$C_7$ alkyl (optionally substituted with $C_1$-$C_3$ alkyl and $C_1$-$C_3$ alkoxy), —F, —Cl, —Br, —I, —OH, —SH, —C≡N, —CF$_3$, $C_1$-$C_3$ alkoxy, —NR$_{1-a}$R$_{1-b}$ where R$_{1-a}$ and R$_{1-b}$ are —H or $C_1$-$C_6$ alkyl, and —OC=O NR$_{1-a}$R$_{1-b}$ where R$_{1-a}$ and R$_{1-b}$ are as defined above,
- (II) —CH$_2$—S(O)$_{0-2}$—($C_1$-$C_6$ alkyl),
- (III) —CH$_2$—CH$_2$—S(O)$_{0-2}$—($C_1$-$C_6$ alkyl),
- (IV) $C_2$-$C_6$ alkenyl with one or two double bonds, optionally substituted with one, two or three substituents selected from the group consisting of —F, —Cl, —OH, —SH, —C≡N, —CF$_3$, $C_1$-$C_3$ alkoxy, and —NR$_{1-a}$R$_{1-b}$ where R$_{1-a}$ and R$_{1-b}$ are —H or $C_1$-$C_6$ alkyl,
- (V) $C_2$-$C_6$ alkynyl with one or two triple bonds, optionally substituted with one, two or three substituents selected from the group consisting of —F, —Cl, —OH, —SH, —C≡N, —CF$_3$, $C_1$-$C_3$ alkoxy, and —NR$_{1-a}$R$_{1-b}$ where R$_{1-a}$ and R$_{1-b}$ are —H or $C_1$-$C_6$ alkyl,
- (VI) —(CH$_2$)$_{n1}$—(R$_{1-aryl}$) where n$_1$ is zero or one and where R$_{1-aryl}$ is phenyl, 1-naphthyl, 2-naphthyl and indanyl, indenyl, dihydronaphthalyl, or tetralinyl optionally substituted with one, two, three, or four of the following substituents on the aryl ring:
  - (A) $C_1$-$C_6$ alkyl optionally substituted with one, two or three substituents selected from the group consisting of $C_1$-$C_3$ alkyl, —F, —Cl, —Br, —I, —OH, —SH, —C≡N, —CF$_3$, $C_1$-$C_3$ alkoxy, and —NR$_{1-a}$ R$_{1-b}$ where R$_{1-a}$ and R$_{1-b}$ are as defined above,
  - (B) $C_2$-$C_6$ alkenyl with one or two double bonds, optionally substituted with one, two or three substituents selected from the group consisting of —F, —Cl, —OH, —SH, —C≡N, —CF$_3$, $C_1$-$C_3$ alkoxy, —NR$_{1-a}$R$_{1-b}$ where R$_{1-a}$ and R$_{1-b}$ are —H or $C_1$-$C_6$ alkyl,
  - (C) $C_2$-$C_6$ alkynyl with one or two triple bonds, optionally substituted with one, two or three substituents selected from the group consisting of —F, —Cl, —OH, —SH, —C≡N, —CF$_3$, $C_1$-$C_3$ alkoxy, and —NR$_{1-a}$R$_{1-b}$ where R$_{1-a}$ and R$_{1-b}$ are —H or $C_1$-$C_6$ alkyl,
  - (D) —F, Cl, —Br or —I,
  - (F) —$C_1$-$C_6$ alkoxy optionally substituted with one, two, or three —F,
  - (G) —NR$_{N-2}$R$_{N-3}$ where R$_{N-2}$ and R$_{N-3}$ are as defined below,
  - (H) —OH,
  - (I) —C≡N,
  - (J) $C_3$-$C_7$ cycloalkyl, optionally substituted with one, two or three substituents selected from the group consisting of —F, —Cl, —OH, —SH, —C≡N, —CF$_3$, $C_1$-$C_3$ alkoxy, and —NR$_{1-a}$R$_{1-b}$ where R$_{1-a}$ and R$_{1-b}$ are —H or $C_1$-$C_6$ alkyl,
  - (K) —CO—($C_1$-$C_4$ alkyl),
  - (L) —SO$_2$—NR$_{1-a}$R$_{1-b}$ where R$_{1-a}$ and R$_{1-b}$ are as defined above,
  - (M) —CO—NR$_{1-a}$R$_{1-b}$ where R$_{1-a}$ and R$_{1-b}$ are as defined above, or
  - (N) —SO$_2$—($C_1$-$C_4$ alkyl),
- (VII) —(CH$_2$)$_{n1}$—(R$_{1-heteroaryl}$) where n$_1$ is as defined above and where R$_{1-heteroaryl}$ is selected from the group consisting of:
  - pyridinyl,
  - pyrimidinyl,
  - quinolinyl,
  - benzothienyl,
  - indolyl,
  - indolinyl,
  - pryidazinyl,
  - pyrazinyl,
  - isoquinolyl,
  - quinazolinyl,
  - quinoxalinyl,
  - phthalazinyl,
  - imidazolyl,
  - isoxazolyl,
  - pyrazolyl,
  - oxazolyl,
  - thiazolyl,
  - indolizinyl,
  - indazolyl,
  - benzothiazolyl,
  - benzimidazolyl,
  - benzofuranyl,
  - furanyl,
  - thienyl,
  - pyrrolyl,
  - oxadiazolyl,
  - thiadiazolyl,
  - triazolyl,
  - tetrazolyl,
  - oxazolopyridinyl,
  - imidazopyridinyl,
  - isothiazolyl,
  - naphthyridinyl,
  - cinnolinyl,
  - carbazolyl,
  - beta-carbolinyl,
  - isochromanyl,
  - chromanyl,
  - tetrahydroisoquinolinyl,
  - isoindolinyl,
  - isobenzotetrahydrofuranyl,
  - isobenzotetrahydrothienyl, isobenzothienyl,
benzoxazolyl,
pyridopyridinyl,
benzotetrahydrofuranyl,
benzotetrahydrothienyl,
purinyl,
benzodioxolyl,
triazinyl,
phenoxazinyl,
phenothiazinyl,
pteridinyl,
benzothiazolyl,
imidazopyridinyl,
imidazothiazolyl,
dihydrobenzisoxazinyl,
benzisoxazinyl,
benzoxazinyl,
dihydrobenzisothiazinyl,
benzopyranyl,
benzothiopyranyl,
coumarinyl,
isocoumarinyl,
chromonyl,
chromanonyl,
pyridinyl-N-oxide,
tetrahydroquinolinyl
dihydroquinolinyl
dihydroquinolinonyl
dihydroisoquinolinonyl
dihydrocoumarinyl
dihydroisocoumarinyl
isoindolinonyl
benzodioxanyl
benzoxazolinonyl
pyrrolyl N-oxide,
pyrimidinyl N-oxide,
pyridazinyl N-oxide,
pyrazinyl N-oxide,
quinolinyl N-oxide,
indolyl N-oxide,
indolinyl N-oxide,
isoquinolyl N-oxide,
quinazolinyl N-oxide,
quinoxalinyl N-oxide,
phthalazinyl N-oxide,
imidazolyl N-oxide,
isoxazolyl N-oxide,
oxazolyl N-oxide,
thiazolyl N-oxide,
indolizinyl N-oxide,
indazolyl N-oxide,
benzothiazolyl N-oxide,
benzimidazolyl N-oxide,
pyrrolyl N-oxide,
oxadiazolyl N-oxide,
thiadiazolyl N-oxide,
triazolyl N-oxide,
tetrazolyl N-oxide,
benzothiopyranyl S-oxide, and
benzothiopyranyl S,S-dioxide,
where the $R_{1\text{-}heteroaryl}$ group is bonded to $-(CH_2)_{n1}-$ by any ring atom of the parent $R_{N\text{-}heteroaryl}$ group substituted by hydrogen such that the new bond to the $R_{1\text{-}heteroaryl}$ group replaces the hydrogen atom and its bond, where heteroaryl is optionally substituted with one, two, three, or four:
  (1) $C_1$-$C_6$ alkyl optionally substituted with one, two or three substituents selected from the group consisting of $C_1$-$C_3$ alkyl, —F, —Cl, —Br, —I, —OH, —SH, —C≡N, —CF$_3$, $C_1$-$C_3$ alkoxy, and —NR$_{1\text{-}a}$R$_{1\text{-}b}$ where $R_{1\text{-}a}$ and $R_{1\text{-}b}$ are as defined above,
  (2) $C_2$-$C_6$ alkenyl with one or two double bonds, optionally substituted with one, two or three substituents selected from the group consisting of —F, —Cl, —OH, —SH, —C≡N, —CF$_3$, $C_1$-$C_3$ alkoxy, and —NR$_{1\text{-}a}$R$_{1\text{-}b}$ where $R_{1\text{-}a}$ and $R_{1\text{-}b}$ are —H or $C_1$-$C_6$ alkyl,
  (3) $C_2$-$C_6$ alkynyl with one or two triple bonds, optionally substituted with one, two or three substituents selected from the group consisting of —F, —Cl, —OH, —SH, —C≡N, —CF$_3$, $C_1$-$C_3$ alkoxy, and —NR$_{1\text{-}a}$R$_{1\text{-}b}$ where $R_{1\text{-}a}$ and $R_{1\text{-}b}$ are —H or $C_1$-$C_6$ alkyl,
  (4) —F, Cl, —BR, or —I,
  (6) —$C_1$-$C_6$ alkoxy optionally substituted with one, two, or three —F,
  (7) —NR$_{N\text{-}2}$R$_{N\text{-}3}$ where R$_{N\text{-}2}$ and R$_{N\text{-}3}$ are as defined below,
  (8) —OH,
  (9) —C≡N,
  (10) $C_3$-$C_7$ cycloalkyl, optionally substituted with one, two or three substituents selected from the group consisting of —F, —Cl, —OH, —SH, —C≡N, —CF$_3$, $C_1$-$C_3$ alkoxy, and —NR$_{1\text{-}a}$R$_{1\text{-}b}$ where $R_{1\text{-}a}$ and $R_{1\text{-}b}$ are —H or $C_1$-$C_6$ alkyl,
  (11) —CO—($C_1$-$C_4$ alkyl),
  (12) —SO$_2$—NR$_{1\text{-}a}$R$_{1\text{-}b}$ where $R_{1\text{-}a}$ and $R_{1\text{-}b}$ are as defined above,
  (13) —CO—NR$_{1\text{-}a}$R$_{1\text{-}b}$ where $R_{1\text{-}a}$ and $R_{1\text{-}b}$ are as defined above, or
  (14) —SO$_2$—($C_1$-$C_4$ alkyl), with the proviso that when $n_1$ is zero $R_{1\text{-}heteroaryl}$ is not bonded to the carbon chain by nitrogen, or
  (VIII) —(CH$_2$)$_{n1}$—(R$_{1\text{-}heterocycle}$) where $n_1$ is as defined above and $R_{1\text{-}heterocycle}$ is selected from the group consisting of:
    morpholinyl,
    thiomorpholinyl,
    thiomorpholinyl S-oxide,
    thiomorpholinyl S,S-dioxide,
    piperazinyl,
    homopiperazinyl,
    pyrrolidinyl,
    pyrrolinyl,
    tetrahydropyranyl,
    piperidinyl,
    tetrahydrofuranyl,
    tetrahydrothienyl,
    homopiperidinyl,
    homomorpholinyl,
    homothiomorpholinyl,
    homothiomorpholinyl S,S-dioxide,
    oxazolidinonyl,
    dihydropyrazolyl,
    dihydropyrrolyl,
    dihydropyrazinyl,
    dihydropyridinyl,
    dihydropyrimidinyl,
    dihydrofuryl,
    dihydropyranyl,
    tetrahydrothienyl S-oxide,
    tetrahydrothienyl S,S-dioxide, and
    homothiomorpholinyl S-oxide,
where the $R_{1\text{-}heterocycle}$ group is bonded by any atom of the parent $R_{1\text{-}heterocycle}$ group substituted by hydrogen such that the new bond to the $R_{1\text{-}heterocycle}$ group replaces the hydrogen atom and its bond, where heterocycle is optionally substituted with one, two, three, or four:

(1) $C_1$-$C_6$ alkyl optionally substituted with one, two or three substituents selected from the group consisting of $C_1$-$C_3$ alkyl, —F, —Cl, —Br, —I, —OH, —SH, —C≡N, —CF$_3$, $C_1$-$C_3$ alkoxy, and —NR$_{1-a}$R$_{1-b}$ where R$_{1-a}$ and R$_{1-b}$ are as defined above, (2) $C_2$-$C_6$ alkenyl with one or two double bonds, optionally substituted with one, two or three substituents selected from the group consisting of —F, —Cl, —OH, —SH, —C≡N, —CF$_3$, $C_1$-$C_3$ alkoxy, and —NR$_{1-a}$R$_{1-b}$ where R$_{1-a}$ and R$_{1-b}$ are —H or $C_1$-$C_6$ alkyl, (3) $C_2$-$C_6$ alkynyl with one or two triple bonds, optionally substituted with one, two or three substituents selected from the group consisting of —F, —Cl, —OH, —SH, —C≡N, —CF$_3$, $C_1$-$C_3$ alkoxy, and —NR$_{1-a}$R$_{1-b}$ where R$_{1-a}$ and R$_{1-b}$ are —H or $C_1$-$C_6$ alkyl, (4) —F, Cl, —Br, or —I, (5) $C_1$-$C_6$ alkoxy, (6) —$C_1$-$C_6$ alkoxy substituted with one, two, or three —F, (7) —NR$_{N-2}$R$_{N-3}$ where R$_{N-2}$ and R$_{N-3}$ are as defined below, (8) —OH, (9) —C≡N,

(10) $C_3$-$C_7$ cycloalkyl, optionally substituted with one, two or three substituents selected from the group consisting of —F, —Cl, —OH, —SH, —C≡N, —CF$_3$, $C_1$-$C_3$ alkoxy, and —NR$_{1-a}$R$_{1-b}$ where R$_{1-a}$ and R$_{1-b}$ are —H or $C_1$-$C_6$ alkyl,

(11) —CO—($C_1$-$C_4$ alkyl),

(12) —SO$_2$—NR$_{1-a}$R$_{1-b}$ where R$_{1-a}$ and R$_{1-b}$ are as defined above,

(13) —CO—NR$_{1-a}$R$_{1-b}$ where R$_{1-a}$ and R$_{1-b}$ are as defined above,

(14) —SO$_2$—($C_1$-$C_4$ alkyl), or

(15) =O, with the proviso that when n$_1$ is zero R$_{1-heterocycle}$ is not bonded to the carbon chain by nitrogen;

where R$_2$ is:

(I) —H, (II) $C_1$-$C_6$ alkyl, optionally substituted with one, two or three substituents selected from the group consisting of $C_1$-$C_3$ alkyl, —F, —Cl, —Br, —I, —OH, —SH, —C≡N, —CF$_3$, $C_1$-$C_3$ alkoxy, and —NR$_{1-a}$R$_{1-b}$ where R$_{1-a}$ and R$_{1-b}$ are as defined above, (III) —(CH$_2$)$_{0-4}$—R$_{2-1}$ where R$_{2-1}$ is R$_{1-aryl}$ or R$_{1-heteroaryl}$ where R$_{1-aryl}$ and R$_{1-heteroaryl}$ are as defined above;

(IV) $C_2$-$C_6$ alkenyl with one or two double bonds, optionally substituted with one, two or three substituents selected from the group consisting of —F, —Cl, —OH, —SH, —C≡N, —CF$_3$, $C_1$-$C_3$ alkoxy, and —NR$_{1-a}$R$_{1-b}$ where R$_{1-a}$ and R$_{1-b}$ are —H or $C_1$-$C_6$ alkyl, (V) $C_2$-$C_6$ alkynyl with one or two triple bonds, optionally substituted with one, two or three substituents selected from the group consisting of —F, —Cl, —OH, —SH, —C≡N, —CF$_3$, $C_1$-$C_3$ alkoxy, and —NR$_{1-a}$R$_{1-b}$ where R$_{1-a}$ and R$_{1-b}$ are —H or $C_1$-$C_6$ alkyl, or (VI) —(CH$_2$)$_{0-4}$—$C_3$-$C_7$ cycloalkyl, optionally substituted with one, two or three substituents selected from the group consisting of —F, —Cl, —OH, —SH, —C≡N, —CF$_3$, $C_1$-$C_3$ alkoxy, and —NR$_{1-a}$R$_{1-b}$ where R$_{1-a}$ and R$_{1-b}$ are —H or $C_1$-$C_6$ alkyl, where R$_3$ is:

(I) —H, (II) $C_1$-$C_6$ alkyl, optionally substituted with one, two or three substituents selected from the group consisting of $C_1$-$C_3$ alkyl, —F, —Cl, —Br, —I, —OH, —SH, —C≡N, —CF$_3$, $C_1$-$C_3$ alkoxy, and —NR$_{1-a}$R$_{1-b}$ where R$_{1-a}$ and R$_{1-b}$ are as defined above, (III) —(CH$_2$)$_{0-4}$—R$_{2-1}$ where R$_{2-1}$ is R$_{1-aryl}$ or R$_{1-heteroaryl}$ where R$_{1-aryl}$ and R$_{1-heteroaryl}$ are as defined above;

(IV) $C_2$-$C_6$ alkenyl with one or two double bonds, (V) $C_2$-$C_6$ alkynyl with one or two triple bonds, or (VI) —(CH$_2$)$_{0-4}$—$C_3$-$C_7$ cycloalkyl, optionally substituted with one, two or three substituents selected from the group consisting of —F, —Cl, —OH, —SH, —C≡N, —CF$_3$, $C_1$-$C_3$ alkoxy, and —NR$_{1-a}$R$_{1-b}$ where R$_{1-a}$ and R$_{1-b}$ are —H or $C_1$-$C_6$ alkyl, where R$_2$ and R$_3$ are taken together with the carbon to which they are attached to form a carbocycle of three, four, five, six or seven carbon atoms, optionally where one carbon atom is replaced by a heteroatom selected from the group consisting of —O—, —S—, —SO$_2$—, and —NR$_{N-2}$—, where R$_{N-2}$ is selected from the group consisting of:

(a) —H, (b) —$C_1$-$C_6$ alkyl optionally substituted with one substituent selected from the group consisting of:

(i) —OH, and (ii) —NH$_2$, (c) —$C_1$-$C_6$ alkyl optionally substituted with one to three —F, —Cl, —Br, or —I, (d) —$C_3$-$C_7$ cycloalkyl, (e) —($C_1$-$C_2$ alkyl)-($C_3$-$C_7$ cycloalkyl), (f) —($C_1$-$C_6$ alkyl)-O—($C_1$-$C_3$ alkyl), (g) —$C_2$-$C_6$ alkenyl with one or two double bonds, (h) —$C_2$-$C_6$ alkynyl with one or two triple bonds, (i) —$C_1$-$C_6$ alkyl chain with one double bond and one triple bond, (j) —R$_{1-aryl}$ where R$_{1-aryl}$ is as defined above, and (k) —R$_{1-heteroaryl}$ where R$_{1-heteroaryl}$ is as defined above;

where one X is —C(O)— and the other is —CH2—, wherein in the rings drawn, a dotted line indicates an optional double bond or an optional ring;

wherein ring A is phenyl; and where R$_{N-1}$ is selected from the group consisting of:

(1) $C_1$-$C_6$ alkyl, optionally substituted with one, two or three substituents selected from the group consisting of $C_1$-$C_3$ alkyl, —F, —Cl, —Br, —I, —OH, —SH, —C≡N, —CF$_3$, $C_1$-$C_3$ alkoxy, and —NR$_{1-a}$R$_{1-b}$ where R$_{1-a}$ and R$_{1-b}$ are as defined above, (2) —OH, (3) —NO$_2$, (4) —F, —Cl, —Br, or —I, (5) —CO—OH, (6) —C≡N, (7) —(CH$_2$)$_{0-4}$—CO—NR$_{N-2}$R$_{N-3}$ where R$_{N-2}$ and R$_{N-3}$ are the same or different and are selected from the group consisting of:

(a) —H, (b) —$C_1$-$C_6$ alkyl optionally substituted with one substituent selected from the group consisting of:

(i) —OH, and (ii) —NH$_2$, (c) —$C_1$-$C_6$ alkyl optionally substituted with one to three —F, —Cl, —Br, or —I, (d) —$C_3$-$C_7$ cycloalkyl, (e) —($C_1$-$C_2$ alkyl)-($C_3$-$C_7$ cycloalkyl), (f) —($C_1$-$C_6$ alkyl)-O—($C_1$-$C_3$ alkyl), (g) —$C_2$-$C_6$ alkenyl with one or two double bonds, (h) —$C_2$-$C_6$ alkynyl with one or two triple bonds, (i) —$C_1$-$C_6$ alkyl chain with one double bond and one triple bond, (j) —$R_{1\text{-}aryl}$ where $R_{1\text{-}aryl}$ is as defined above, and (k) —$R_{1\text{-}heteroaryl}$ where $R_{1\text{-}heteroaryl}$ is as defined above, (8) —$(CH_2)_{0\text{-}4}$—CO—$(C_1\text{-}C_{12}$ alkyl), (9) —$(CH_2)_{0\text{-}4}$—CO—$(C_2\text{-}C_{12}$ alkenyl with one, two, or three double bonds),

(10) —$(CH_2)_{0\text{-}4}$—CO—$(C_2\text{-}C_{12}$ alkynyl with one, two, or three triple bonds),

(11) —$(CH_2)_{0\text{-}4}$—CO—$(C_3\text{-}C_7$ cycloalkyl),

(12) —$(CH_2)_{0\text{-}4}$—CO—$R_{1\text{-}aryl}$ where $R_{1\text{-}aryl}$ is as defined above,

(13) —$(CH_2)_{0\text{-}4}$—CO—$R_{1\text{-}heteroaryl}$ where $R_{1\text{-}heteroaryl}$ is as defined above,

(14) —$(CH_2)_{0\text{-}4}$—CO—$R_{1\text{-}heterocycle}$ where $R_{1\text{-}heterocycle}$ is as defined above,

(15) —$(CH_2)_{0\text{-}4}$—CO—$R_{N\text{-}4}$ where $R_{N\text{-}4}$ is selected from the group consisting of morpholinyl, thiomorpholinyl, piperazinyl, piperidinyl, homomorpholinyl, homothiomorpholinyl, homoythiomorpholinyl S-oxide, homothiomorpholinyl S,S-dioxide, pyrrolinyl and pyrrolidinyl where each group is optionally substituted with one, two, three, or four of: $C_1\text{-}C_6$ alkyl,

(16) —$(CH_2)_{0\text{-}4}$—CO—O—$R_{N\text{-}5}$ where $R_{N\text{-}5}$ is selected from the group consisting of:
(a) $C_1\text{-}C_6$ alkyl,
(b) —$(CH_2)_{0\text{-}2}$—$(R_{1\text{-}aryl})$ where $R_{1\text{-}aryl}$ is as defined above,
(c) $C_2\text{-}C_6$ alkenyl containing one, or two double bonds,
(d) $C_2\text{-}C_6$ alkynyl containing one, or two triple bonds,
(e) $C_3\text{-}C_7$ cycloalkyl, and
(f) —$(CH_2)_{0\text{-}2}$—$(R_{1\text{-}heteroaryl})$ where $R_{1\text{-}heteroaryl}$ is as defined above,

(17) —$(CH_2)_{0\text{-}4}$—$SO_2$—$NR_{N\text{-}2}R_{N\text{-}3}$ where $R_{N\text{-}2}$ and $R_{N\text{-}3}$ are as defined above,

(18) —$(CH_2)_{0\text{-}4}$—SO—$(C_1\text{-}C_8$ alkyl),

(19) —$(CH_2)_{0\text{-}4}$—$SO_2$—$(C_1\text{-}C_{12}$ alkyl),

(20) —$(CH_2)_{0\text{-}4}$—$SO_2$—$(C_3\text{-}C_7$ cycloalkyl),

(21) —$(CH_2)_{0\text{-}4}$—N(H or $R_{N\text{-}5}$)—CO—O—$R_{N\text{-}5}$ where $R_{N\text{-}5}$ can be the same or different and is as defined above,

(22) —$(CH_2)_{0\text{-}4}$—N(H or $R_{N\text{-}5}$)—CO—$N(R_{N\text{-}5})_2$, where $R_{N\text{-}5}$ can be the same or different and is as defined above,

(23) —$(CH_2)_{0\text{-}4}$—N—CS—$N(R_{N\text{-}5})_2$, where $R_{N\text{-}5}$ can be the same or different and is as defined above,

(24) —$(CH_2)_{0\text{-}4}$—N(—H or $R_{N\text{-}5}$)—CO—$R_{N\text{-}2}$ where $R_{N\text{-}5}$ and $R_{N\text{-}2}$ can be the same or different and are as defined above,

(25) —$(CH_2)_{0\text{-}4}$—$NR_{N\text{-}2}R_{N\text{-}3}$ where $R_{N\text{-}2}$ and $R_{N\text{-}3}$ can be the same or different and are as defined above,

(26) —$(CH_2)_{0\text{-}4}$—$R_{N\text{-}4}$ where $R_{N\text{-}4}$ is as defined above,

(27) —$(CH_2)_{0\text{-}4}$—O—CO—$(C_1\text{-}C_6$ alkyl),

(28) —$(CH_2)_{0\text{-}4}$—O—P(O)—$(OR_{N\text{-}aryl\text{-}1})_2$ where $R_{N\text{-}aryl\text{-}1}$ is H or $C_1\text{-}C_4$ alkyl,

(29) —$(CH_2)_{0\text{-}4}$—O—CO—$N(R_{N\text{-}5})_2$ where $R_{N\text{-}5}$ is as defined above,

(30) —$(CH_2)_{0\text{-}4}$—O—CS—$N(R_{N\text{-}5})_2$ where $R_{N\text{-}5}$ is as defined above,

(31) —$(CH_2)_{0\text{-}4}$—O—$(R_{N\text{-}5})_2$ where $R_{N\text{-}5}$ is as defined above,

(32) —$(CH_2)_{0\text{-}4}$—O—$(R_{N\text{-}5})_2$—COOH where $R_{N\text{-}5}$ is as defined above,

(33) —$(CH_2)_{0\text{-}4}$—S—$(R_{N\text{-}5})_2$ where $R_{N\text{-}5}$ is as defined above,

(34) —$(CH_2)_{0\text{-}4}$—O—$(C_1\text{-}C_6$ alkyl optionally substituted with one, two, three, four, or five of: —F),

(35) $C_3\text{-}C_7$ cycloalkyl,

(36) $C_2\text{-}C_6$ alkenyl with one or two double bonds optionally substituted with $C_1\text{-}C_3$ alkyl, —F, —Cl, —Br, —I, —OH, —SH, —C≡N, —$CF_3$, $C_1\text{-}C_3$ alkoxy, or —$NR_{1\text{-}a}R_{1\text{-}b}$ where $R_{1\text{-}a}$ and $R_{1\text{-}b}$ are as defined above,

(37) $C_2\text{-}C_6$ alkynyl with one or two triple bonds optionally substituted with $C_1\text{-}C_3$ alkyl, —F, —Cl, —Br, —I, —OH, —SH, —C≡N, —$CF_3$, $C_1\text{-}C_3$ alkoxy, or —$NR_{1\text{-}a}R_{1\text{-}b}$ where $R_{1\text{-}a}$ and $R_{1\text{-}b}$ are as defined above,

(38) —$(CH_2)_{0\text{-}4}$—N(—H or $R_{N\text{-}5}$)—$SO_2$—$R_{N\text{-}2}$ where $R_{N\text{-}5}$ and $R_{N\text{-}2}$ can be the same of different and are as described above, and

(39) —$(CH_2)_{0\text{-}4}$—$C_3\text{-}C_7$ cycloalkyl;

where n is equal to 0, 1, 2 or 3;

where Z is selected from the group consisting of:

(A) —C(O)—, (B) —$S(O)_{1\text{-}2}$—, (C) —C(O)—$X_{N\text{-}1}$— where $X_{N\text{-}1}$ is selected from the group consisting of —O—, —S— and —NR'— and where R' is as defined above; and (D) a single bond;

where $R_C$ is:

(I) —$C_1\text{-}C_{10}$ alkyl optionally substituted with one, two or three substituents selected from the group consisting of $C_1\text{-}C_3$ alkyl, —F, —Cl, —Br, —I, —OH, —SH, —C≡N, —$CF_3$, $C_1\text{-}C_6$ alkoxy, —O-phenyl, —$NR_{1\text{-}a}R_{1\text{-}b}$ where $R_{1\text{-}a}$ and $R_{1\text{-}b}$ are as defined above, —OC=O $NR_{1\text{-}a}R_{1\text{-}b}$ where $R_{1\text{-}a}$ and $R_{1\text{-}b}$ are as defined above, —$S(=O)_{0\text{-}2}$ $R_{1\text{-}a}$ where $R_{1\text{-}a}$ is as defined above, —$NR_{1\text{-}a}C=O$ $NR_{1\text{-}a}R_{1\text{-}b}$ where $R_{1\text{-}a}$ and $R_{1\text{-}b}$ are as defined above, —C=O $NR_{1\text{-}a}R_{1\text{-}b}$ where $R_{1\text{-}a}$ and $R_{1\text{-}b}$ are as defined above, and —$S(=O)_2$ $NR_{1\text{-}a}R_{1\text{-}b}$ where $R_{1\text{-}a}$ and $R_{1\text{-}b}$ are as defined above, (II) —$(CH_2)_{0\text{-}3}$—$(C_3\text{-}C_8)$ cycloalkyl where cycloalkyl can be optionally substituted with one, two, or three substituents selected from the group consisting of $C_1\text{-}C_3$ alkyl, —F, —Cl, —Br, —I, —OH, —SH, —C≡N, —$CF_3$, $C_1\text{-}C_6$ alkoxy, —O-phenyl, —CO—OH, —CO—O—$(C_1\text{-}C_4$ alkyl), and —$NR_{1\text{-}a}R_{1\text{-}b}$ where $R_{1\text{-}a}$ and $R_{1\text{-}b}$ are as defined above, (III) —$(CR_{C\text{-}x}R_{C\text{-}y})_{0\text{-}4}$—$R_{C\text{-}aryl}$ where $R_{C\text{-}x}$ and $R_{C\text{-}y}$ are
(A) —H,
(B) $C_1\text{-}C_4$ alkyl optionally substituted with one or two —OH,
(C) $C_1\text{-}C_4$ alkoxy optionally substituted with one, two, or three —F,
(D) —$(CH_2)_{0\text{-}4}$—$C_3\text{-}C_7$ cycloalkyl,
(E) $C_2\text{-}C_6$ alkenyl containing one or two double bonds,
(F) $C_2\text{-}C_6$ alkynyl contianing one or two triple bonds,
(G) phenyl-,
(H) $C_0\text{-}C_4$ alkylC(O) $NR_{1\text{-}a}R_{1\text{-}b}$ where $R_{1\text{-}a}$ and $R_{1\text{-}b}$ are as defined above, and where $R_{C\text{-}x}$ and $R_{C\text{-}y}$ are taken together with the carbon to which they are attached to form a carbocycle of three, four, five, six, or seven carbon atoms, optionally where one carbon atom is replaced by a heteroatom selected from the group consisting of —O—, —S—, —$SO_2$—, —$NR_{N\text{-}2}$— and $R_{C\text{-}aryl}$ is the same as $R_{N\text{-}aryl}$ and where $R_{C\text{-}aryl}$ may optionally be substituted with —$C_0\text{-}C_4$ alkyl-C(O) $NR_{1\text{-}a}R_{1\text{-}b}$, $C_0\text{-}C_4$ alkylC(O) $OR_{1\text{-}a}$ where $R_{1\text{-}a}$ and $R_{1\text{-}b}$ are as defined above, (IV) —$(CR_{C-x}R_{C-y})_{0-4}$—$R_{C\text{-}heteroaryl}$ where $R_{C\text{-}heteroaryl}$ is the same as $R_{N\text{-}heteroaryl}$ and $R_{C-x}$ and $R_{C-y}$, are as defined above, (V) —$(CR_{C-x}R_{C-y})_{0-4}$—$R_{C\text{-}aryl}$-$R_{C\text{-}aryl}$ where $R_{C\text{-}aryl}$, $R_{C-x}$ and $R_{C-y}$ are as defined above, (VI) —$(CR_{C-x}R_{C-y})_{0-4}$—$R_{C\text{-}aryl}$-$R_{C\text{-}heteroaryl}$ where $R_{C\text{-}aryl}$, $R_{C\text{-}heteroaryl}$ $R_{C-x}$ and $R_{C-y}$ are as defined above, (VII) —$(CR_{C-x}R_{C-y})_{0-4}$—$R_{C\text{-}heteroaryl}$-$R_{C\text{-}aryl}$ where $R_{C\text{-}heteroaryl}$, $R_{C\text{-}aryl}$ $R_{C-x}$ and $R_{C-y}$ are as defined above, (VIII) —$(CR_{C-x}R_{C-y})_{0-4}$—$R_{C\text{-}heteroaryl}$-$R_{C\text{-}heteroaryl}$ where $R_{C\text{-}heteroaryl}$, $R_{C-x}$ and $R_{C-y}$ are as defined above, (IX) —$(CR_{C-x}R_{C-y})_{0-4}$—$R_{C\text{-}aryl}$-$R_{C\text{-}heterocycle}$ where $R_{C\text{-}heterocycle}$ is the same as $R_{1\text{-}heterocycle}$, and $R_{C\text{-}aryl}$, $R_{C-x}$ and $R_{C-y}$ are as defined above, (X) —$(CR_{C-x}R_{C-y})_{0-4}$—$R_{C\text{-}heteroaryl}$-$R_{C\text{-}heterocycle}$ where $R_{C\text{-}heteroaryl}$, $R_{C\text{-}heterocycle}$, $R_{C-x}$ and $R_{C-y}$ are as defined above, (XI) —$(CR_{C-x}R_{C-y})_{0-4}$—$R_{C\text{-}heterocycle}$-$R_{C\text{-}aryl}$ where $R_{C\text{-}heterocycle}$, $R_{C\text{-}aryl}$, $R_{C-x}$ and $R_{C-y}$ are as defined above, (XII) —$(CR_{C-x}R_{C-y})_{0-4}$—$R_{C\text{-}heterocycle}$-$R_{C\text{-}heteroaryl}$ where $R_{C\text{-}heterocycle}$, $R_{C\text{-}heteroaryl}$, $R_{C-x}$ and $R_{C-y}$ are as defined above, (XIII) —$(CR_{C-x}R_{C-y})_{0-4}$—$R_{C\text{-}heterocycle}$-$R_{C\text{-}heterocycle}$ where $R_{C\text{-}heterocycle}$, $R_{C-x}$ and $R_{C-y}$ are as defined above, (XIV) —$(CR_{C-x}R_{C-y})_{0-4}$—$R_{C\text{-}heterocycle}$ where $R_{C\text{-}heterocycle}$, $R_{C-x}$ and $R_{C-y}$ are as defined above, (XV) —$[C(R_{C-1})(R_{C-2})]_{1-3}$—CO—N—$(R_{C-3})_2$ where $R_{C-3}$ is as defined below and $R_{C-1}$, $R_{C-2}$ are the same or different and are selected from the group consisting of:

(A) —H, (B) —$C_1$-$C_6$ alkyl, optionally substituted with one, two, or three substituents independently selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above, (D) $C_2$-$C_6$ alkenyl with one, or two double bonds, optionally substituted with one, two, or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above, (E) $C_2$-$C_6$ alkynyl with one or two triple bonds, optionally substituted with one, two, or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above, (F) —$(CH_2)_{1-2}$—$S(O)_{0-2}$—$(C_1$-$C_6$ alkyl), (F) —$(CH_2)_{0-4}$—$C_3$-$C_7$ cycloalkyl, optionally substituted with one, two, or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above, (G) —$(C_1$-$C_4$ alkyl)-$R_{C'\text{-}aryl}$ where $R_{C'\text{-}aryl}$ is as defined for $R_{1\text{-}aryl}$, (H) —$(C_1$-$C_4$ alkyl)-$R_{C\text{-}heteroaryl}$ where $R_{C\text{-}heteroaryl}$ is as defined above, (I) —$(C_1$-$C_4$ alkyl)-$R_{C\text{-}heterocycle}$ where $R_{C\text{-}heterocycle}$ is as defined above, (J) —$R_{C\text{-}heteroaryl}$ where $R_{C\text{-}heteroaryl}$ is as defined above, (K) —$R_{C\text{-}heterocycle}$ where $R_{C\text{-}heterocycle}$ is as defined above, (M) —$(CH_2)_{1-4}$—$R_{C-4}$—$(CH_2)_{0-4}$—$R_{C'\text{-}aryl}$ where $R_{C-4}$ is —O—, —S— or —$NR_{C-5}$— where $R_{C-5}$ is $C_1$-$C_6$ alkyl, and where $R_{C'\text{-}aryl}$ is defined above, (N) —$(CH_2)_{1-4}$—$R_{C-4}$—$(CH_2)_{0-4}$—$R_{C\text{-}heteroaryl}$ where $R_{C-4}$ and $R_{C\text{-}heteroaryl}$ are as defined above, and (O) —$R_{C'\text{-}aryl}$ where $R_{C'\text{-}aryl}$ is as defined above, and where $R_{C-3}$ is the same or different and is:

(a) —H, (b) —$C_1$-$C_6$ alkyl optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above, (c) $C_2$-$C_6$ alkenyl with one or two double bonds, optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above, (d) $C_2$-$C_6$ alkynyl with one, or two triple bonds, optionally substituted with one, two or three substituents selected from the group consisting of $C_1$-$C_3$ alkyl, —F, —Cl, —Br, —I, —OH, —SH —C≡N, —$CF_3$, $C_1$-$C_6$ alkoxy, —O-phenyl, and —$NR_{1-a}R_{1-b}$ where $R_{1-a}$ and $R_{1-b}$ are as defined above, (e) —$(CH_2)_{0-4}$—$C_3$-$C_7$ cycloalkyl, optionally substituted with one, two or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above, (f) —$R_{C'\text{-}aryl}$ where $R_{C'\text{-}aryl}$ is as defined above, (g) —$R_{C\text{-}heterocycle}$ where $R_{C\text{-}heteroaryl}$ is as defined above, (h) —$R_{C\text{-}heterocycle}$ where $R_{C\text{-}heterocycle}$ is as defined above, (i) —$(C_1$-$C_4$ alkyl)-$R_{C'\text{-}aryl}$ where $R_{C'\text{-}aryl}$ is as defined above, (j) —$(C_1C_4$ alkyl)-$R_{C\text{-}heterocycle}$ where $R_{C\text{-}heteroaryl}$ is as defined above, (k) —$(C_1$-$C_4$ alkyl)-$R_{C\text{-}heterocycle}$ where $R_{C\text{-}heterocycle}$ is as defined above, (XVI) —$CH(R_{C\text{-}aryl})_2$ where $R_{C\text{-}aryl}$ are the same or different and are as defined above, (XVII) —$CH(R_{C\text{-}heteroaryl})_2$ where $R_{C\text{-}heteroaryl}$ are the same or different and are as defined above, (XVIII) —$CH(R_{C\text{-}aryl})(R_{C\text{-}heteroaryl})$ where $R_{C\text{-}aryl}$ and $R_{C\text{-}heteroaryl}$ are as defined above, (XIX) -cyclopentyl, -cyclohexyl, or -cycloheptyl ring fused to $R_{C\text{-}aryl}$ or $R_{C\text{-}heteroaryl}$ or $R_{C\text{-}heterocycle}$ where $R_{C\text{-}aryl}$ or $R_{C\text{-}heteroaryl}$ or $R_{C\text{-}heterocycle}$ are as defined above where one carbon of cyclopentyl, cyclohexyl, or cycloheptyl is optionally replaced with NH, $NR_{N-5}$, O or $S(=O)_{0-2}$, and where cyclopentyl, cyclohexyl, or cycloheptyl can be optionally substituted with one, or two —$C_1$-$C_3$ alkyl, —F, —OH, —SH, —C≡N, —$CF_3$, $C_1$-$C_6$ alkoxy, =O, or —$NR_{1-a}R_{1-b}$ where $R_{1-a}$ and $R_{1-b}$ are as defined above, (XX) $C_2$-$C_{10}$ alkenyl containing one or two double bonds optionally substituted with one, two, or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above, (XXI) $C_2$-$C_{10}$ alkynyl containing one, or two triple bonds optionally substituted with one, two, or three substituents selected from the group consisting of $C_1$-$C_3$ alkyl, —F, —Cl, —Br, —I, —OH, —SH, —C≡N, —$CF_3$, $C_1$-$C_6$ alkoxy, —O-phenyl, and —$NR_{1-a}R_{1-b}$ where $R_{1-a}$ and $R_{1-b}$ are as defined above, (XXI) —$(CH_2)_{0-1}$—$CHR_{C-6}$—$(CH_2)_{0-1}$—$R_{C-aryl}$ where $R_{C-aryl}$ is as defined above and $R_{C-6}$ is —$(CH_2)_{0-6}$—OH, (XXII) —$(CH_2)_{0-1}$—$CHR_{C-6}$—$(CH_2)_{0-1}$—$R_{C-heteroaryl}$ where $R_{C-heteroaryl}$ and $R_{C-6}$ is as defined above, (XXIII) —CH(-$R_{C-aryl}$ or $R_{C-heteroaryl}$)-CO—O($C_1$-$C_4$ alkyl) where $R_{C-aryl}$ and $R_{C-heteroaryl}$ are as defined above, (XXIV) —CH(—$CH_2$—OH)—CH(—OH)-phenyl-$NO_2$, (XXV) ($C_1$-$C_6$ alkyl)-O—($C_1$-$C_6$ alkyl)-OH, (XXVII) —$CH_2$—NH—$CH_2$—CH(—O—$CH_2$—$CH_3$)$_2$, or (XXVIII) —$(CH_2)_{0-6}$—C(=$NR_{1-a}$)($NR_{1-a}R_{1-b}$) where $R_{1-a}$ and $R_{1-b}$ are as defined above, and where $R_{C-A}$ is H, $C_1$-$C_{10}$ alkyl, $C_2$-$C_{10}$ alkenyl and alkynyl, phenyl, $C_1$-$C_4$ alkyl-$R_{N-aryl}$, $C_1$-$C_4$ alkyl-$R_{N-heteroaryl}$, $C_1$-$C_4$ alkyl-C3-C7 cycloalkyl, or $C_1$-$C_4$ alkyl-$R_{1-heterocycle}$, wherein each multi-atom group may be optionally substituted with one, two, or three substituents independently selected from the group consisting of —F, —Cl, —OH, —SH, —C≡N, —$CF_3$, $C_1$-$C_3$ alkoxy, —C(O)O—$R_{1-a}$, and —$NR_{1-a}R_{1-b}$ where $R_{1-a}$ and $R_{1-b}$ are —H, $C_1$-$C_6$ alkyl or phenyl;

where $R_{C-A}$, -Z-$R_C$, and the nitrogen atom to which they attach may cyclize to form a ring or fused rings chosen from the group consisting of 5-8 membered heterocyclics having up to 2 heteroatoms in addition to the ring nitrogen defined above chosen from the group consisting of N, O, and S, which may optionally be fused with one, or two phenyl, pyridyl, cyclohexyl, piperidinyl or morpholinyl, where the ring or fused rings may optionally have one, two, or three substituents independently chosen from the group of:

(1) $C_1$-$C_6$ alkyl,
$C_2$-$C_6$ alkenyl with one or two double bonds, or
$C_2$-$C_6$ alkynyl with one or two triple bonds, wherein each may be optionally substituted with one, two, or three substituents selected from the group consisting of —F, —Cl, —OH, —SH, —C≡N, —$CF_3$, $C_1$-$C_3$ alkoxy, and —$NR_{1-a}R_{1-b}$ where $R_{1-a}$ and $R_{1-b}$ are —H or $C_1$-$C_6$ alkyl, (2) —F, Cl, —Br, or —I, (3) —$C_1$-$C_6$ alkoxy optionally substituted with one, two, or three —F, (4) —$NR_{N-2}R_{N-3}$ where $R_{N-2}$ and $R_{N-3}$ are as defined below, (5) —OH, (6) —C≡N, (7) =O (oxo), (8) —CO—($C_1$-$C_4$ alkyl), (9) —$SO_2$—$NR_{1-a}R_{1-b}$ where $R_{1-a}$ and $R_{1-b}$ are as defined above, or

(10) —CO—$NR_{1-a}R_{1-b}$ where $R_{1-a}$ and $R_{1-b}$ are as defined above, or a pharmaceutically acceptable salt thereof.

2. A compound according to claim 1, wherein $R_1$ is:
—$(CH_2)_{0-1}$—($R_{1-aryl}$), or
—$(CH_2)_{n-1}$—($R_{1-heteroaryl}$).

3. A compound according to claim 2, wherein $R_1$ is:
—$(CH_2)$—($R_{1-aryl}$), or
—$(CH_2)$—($R_{1-heteroaryl}$).

4. A compound according to claim 3, wherein $R_1$ is —$(CH_2)$—($R_{1-aryl}$) where $R_{1-aryl}$ is phenyl.

5. A compound according to claim 4, wherein $R_1$ is substituted with two —F.

6. A compound according to claim 1, wherein $R_2$ and $R_3$ are both —H.

7. A compound according to claim 1, wherein $R_C$ is:
—$C_1$-$C_8$ alkyl,
—$(CH_2)_{0-3}$—($C_3$-$C_7$) cycloalkyl,
—$(CR_{C-x}R_{C-y})_{0-4}$—$R_{C-aryl}$,
—$(CR_{C-x}R_{C-y})_{0-4}$—$R_{C-heteroary}$,
—$(CR_{C-x}R_{C-y})_{0-4}$—$R_{C-heterocycle}$, or
-cyclopentyl or -cyclohexyl ring fused to $R_{C-aryl}$ or $R_{C-heteroaryl}$ or $R_{C-heterocycle}$.

8. A compound according to claim 7, wherein $R_C$ is:
—$(CH_2)_{0-3}$—($C_3$-$C_7$) cycloalkyl,
—$(CR_{C-x}R_{C-y})_{0-4}$—$R_{C-aryl}$,
—$(CR_{C-x}R_{C-y})_{0-4}$—$R_{C-heteroaryl}$,
—$(CR_{C-x}R_{C-y})_{0-4}$—$R_{C-heterocycle}$,
-cyclopentyl or -cyclohexyl ring fused to a $R_{C-aryl}$ $R_{C-heteroaryl}$ or $R_{C-heterocycle}$.

9. A compound according to claim 8, wherein $R_C$ is:
—$(CR_{C-x}R_{C-y})_{0-4}$—$R_{C-aryl}$,
—$(CR_{C-x}R_{C-y})_{0-4}$—$R_{C-heteroaryl}$,
-cyclopentyl or -cyclohexyl ring fused to a $R_{C-aryl}$ $R_{C-heteroaryl}$ or $R_{C-heterocycle}$.

10. A compound according to claim 9, wherein $R_C$ is:
—$(CR_{C-x}R_{C-y})_{0-4}$—$R_{C-aryl}$ where $R_{C-aryl}$ is phenyl.

11. A compound according to claim 10, wherein said phenyl is substituted in the 3-position or 3,5-positions.

12. A compound according to claim 1, wherein $R_{C-A}$ is:
-methyl, or
-ethyl.

13. A compound according to claim 1, wherein Z is:
—C(O)—, or
—C(O)—$X_{N-1}$-where $X_{N-1}$ is selected from the group consisting of —O—, —S—and —NR'—.

14. A composition comprising a compound according to claim 1, and a binder, excipient, disintegrating agent, lubricant, or glidant.

* * * * *

SEQUENCE LISTING

```
<160> NUMBER OF SEQ ID NOS: 9

<210> SEQ ID NO 1
<211> LENGTH: 13
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (11)..(11)
<223> OTHER INFORMATION: covalent attachment of oregon green

<400> SEQUENCE: 1

Ser Glu Val Asn Leu Asp Ala Glu Phe Arg Cys Lys Lys
1               5                   10

<210> SEQ ID NO 2
<211> LENGTH: 13
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (11)..(11)
<223> OTHER INFORMATION: covalent attachment of oregon green
```

```
<400> SEQUENCE: 2

Ser Glu Val Lys Met Asp Ala Glu Phe Arg Cys Lys Lys
1               5                   10

<210> SEQ ID NO 3
<211> LENGTH: 22
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (20)..(20)
<223> OTHER INFORMATION: covalent attachment of oregon green

<400> SEQUENCE: 3

Gly Leu Asn Ile Lys Thr Glu Glu Ile Ser Glu Ile Ser Tyr Glu Val
1               5                   10                  15

Glu Phe Arg Cys Lys Lys
            20

<210> SEQ ID NO 4
<211> LENGTH: 34
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (32)..(32)
<223> OTHER INFORMATION: covalent attachment of oregon green

<400> SEQUENCE: 4

Ala Asp Arg Gly Leu Thr Thr Arg Pro Gly Ser Gly Leu Thr Asn Ile
1               5                   10                  15

Lys Thr Glu Glu Ile Ser Glu Val Asn Leu Asp Ala Glu Phe Arg Cys
            20                  25                  30

Lys Lys

<210> SEQ ID NO 5
<211> LENGTH: 33
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (7)..(7)
<223> OTHER INFORMATION: oxidized cysteine
<220> FEATURE:
<221> NAME/KEY: MISC_FEATURE
<222> LOCATION: (19)..(19)
<223> OTHER INFORMATION: oxidized cysteine
<220> FEATURE:
<221> NAME/KEY: MISC_FEATURE
<222> LOCATION: (31)..(31)
<223> OTHER INFORMATION: covalent attachment of oregon green
```

```
<400> SEQUENCE: 5

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Ala Cys Lys
            20                  25                  30

Lys

<210> SEQ ID NO 6
<211> LENGTH: 33
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin

<400> SEQUENCE: 6

Cys Gly Gly Ala Asp Arg Gly Leu Thr Thr Arg Pro Gly Ser Gly Leu
1               5                   10                  15

Thr Asn Ile Lys Thr Glu Glu Ile Ser Glu Val Asn Leu Asp Ala Glu
            20                  25                  30

Phe

<210> SEQ ID NO 7
<211> LENGTH: 29
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin

<400> SEQUENCE: 7

Cys Gly Gly Ala Asp Arg Gly Leu Thr Thr Arg Pro Gly Ser Gly Leu
1               5                   10                  15

Thr Asn Ile Lys Thr Glu Glu Ile Ser Glu Val Asn Leu
            20                  25

<210> SEQ ID NO 8
<211> LENGTH: 9
<212> TYPE: PRT
<213> ORGANISM: Artificial sequence
<220> FEATURE:
<223> OTHER INFORMATION: synthetic peptide

<400> SEQUENCE: 8

Ser Glu Val Asn Leu Asp Ala Glu Phe
1               5

<210> SEQ ID NO 9
<211> LENGTH: 30
<212> TYPE: PRT
<213> ORGANISM: Artificial sequence
<220> FEATURE:
<223> OTHER INFORMATION: synthetic peptide

<400> SEQUENCE: 9

Ala Asp Arg Gly Leu Thr Thr Arg Pro Gly Ser Gly Leu Thr Asn Ile
1               5                   10                  15
```

```
-continued
Lys Thr Glu Glu Ile Ser Glu Val Asn Leu Asp Ala Glu Phe
         20              25              30
```